(12) United States Patent
Stenkamp et al.

(10) Patent No.: US 8,618,132 B2
(45) Date of Patent: *Dec. 31, 2013

(54) ALKYNE COMPOUNDS WITH MCH ANTAGONISTIC ACTIVITY AND MEDICAMENTS COMPRISING THESE COMPOUNDS

(75) Inventors: Dirk Stenkamp, Biberach (DE); Stephan Georg Mueller, Warthausen (DE); Gerald Juergen Roth, Biberach an der Riss (DE); Thorsten Lehmann-Lintz, Ochsenhausen (DE); Klaus Rudolf, Warthausen (DE); Philipp Lustenberger, Allschwil (CH); Kristen Arndt, Ravensburg (DE); Ralf R. H. Lotz, Schemmerhofen (DE); Martin Lenter, Neu-Ulm (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 550 days.

This patent is subject to a terminal disclaimer.

(21) Appl. No.: 12/121,251

(22) Filed: May 15, 2008

(65) Prior Publication Data

US 2009/0069282 A1    Mar. 12, 2009

Related U.S. Application Data

(63) Continuation of application No. 10/697,443, filed on Oct. 30, 2003, now Pat. No. 7,452,911.

(60) Provisional application No. 60/456,543, filed on Mar. 21, 2003.

(30) Foreign Application Priority Data

Oct. 31, 2002   (DE) .................................. 102 50 708

(51) Int. Cl.
*A61K 31/444* (2006.01)
*C07D 401/12* (2006.01)

(52) U.S. Cl.
USPC .......................................... 514/318; 546/194

(58) Field of Classification Search
USPC .......................................... 546/194; 514/318
See application file for complete search history.

(56) References Cited

U.S. PATENT DOCUMENTS

| | | | |
|---|---|---|---|
| 4,594,352 A | 6/1986 | Massardo et al. | |
| 4,663,334 A | 5/1987 | Carson | |
| 5,130,315 A | 7/1992 | Ong et al. | |
| 5,622,954 A | 4/1997 | Henrie, II et al. | |
| 5,856,510 A | 1/1999 | Meng et al. | |
| 6,366,268 B1 | 4/2002 | Forrest et al. | |
| 7,592,358 B2 * | 9/2009 | Stenkamp et al. ............ 514/314 |
| 2002/0019370 A1 | 2/2002 | Hegde et al. | |
| 2002/0052383 A1 | 5/2002 | Bakthavatchalam et al. | |

FOREIGN PATENT DOCUMENTS

| | | |
|---|---|---|
| CA | 2 407 149 A1 | 11/2001 |
| CA | 2 559 698 A1 | 10/2005 |
| CA | 2 559 021 A1 | 11/2005 |
| CA | 2 559 688 A1 | 11/2005 |
| CA | 2558755 A1 | 11/2005 |
| CA | 2559237 A1 | 11/2005 |
| EP | 124052 | 11/1984 |
| EP | 0494604 | 7/1992 |
| EP | 0555235 | 8/1993 |
| EP | 1 283 199 A1 | 2/2003 |
| EP | 1300405 | 4/2003 |
| JP | 60034940 | 2/1985 |
| JP | 10195063 | 7/1998 |
| JP | 2002167382 | 6/2002 |
| WO | 9206092 | 4/1992 |
| WO | 9745402 | 12/1997 |
| WO | 98/38156 A1 | 9/1998 |
| WO | 99/02497 A2 | 1/1999 |
| WO | 0015213 | 3/2000 |
| WO | 01/21577 A2 | 3/2001 |
| WO | 01/55066 A2 | 8/2001 |
| WO | 01/72712 A1 | 10/2001 |
| WO | 01/82925 A1 | 11/2001 |
| WO | 02/04433 A2 | 1/2002 |
| WO | 02/28182 A1 | 4/2002 |
| WO | 03/013247 A1 | 2/2003 |
| WO | 03/014111 A1 | 2/2003 |
| WO | 03/018579 A1 | 3/2003 |
| WO | 03/050087 A2 | 6/2003 |
| WO | 2005/100285 A2 | 10/2005 |
| WO | 2005/103002 A2 | 11/2005 |
| WO | 2005/103031 A1 | 11/2005 |
| WO | 2005103029 A1 | 11/2005 |
| WO | 2005103032 A2 | 11/2005 |

* cited by examiner

*Primary Examiner* — Patricia L Morris
(74) *Attorney, Agent, or Firm* — Michael P. Morris; Mary-Ellen M. Devlin

(57) ABSTRACT

The present invention relates to alkyne compounds of general formula I

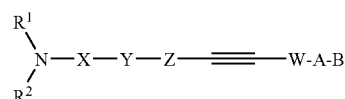

wherein the groups and residues A, B, W, X, Y, Z, $R^1$ and $R^2$ have the meanings given in claim 1. The invention further relates to pharmaceutical compositions containing at least one alkyne according to the invention. In view of their MCH-receptor antagonistic activity the pharmaceutical compositions according to the invention are suitable for the treatment of metabolic disorders and/or eating disorders, particularly obesity, bulimia, anorexia, hyperphagia and diabetes.

8 Claims, No Drawings

ALKYNE COMPOUNDS WITH MCH ANTAGONISTIC ACTIVITY AND MEDICAMENTS COMPRISING THESE COMPOUNDS

The present invention relates to new alkyne compounds, the physiologically acceptable salts thereof as well as their use as MCH antagonists and their use in preparing a pharmaceutical preparation which is suitable for the prevention and/or treatment of symptoms and/or diseases caused by MCH or causally connected with MCH in some other way. The invention also relates to the use of a compound according to the invention for influencing eating behaviour and for reducing body weight and/or for preventing any increase in body weight in a mammal. It further relates to compositions and medicaments containing a compound according to the invention and processes for preparing them.

BACKGROUND TO THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialised countries, have promoted obesity in recent decades. In affected people, obesity leads directly to restricted mobility and a reduction in the quality of life. There is the additional factor that obesity often leads to other diseases such as, for example, diabetes, dyslipidaemia, high blood pressure, arteriosclerosis and coronary heart disease. Moreover, high body weight alone puts an increased strain on the support and mobility apparatus, which can lead to chronic pain and diseases such as arthritis or osteoarthritis. Thus, obesity is a serious health problem for society.

The term obesity means an excess of adipose tissue. In this connection, obesity is fundamentally to be seen as the increased level of fatness which leads to a health risk. In the last analysis it is not precisely possible to draw a distinction between normal individuals and those suffering from obesity, but the health risk accompanying obesity is presumed to rise continuously as the level of fatness increases. For simplicity's sake, in the present invention, individuals with a Body Mass Index (BMI), which is defined as the body weight measured in kilograms divided by the height (in meters) squared, above a value of 25 and more particularly above 30 are preferably regarded as suffering from obesity.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity. One approach which has been proposed very recently is the therapeutic use of MCH antagonists (cf. inter alia WO 01/21577, WO 01/82925).

Melanin-concentrating hormone (MCH) is a cyclic neuropeptide consisting of 19 amino acids. It is synthesised predominantly in the hypothalamus in mammals and from there travels to other parts of the brain by the projections of hypothalamic neurones. Its biological activity is mediated in humans through two different G-protein-coupled receptors (GPCRs) from the family of rhodopsin-related GPCRs, namely the MCH receptors 1 and 2 (MCH-1R, MCH-2R).

Investigations into the function of MCH in animal models have provided good indications for a role of the peptide in regulating the energy balance, i.e. changing metabolic activity and food intake [1,2]. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are mediated in rodents through the $G_{V_s}$-coupled MCH-1R [3-6]. Unlike primates, ferrets and dogs, no second receptor has hitherto been found in rodents. After losing the MCH-1R, knock-out mice have a lower fat mass, an increased energy conversion and, when fed on a high fat diet, do not put on weight, compared with control animals. Another indication of the importance of the MCH-MCH-1R system in regulating the energy balance results from experiments with a receptor antagonist (SNAP-7941) [3]. In long term trials the animals treated with the antagonist lose significant amounts of weight.

In addition to its anorectic effect, the MCH-1R antagonist SNAP-7941 also achieves additional anxiolytic and antidepressant effects in behavioural experiments on rats [3]. Thus, there are clear indications that the MCH-MCH-1R system is involved not only in regulating the energy balance but also in affectivity.

Literature:
1. Qu, D., et al., A role for melanin-concentrating hormone in the central regulation of feeding behaviour. Nature, 1996. 380(6571): p. 243-7.
2. Shimada, M., et al., Mice lacking melanin-concentrating hormone are hypophagic and lean. Nature, 1998. 396(6712): p. 670-4.
3. Borowsky, B., et al., Antidepressant, anxiolytic and anorectic effects of a melanin-concentrating hormone-1 receptor antagonist. Nat Med, 2002. 8(8): p. 825-30.
4. Chen, Y., et al., Targeted disruption of the melanin-concentrating hormone receptor-1 results in hyperphagia and resistance to diet-induced obesity. Endocrinology, 2002. 143(7): p. 2469-77.
5. Marsh, D. J., et al., Melanin-concentrating hormone 1 receptor-deficient mice are lean, hyperactive, and hyperphagic and have altered metabolism. Proc Natl Acad Sci USA, 2002. 99(5): p. 3240-5.
6. Takekawa, S., et al., T-226296: A novel, orally active and selective melanin-concentrating hormone receptor antagonist. Eur J Pharmacol, 2002. 438(3): p. 129-35.

In the patent literature certain amine compounds are proposed as MCH antagonists. Thus, WO 01/21577 (Takeda) describes compounds of formula

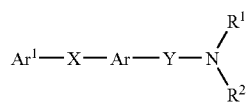

wherein $Ar^1$ denotes a cyclic group, X denotes a spacer, Y denotes a bond or a spacer, Ar denotes an aromatic ring which may be fused with a non-aromatic ring, $R^1$ and $R^2$ independently of one another denote H or a hydrocarbon group, while $R^1$ and $R^2$ together with the adjacent N atom may form an N-containing hetero ring and R² with Ar may also form a spirocyclic ring, R together with the adjacent N atom and Y may form an N-containing hetero ring, as MCH antagonists for the treatment of obesity.

Moreover WO 01/82925 (Takeda) also describes compounds of formula

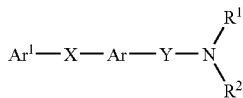

wherein Ar¹ denotes a cyclic group, X and Y represent spacer groups, Ar denotes an optionally substituted fused polycyclic aromatic ring, R¹ and R² independently of one another represent H or a hydrocarbon group, while R¹ and R² together with the adjacent N atom may form an N-containing heterocyclic ring and R² together with the adjacent N atom and Y may form an N-containing hetero ring, as MCH antagonists for the treatment of obesity, inter alia.

Aim of the Invention

The aim of the present invention is to discover new alkyne compounds, particularly those which have an activity as MCH antagonists.

A further aim of the invention is to provide new alkyne compounds which make it possible to influence the eating behaviour of mammals and in particular achieve a reduction in body weight and/or prevent an increase in body weight in mammals.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the alkyne compounds according to the invention. Other aims of the present invention will be immediately apparent to the skilled man from the foregoing remarks and those that follow.

Subject Matter of the Invention

A first object of the present invention comprises alkyne compounds of general formula I

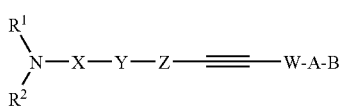

wherein

R¹, R² independently of one another denote H, a $C_{1-8}$-alkyl or $C_{3-7}$-cycloalkyl group optionally substituted by the group R¹¹, while a —CH₂— group in position 3 or 4 of a 5-, 6- or 7-membered cycloalkyl group may be replaced by —O—, —S— or —NR¹³—, or a phenyl or pyridinyl group optionally mono- or polysubstituted by the group R¹² and/or monosubstituted by nitro, or R¹ and R² form a $C_{2-8}$-alkylene bridge wherein
  one or two —CH₂— groups may be replaced independently of one another by —O—, —S—, —SO—, —(SO₂)—, —C=N—R¹⁸—, —C=N—O—R¹⁸—, —CO—, —C(=CH₂)— or —NR¹³— in such a way that heteroatoms are not directly connected to one another,
  while in the above-defined alkylene bridge one or more H atoms may be replaced by R¹⁴, and
  while the above-defined alkylene bridge may be substituted by one or two identical or different carbo- or heterocyclic groups Cy in such a way that the bond between the alkylene bridge and the group Cy is formed
  via a single or double bond,
  via a common C atom forming a spirocyclic ring system,
  via two common, adjacent C and/or N atoms forming a fused bicyclic ring system or
  via three or more C and/or N atoms forming a bridged ring system, X denotes a single bond or a $C_{1-6}$-alkylene bridge wherein
  a —CH₂— group may be replaced by —CH=CH— or —C≡C— and/or
  one or two —CH₂— groups may be replaced independently of one another by —O—, —S—, —(SO)—, —(SO₂)—, —CO— or —NR⁴— in such a way that in each case two O, S or N atoms or an O and an S atom are not directly connected to one another,
  while the bridge X may be attached to R¹ including the N atom attached to R¹ and X forming a heterocyclic group, while the bridge X may additionally also be attached to R², including the N-atom attached to R² and X, forming a heterocyclic group, and
  two C atoms or one C and one N atom of the alkylene bridge may be joined together by an additional $C_{1-4}$-alkylene bridge, and
  a C atom may be substituted by R¹⁰ and/or one or two C atoms in each case may be substituted with one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system,
  and W, Z independently of one another denote a single bond or a $C_{1-4}$-alkylene bridge,
  while in the group W and/or Z a —CH₂— group not adjacent to the —C≡C— group may be replaced by —O— or —NR⁵—, and
  two adjacent C atoms or one C atom and an adjacent N atom may be joined together by an additional $C_{1-4}$-alkylene bridge, and
  in the alkylene bridge and/or in the additional alkylene bridge a C atom may be substituted by R¹⁰ and/or one or two C atoms independently of one another may be substituted by one or two identical or different $C_{1-6}$-alkyl groups, while two alkyl groups may be joined together, forming a carbocyclic ring, and Y denotes one of the meanings given for Cy,
  while R¹ may be attached to Y including the group X and the N atom attached to R¹ and X, forming a heterocyclic group fused to Y, and/or
  X may be attached to Y forming a carbo- or heterocyclic group fused to Y, and A denotes one of the meanings given for Cy and B denotes one of the meanings given for Cy or
  $C_{1-6}$-alkyl, $C_{1-6}$-alkenyl, $C_{1-6}$-alkynyl, $C_{3-7}$-cycloalkyl-$C_{1-3}$-alkyl, $C_{3-7}$-cycloalkenyl-$C_{1-3}$-alkyl, $C_{3-7}$-cycloalkyl-$C_{1-3}$-alkenyl or $C_{3-7}$-cycloalkyl-$C_{1-3}$-alkynyl, wherein one or more C atoms may be mono- or polysubstituted by halogen and/or may be monosubstituted by hydroxy or cyano and/or cyclic groups may be mono- or polysubstituted by $R^{20}$, Cy denotes a carbo- or heterocyclic group selected from one of the following meanings
- a saturated 3- to 7-membered carbocyclic group,
- an unsaturated 4- to 7-membered carbocyclic group,
- a phenyl group,
- a saturated 4- to 7-membered or unsaturated 5- to 7-membered heterocyclic group with an N, O or S atom as heteroatom,
- a saturated or unsaturated 5- to 7-membered heterocyclic group with two or more N atoms or with one or two N atoms and an O or S atom as heteroatoms,
- an aromatic heterocyclic 5- or 6-membered group with one or more identical or different heteroatoms selected from N, O and/or S,
- while the above-mentioned 4-, 5-, 6- or 7-membered groups may be attached via two common, adjacent C atoms fused to a phenyl or pyridine ring, and
- in the above-mentioned 5-, 6- or 7-membered groups one or two non-adjacent —$CH_2$— groups may be replaced independently of one another by a —CO—, —C(=$CH_2$)—, —(SO)— or —($SO_2$)— group, and
- the above-mentioned saturated 6- or 7-membered groups may also be present as bridged ring systems with an imino, ($C_{1-4}$-alkyl)-imino, methylene, ($C_{1-4}$-alkyl)-methylene or di-($C_{1-4}$-alkyl)-methylene bridge, and
- the above-mentioned cyclic groups may be mono- or polysubstituted at one or more C atoms with $R^{20}$, in the case of a phenyl group they may also additionally be monosubstituted with nitro, and/or one or more NH groups may be substituted with $R^{21}$, $R^4$, $R^5$ independently of one another have one of the meanings given for $R^{17}$, $R^{10}$ denotes hydroxy, ω-hydroxy-$C_{1-3}$-alkyl, $C_{1-4}$-alkoxy, ω-($C_{1-4}$-alkoxy)-$C_{1-3}$-alkyl, carboxy, $C_{1-4}$-alkoxycarbonyl, amino, $C_{1-4}$-alkyl-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, amino-$C_{2-3}$-alkoxy, $C_{1-4}$-alkyl-amino-$C_{2-3}$-alkoxy, di-($C_{1-4}$-alkyl)-amino-$C_{2-3}$-alkoxy, cyclo-$C_{3-6}$-alkyleneimino-$C_{2-3}$-alkoxy, aminocarbonyl, $C_{1-4}$-alkyl-aminocarbonyl, di-($C_{1-4}$-alkyl)-aminocarbonyl, cyclo-$C_{3-6}$-alkyleneimino-carbonyl, $R^{11}$ denotes $C_{2-6}$-alkenyl, $C_{2-6}$-alkynyl, $R^{15}$—O, $R^{15}$—O—CO, $R^{15}$—CO—O, $R^{16}R^{17}$N, $R^{18}R^{19}$N—CO or Cy, $R^{12}$ has one of the meanings given for $R^{20}$, $R^{13}$ has one of the meanings given for $R^{17}$, with the exception of carboxy, $R^{14}$ denotes halogen, $C_{1-6}$-alkyl, $C_{2-6}$-alkenyl, $C_{2-6}$-alkynyl, $R^{15}$—O, $R^{15}$—O—CO, $R^{15}$—CO, $R^{15}$—CO—O, $R^{16}R^{17}$N, $R^{18}R^{19}$N—CO, $R^{15}$—O—$C_{1-3}$-alkyl, $R^{15}$—O—CO—$C_{1-3}$-alkyl, $R^{15}$—O—CO—NH, $R^{15}$—$SO_2$—NH, $R^{15}$—O—CO—NH—$C_{1-3}$-alkyl, $R^{15}$—$SO_2$—NH—$C_{1-3}$-alkyl, $R^{15}$—CO—$C_{1-3}$-alkyl, $R^{15}$—CO—O—$C_{1-3}$-alkyl, $R^{16}R^{17}$N—$C_{1-3}$-alkyl, $R^{18}R^{19}$N—CO—$C_{1-3}$-alkyl or Cy-$C_{1-3}$-alkyl, $R^{15}$ denotes H, $C_{1-4}$-alkyl, $C_{3-7}$-cycloalkyl, $C_{3-7}$-cycloalkyl-$C_{1-3}$-alkyl, phenyl, phenyl-$C_{1-3}$-alkyl, pyridinyl or pyridinyl-$C_{1-3}$-alkyl, $R^{16}$ denotes H, $C_{1-6}$-alkyl, $C_{3-7}$-cycloalkyl, $C_{3-7}$-cycloalkyl-$C_{1-3}$-alkyl, $C_{4-7}$-cycloalkenyl, $C_{4-7}$-cycloalkenyl-$C_{1-3}$-alkyl, ω-hydroxy-$C_{2-3}$-alkyl, ω-($C_{1-4}$-alkoxy)-$C_{2-3}$-alkyl, amino-$C_{2-6}$-alkyl, $C_{1-4}$-alkyl-amino-$C_{2-6}$-alkyl, di-($C_{1-4}$-alkyl)-amino-$C_{2-6}$-alkyl or cyclo-$C_{3-6}$-alkyleneimino-$C_{2-6}$-alkyl, $R^{17}$ has one of the meanings given for $R^{16}$ or denotes phenyl, phenyl-$C_{1-3}$-alkyl, pyridinyl, dioxolan-2-yl, —CHO, $C_{1-4}$-alkylcarbonyl, carboxy, hydroxycarbonyl-$C_{1-3}$-alkyl, $C_{1-4}$-alkoxycarbonyl, $C_{1-4}$-alkoxycarbonyl-$C_{1-3}$-alkyl, $C_{1-4}$-alkylcarbonylamino-$C_{2-3}$-alkyl, N—($C_{1-4}$-alkylcarbonyl)-N—($C_{1-4}$-alkyl)-amino-$C_{2-3}$-alkyl, $C_{1-4}$-alkylsulphonyl, $C_{1-4}$-alkylsulphonylamino-$C_{2-3}$-alkyl or N—($C_{1-4}$-alkylsulphonyl)-N—($C_{1-4}$-alkyl)-amino-$C_{2-3}$-alkyl $R^{18}$, $R^{19}$ independently of one another denote H or $C_{1-6}$-alkyl, $R^{20}$ denotes halogen, hydroxy, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy-$C_{1-3}$-alkyl, $R^{22}$—$C_{1-3}$-alkyl or has one of the meanings given for $R^{22}$, $R^{21}$ denotes $C_{1-4}$-alkyl, ω-hydroxy-$C_{2-6}$-alkyl, ω-$C_{1-4}$-alkoxy-$C_{2-6}$-alkyl, ω-$C_{1-4}$-alkyl-amino-$C_{2-6}$-alkyl, ω-di-($C_{1-4}$-alkyl)-amino-$C_{2-6}$-alkyl, ω-cyclo-$C_{3-6}$-alkyleneimino-$C_{2-6}$-alkyl, phenyl, phenyl-$C_{1-3}$-alkyl, $C_{1-4}$-alkyl-carbonyl, $C_{1-4}$-alkoxy-carbonyl, $C_{1-4}$-alkylsulphonyl, phenylcarbonyl or phenyl-$C_{1-3}$-alkyl-carbonyl, $R^{22}$ denotes pyridinyl, phenyl, phenyl-$C_{1-3}$-alkoxy, OHC, HO—N=HC, $C_{1-4}$-alkoxy-N=HC, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylamino-carbonyl, di-($C_{1-4}$-alkyl)-aminocarbonyl, cyclo-$C_{3-6}$-alkyl-aminocarbonyl, cyclo-$C_{3-6}$-alkyleneimino-carbonyl, cyclo-$C_{3-6}$-alkyleneimino-$C_{2-4}$-alkyl-aminocarbonyl, $C_{1-4}$-alkyl-sulphonyl, $C_{1-4}$-alkyl-sulphinyl, $C_{1-4}$-alkyl-sulphonylamino, amino, $C_{1-4}$-alkylamino, di-($C_{1-4}$-alkyl)-amino, $C_{1-4}$-alkyl-carbonyl-amino, cyclo-$C_{3-6}$-alkyleneimino, phenyl-$C_{1-3}$-alkylamino, N—($C_{1-4}$-alkyl)-phenyl-$C_{1-3}$-alkylamino, acetylamino, propionylamino, phenylcarbonyl, phenylcarbonylamino, phenylcarbonylmethylamino, hydroxy-$C_{2-3}$-alkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino or alkylaminocarbonylamino, while in the above-mentioned groups and residues, particularly in A, B, W, X, Y, Z, $R^1$ to $R^5$ and $R^{10}$ to $R^{22}$, in each case one or more C atoms may additionally be mono- or polysubstituted by F and/or in each case one or two C atoms independently of one another may additionally be monosubstituted by Cl or Br and/or in each case one or more phenyl rings independently of one another additionally have one, two or three substituents selected from among F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl- and/or may be monosubstituted by nitro, and the H atom of any carboxy group present or an H atom bound to an N atom may each be replaced by a group which can be cleaved in vivo, the tautomers, the diastereomers, the enantiomers, the mixtures thereof and the salts thereof.

The invention also relates to the compounds in the form of the individual optical isomers, mixtures of the individual enantiomers or racemates, in the form of the tautomers and in the form of the free bases or the corresponding acid addition salts with pharmacologically safe acids. The subject of the invention also includes the compounds according to the invention, including the salts thereof, wherein one or more hydrogen atoms are replaced by deuterium.

This invention also includes the physiologically acceptable salts of the alkyne compounds according to the invention as described above and hereinafter.

This invention also relates to compositions containing at least one alkyne compound according to the invention and/or a salt according to the invention optionally together with one or more physiologically acceptable excipients.

Also covered by this invention are pharmaceutical compositions containing at least one alkyne compound according to the invention and/or a salt according to the invention optionally together with one or more inert carriers and/or diluents.

This invention also relates to the use of at least one alkyne compound according to the invention and/or a salt according to the invention for influencing the eating behaviour of a mammal.

The invention further relates to the use of at least one alkyne compound according to the invention and/or a salt according to the invention for reducing the body weight and/or for preventing an increase in the body weight of a mammal.

The invention also relates to the use of at least one alkyne compound according to the invention and/or a salt according to the invention for preparing a pharmaceutical composition with an MCH receptor-antagonistic activity, particularly with an MCH-1 receptor-antagonistic activity.

This invention also relates to the use of at least one alkyne compound according to the invention and/or a salt according to the invention for preparing a pharmaceutical composition which is suitable for the prevention and/or treatment of symptoms and/or diseases which are caused by MCH or are otherwise causally connected with MCH.

A further object of this invention is the use of at least one alkyne compound according to the invention and/or a salt according to the invention for preparing a pharmaceutical composition which is suitable for the prevention and/or treatment of metabolic disorders and/or eating disorders, particularly obesity, bulimia, bulimia nervosa, cachexia, anorexia, anorexia nervosa and hyperphagia The invention also relates to the use of at least one alkyne compound according to the invention and/or a salt according to the invention for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis and gonitis.

In addition the present invention relates to the use of at least one alkyne compound according to the invention and/or a salt according to the invention for preparing a pharmaceutical composition which is suitable for the prevention and/or treatment of hyperlipidaemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia and hormonal disorders.

The invention also relates to the use of at least one alkyne compound according to the invention and/or a salt according to the invention for preparing a pharmaceutical composition which is suitable for the prevention and/or treatment of urinary problems, such as for example urinary incontinence, overactive bladder, urgency, nycturia and enuresis.

The invention further relates to processes for preparing for preparing a pharmaceutical composition according to the invention, characterised in that at least one alkyne compound according to the invention and/or a salt according to the invention is incorporated in one or more inert carriers and/or diluents by a non-chemical method.

The invention also relates to a pharmaceutical composition containing a first active substance which is selected from the alkyne compounds according to the invention and/or the corresponding salts as well as a second active substance which is selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of hyperlipidaemia, including arteriosclerosis, active substances for the treatment of arthritis, active substances for the treatment of anxiety states and active substances for the treatment of depression, optionally together with one or more inert carriers and/or diluents.

This invention further relates to a process for preparing alkyne compounds of formula A.5

  (A.5)

while in formulae A.1, A.2, A.3, A.4 and A.5 $R^1$, $R^2$, X, Y, W, A and B have one of the meanings given hereinbefore and hereinafter and Y denotes aryl or heteroaryl,
wherein a halogen compound of formula A.1

  (A.1)

wherein Hal denotes chlorine, bromine or iodine, preferably bromine or iodine,
is reacted with an alkyne compound of formula A.2

  (A.2)

in the presence of a suitable palladium catalyst, a suitable base and copper(I)iodide in a suitable solvent, and
the resulting compound of formula A.3

  (A.3)

is reacted with methanesulphonic acid chloride (MsCl) to form the methanesulphonate derivative A.4,

  (A.4)

which is further reacted with an amine of formula H—$NR^1R^2$ to obtain the end product A.5.

This invention further relates to a process for preparing alkyne compounds of formula B.5

  (B.5)

while in formulae B.1, B.2, B.3, B.4 and B.5 $R^1$, $R^2$, X, Y, Z, A and B have one of the meanings given hereinbefore and hereinafter and A particularly denotes aryl or heteroaryl,
wherein a halogen compound of formula B.1

  (B.1)

wherein Hal denotes chlorine, bromine or iodine, preferably bromine or iodine,
is reacted with an alkyne compound of formula B.2

  (B.2)

in the presence of a suitable palladium catalyst, a suitable base and copper(I)iodide in a suitable solvent, and
the resulting compound of formula B.3

  (B.3)

is reacted with methanesulphonic acid chloride (MsCl) to form the methanesulphonate derivative B.4, $$\text{MsO—X—Y-Z-C} \equiv \text{C-A-B} \qquad (B.4)$$

which is further reacted with an amine of formula H—NR$^1$R$^2$ to obtain the end product B.5.

Moreover this invention relates to a process for preparing alkyne compounds of formula C.3

$$R^1R^2N\text{—X—Y—C} \equiv \text{C—W-A-B} \qquad (C.3)$$

while in formulae C.1, C.2 and C.3 R$^1$, R$^2$, X, Y, W, A and B have one of the meanings given hereinbefore and hereinafter and Y denotes aryl or heteroaryl,
wherein a halogen compound of formula C.1

$$R^1R^2N\text{—X—Y-Hal} \qquad (C.1)$$

wherein Hal denotes chlorine, bromine or iodine, preferably bromine or iodine,
is further reacted with an alkyne compound of formula C.2

$$H\text{—C} \equiv \text{C—W-A-B} \qquad (C.2)$$

in the presence of a suitable palladium catalyst, a suitable base and copper(I)iodide in a suitable solvent to obtain the end product C.3.

This invention further relates to a process for preparing alkyne compounds of formula D.3

$$R^1R^2N\text{—X—Y-Z-C} \equiv \text{C-A-B} \qquad (D.3)$$

while in formulae D.1, D.2 and D.3 R$^1$, R$^2$, X, Y, Z, A and B have one of the meanings given hereinbefore and hereinafter and A particularly denotes aryl or heteroaryl,
wherein a halogen compound of formula D.2

$$\text{Hal-A-B} \qquad (D.2)$$

wherein Hal denotes chlorine, bromine or iodine, preferably bromine or iodine, is reacted with an alkyne compound of formula D.1

$$R^1R^2N\text{—X—Y-Z-C} \equiv \text{C—H} \qquad (D.1)$$

in the presence of a suitable palladium catalyst, a suitable base and copper(I)iodide in a suitable solvent to obtain the end product D.3.

MORE DETAILED DESCRIPTION OF THE INVENTION

Unless otherwise specified the groups, residues and substituents, particularly A, B, W, X, Y, Z, R$^1$ to R$^5$ and R$^{10}$ to R$^{22}$, have the meanings given hereinbefore and hereinafter.

According to one embodiment of the invention the groups R$^1$, R$^2$, X, W, Z, B, R$^{10}$, R$^{13}$, R$^{14}$, R$^{15}$, R$^{17}$, R$^{20}$, R$^{22}$ have the following meanings:

R$^1$, R$^2$ independently of one another denote H, a C$_{1-8}$-alkyl or C$_{3-7}$-cycloalkyl group optionally substituted by the group R$^{11}$ or a phenyl group optionally mono- or polysubstituted by the group R$^{12}$ and/or monosubstituted by nitro, or R$^1$ and R$^2$ form a C$_{2-8}$-alkylene bridge, wherein
one or two —CH$_2$— groups independently of one another may be replaced by —CH=N— or —CH=CH— and/or
one or two —CH$_2$— groups independently of one another may be replaced by —O—, —S—, —CO—, —C(=CH$_2$)— or —NR$^{13}$— in such a way that heteroatoms are not directly joined together,
while in the alkylene bridge defined hereinbefore one or more H atoms may be replaced by R$^{14}$, and
the alkylene bridge defined hereinbefore may be substituted by one or two identical or different carbo- or heterocyclic groups Cy in such a way that the bond between the alkylene bridge and the group Cy is made
via a single or double bond,
via a common C atom forming a spirocyclic ring system,
via two common adjacent C— and/or N atoms forming a fused bicyclic ring system or
via three or more C— and/or N atoms forming a bridged ring system, X denotes a single bond or a C$_{1-6}$-alkylene bridge, wherein
a —CH$_2$— group may be replaced by —CH=CH— or —C≡C— and/or
one or two —CH$_2$— groups independently of one another may be replaced by —O—, —S—, —(SO)—, —(SO$_2$)—, —CO— or —NR$^4$— in such a way that in each case two O, S or N atoms or an O and an S atom are not directly joined together,
while the bridge X may be attached to R$^1$ including the N atom attached to R$^1$ and X, forming a heterocyclic group, and
while two C atoms or a C and an N atom of the alkylene bridge may be joined together by an additional C$_{1-4}$-alkylene bridge, and
a C atom may be substituted by R$^{10}$ and/or one or two C atoms in each case may be substituted by one or two identical or different C$_{1-6}$-alkyl groups, and W, Z independently of one another denote a single bond or a C$_{1-4}$-alkylene bridge,
while in the group W and/or Z a —CH$_2$— group not adjacent to the —C≡C— group may be replaced by —O— or —NR$^5$—, and
two adjacent C atoms or a C atom and an adjacent N atom may be joined together by an additional C$_{1-4}$-alkylene bridge, and
in the alkylene bridge and/or in the additional alkylene bridge a C atom may be substituted by R$^{10}$ and/or one or two C atoms independently of one another may be substituted by one or two identical or different C$_{1-6}$-alkyl groups, and B has one of the meanings given for Cy or
denotes C$_{1-6}$-alkyl, C$_{1-6}$-alkenyl, C$_{1-6}$-alkynyl, C$_{3-7}$-cycloalkyl-C$_{1-3}$-alkyl, C$_{3-7}$-cycloalkenyl-C$_{1-3}$-alkyl, C$_{3-7}$-cycloalkyl-C$_{1-3}$-alkenyl or C$_{3-7}$-cycloalkyl-C$_{1-3}$-alkynyl, wherein one or more C atoms may be mono- or polysubstituted by fluorine and cyclic groups may be mono- or polysubstituted by R$^{20}$, R$^{10}$ denotes hydroxy, ω-hydroxy-C$_{1-3}$-alkyl, C$_{1-4}$-alkoxy, ω-(C$_{1-4}$-alkoxy)-C$_{1-3}$-alkyl, amino, C$_{1-4}$-alkyl-amino, di-(C$_{1-4}$-alkyl)-amino, cyclo-C$_{3-6}$-alkyleneimino, amino-C$_{1-3}$-alkyl, C$_{1-4}$-alkyl-amino-C$_{1-3}$-alkyl, di-(C$_{1-4}$-alkyl)-amino-C$_{1-3}$-alkyl, cyclo-C$_{3-6}$-alkyleneimino-C$_{1-3}$-alkyl, amino-C$_{2-3}$-alkoxy, C$_{1-4}$-alkyl-amino-C$_{2-3}$-alkoxy, di-(C$_{1-4}$-alkyl)-amino-C$_{2-3}$-alkoxy or cyclo-C$_{3-6}$-alkyleneimino-C$_{2-3}$-alkoxy, R$^{13}$ has one of the meanings given for R$^{17}$, R$^{14}$ denotes halogen, C$_{1-6}$-alkyl, R$^{15}$—O, R$^{15}$—O—CO, R$^{15}$—CO, R$^{15}$—CO—O, R$^{16}$R$^{17}$N, R$^{18}$R$^{19}$N—CO, R$^{15}$—O—C$_{1-3}$-alkyl, R$^{15}$—O—CO—C$_{1-3}$-alkyl, R$^{15}$—CO—C$_{1-3}$-alkyl, R$^{15}$—CO—O—C$_{1-3}$-alkyl, R$^{16}$R$^{17}$N—C$_{1-3}$-alkyl, R$^{18}$R$^{19}$N—CO—C$_{1-3}$-alkyl or Cy-C$_{1-3}$-alkyl, R$^{15}$ denotes H, C$_{1-4}$-alkyl, C$_{3-7}$-cycloalkyl, C$_{3-7}$-cycloalkyl-C$_{1-3}$-alkyl, phenyl or phenyl-C$_{1-3}$-alkyl, R$^{17}$ has one of the meanings given for R$^{16}$ or denotes phenyl, phenyl-C$_{1-3}$-alkyl, C$_{1-4}$-alkylcarbonyl, hydroxycarbonyl-$C_{1-3}$-alkyl, $C_{1-4}$-alkylcarbonylamino-$C_{2-3}$-alkyl, N—($C_{1-4}$-alkylcarbonyl)-N—($C_{1-4}$-alkyl)-amino-$C_{2-3}$-alkyl, $C_{1-4}$-alkylsulphonyl, $C_{1-4}$-alkylsulphonylamino-$C_{2-3}$-alkyl or N—($C_{1-4}$-alkylsulphonyl)-N($C_{1-4}$-alkyl)-amino-$C_{2-3}$-alkyl $R^{20}$ denotes halogen, hydroxy, cyano, $C_{1-6}$-alkyl, $C_{3-7}$-cycloalkyl, $C_{3-7}$-cycloalkyl-$C_{1-3}$-alkyl, hydroxy-$C_{1-3}$-alkyl, $R^{22}$—$C_{1-3}$-alkyl or has one of the meanings given for $R^{22}$, $R^{22}$ denotes phenyl, phenyl-$C_{1-3}$-alkoxy, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, cyclo-$C_{3-6}$-alkyleneimino-carbonyl, $C_{1-4}$-alkyl-sulphonyl, $C_{1-4}$-alkyl-sulphinyl, $C_{1-4}$-alkyl-sulphonylamino, amino, $C_{1-4}$-alkylamino, di-($C_{1-4}$-alkyl)-amino, cyclo-$C_{3-6}$-alkyleneimino, phenyl-$C_{1-3}$-alkylamino, N—($C_{1-4}$-alkyl)-phenyl-$C_{1-3}$-alkylamino, acetylamino, propionylamino, phenylcarbonyl, phenylcarbonylamino, phenylcarbonylmethylamino, hydroxyalkylaminocarbonyl, (4-morpholinyl)carbonyl, (1-pyrrolidinyl)-carbonyl, (1-piperidinyl)carbonyl, (hexahydro-1-azepinyl)carbonyl, (4-methyl-1-piperazinyl)carbonyl, methylenedioxy, aminocarbonylamino or alkylaminocarbonylamino, while $R^4$, $R^{11}$, $R^{12}$, $R^{16}$, $R^{18}$, $R^{19}$ and Cy are as hereinbefore defined.

If $R^1$ and $R^2$ are not joined together via an alkylene bridge, $R^1$ and $R^2$ independently of one another preferably denote a $C_{1-8}$-alkyl or $C_{3-7}$-cycloalkyl group optionally substituted by the group $R^{11}$, while a —$CH_2$— group in position 3 or 4 of a 5-, 6- or 7-membered cycloalkyl group may be replaced by —O—, —S— or —NH—, —N($C_{1-4}$-alkyl)- or —N(CO—O—$C_{1-4}$-alkyl)-, or phenyl or pyridinyl group optionally mono- or polysubstituted by the group $R^{12}$ and/or monosubstituted by nitro, and one of the groups $R^1$ and $R^2$ may also denote H.

Preferably, the groups $R^1$, $R^2$ independently of one another represent H, $C_{1-6}$-alkyl, $C_{3-7}$-cycloalkyl, $C_{3-7}$-cycloalkyl-$C_{1-3}$-alkyl, ω-hydroxy-$C_{2-3}$-alkyl, CO—($C_{1-4}$-alkoxy)-$C_{2-3}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$-alkyl, pyrrolidin-3-yl, N—($C_{1-4}$-alkyl)-pyrrolidinyl, pyrrolidinyl-$C_{1-3}$-alkyl, N—($C_{1-4}$-alkyl)-pyrrolidinyl-$C_{1-3}$-alkyl, piperidinyl, N—($C_{1-4}$-alkyl)-piperidinyl, piperidinyl-$C_{1-3}$-alkyl, N—($C_{1-4}$-alkyl)-piperidinyl-$C_{1-3}$-alkyl, phenyl, phenyl-$C_{1-3}$-alkyl, pyridyl or pyridyl-$C_{1-3}$-alkyl, while in the above-mentioned groups and residues one or more C atoms may be mono- or polysubstituted by F and/or one or two C atoms may be monosubstituted independently of one another by Cl or Br, and the phenyl or pyridyl group may be mono- or polysubstituted by the above-defined group $R^{12}$ and/or may be monosubstituted by nitro. Preferred substituents of the above-mentioned phenyl or pyridyl groups are selected from among F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl- and di-($C_{1-3}$-alkyl)-amino-$C_{1-3}$-alkyl, while a phenyl group may also be monosubstituted by nitro.

Particularly preferably, at least one of the groups $R^1$, $R^2$, and most particularly preferably both groups, have a meaning other than H.

If $R^1$ and $R^2$ form an alkylene bridge, it is preferably a $C_{3-7}$-alkylene bridge, wherein a —$CH_2$— group not adjacent to the N atom of the $R^1R^2N$ group may be replaced by —CH=N— or —CH=CH— and/or a —$CH_2$— group which is preferably not adjacent to the N atom of the $R^1R^2N$ group may be replaced by —O—, —S—, —C(=N—$R^{18}$)—, —C—O, —C(=$CH_2$)— or —$NR^{13}$— in such a way that heteroatoms are not directly joined together, while in the alkylene bridge defined hereinbefore one or more H atoms may be replaced by $R^{14}$, and the alkylene bridge defined hereinbefore may be substituted by a carbo- or heterocyclic group Cy in such a way that the bond between the alkylene bridge and the group Cy is made
via a single bond,
via a common C atom forming a spirocyclic ring system,
via two common adjacent C and/or N atoms forming a fused bicyclic ring system or
via three or more C and/or N atoms forming a bridged ring system.

Also preferably, $R^1$ and $R^2$ form an alkylene bridge in such a way that $R^1R^2N$— denotes a group selected from azetidine, pyrrolidine, piperidine, azepan, 2,5-dihydro-1H-pyrrole, 1,2,3,6-tetrahydro-pyridine, 2,3,4,7-tetrahydro-1H-azepine, 2,3,6,7-tetrahydro-1H-azepine, piperazine, wherein the free imine function is substituted by $R^{13}$, piperidin-4-one, piperidin-4-one-oxime, piperidin-4-one-O—$C_{1-4}$-alkyl-oxime, morpholine and thiomorpholine, while according to the general definition of $R^1$ and $R^2$ one or more H atoms may be replaced by $R^{14}$, and/or the above-mentioned groups may be substituted by one or two identical or different carbo- or heterocyclic groups Cy in a manner specified according to the general definition of $R^1$ and $R^2$. Particularly preferred groups Cy are $C_{3-7}$-cycloalkyl, aza-$C_{4-7}$-cycloalkyl, particularly cyclo-$C_{3-6}$-alkyleneimino, as well as 1-$C_{1-4}$-alkyl-aza-$C_{4-7}$-cycloalkyl.

The $C_{2-8}$-alkylene bridge formed by $R^1$ and $R^2$, wherein —$CH_2$— groups may be replaced as specified, may be substituted by one or two identical or different carbo- or heterocyclic groups Cy, as described.

In the event that the alkylene bridge is linked to a group Cy via a single bond, Cy is preferably selected from among $C_{3-7}$-cycloalkyl, cyclo-$C_{3-6}$-alkyleneimino, 1H-imidazole, thienyl and phenyl.

In the event that the alkylene bridge is linked to a group Cy via a common C atom forming a spirocyclic ring system, Cy is preferably selected from among $C_{3-7}$-cycloalkyl, aza-$C_{4-8}$-cycloalkyl, oxa-$C_{4-8}$-cycloalkyl, 2,3-dihydro-1H-quinazolin-4-one.

In the event that the alkylene bridge is linked to a group Cy via two common adjacent C and/or N atoms forming a fused bicyclic ring system, Cy is preferably selected from among $C_{4-7}$-cycloalkyl, phenyl, thienyl.

In the event that the alkylene bridge is linked to a group Cy via three or more C and/or N atoms forming a bridged ring system, Cy preferably denotes $C_{4-8}$-cycloalkyl or aza-$C_{4-8}$-cycloalkyl.

Particularly preferably, the group

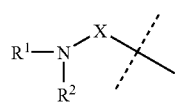

is defined according to one of the following partial formulae
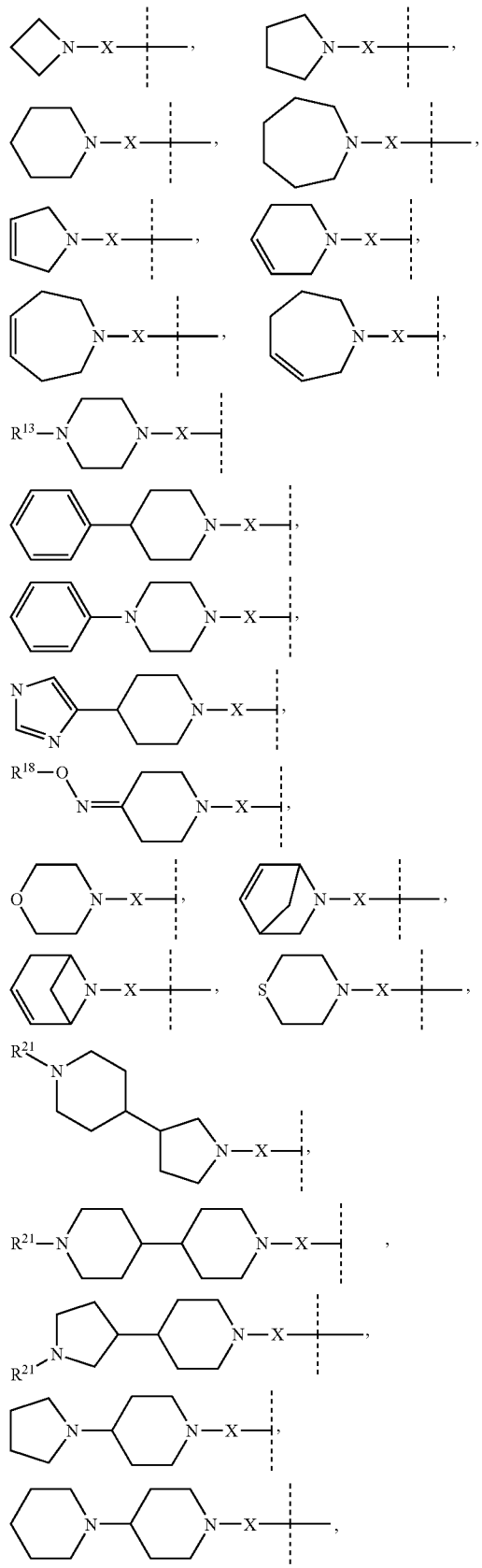
-continued
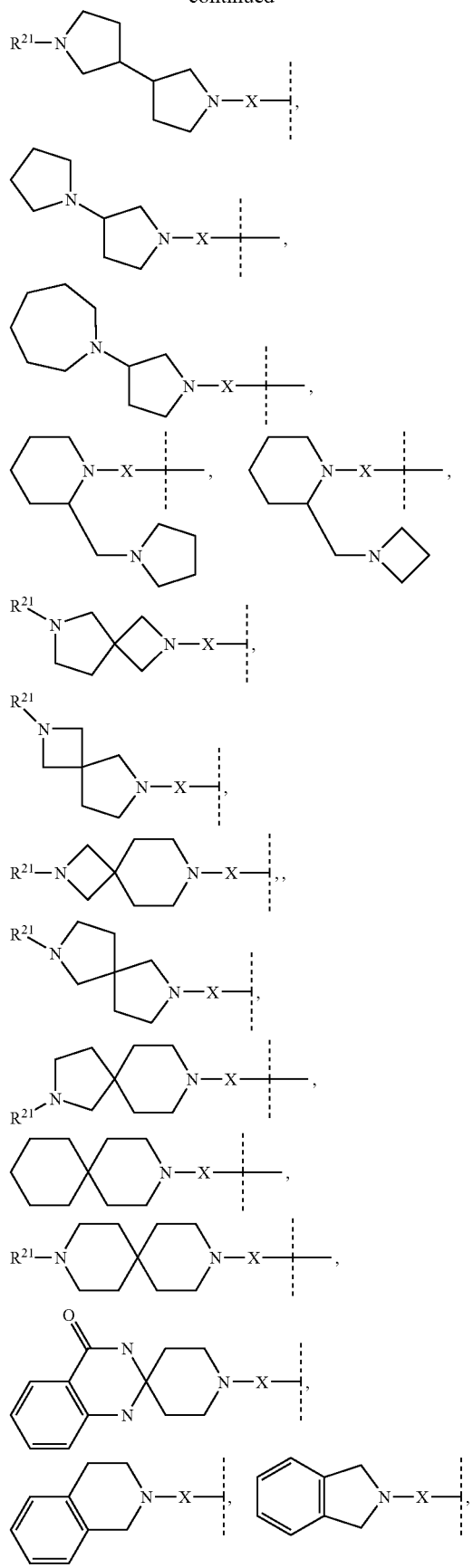

-continued

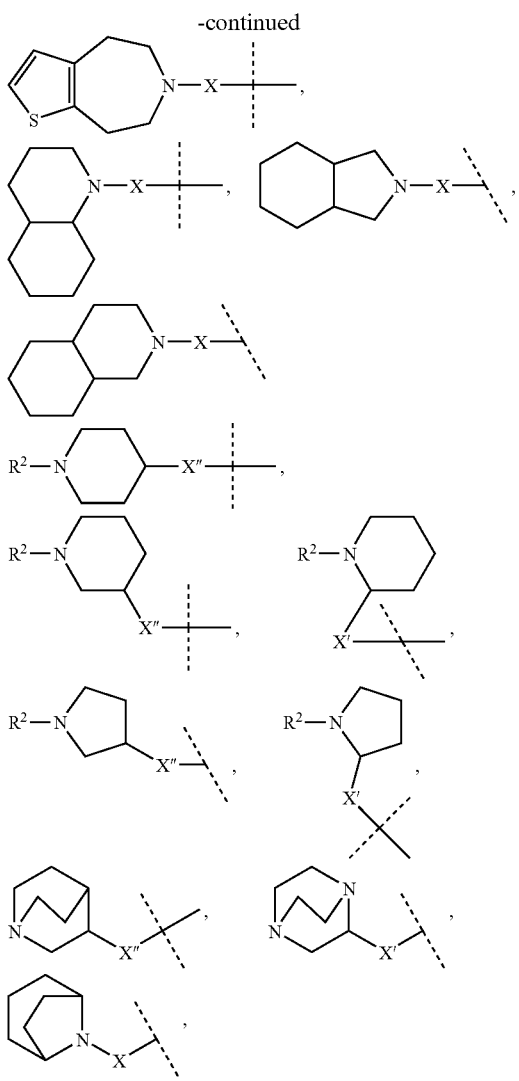

wherein one or more H atoms of the heterocycle formed by the group $R^1R^2N—$ may be replaced by $R^{14}$ and the ring attached to the heterocycle formed by the group $R^1R^2N—$ may be mono- or polysubstituted by $R^{20}$ at one or more C atoms, in the case of a phenyl ring may also additionally be monosubstituted by nitro and X', X" independently of one another denote a single bond or $C_{1-3}$-alkylene and
in the event that the group Y is linked to X' or X" via a C atom, also denotes —$C_{1-3}$-alkylene-O—, —$C_{1-3}$-alkylene-NH— or —$C_{1-3}$-alkylene-N($C_{1-3}$-alkyl)-, and X" additionally also denotes —O—$C_{1-3}$-alkylene-, —NH—$C_{1-3}$-alkylene- or —N($C_{1-3}$-alkyl)-$C_{1-3}$-alkylene- and
in the event that the group Y is linked to X" via a C atom, also denotes —NH—, —N($C_{1-3}$-alkyl)- or —O—,
while in the meanings given for X', X" hereinbefore, in each case a C atom may be substituted by $R^{10}$, preferably by a hydroxy, ω-hydroxy-$C_{1-3}$-alkyl, O—($C_{1-4}$-alkoxy)-$C_{1-3}$-alkyl and/or $C_{1-4}$-alkoxy group, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, and in X', X" independently of one another in each case one or more C atoms may be mono- or polysubstituted by F and/or in each case one or two C atoms independently of one another may be monosubstituted by Cl or Br and wherein $R^2$, $R^{10}$, $R^{13}$, $R^{14}$, $R^{20}$, $R^{21}$ and X have the meanings given above and hereinafter.

In the preferred and particularly preferred meanings of $R^1R^2N$ listed above the following definitions of the substituent $R^{14}$ are preferred: $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, ω-hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, carboxy, $C_{1-4}$-alkoxy-carbonyl, hydroxy-carbonyl-$C_{1-3}$-alkyl, $C_{1-4}$-alkoxycarbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkyl-amino, $C_{3-7}$-cycloalkyl-amino, N—($C_{3-7}$-cycloalkyl)-N—($C_{1-4}$-alkyl)-amino, di-($C_{1-4}$-alkyl)-amino, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, $C_{1-4}$-alkyl-amino-carbonyl, $C_{3-7}$-cycloalkyl-amino-carbonyl, N—($C_{3-7}$-cycloalkyl)-N—($C_{1-4}$-alkyl)-amino-carbonyl, di-($C_{1-4}$-alkyl)-amino-carbonyl, pyridinyl-oxy, pyridinyl-amino, pyridinyl-$C_{1-3}$-alkyl-amino.

Most particularly preferred meanings of the substituent $R^{14}$ are $C_{1-4}$-alkyl, hydroxy, ω-hydroxy-$C_{1-3}$-alkyl, $C_{1-4}$-alkoxy and O—($C_{1-4}$-alkoxy)-$C_{1-3}$-alkyl.

Preferably X denotes a single bond or a $C_{1-4}$-alkylene bridge, wherein
a —$CH_2$— group may be replaced by —CH=CH— or —C≡C— and/or
a —$CH_2$— group may be replaced by —O—, —S—, —CO— or —$NR^4$— in such a way that in each case two O, S or N atoms or an O and an S atom are not directly joined together,
while the bridge X may be attached to $R^1$ including the N atom attached to $R^1$ and X, forming a heterocyclic group, while the bridge X may additionally also be linked to $R^2$ including the N atom attached to $R^2$ and X, forming a heterocyclic group, and
while two C atoms or a C and an N atom of the alkylene bridge may be joined together by an additional $C_{1-4}$-alkylene bridge, and
a C atom may be substituted by $R^{10}$ and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, particularly a cyclopropyl, cyclobutyl or cyclopentyl group.

If in the group X a —$CH_2$— group of the alkylene bridge is replaced according to the invention, this —$CH_2$— group is preferably not attached directly to a heteroatom, a double or triple bond.

Preferably the alkylene bridge X, X' or X" has no or at most one imino group. The position of the imino group within the alkylene bridge X, X' or X" is preferably selected so that no aminal function is formed together with the amino group $NR^1R^2$ or another adjacent amino group or two N atoms are not adjacent to each other.

Preferably X denotes a single bond or $C_{1-4}$-alkylene and in the event that the group Y is linked to X via a C atom, it also denotes —$CH_2$—CH=CH—, —$CH_2$—C≡C—, $C_{2-4}$-alkylenoxy, $C_{2-4}$-alkylene-$NR^4$, $C_{2-4}$-alkylene-$NR^4$—$C_{2-4}$-alkylene-O, 1,2- or 1,3-pyrrolidinylene or 1,2-, 1,3- or 1,4-piperidinylene, while the pyrrolidinylene and piperidinylene groups are bound to Y via the imino group, while the bridge X may be attached to $R^1$ including the N atom attached to $R^1$ and X, forming a heterocyclic group, and the bridge X may additionally also be attached to $R^2$, including the N atom attached to $R^2$ and X, forming a heterocyclic group, and in X a C atom may be substituted by $R^{10}$, preferably a hydroxy, ω-hydroxy-$C_{1-3}$-alkyl, ω-($C_{1-4}$-alkoxy)-$C_{1-3}$-alkyl- and/or $C_{1-4}$-alkoxy group, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, and in the above-mentioned groups and residues one or more C atoms may be mono- or polysubstituted by F and/or one or two C atoms independently of one another may be monosubstituted by Cl or Br and $R^1$, $R^4$ and $R^{10}$ are as hereinbefore defined.

Particularly preferably X denotes —$CH_2$—, —$CH_2$—$CH_2$— or —$CH_2$—$CH_2$—$CH_2$— and in the event that the group Y is bonded to X via a C atom, it also denotes —$CH_2$—C≡C— —$CH_2$—$CH_2$—O—, —$CH_2$—$CH_2$—$NR^4$— or 1,3-pyrrolidinylene, while the pyrrolidinylene group is linked to Y via the imino group, and the bridge X may be attached to $R^1$ including the N atom attached to $R^1$ and X, forming a heterocyclic group, and the bridge X may additionally also be attached to $R^2$, including the N atom attached to $R^2$ and X, forming a heterocyclic group, and in X a C atom may be substituted by $R^{10}$, preferably a hydroxy, ω-hydroxy-$C_{1-3}$-alkyl, ω-($C_{1-4}$-alkoxy)-$C_{1-3}$-alkyl and/or $C_{1-4}$-alkoxy group, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents may be joined together, forming a carbocyclic ring system, and in each case one or more C atoms may be mono- or polysubstituted by F and/or in each case one or two C atoms independently of one another may be monosubstituted by Cl or Br.

If in the group X, X' or X" one or more C atoms is or are substituted by a hydroxy and/or $C_{1-4}$-alkoxy group, the substituted C atom is preferably not directly adjacent to another heteroatom.

If in X, X' or X" a C atom is substituted, preferred substituents are selected from among $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, ω-hydroxy-$C_{1-3}$-alkyl, ω-($C_{1-4}$-alkoxy)-$C_{1-3}$-alkyl- and $C_{1-4}$-alkoxy groups. Moreover in X, X' or X" a C atom may be disubstituted and/or one or two C atoms may be mono- or disubstituted, while preferred substituents are selected from among $C_{1-4}$-alkyl, $C_{2-4}$-alkenyl, $C_{2-4}$-alkynyl, $C_{3-7}$-cycloalkyl and $C_{3-7}$-cycloalkyl-$C_{1-3}$-alkyl, and two $C_{1-4}$-alkyl and/or $C_{2-4}$-alkenyl substituents may also be joined together, forming a saturated or monounsaturated carbocyclic ring.

Most particularly preferred substituents of one or two C atoms in X, X' or X" are selected from methyl, ethyl, n-propyl, i-propyl, cyclopropyl, cyclopropylmethyl, while two alkyl substituents may also be joined together at a C atom, forming a carbocyclic ring.

If X denotes an alkylene bridge, the —$CH_2$— group adjacent to the $R^1R^2N$— group is preferably not replaced by —O—, —S—, —(SO)—, —($SO_2$)—, —CO— or —$NR^4$—.

Most particularly preferably, X denotes —$CH_2$—, —$CH_2$—$CH_2$— or —$CH_2$—$CH_2$—$CH_2$— and in the event that the group Y is attached to X via a C atom, also denotes —$CH_2$—$CH_2$—O—, —$CH(CH_3)$—$CH_2$—O—, —$CH_2$—$CH(CH_3)$—O—, —$CH_2$—$CH_2$—NH—, —$CH(CH_3)$—$CH_2$—NH— or —$CH_2$—$CH_2$—$N(CH_3)$—. In the event that $R^1$ and/or $R^2$ have an amine function, which may also be substituted, another particularly preferred meaning of X is a single bond.

According to a first preferred embodiment according to the invention Z denotes a single bond.

In a second preferred embodiment according to the invention Z is a $C_{1-4}$-alkylene bridge, which may be substituted and/or wherein a —$CH_2$— group may be replaced as specified.

Preferred definitions of the groups W and/or Z, particularly the group Z, are, independently of one another, a single bond or a bridge selected from among —$CH_2$—, —$CH_2$—$CH_2$—, —$CH_2$—$CH(CH_3)$—, —$CH_2$—$C(CH_3)_2$—, —$CH(CH_3)$—$CH_2$—, —$C(CH_3)_2$—$CH_2$—, cyclopropylene, —$CH_2$—CH($R^{10}$)— and —$CH(R^{10})$—$CH_2$—. Additional particularly preferred definitions of the group W are also —$CH_2$—O— or —$CH_2$—$NR^4$—. Additional particularly preferred definitions of the group Z are also —O—$CH_2$— or —$NR^4$—$CH_2$—.

According to one preferred embodiment according to the invention W denotes a single bond.

Preferably W and/or Z independently of one another represent a single bond, —$CH_2$—, —$CH_2$—$CH_2$—, —$CH_2$—$CH_2$—$CH_2$, 1,1-cyclopropylene or 1,2-cyclopropylene.

W may preferably additionally also represent —$CH_2$—O—, —$CH_2$—$CH_2$—O—, —$CH_2$—$NR^4$— or —$CH_2$—$CH_2$—$NR^4$—.

In addition to the definitions given above Z may also preferably represent —O—$CH_2$—, —O—$CH_2$—$CH_2$—, —$NR^4$—$CH_2$— or —$NR^4$—$CH_2$—$CH_2$—.

In the above-mentioned definitions of the groups W and Z a C atom may be substituted by $R^{10}$, preferably by a hydroxy, ω-hydroxy-$C_{1-3}$-alkyl, ω-($C_{1-4}$-alkoxy)-$C_{1-3}$-alkyl and/or $C_{1-4}$-alkoxy group, and/or one or two C atoms may each independently of one another be substituted by one or two identical or different $C_{1-4}$-alkyl groups, while two alkyl groups may be joined together, forming a carbocyclic group, particularly a cyclopropyl, cyclobutyl or cyclopentyl group. Moreover in each case one or more C atoms in the groups W and Z may be mono- or polysubstituted by F and/or in each case one or two C atoms may each independently of one another be monosubstituted by Cl or Br.

In the event that the bridge X comprises a carbonyl group, W and Z preferably do not contain an —O— bridge.

In the definitions of the groups W and/or Z, $R^4$ has the meanings given above, preferably —H, methyl, ethyl, propyl or iso-propyl.

In the definitions of the groups W and/or Z, $R^{10}$ has the meanings given above, preferably —OH, N-pyrrolidinyl, amino-ethoxy, $C_{1-4}$-alkyl-amino-ethoxy or di-($C_{1-4}$-alkyl)-amino-ethoxy.

In the above-mentioned definitions of the groups W and/or Z in each case one or more C atoms may be mono- or polysubstituted by F and/or in each case one or two C atoms independently of one another may be monosubstituted by Cl or Br.

If in the group W and/or Z one or two C atoms are substituted by a hydroxy and/or $C_{1-3}$-alkoxy group, the substituted C atom is preferably not immediately adjacent to another heteroatom.

According to one embodiment compounds of formula I according to the invention have W and Z bridges, while precisely one or both of the bridges W and Z represent a single bond.

A preferred definition of the group Y is aryl or heteroaryl.

The group Y preferably has a meaning which is selected from the group of the bivalent cyclic groups phenyl, naphthyl, thienyl, benzothienyl, tetrahydronaphthyl, pyridinyl, pyrimidinyl, pyrazinyl, pyridazinyl, indolyl, dihydroindolyl, dihydroindolonyl, quinolinyl, tetrahydroquinolinyl, isoquinolinyl, tetrahydroisoquinolinyl, indazolyl, benzimidazolyl, benzofuranyl or benzoxazolyl, while the above-mentioned cyclic groups may be mono- or polysubstituted at one or more C atoms by $R^{20}$, or in the case of a phenyl group may also additionally be monosubstituted by nitro, and/or substituted by $R^{21}$ at one or more N atoms. $R^1$ may be attached to Y and/or X may be attached to Y as hereinbefore defined.

Particularly preferably, a definition of the group Y is selected from among the bivalent cyclic groups

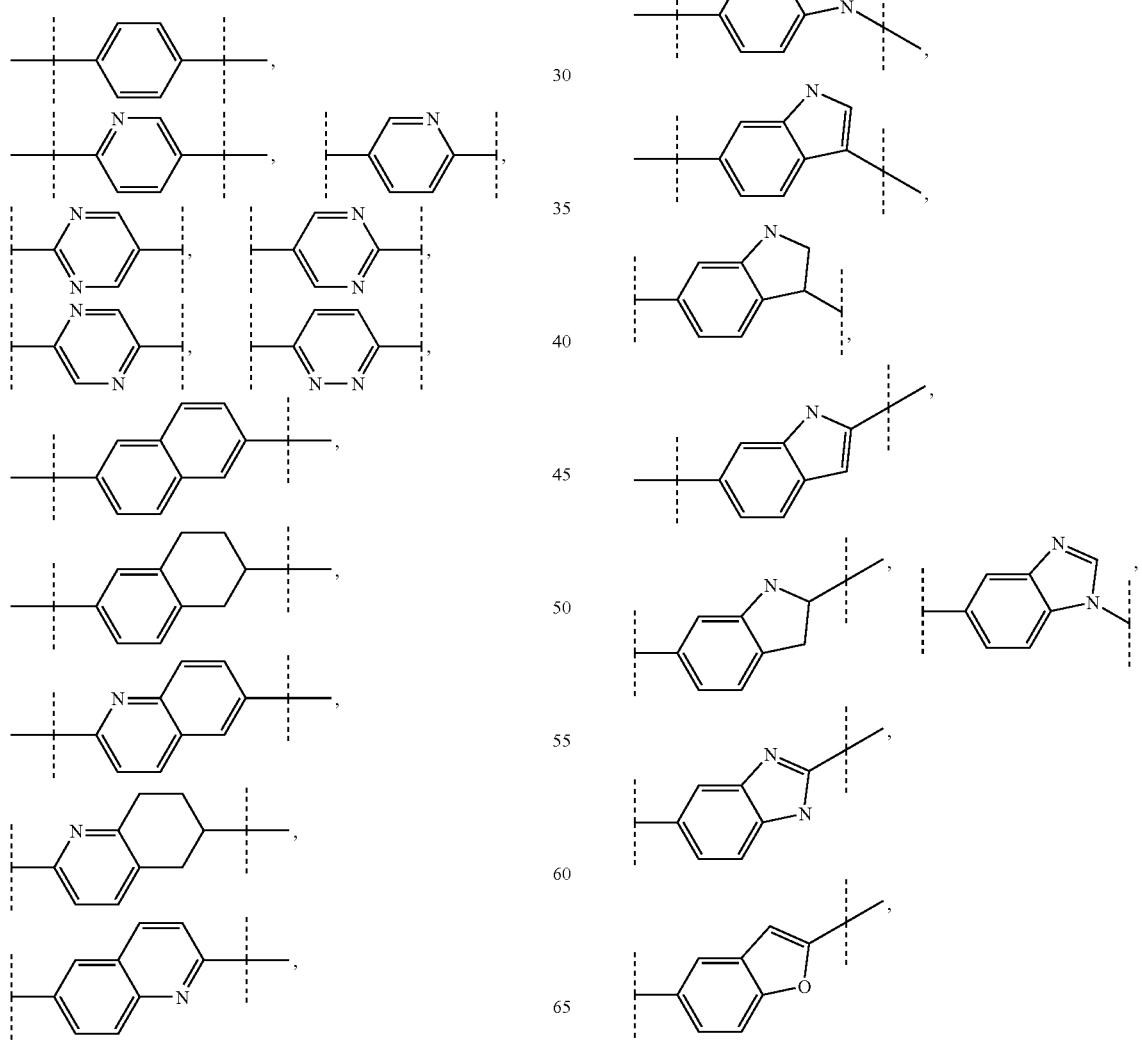

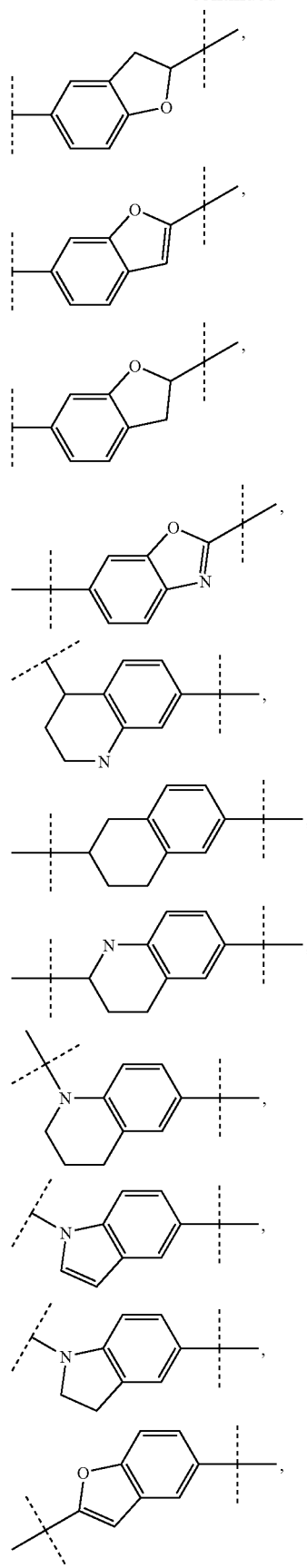
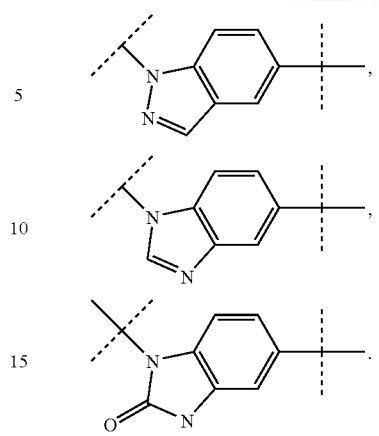
The cyclic groups listed above may be mono- or polysubstituted by $R^{20}$ at one or more C atoms, and in the case of a phenyl group may also additionally be monosubstituted by nitro, and/or one or more NH groups may be substituted by $R^{21}$.
Most particularly preferably, Y is one of the groups listed below
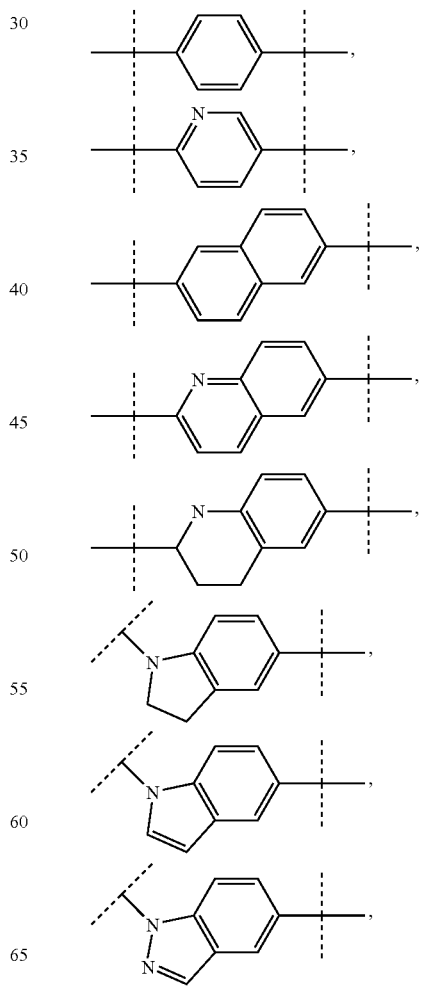

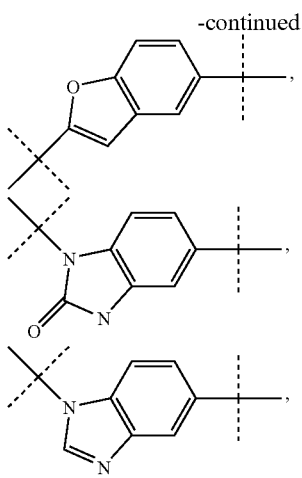

particularly a 1,4-phenylene group, while the groups listed may be substituted as specified.

Particularly preferred substituents $R^{20}$ of the group Y are selected from among fluorine, chlorine, bromine, $C_{1-4}$-alkyl, $C_{2-6}$-alkenyl, —CHO, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, aminocarbonyl, $C_{1-4}$-alkyl-amino-carbonyl, di-($C_{1-4}$-alkyl)-amino-carbonyl, —CH=N—OH and —CH=N—O—$C_{1-4}$-alkyl.

A preferred definition of the group A is aryl or heteroaryl.

Preferably the group A is selected from among the bivalent cyclic groups phenyl, pyridinyl, pyrimidinyl, pyrazinyl or pyridazinyl, which may be may be mono- or polysubstituted at one or more C atoms by $R^{20}$, and in the case of a phenyl ring may also additionally be monosubstituted by nitro.

Most particularly preferably, A is one of the groups listed below

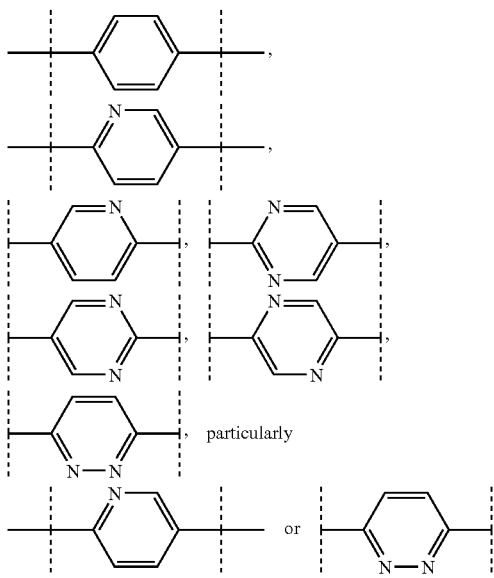

particularly while the groups listed may be substituted as specified hereinbefore.

Particularly preferred substituents $R^{20}$ of the group A are fluorine, chlorine, bromine, methoxy and $C_{1-3}$-alkyl.

Preferably the groups A and/or Y are unsubstituted or monosubstituted by $R^{20}$ as specified. The group A is preferably unsubstituted or monofluorinated.

According to a first embodiment, the definition of the group B is preferably selected from among the unsaturated carbo- and heterocycles phenyl, thienyl and furanyl. Particularly preferably, the group B denotes phenyl. The group B in the definitions provided may be mono- or polysubstituted by $R^{20}$, a phenyl group may additionally also be monosubstituted by nitro. Preferably the group B is mono-, di- or trisubstituted, particularly mono- or disubstituted. In the case of a monosubstitution the substituent is preferably in the para position to the group A.

Particularly preferred substituents $R^{20}$ of the group B are selected from among fluorine, chlorine, bromine, cyano, nitro, $C_{1-4}$-alkyl, hydroxy, ω-hydroxy-$C_{1-3}$-alkyl, $C_{1-4}$-alkoxy, difluoromethyl, trifluoromethyl, difluoromethoxy, trifluoromethoxy, $C_{2-4}$-alkynyl, carboxy, $C_{1-4}$-alkoxycarbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, aminocarbonyl, $C_{1-4}$-alkyl-amino-carbonyl and di-($C_{1-4}$-alkyl)-amino-carbonyl.

Most particularly preferred substituents $R^{20}$ of the group B are selected from among fluorine, chlorine, bromine, $CF_3$, $C_{1-3}$-alkyl and $C_{1-4}$-alkoxy.

According to a second embodiment the definition of the group B is preferably selected from $C_{1-6}$-alkyl, $C_{2-6}$-alkenyl, $C_{2-6}$-alkynyl, $C_{3-7}$-cycloalkyl-$C_{1-3}$-alkyl, $C_{3-7}$-cycloalkenyl-$C_{1-3}$-alkyl, $C_{3-7}$-cycloalkyl-$C_{1-3}$-alkenyl, $C_{3-7}$-cycloalkyl-$C_{1-3}$-alkynyl, while one or more C atoms in the groups mentioned for B hereinbefore may be mono- or polysubstituted by fluorine.

In the cyclic groups according to the embodiment mentioned hereinbefore one or more C atoms may be substituted by $R^{20}$.

Particularly preferred according to this embodiment are the groups $C_{3-6}$-alkyl, $C_{3-6}$-alkenyl, $C_{3-6}$-alkynyl, cyclopentyl, cyclopentenyl, cyclohexyl, cyclohexenyl, cycloheptyl, cycloheptenyl, cyclopentyl-$C_{1-3}$-alkyl, cyclopentenyl-$C_{1-3}$-alkyl, cyclohexyl-$C_{1-3}$-alkyl, cyclohexenyl-$C_{1-3}$-alkyl, cycloheptyl-$C_{1-3}$-alkyl, cycloheptenyl-$C_{1-3}$-alkyl, while one or more C atoms in the groups mentioned for B hereinbefore may be mono- or polysubstituted by fluorine.

$R^4$ and/or $R^5$ have one of the meanings given for $R^{17}$, preferably for $R^{16}$. Particularly preferred meanings of $R^4$ and/or $R^5$ are H, $C_{1-4}$-alkyl, $C_{3-7}$-cycloalkyl and $C_{3-7}$-cycloalkyl-$C_{1-3}$-alkyl.

If $R^{11}$ is a $C_{2-6}$-alkenyl or $C_{2-6}$-alkynyl group, the meanings —CH=CH$_2$, —CH=CH(CH$_3$), —CH=C(CH$_3$)$_2$ and —C≡CH, —C≡C—CH$_3$ are preferred.

Preferred definitions of the group $R^{20}$ are halogen, hydroxy, cyano, $C_{1-4}$-alkyl, $C_{1-4}$-alkoxy, $C_{3-7}$-cycloalkyl and $C_{1-4}$-alkoxy-$C_{1-3}$-alkyl, while C atoms may be mono- or polysubstituted by fluorine and monosubstituted by Cl or Br. Particularly preferably, $R^{20}$ denotes F, Cl, Br, I, OH, cyano, methyl, difluoromethyl, trifluoromethyl, ethyl, n-propyl, iso-propyl, methoxy, difluoromethoxy, trifluoromethoxy, ethoxy, n-propoxy or iso-propoxy.

Preferred definitions of the group $R^{21}$ are $C_{1-4}$-alkyl, $C_{1-4}$-alkylcarbonyl, $C_{1-4}$-alkylsulphonyl, —SO$_2$—NH$_2$, —SO$_2$—NH—$C_{1-3}$-alkyl, —SO$_2$—N($C_{1-3}$-alkyl)$_2$ and cyclo-$C_{3-6}$-alkyleneimino-sulphonyl.

Cy preferably denotes a $C_{3-7}$-cycloalkyl, particularly a $C_{5-7}$-cycloalkyl group, a $C_{5-7}$-cycloalkenyl group, aryl or heteroaryl, while aryl or heteroaryl preferably denotes a monocyclic or fused bicyclic ring system, and the above-mentioned cyclic groups may be mono- or polysubstituted by $R^{20}$ at one or more C atoms, and in the case of a phenyl group may also additionally be monosubstituted by nitro, and/or one or more NH groups may be substituted by $R^{21}$.

Preferred compounds according to the invention are those wherein one or more of the groups, residues, substituents and/or indices have one of the meanings mentioned above as being preferred.

Particularly preferred compounds according to the invention are those wherein

Y has one of the meanings mentioned above as being preferred, most preferably a group selected from

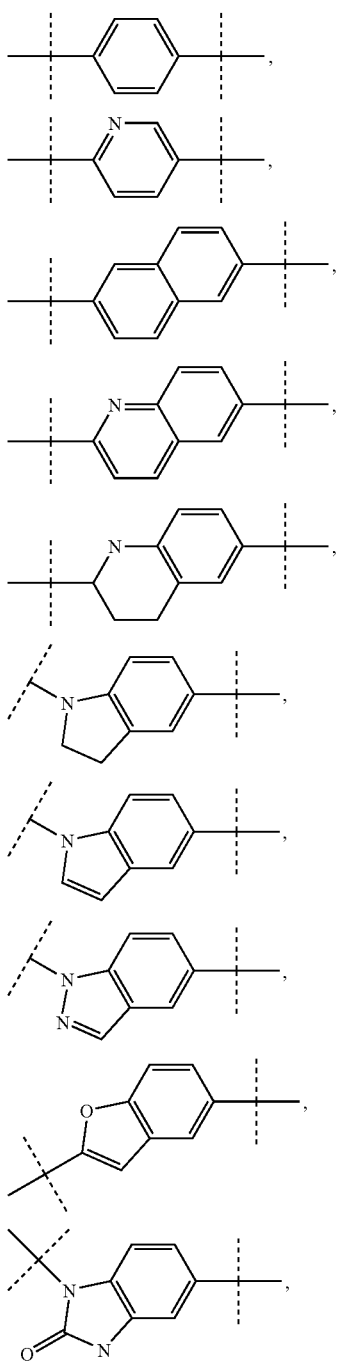

and/or

A has one of the meanings mentioned above as being preferred, and most preferably denotes

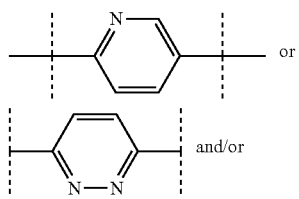

B has one of the meanings mentioned above as being preferred, most preferably phenyl, while A, B and/or Y may be mono- or disubstituted, B may also be trisubstituted by, or substituted by $R^{20}$ at one or more C atoms, and in the case of a phenyl ring may also additionally be monosubstituted by nitro.

Most particularly preferred compounds according to the invention are those wherein A, B, X, Y, Z, $R^1$, $R^2$ and W independently of one another have the preferred meanings given above.

Particularly preferred compounds according to the invention are therefore described by one of general formulae IIa to IIL

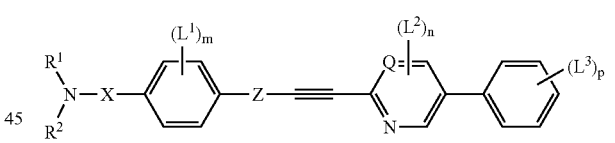

IIa

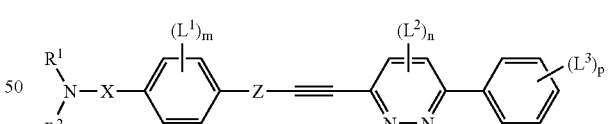

IIb

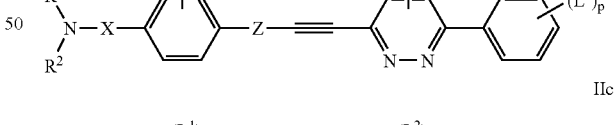

IIc

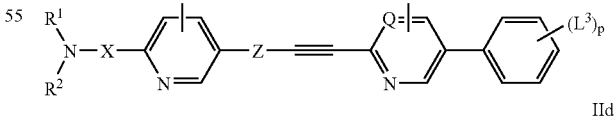

IId

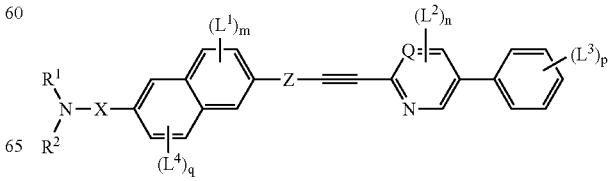

-continued

IIe
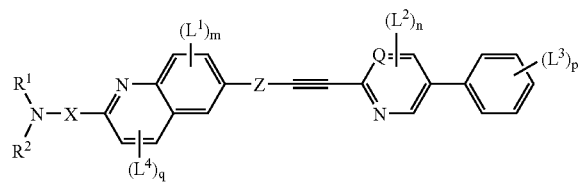

IIf
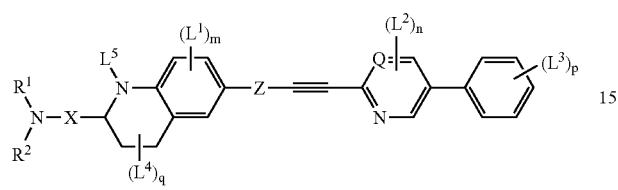

IIg
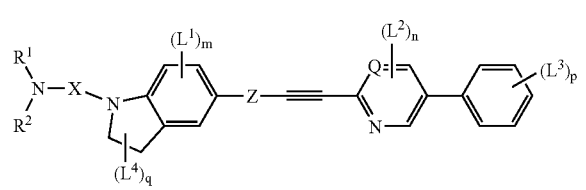

IIh
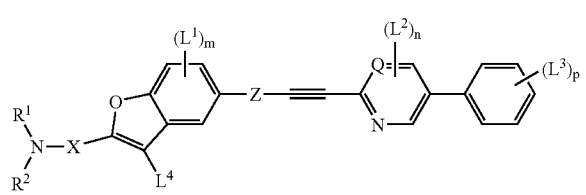

IIi
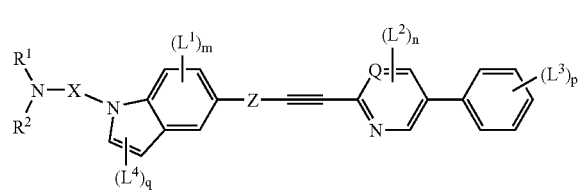

IIj
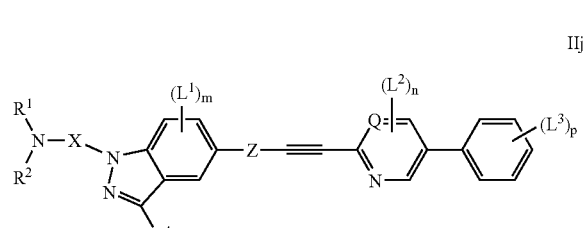

IIk
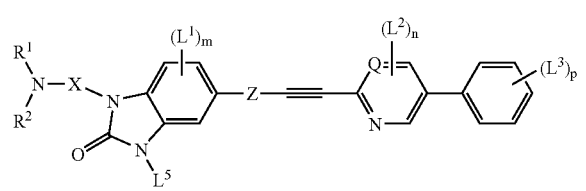

-continued

IIL
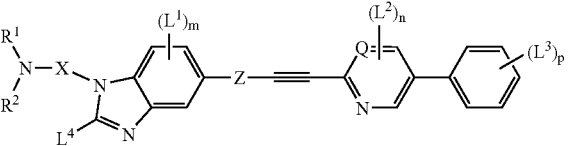

wherein
R$^1$, R$^2$, X and Z have the above-mentioned meanings and Q denotes —CH— or N, preferably —CH—, and
L$^1$, L$^2$, L$^3$, L$^4$ denote H or have one of the meanings given for R$^{20}$, and
L$^5$ denote H or has one of the meanings given for R$^{21}$, and
m, n, p, q independently of one another represent the values 0, 1 or 2, and p may also have the value 3.

One group of most particularly preferred compounds can be described by the formula IIa wherein the group Q denotes —CH—.

Preferably, particularly in formulae IIa to IIL, the above-mentioned groups have the following meanings:
X denotes —CH$_2$—, —CH$_2$—CH$_2$— or —CH$_2$—CH$_2$—CH$_2$—,
in formulae IIa to IIe it also denotes —CH$_2$—C≡C—, —CH$_2$—CH$_2$—O—, —CH$_2$—CH$_2$—NR$^4$— or 1,3-pyrrolidinylene, while the pyrrolidinylene group is linked to Y via the imino group,
while in the definitions given hereinbefore one or two —CH$_2$— groups may be substituted by one or two methyl groups,
while the bridge X may be connected to R$^1$ including the N atom attached to R$^1$ and X, forming a heterocyclic group, and
Z denotes a single bond or a bridge selected from among —CH$_2$—, —CH$_2$—CH$_2$—, —CH$_2$—CH(CH$_3$)—, —CH$_2$—C(CH$_3$)$_2$—, —CH(CH$_3$)—CH$_2$—, —C(CH$_3$)$_2$—CH$_2$—, cyclopropylene, —CH$_2$—CH(R$^{10}$)— and —CH(R$^{10}$)—CH$_2$—, —O—CH$_2$— or —NR$^4$—CH$_2$—.

In the definitions of X and Z provided hereinbefore, in each case a C atom may be substituted by a hydroxy, ω-hydroxy-C$_{1-3}$-alkyl, ω-(C$_{1-4}$-alkoxy)-C$_{1-3}$-alkyl and/or C$_{1-4}$-alkoxy group, and/or one or two C atoms independently of one another may each be substituted by one or two identical or different C$_{1-4}$-alkyl groups, while the alkyl groups may be joined together, forming a carbocyclic ring. In addition, in the groups X and Z in each case one or more C atoms may be mono- or polysubstituted by F and/or in each case one or two C atoms independently of one another may be monosubstituted by Cl or Br.

In the definitions of X and Z R$^4$ has the meanings given hereinbefore, preferably —H, methyl, ethyl, propyl or iso-propyl.

In the definitions of X and Z R$^{10}$ has the meanings given hereinbefore, preferably —OH, N-pyrrolidinyl, amino-ethoxy, C$_{1-4}$-alkyl-amino-ethoxy or di-(C$_{1-4}$-alkyl)-amino-ethoxy.

Most particularly preferably,
X denotes —CH$_2$—, —CH$_2$—CH$_2$— or —CH$_2$—CH$_2$—CH$_2$—,
and in formulae IIa to IIe it also denotes —CH$_2$—CH═CH—, —CH$_2$—C≡C—, —CH$_2$—CH$_2$—O—, —CH(CH$_3$)—CH$_2$—O— or —CH$_2$—CH(CH$_3$)—O—, and/or Z denotes a single bond, —CH$_2$—, —CH$_2$—CH$_2$— or —O—CH$_2$—, particularly a single bond or —CH$_2$—CH$_2$— and/or L$^1$, L$^2$, L$^3$, L$^4$, independently of one another denote F, Cl, Br, I, OH, cyano, C$_{1-4}$-alkyl, C$_{2-4}$-alkynyl, C$_{1-4}$-alkoxy, difluoromethyl, trifluoromethyl, amino, C$_{1-4}$-alkylamino, di-(C$_{1-4}$-alkyl)-amino, acetylamino, aminocarbonyl, difluoromethoxy, trifluoromethoxy, amino-C$_{1-3}$-alkyl, C$_{1-4}$-alkylamino-C$_{1-3}$-alkyl or di-(C$_{1-4}$-alkyl)-amino-C$_{1-3}$-alkyl or nitro, with the proviso that a phenyl may only be monosubstituted by nitro, and/or L$^1$ additionally also denotes —CH=N—OH or —CH=N—O—C$_{1-4}$-alkyl, m, n, q denote 0 or 1 and/or p denotes 1, 2 or 3, particularly 1 or 2.

The following individual compounds are particularly preferred:

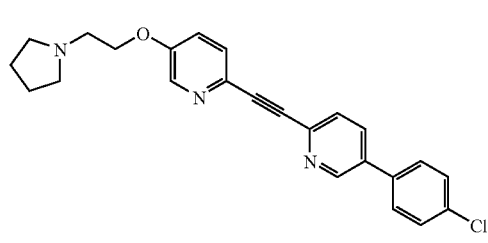

(1)

5-(4-chloro-phenyl)-2-[5-(2-pyrrolidin-1-yl-ethoxy)-pyridin-2-yl-ethynyl]-pyridine

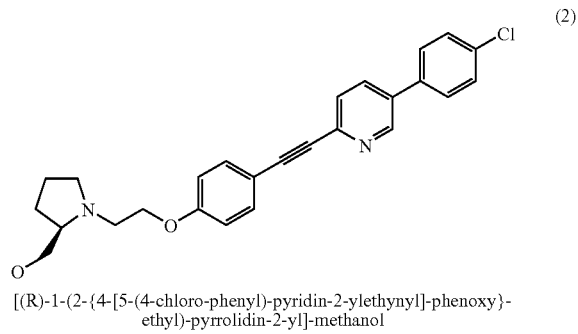

(2)

[(R)-1-(2-{4-[5-(4-chloro-phenyl)-pyridin-2-ylethynyl]-phenoxy}-ethyl)-pyrrolidin-2-yl]-methanol

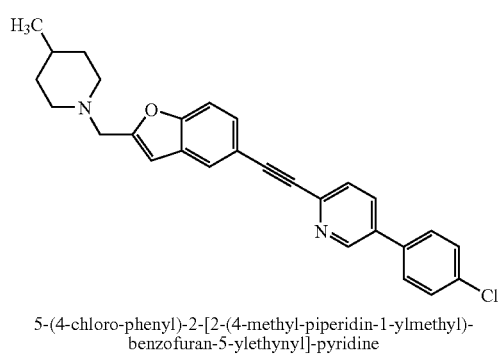

(3)

5-(4-chloro-phenyl)-2-[2-(4-methyl-piperidin-1-ylmethyl)-benzofuran-5-ylethynyl]-pyridine

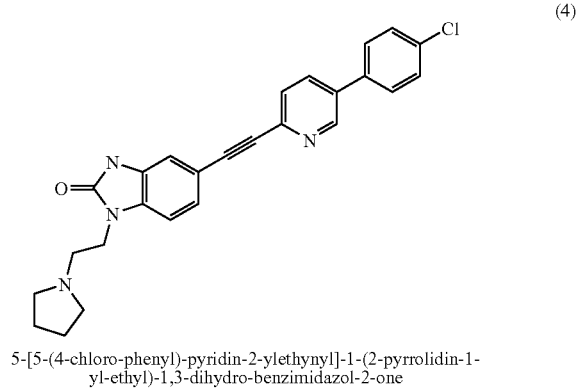

(4)

5-[5-(4-chloro-phenyl)-pyridin-2-ylethynyl]-1-(2-pyrrolidin-1-yl-ethyl)-1,3-dihydro-benzimidazol-2-one

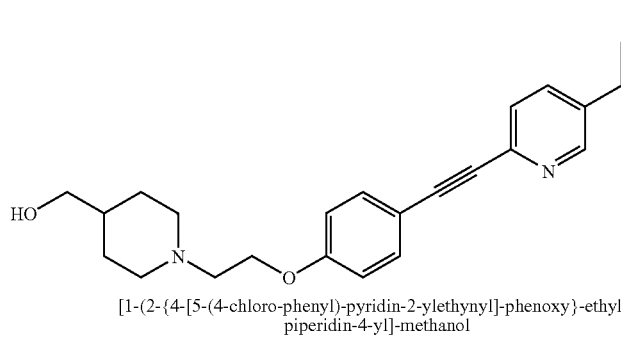

(5)

[1-(2-{4-[5-(4-chloro-phenyl)-pyridin-2-ylethynyl]-phenoxy}-ethyl)-piperidin-4-yl]-methanol

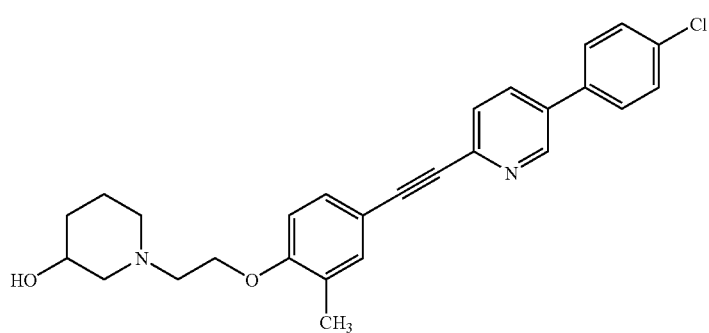

(6)

1-(2-{4-[5-(4-chloro-phenyl)-pyridin-2-ylethynyl]-2-methyl-phenoxy}-ethyl)-piperidin-3-ol -continued

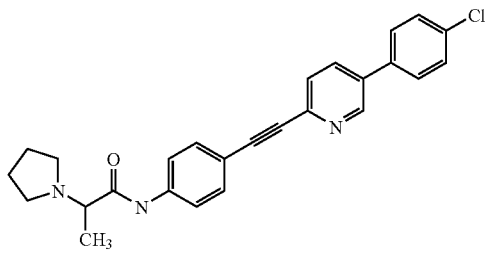

N-{4-[5-(4-chloro-phenyl)-pyridin-2-ylethynyl]-phenyl}-2-pyrrolidin-1-yl-propionamide
(7)

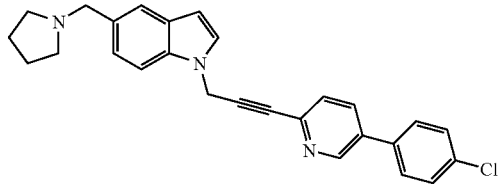

1-{3-[5-(4-chloro-phenyl)-pyridin-2-yl]-prop-2-ynyl}-5-pyrrolidin-1-ylmethyl-1H-indole
(8)

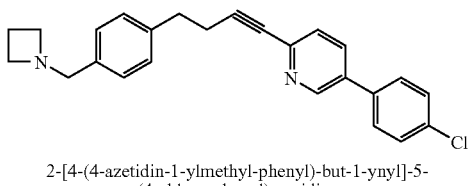

2-[4-(4-azetidin-1-ylmethyl-phenyl)-but-1-ynyl]-5-(4-chloro-phenyl)-pyridine
(9)

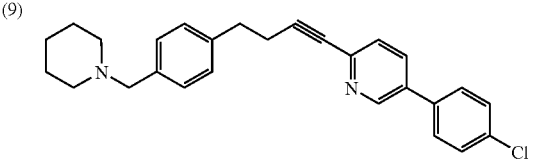

5-(4-chloro-phenyl)-2-[4-(4-piperidin-1-ylmethyl-phenyl)-but-1-ynyl]-pyridine
(10)

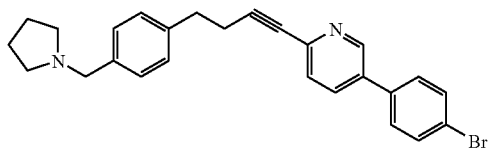

5-(4-bromo-phenyl)-2-[4-(4-pyrrolidin-1-ylmethyl-phenyl)-but-1-ynyl]-pyridine
(11)

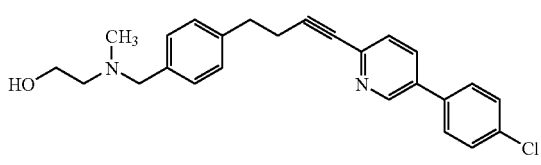

2-[(4-{4-[5-(4-chloro-phenyl)-pyridin-2-yl]-but-3-ynyl}-benzyl)-methyl-amino]-ethanol
(12)

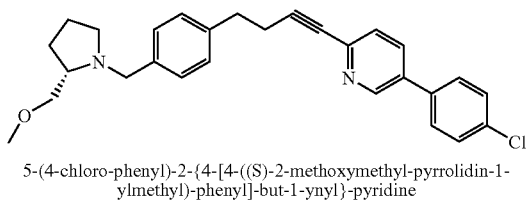

5-(4-chloro-phenyl)-2-{4-[4-((S)-2-methoxymethyl-pyrrolidin-1-ylmethyl)-phenyl]-but-1-ynyl}-pyridine
(13)

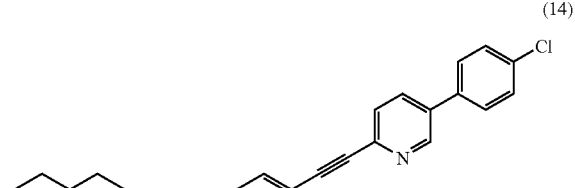

5-(4-chloro-phenyl)-2-{4-[2-(4-propyl-piperidin-1-yl)-ethoxy]-phenylethynyl}-pyridine
(14)

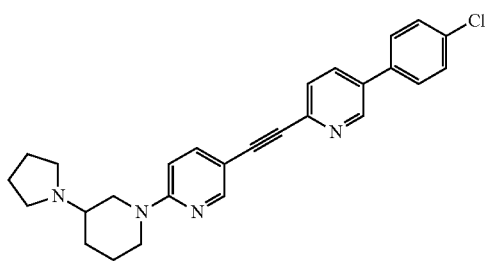

5'-[5-(4-chloro-phenyl)-pyridin-2-ylethynyl]-3-pyrrolidin-1-yl-3,4,5,6-tetrahydro-2H-[1,2']bipyridinyl
(15)

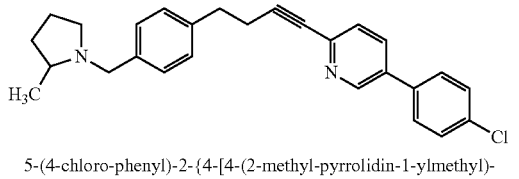

5-(4-chloro-phenyl)-2-{4-[4-(2-methyl-pyrrolidin-1-ylmethyl)-phenyl]-but-1-ynyl}-pyridine
(16)

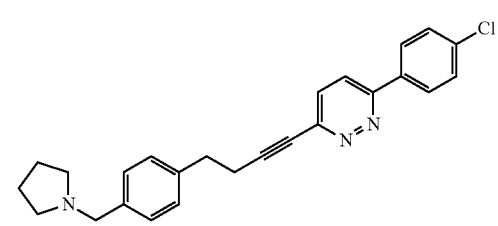

3-(4-chloro-phenyl)-6-[4-(4-pyrrolidin-1-ylmethyl-phenyl)-but-1-ynyl]-pyridazine
(17)

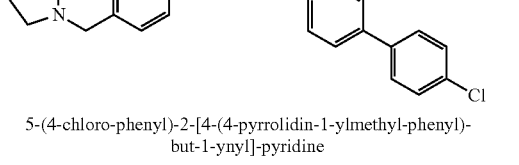

5-(4-chloro-phenyl)-2-[4-(4-pyrrolidin-1-ylmethyl-phenyl)-but-1-ynyl]-pyridine
(18)

-continued

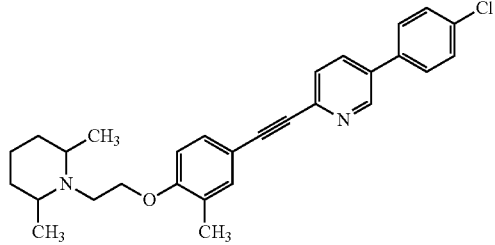

(19) 5-(4-chloro-phenyl)-2-{4-[2-(2,6-dimethyl-piperidin-1-yl)-ethoxy]-3-methyl-phenylethynyl}-pyridine

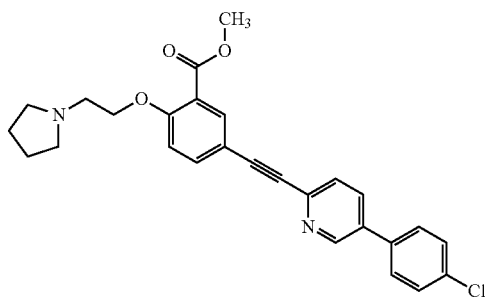

(20) methyl 5-[5-(4-chloro-phenyl)-pyridin-2-ylethynyl]-2-(2-pyrrolidin-1-yl-ethoxy)-benzoate

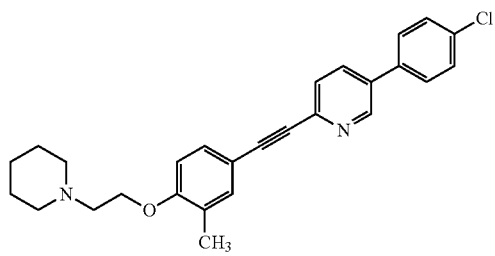

(21) 5-(4-chloro-phenyl)-2-[3-methyl-4-(2-piperidin-1-yl-ethoxy)-phenylethynyl]-pyridine

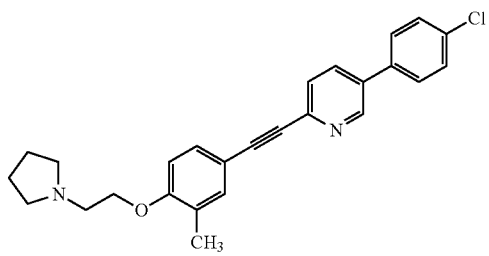

(22) 5-(4-chloro-phenyl)-2-[3-methyl-4-(2-pyrrolidin-1-yl-ethoxy)-phenylethynyl]-pyridine

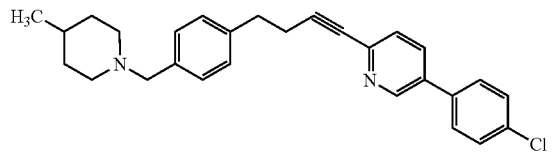

(23) 5-(4-chloro-phenyl)-2-{4-[4-(4-methyl-piperidin-1-ylmethyl)-phenyl]-but-1-ynyl}-pyridine

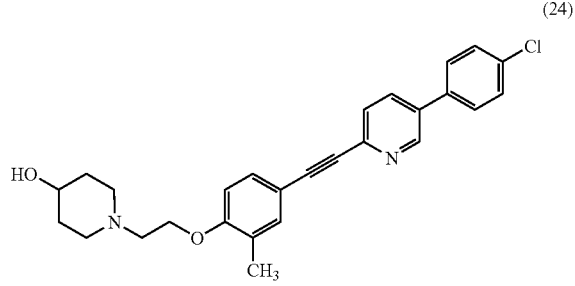

(24) 1-(2-{4-[5-(4-chloro-phenyl)-pyridin-2-ylethynyl]-2-methyl-phenoxy}-ethyl)-piperidin-4-ol

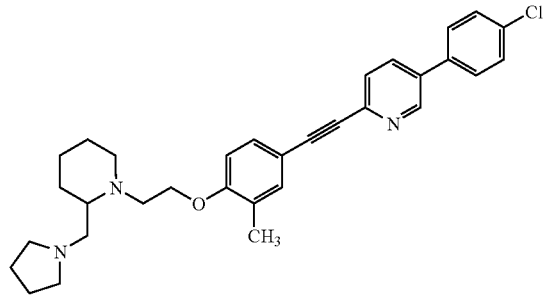

(25) 5-(4-chloro-phenyl)-2-{3-methyl-4-[2-(2-pyrrolidin-1-ylmethyl-piperidin-1-yl)-ethoxy]-phenylethynyl}-pyridine

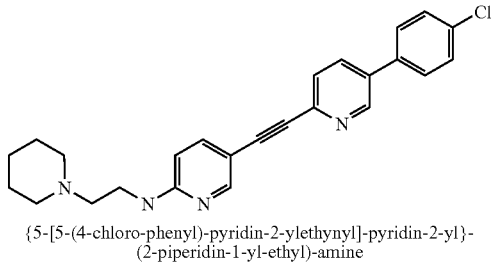

(26) {5-[5-(4-chloro-phenyl)-pyridin-2-ylethynyl]-pyridin-2-yl}-(2-piperidin-1-yl-ethyl)-amine

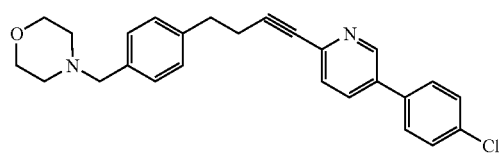

(27) 4-(4-{4-[5-(4-chloro-phenyl)-pyridin-2-yl]-but-3-ynyl}-benzyl)-morpholine

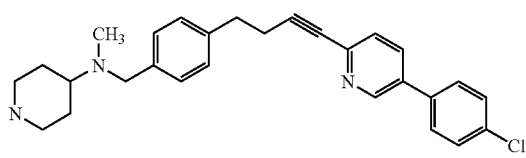

(28) (4-{4-[5-(4-chloro-phenyl)-pyridin-2-yl]-but-3-ynyl}-benzyl)-methyl-piperidin-4-yl-amine

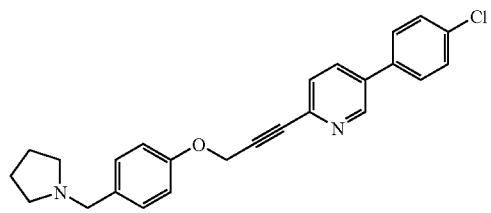

5-(4-chloro-phenyl)-2-[3-(4-pyrrolidin-1-ylmethyl-phenoxy)-prop-1-ynyl]-pyridine (29)

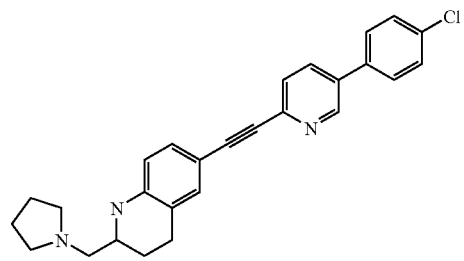

6-[5-(4-chloro-phenyl)-pyridin-2-ylethynyl]-2-pyrrolidin-1-ylmethyl-1,2,3,4-tetrahydro-quinoline (30)

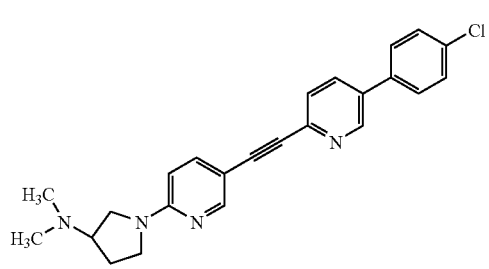

(1-{5-[5-(4-chloro-phenyl)-pyridin-2-ylethynyl]-pyridin-2-yl}-pyrrolidin-3-yl)-dimethyl-amine (31)

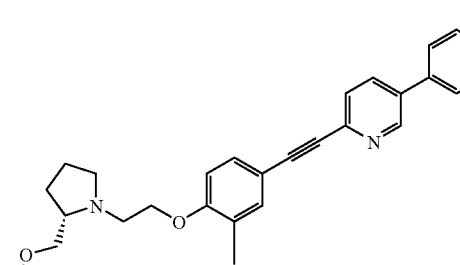

[(S)-1-(2-{4-[5-(4-chloro-phenyl)-pyridin-2-ylethynyl]-2-methyl-phenoxy}-ethyl)-pyrrolidin-2-yl]-methanol (32)

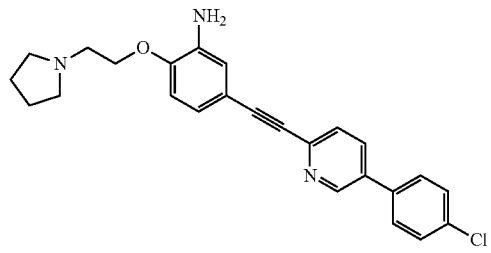

5-[5-(4-chloro-phenyl)-pyridin-2-ylethynyl]-2-(2-pyrrolidin-1-yl-ethoxy)-phenylamine (33)

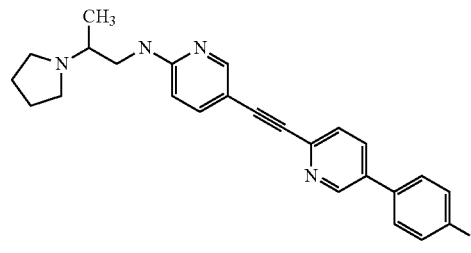

{5-[5-(4-chloro-phenyl)-pyridin-2-ylethynyl]-pyridin-2-yl}-(2-pyrrolidin-1-yl-propyl)-amine (34)

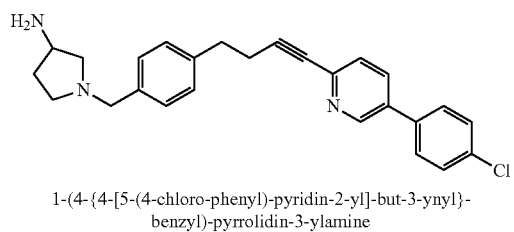

1-(4-{4-[5-(4-chloro-phenyl)-pyridin-2-yl]-but-3-ynyl}-benzyl)-pyrrolidin-3-ylamine (35)

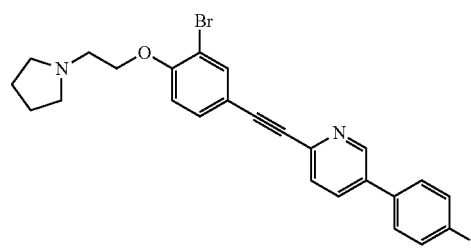

2-[3-bromo-4-(2-pyrrolidin-1-yl-ethoxy)-phenylethynyl]-5-(4-chloro-phenyl)-pyridine (36)

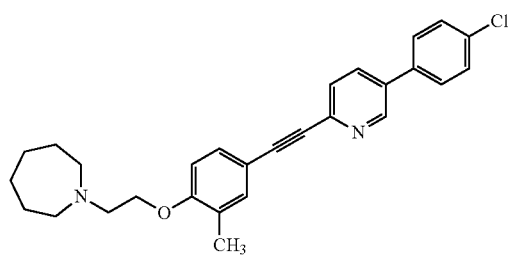

1-(2-{4-[5-(4-chloro-phenyl)-pyridin-2-ylethynyl]-2-methyl-phenoxy}-ethyl)-azepan (37)

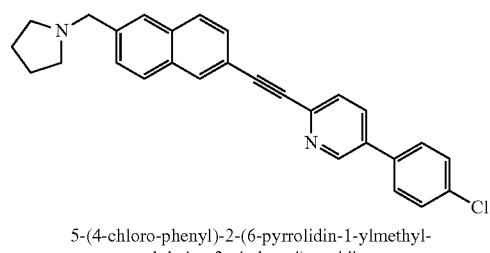

5-(4-chloro-phenyl)-2-(6-pyrrolidin-1-ylmethyl-naphthalen-2-ylethynyl)-pyridine (38)

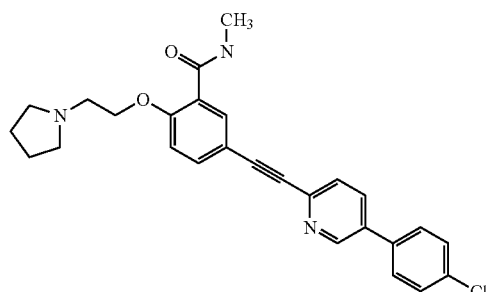

(39)

5-[5-(4-chloro-phenyl)-pyridin-2-ylethynyl]-N-methyl-
2-(2-pyrrolidin-1-yl-ethoxy)-benzamide

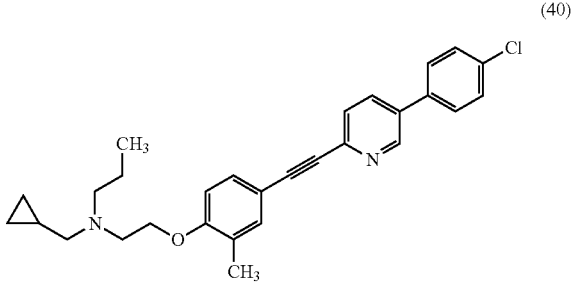

(40)

(2-{4-[5-(4-chloro-phenyl)-pyridin-2-ylethynyl]-2-methyl-
phenoxy}-ethyl)-cyclopropylmethyl-propyl-amine

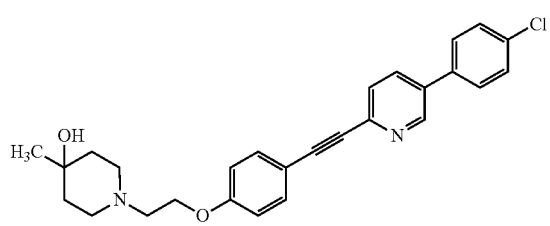

(41)

1-(2-{4-[5-(4-chloro-phenyl)-pyridin-2-ylethynyl]-
phenoxy}-ethyl)-4-methyl-piperidin-4-ol

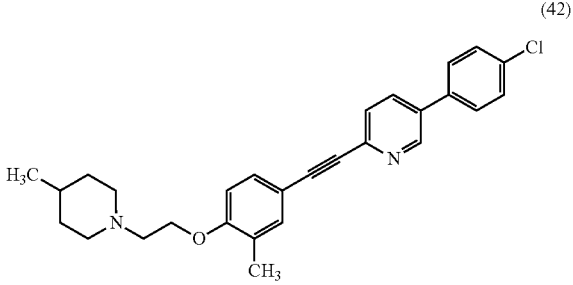

(42)

5-(4-chloro-phenyl)-2-{3-methyl-4-[2-(4-methyl-piperidin-1-yl)-
ethoxy]-phenylethynyl}-pyridine

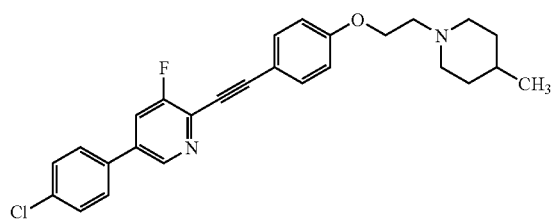

(43)

5-(4-chloro-phenyl)-3-fluoro-2-{4-[2-(4-methyl-piperidin-1-yl)-
ethoxy]-phenylethynyl}-pyridine

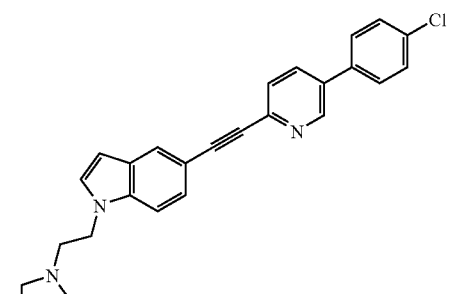

(44)

5-[5-(4-chloro-phenyl)-pyridin-2-ylethynyl]-1-(2-pyrrolidin-
1-yl-ethyl)-1H-indole

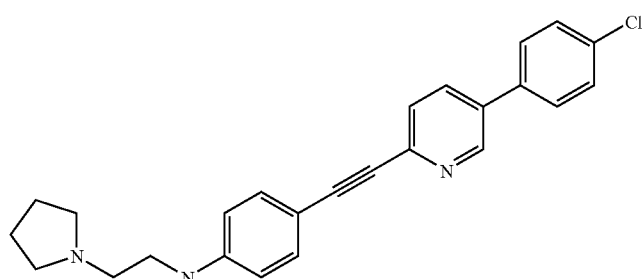

(45)

{4-[5-(4-chloro-phenyl)-pyridin-2-ylethynyl]-phenyl}-(2-pyrrolidin-1-yl-
ethyl)-amine

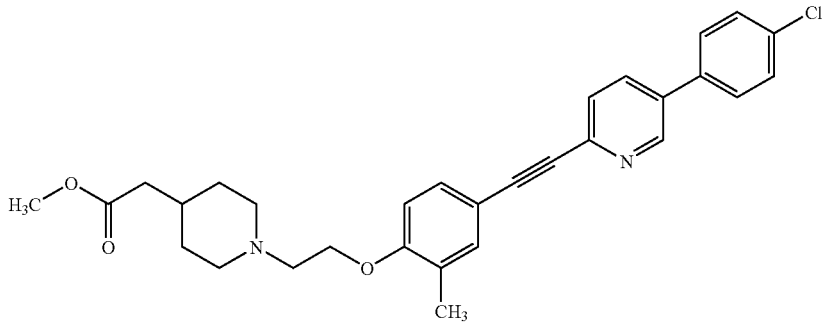

methyl[1-(2-{4-[5-(4-chloro-phenyl)-pyridin-2-ylethynyl]-2-methyl-phenoxy}-ethyl)-piperidin-4-yl]-acetate (46)

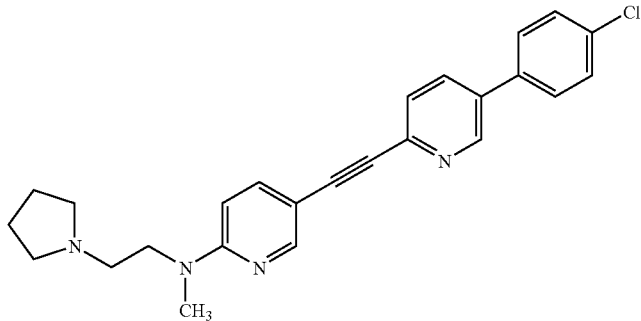

{5-[5-(4-chloro-phenyl)-pyridin-2-ylethynyl]-pyridin-2-yl}-methyl-(2-pyrrolidin-1-yl-ethyl)-amine (47)

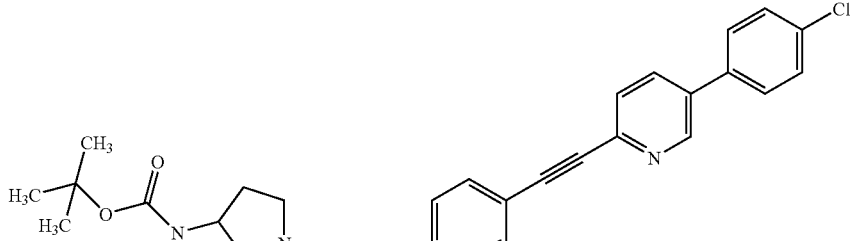

tert-butyl[1-(2-{4-[5-(4-chloro-phenyl)-pyridin-2-ylethynyl]-phenoxy}-ethyl)-pyrrolidin-3-yl]-carbaminate (48)

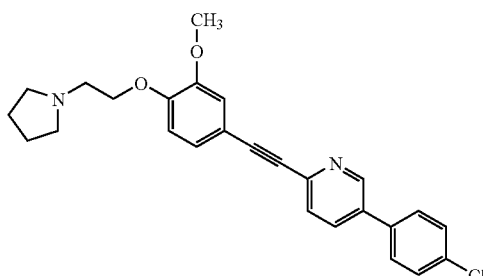

5-(4-chloro-phenyl)-2-[3-methoxy-4-(2-pyrrolidin-1-yl-ethoxy)-phenylethynyl]-pyridine (49)

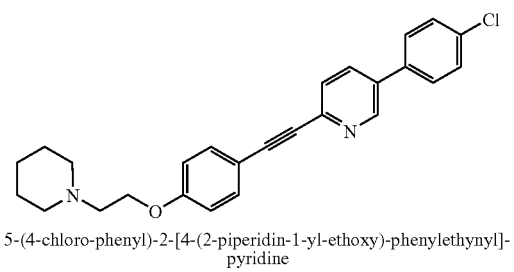

5-(4-chloro-phenyl)-2-[4-(2-piperidin-1-yl-ethoxy)-phenylethynyl]-pyridine (50)

-continued

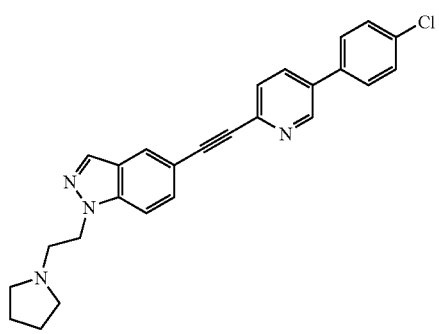

(51)

5-[5-(4-chloro-phenyl)-pyridin-2-ylethynyl]-1-(2-pyrrolidin-1-yl-ethyl)-1H-indazole

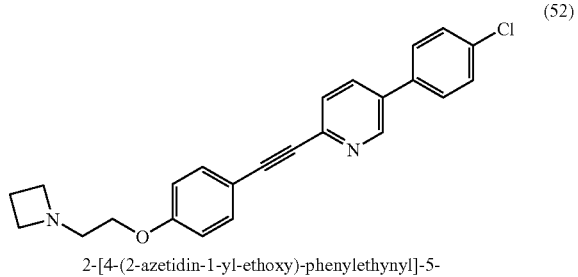

(52)

2-[4-(2-azetidin-1-yl-ethoxy)-phenylethynyl]-5-(4-chloro-phenyl)-pyridine

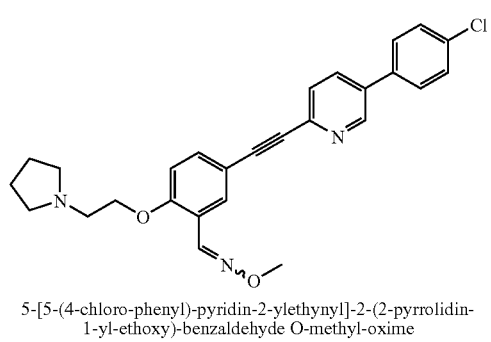

(53)

5-[5-(4-chloro-phenyl)-pyridin-2-ylethynyl]-2-(2-pyrrolidin-1-yl-ethoxy)-benzaldehyde O-methyl-oxime

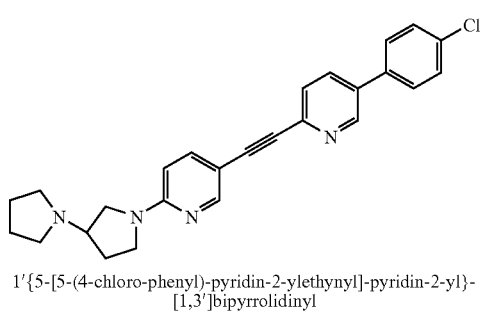

(54)

1′{5-[5-(4-chloro-phenyl)-pyridin-2-ylethynyl]-pyridin-2-yl}-[1,3′]bipyrrolidinyl

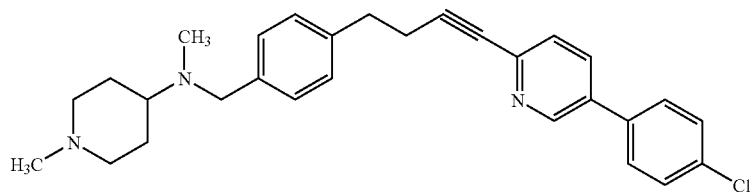

(55)

(4-{4-[5-(4-chloro-phenyl)-pyridin-2-yl]-but-3-ynyl}-benzyl)-methyl-(1-methyl-piperidin-4-yl)-amine

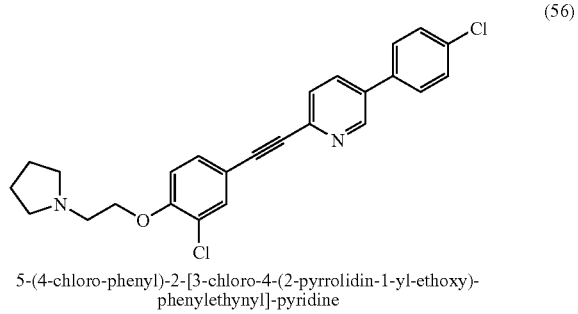

(56)

5-(4-chloro-phenyl)-2-[3-chloro-4-(2-pyrrolidin-1-yl-ethoxy)-phenylethynyl]-pyridine

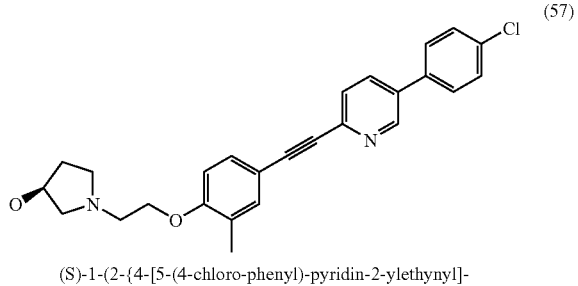

(57)

(S)-1-(2-{4-[5-(4-chloro-phenyl)-pyridin-2-ylethynyl]-2-methyl-phenoxy}-ethyl)-pyrrolidin-3-ol

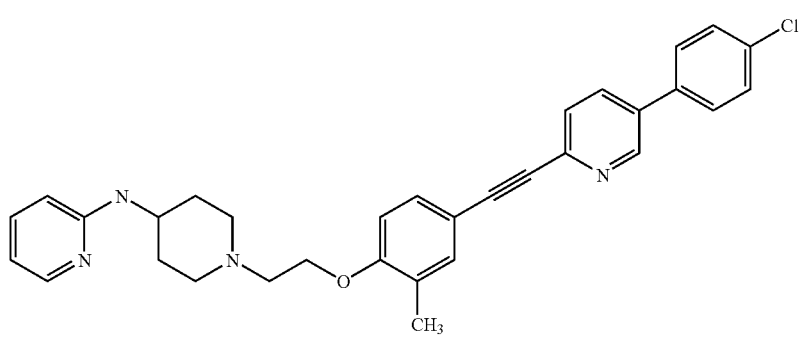

(58)

[1-(2-{4-[5-(4-chloro-phenyl)-pyridin-2-ylethynyl]-2-methyl-phenoxy}-ethyl)-piperidin-4-yl]pyridin-2-yl-amine -continued

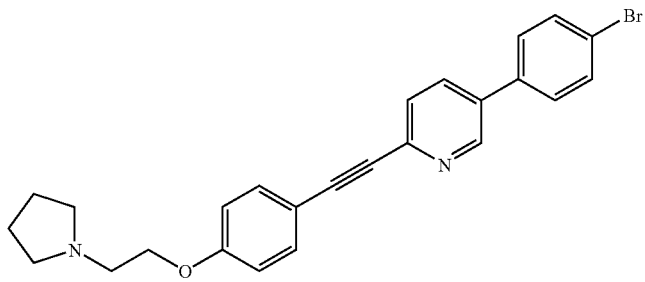

5-(4-bromo-phenyl)-2-[4-(2-pyrrolidin-1-yl-ethoxy)-phenylethynyl]-pyridine (59)

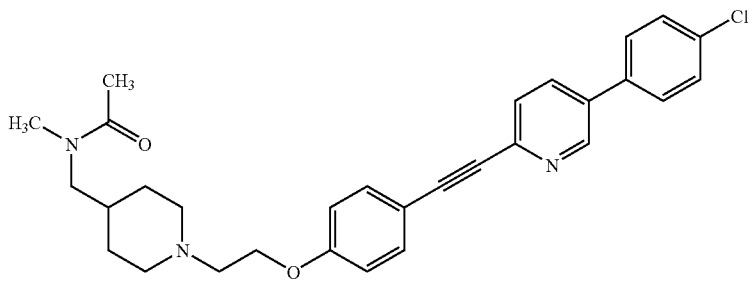

N-[1-(2-{4-[5-(4-chloro-phenyl)-pyridin-2-ylethynyl]-phenoxy}-ethyl)-piperidin-4-ylmethyl]-N-methyl-acetamide (60)

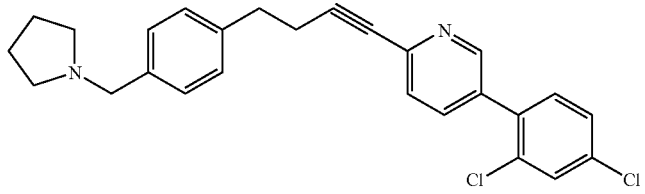

5-(2,4-dichloro-phenyl)-2-[4-(4-pyrrolidin-1-ylmethyl-phenyl)-but-1-ynyl]-pyridine (61)

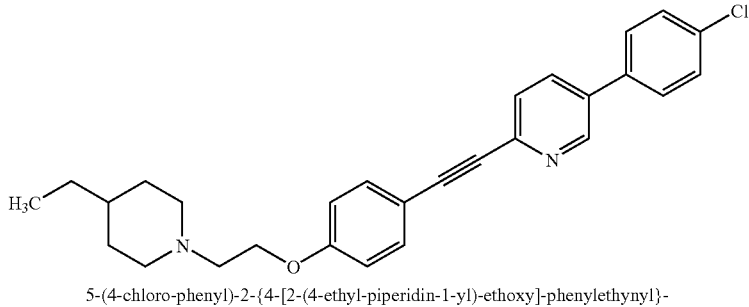

5-(4-chloro-phenyl)-2-{4-[2-(4-ethyl-piperidin-1-yl)-ethoxy]-phenylethynyl}-pyridine (62)

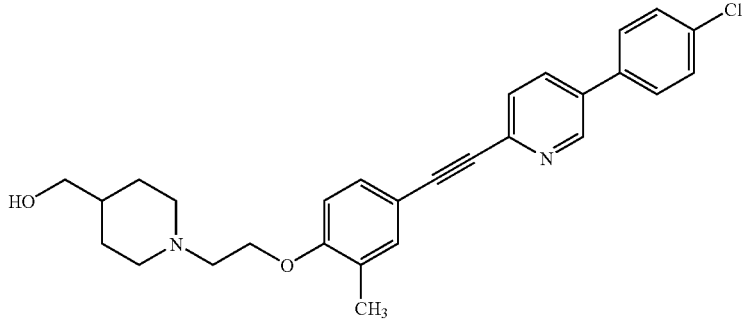

[1-(2-{4-[5-(4-chloro-phenyl)-pyridin-2-ylethynyl]-2-methyl-phenoxy}-ethyl)-piperidin-4-yl]-methanol (63)

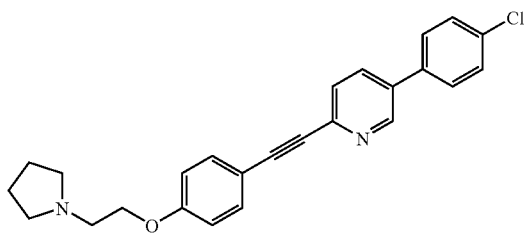

(64) 5-(4-chloro-phenyl)-2-[4-(2-pyrrolidin-1-yl-ethoxy)-phenylethynyl]-pyridine

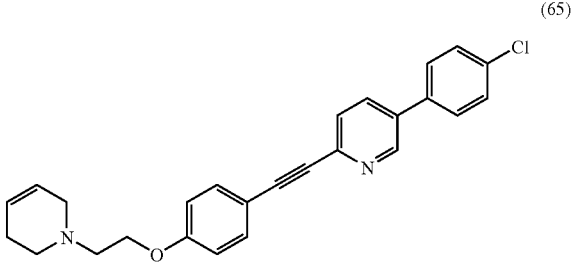

(65) 5-(4-chloro-phenyl)-2-{4-[2-(3,6-dihydro-2H-pyridine-1-yl)-ethoxy]-phenylethynyl}-pyridine

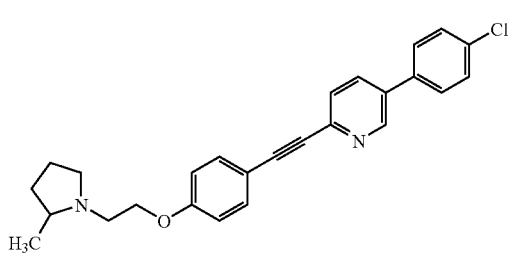

(66) 5-(4-chloro-phenyl)-2-{4-[2-(2-methyl-pyrrolidin-1-yl)-ethoxy]-phenylethynyl}-pyridine

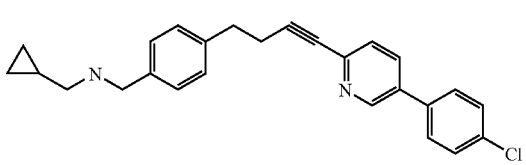

(67) (4-{4-[5-(4-chloro-phenyl)-pyridin-2-yl]-but-3-ynyl}-benzyl)-cyclopropylmethyl-amine

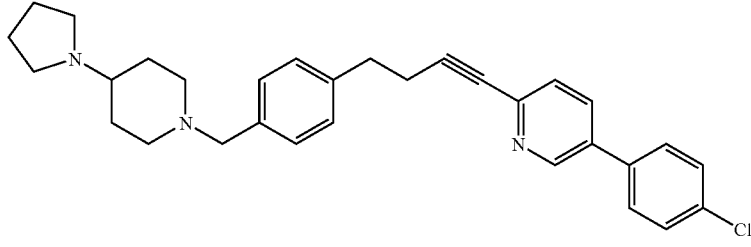

(68) 5-(4-chloro-phenyl)-2-{4-[4-(4-pyrrolidin-1-yl-piperidin-1-ylmethyl)-phenyl]-but-1-ynyl}-pyridine

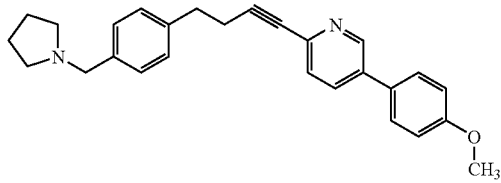

(69) 5-(4-methoxy-phenyl)-2-[4-(4-pyrrolidin-1-ylmethyl-phenyl)-but-1-ynyl]-pyridine

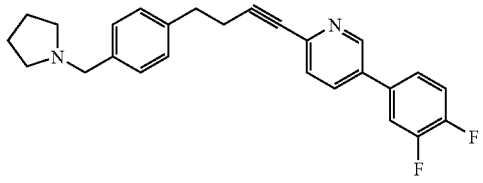

(70) 5-(3,4-difluoro-phenyl)-2-[4-(4-pyrrolidin-1-ylmethyl-phenyl)-but-1-ynyl]-pyridine

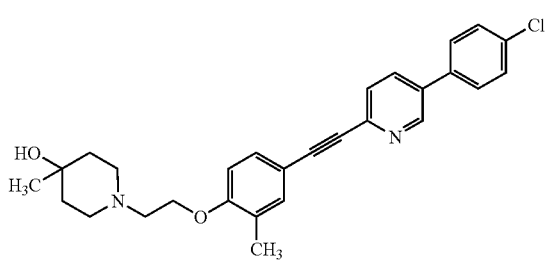

(71) 1-(2-{4-[5-(4-chloro-phenyl)-pyridin-2-ylethynyl]-2-methyl-phenoxy}-ethyl)-4-methyl-piperidin-4-ol

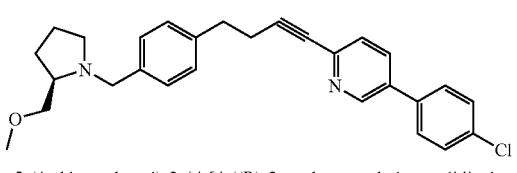

(72) 5-(4-chloro-phenyl)-2-{4-[4-((R)-2-methoxymethyl-pyrrolidin-1-ylmethyl)-phenyl]-but-1-ynyl}-pyridine (73)

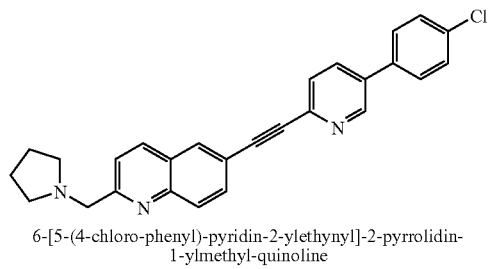

6-[5-(4-chloro-phenyl)-pyridin-2-ylethynyl]-2-pyrrolidin-1-ylmethyl-quinoline (74)

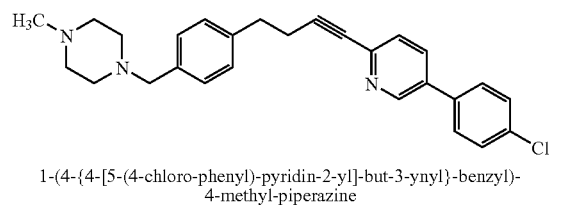

1-(4-{4-[5-(4-chloro-phenyl)-pyridin-2-yl]-but-3-ynyl}-benzyl)-4-methyl-piperazine (75)

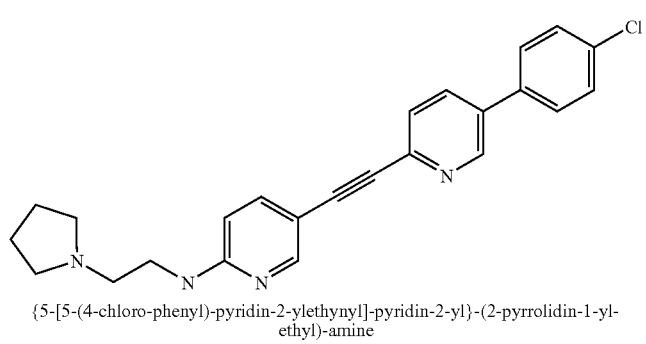

{5-[5-(4-chloro-phenyl)-pyridin-2-ylethynyl]-pyridin-2-yl}-(2-pyrrolidin-1-yl-ethyl)-amine (76)

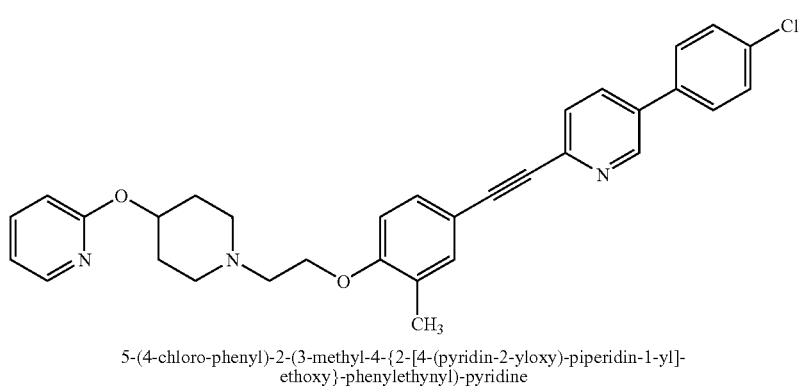

5-(4-chloro-phenyl)-2-(3-methyl-4-{2-[4-(pyridin-2-yloxy)-piperidin-1-yl]-ethoxy}-phenylethynyl)-pyridine (77)

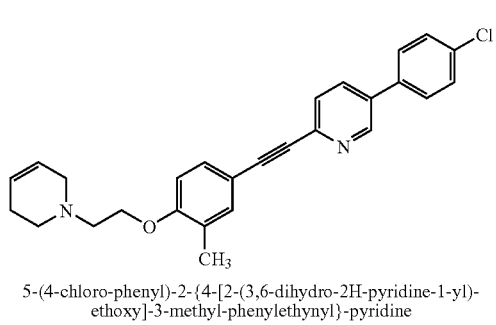

5-(4-chloro-phenyl)-2-{4-[2-(3,6-dihydro-2H-pyridine-1-yl)-ethoxy]-3-methyl-phenylethynyl}-pyridine (78)

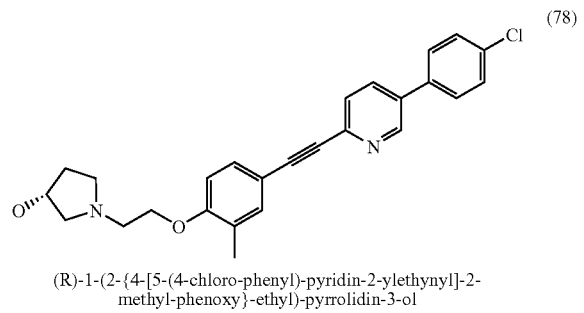

(R)-1-(2-{4-[5-(4-chloro-phenyl)-pyridin-2-ylethynyl]-2-methyl-phenoxy}-ethyl)-pyrrolidin-3-ol -continued (79)

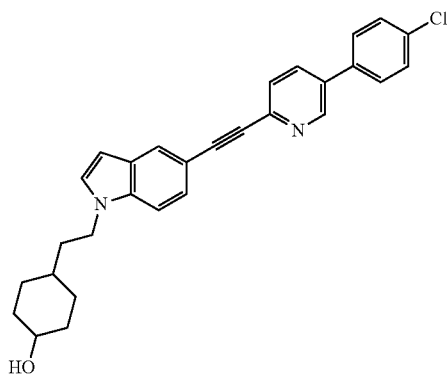

1-(2-{5-[5-(4-chloro-phenyl)-pyridin-2-ylethynyl]-indol-1-yl}-ethyl)-piperidin-4-ol (80)

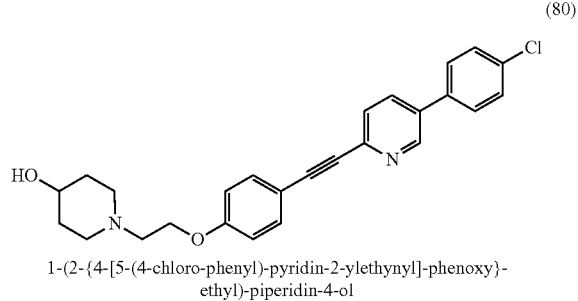

1-(2-{4-[5-(4-chloro-phenyl)-pyridin-2-ylethynyl]-phenoxy}-ethyl)-piperidin-4-ol (81)

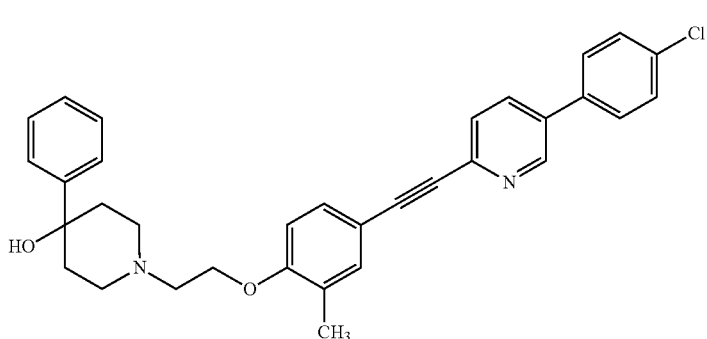

1-(2-{4-[5-(4-chloro-phenyl)-pyridin-2-ylethynyl]-2-methyl-phenoxy}-ethyl)-4-phenyl-piperidin-4-ol (82)

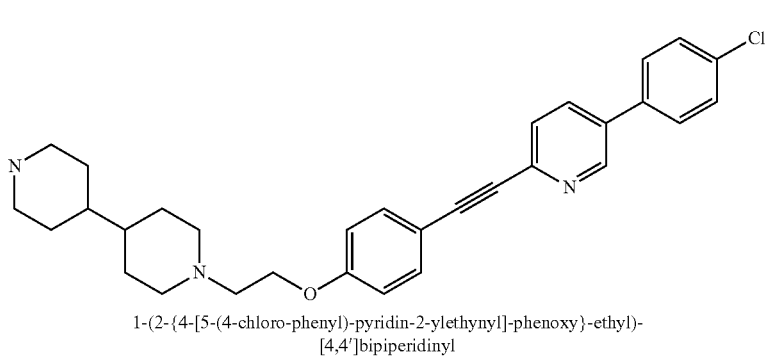

1-(2-{4-[5-(4-chloro-phenyl)-pyridin-2-ylethynyl]-phenoxy}-ethyl)-[4,4']bipiperidinyl (83)

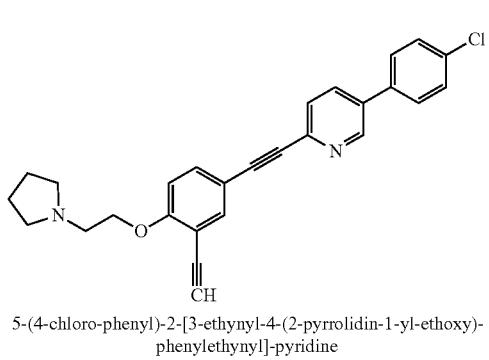

5-(4-chloro-phenyl)-2-[3-ethynyl-4-(2-pyrrolidin-1-yl-ethoxy)-phenylethynyl]-pyridine (84)

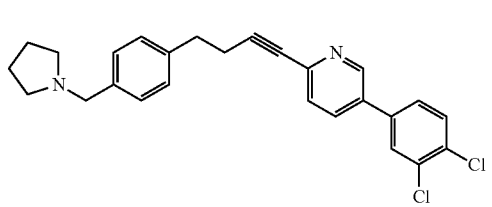

5-(3,4-dichloro-phenyl)-2-[4-(4-pyrrolidin-1-ylmethyl-phenyl)-but-1-ynyl]-pyridine -continued

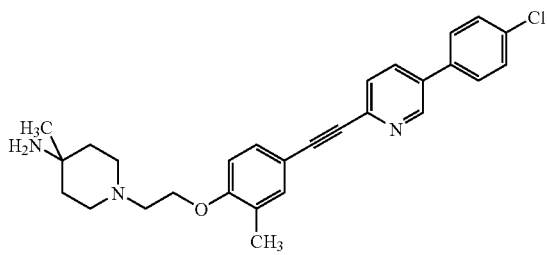

(85)

1-(2-{4-[5-(4-chloro-phenyl)-pyridin-2-ylethynyl]-2-methyl-phenoxy}-ethyl)-4-methyl-piperidin-4-ylamine

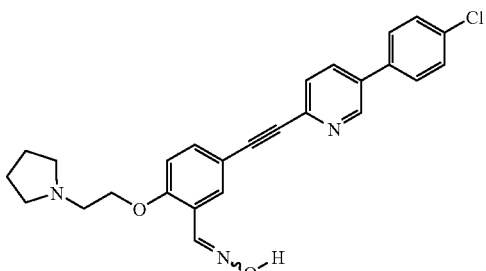

(86)

5-[5-(4-chloro-phenyl)-pyrridin-2-ylethynyl]-2-(2-pyrrolidin-1-yl-ethoxy)-benzaldehyde-oxime

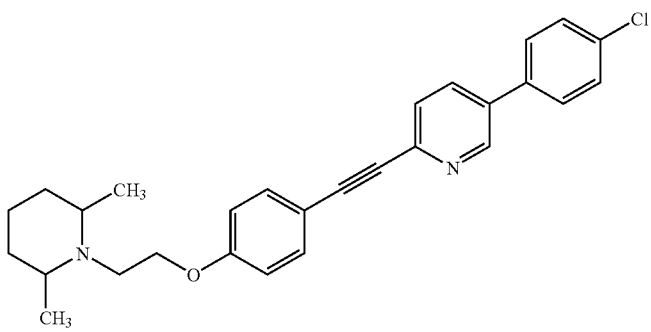

(87)

5-(4-chloro-phenyl)-2-{4-[2-(2,6-dimethyl-piperidin-1-yl)-ethoxy]-phenylethynyl}-pyridine

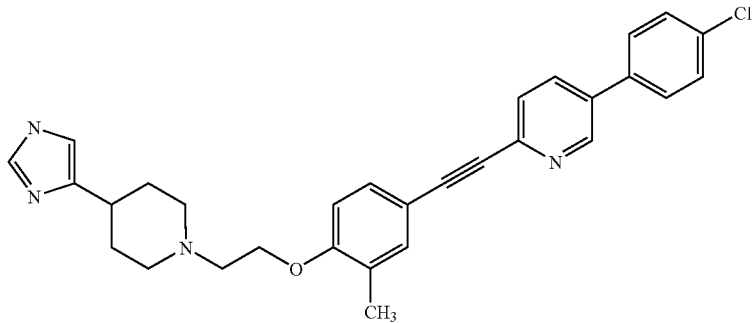

(88)

5-(4-chloro-phenyl)-2-(4-{2-[4-(1H-imidazol-4-yl)-piperidin-1-yl]-ethoxy}-3-methyl-phenylethynyl)-pyridine

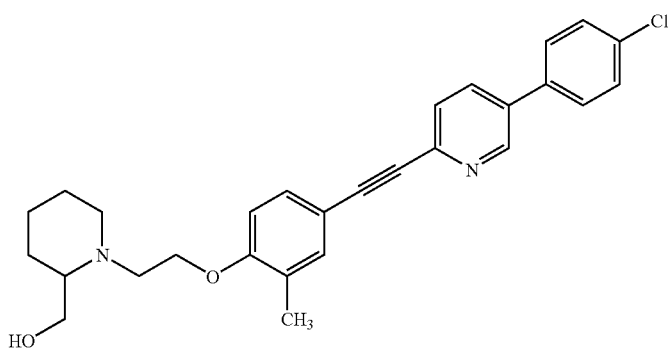

(89)

[1-(2-{4-[5-(4-chloro-phenyl)-pyridin-2-ylethynyl]-2-methyl-phenoxy}-ethyl)-piperidin-2-yl]-methanol (90)

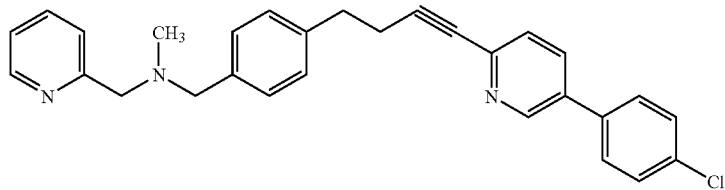

(4-{4-[5-(4-chloro-phenyl)-pyridin-2-yl]-but-3-ynyl}-benzyl)-methyl-pyridin-2-ylmethyl-amine (91)

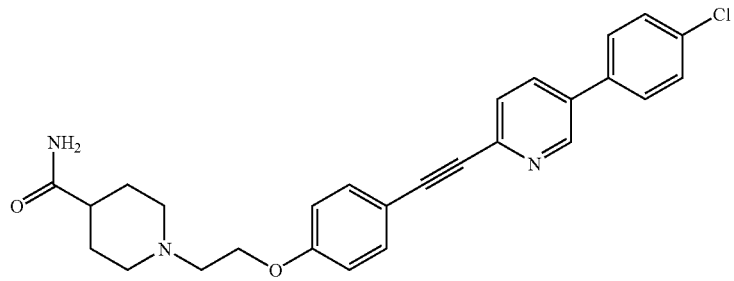

1-(2-{4-[5-(4-chloro-phenyl)-pyridin-2-ylethynyl]-phenoxy}-ethyl)-piperidin-4-carboxylic acid amide (92)

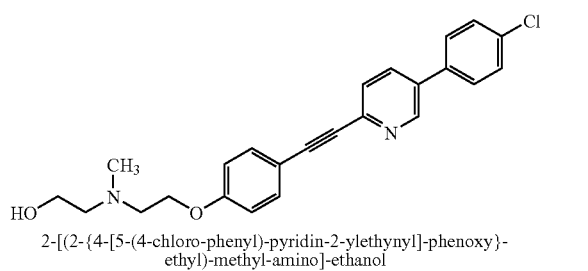

2-[(2-{4-[5-(4-chloro-phenyl)-pyridin-2-ylethynyl]-phenoxy}-ethyl)-methyl-amino]-ethanol (93)

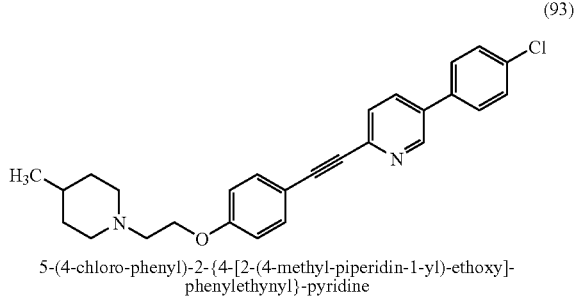

5-(4-chloro-phenyl)-2-{4-[2-(4-methyl-piperidin-1-yl)-ethoxy]-phenylethynyl}-pyridine (94)

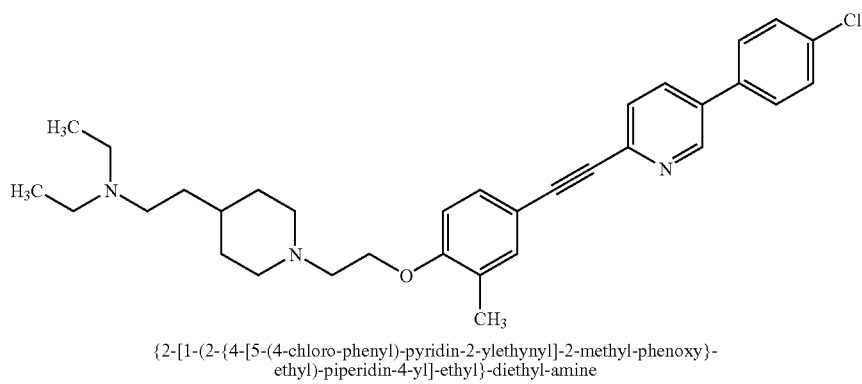

{2-[1-(2-{4-[5-(4-chloro-phenyl)-pyridin-2-ylethynyl]-2-methyl-phenoxy}-ethyl)-piperidin-4-yl]-ethyl}-diethyl-amine (95)

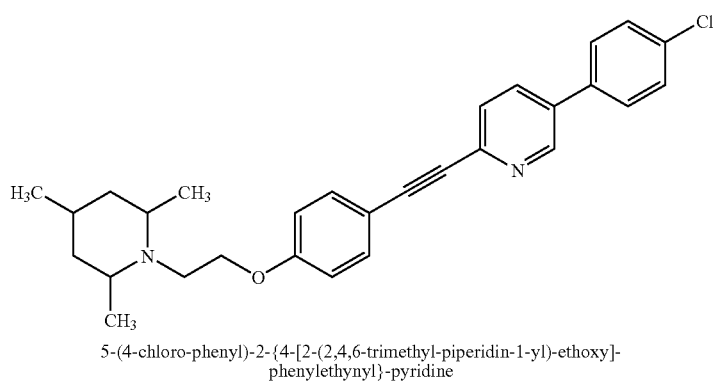

5-(4-chloro-phenyl)-2-{4-[2-(2,4,6-trimethyl-piperidin-1-yl)-ethoxy]-phenylethynyl}-pyridine -continued

(96)
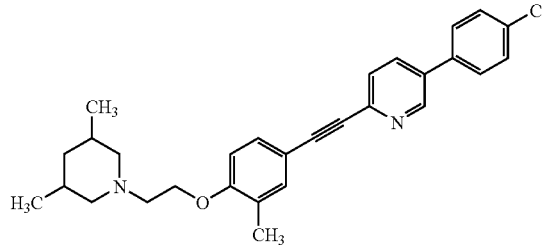
5-(4-chloro-phenyl)-2-{4-[2-(3,5-dimethyl-piperidin-1-yl)-ethoxy]-3-methyl-phenylethynyl}-pyridine

(97)
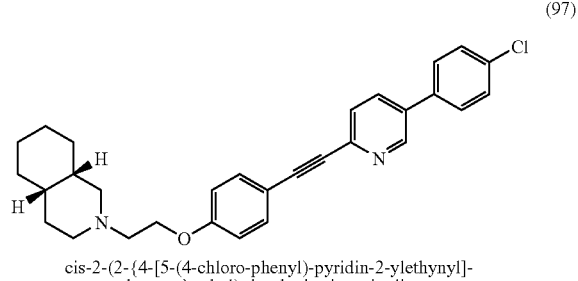
cis-2-(2-{4-[5-(4-chloro-phenyl)-pyridin-2-ylethynyl]-phenoxy}-ethyl)-decahydro-isoquinoline

(98)
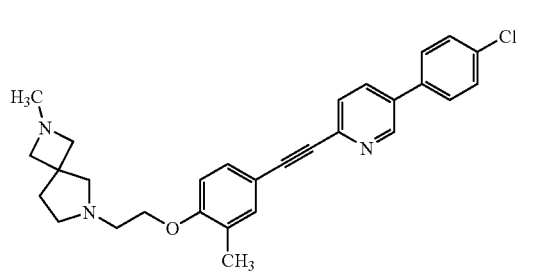
6-(2-{4-[5-(4-chloro-phenyl)-pyridin-2-ylethynyl]-2-methyl-phenoxy}-ethyl)-2-methyl-2,6-diaza-spiro[3.4]octane

(99)
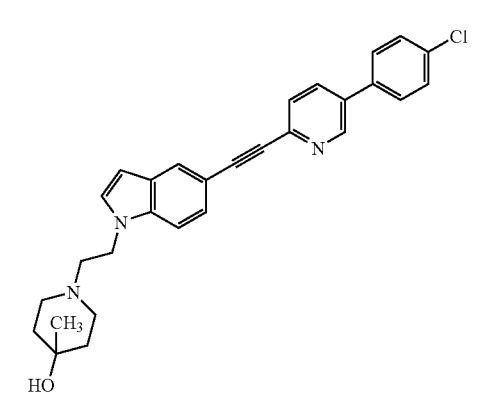
1-(2-{5-[5-(4-chloro-phenyl)-pyridin-2-ylethynyl]-indol-1-yl}-ethyl)-4-methyl-piperidin-4-ol (100)
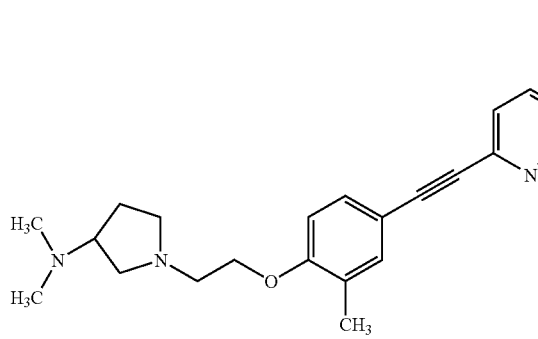
[1-(2-{4-[5-(4-chloro-phenyl)-pyridin-2-ylethynyl]-2-methyl-phenoxy}-ethyl)-pyrrolidin-3-yl]-dimethyl-amine (101)
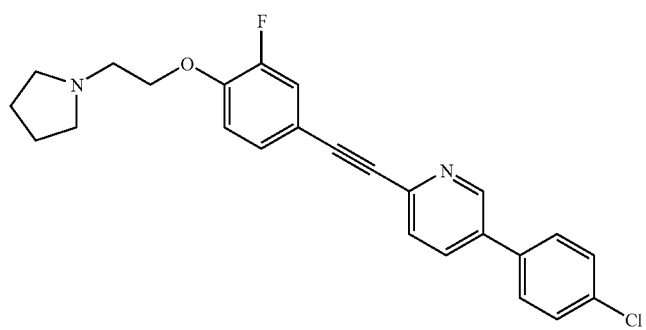
5-(4-chloro-phenyl)-2-[3-fluoro-4-(2-pyrrolidin-1-yl-ethoxy)-phenylethynyl]-pyridine -continued
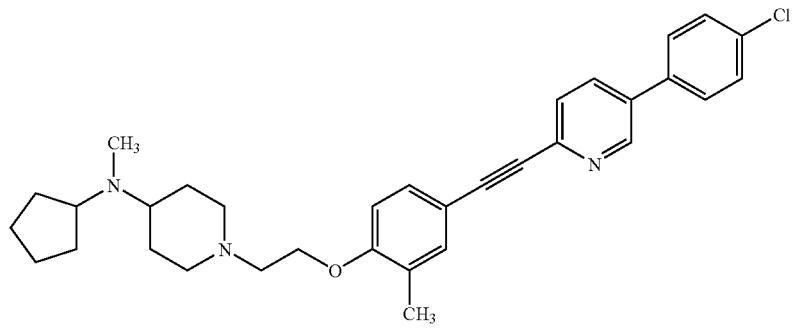
[1-(2-{4-[5-(4-chloro-phenyl)-pyridin-2-ylethynyl]-2-methyl-phenoxy}-ethyl)-piperidin-4-yl]-cyclopentyl-methyl-amine
(102)
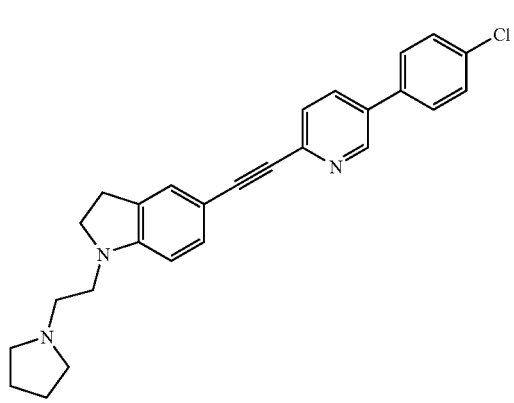
5-[5-(4-chloro-phenyl)-pyridin-2-ylethynyl]-1-(2-pyrrolidin-1-yl-ethyl)-2,3-dihydro-1H-indole
(103)
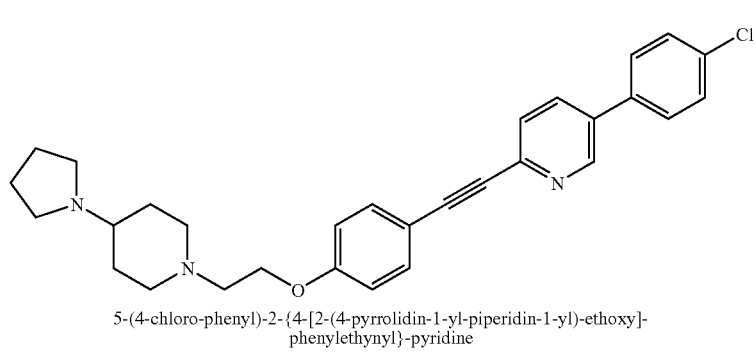
5-(4-chloro-phenyl)-2-{4-[2-(4-pyrrolidin-1-yl-piperidin-1-yl)-ethoxy]-phenylethynyl}-pyridine
(104)
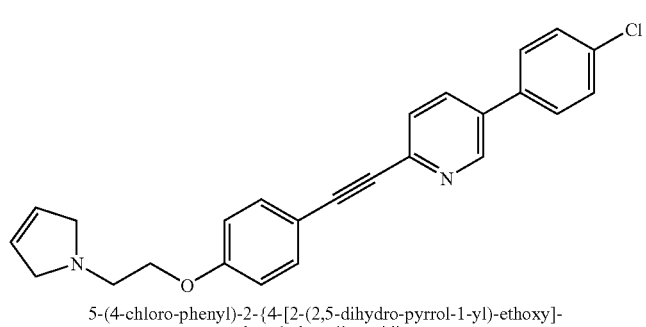
5-(4-chloro-phenyl)-2-{4-[2-(2,5-dihydro-pyrrol-1-yl)-ethoxy]-phenylethynyl}-pyridine
(105)

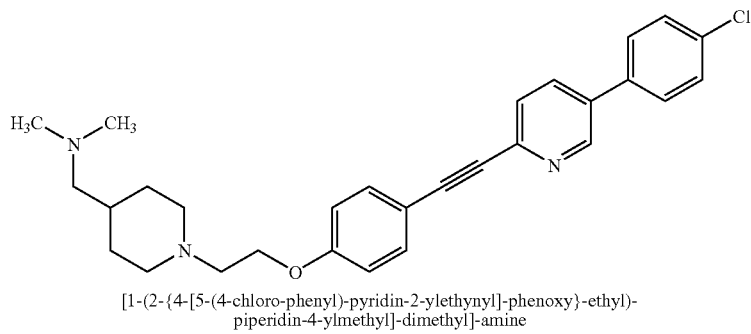
[1-(2-{4-[5-(4-chloro-phenyl)-pyridin-2-ylethynyl]-phenoxy}-ethyl)-piperidin-4-ylmethyl]-dimethyl]-amine
(106)
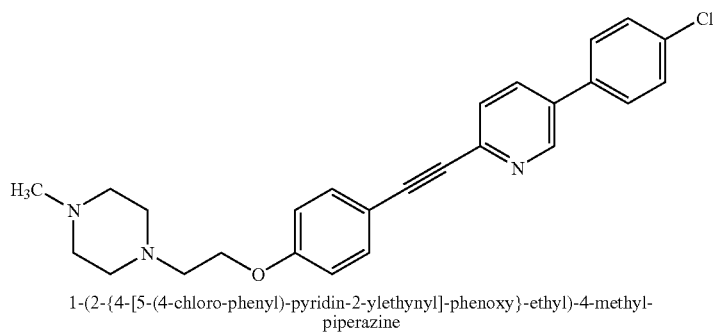
1-(2-{4-[5-(4-chloro-phenyl)-pyridin-2-ylethynyl]-phenoxy}-ethyl)-4-methyl-piperazine
(107)
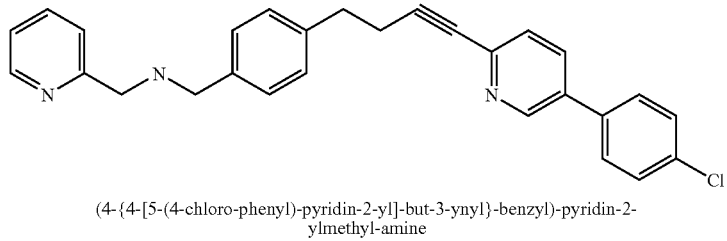
(4-{4-[5-(4-chloro-phenyl)-pyridin-2-yl]-but-3-ynyl}-benzyl)-pyridin-2-ylmethyl-amine
(108)
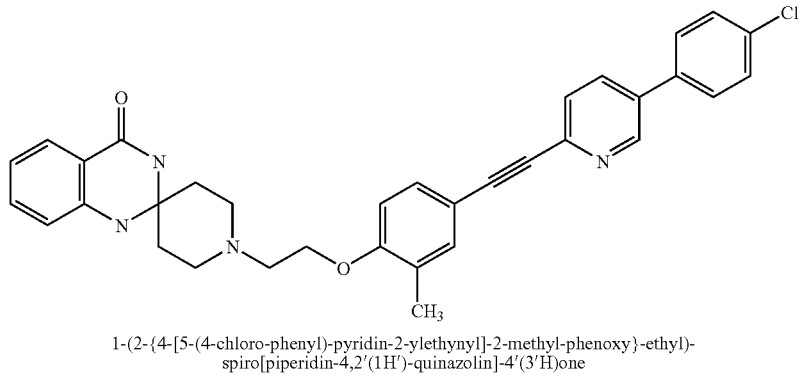
1-(2-{4-[5-(4-chloro-phenyl)-pyridin-2-ylethynyl]-2-methyl-phenoxy}-ethyl)-spiro[piperidin-4,2'(1H')-quinazolin]-4'(3'H)one
(109)

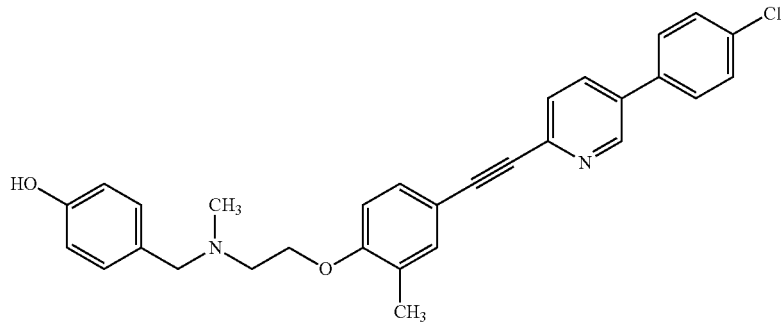

(110)

4-{[(2-{4-[5-(4-chloro-phenyl)-pyridin-2-ylethynyl]-2-methyl-phenoxy}-ethyl)-methyl-amino]-methyl}-phenol

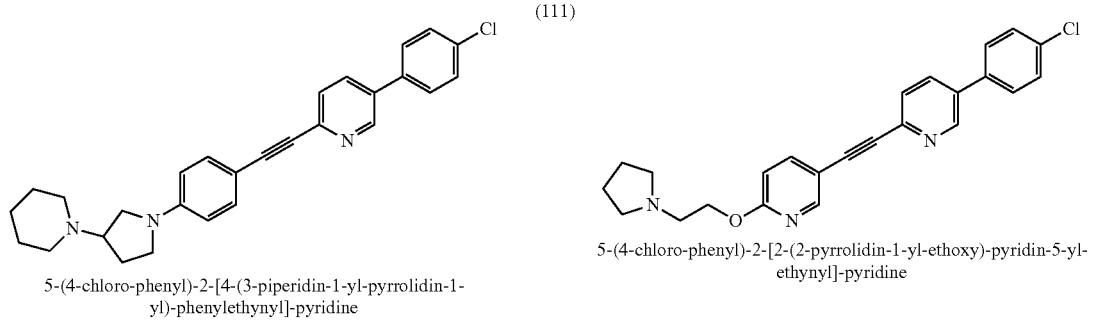

(111) 5-(4-chloro-phenyl)-2-[4-(3-piperidin-1-yl-pyrrolidin-1-yl)-phenylethynyl]-pyridine (112) 5-(4-chloro-phenyl)-2-[2-(2-pyrrolidin-1-yl-ethoxy)-pyridin-5-yl-ethynyl]-pyridine

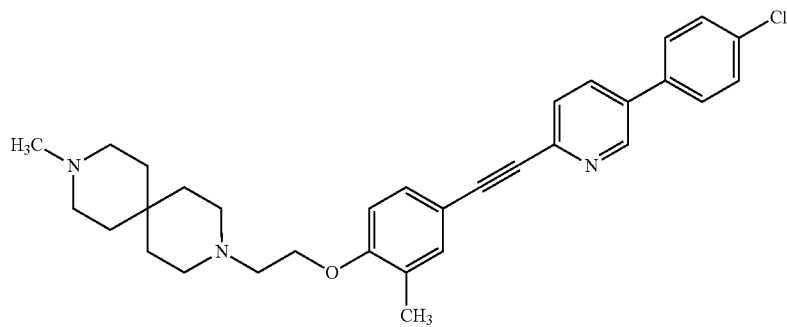

(113)

3-(2-{4-[5-(4-chloro-phenyl)-pyridin-2-ylethynyl]-2-methyl-phenoxy}-ethyl)-9-methyl-3,9-diaza-spiro[5.5]undecane

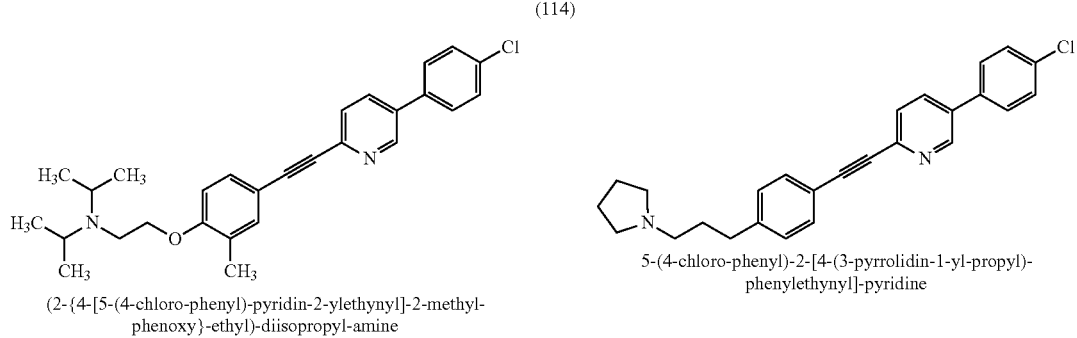

(114) (2-{4-[5-(4-chloro-phenyl)-pyridin-2-ylethynyl]-2-methyl-phenoxy}-ethyl)-diisopropyl-amine (115) 5-(4-chloro-phenyl)-2-[4-(3-pyrrolidin-1-yl-propyl)-phenylethynyl]-pyridine -continued

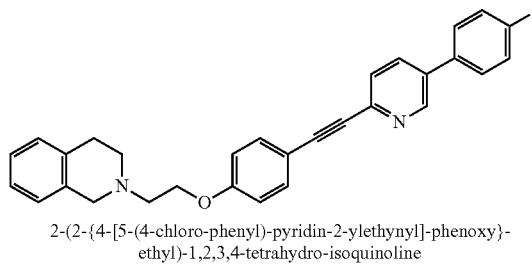

(116)

2-(2-{4-[5-(4-chloro-phenyl)-pyridin-2-ylethynyl]-phenoxy}-
ethyl)-1,2,3,4-tetrahydro-isoquinoline

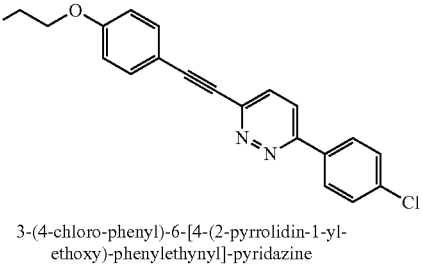

(117)

3-(4-chloro-phenyl)-6-[4-(2-pyrrolidin-1-yl-
ethoxy)-phenylethynyl]-pyridazine

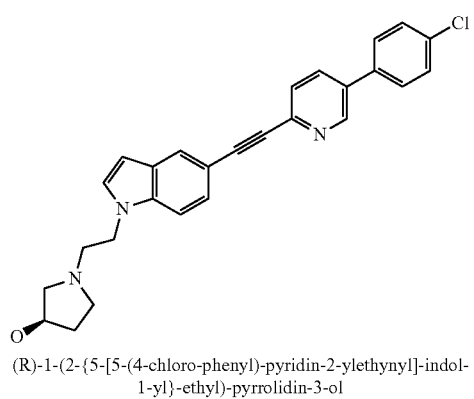

(118)

(R)-1-(2-{5-[5-(4-chloro-phenyl)-pyridin-2-ylethynyl]-indol-
1-yl}-ethyl)-pyrrolidin-3-ol

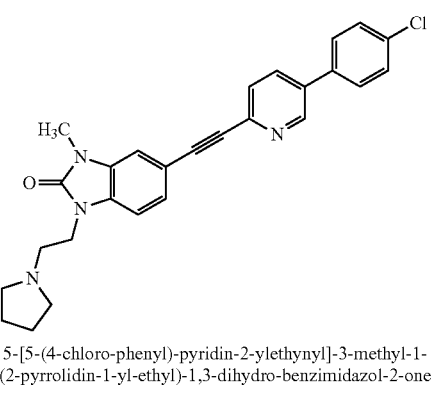

(119)

5-[5-(4-chloro-phenyl)-pyridin-2-ylethynyl]-3-methyl-1-
(2-pyrrolidin-1-yl-ethyl)-1,3-dihydro-benzimidazol-2-one

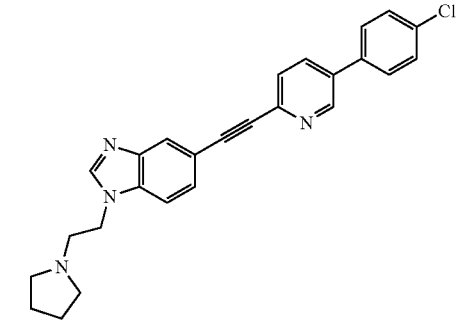

(120)

5-[5-(4-chloro-phenyl)-pyridin-2-ylethynyl]-1-(2-pyrrolidin-1-
yl-ethyl)-1H-benzimidazole

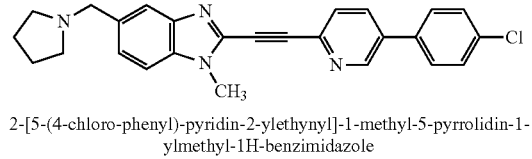

(121)

2-[5-(4-chloro-phenyl)-pyridin-2-ylethynyl]-1-methyl-5-pyrrolidin-1-
ylmethyl-1H-benzimidazole

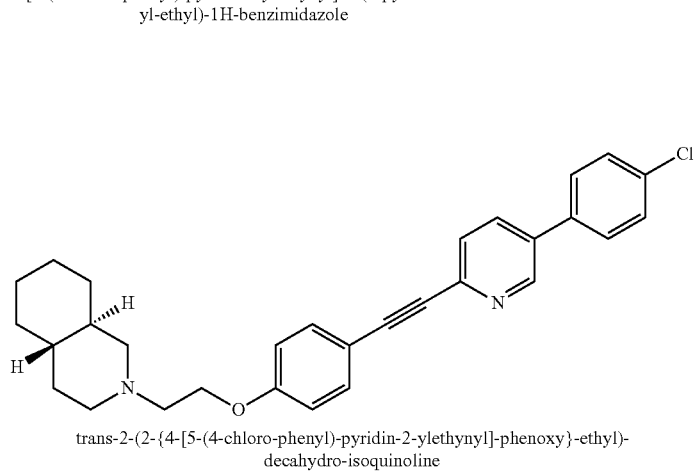

(122)

trans-2-(2-{4-[5-(4-chloro-phenyl)-pyridin-2-ylethynyl]-phenoxy}-ethyl)-
decahydro-isoquinoline including the tautomers, the diastereomers, the enantiomers, the mixtures thereof and the salts thereof.

Some expressions used hereinbefore and below to describe the compounds according to the invention will now be defined more fully.

The term halogen denotes an atom selected from among F, Cl, Br and I, particularly F, Cl and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{1-n}$-alkylene, where n may have a value of 1 to 8, denotes a saturated, branched or unbranched hydrocarbon bridge with 1 to n C atoms. Examples of such groups include methylene (—$CH_2$—), ethylene (—$CH_2$—$CH_2$—), 1-methyl-ethylene (—$CH(CH_3)$—$CH_2$—), 1,1-dimethyl-ethylene (—$C(CH_3)_2$—$CH_2$—), n-prop-1,3-ylene (—$CH_2$—$CH_2$—$CH_2$—), 1-methylprop-1,3-ylene (—$CH(CH_3)$—$CH_2$—$CH_2$—), 2-methylprop-1,3-ylene (—$CH_2$—$CH(CH_3)$—$CH_2$—), etc., as well as the corresponding mirror-symmetrical forms.

The term $C_{2-n}$-alkenyl, where n has a value of 3 to 6, denotes a branched or unbranched hydrocarbon group with 2 to n C atoms and at least one C=C-double bond. Examples of such groups include vinyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, where n has a value of 3 to 6, denotes a branched or unbranched hydrocarbon group with 2 to n C atoms and a C≡C triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{1-n}$-alkoxy denotes a $C_{1-n}$-alkyl-O— group, wherein $C_{1-n}$-alkyl is defined as above. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylthio denotes a $C_{1-n}$-alkyl-S— group, wherein $C_{1-n}$-alkyl is defined as above. Examples of such groups include methylthio, ethylthio, n-propylthio, iso-propylthio, n-butylthio, iso-butylthio, sec-butylthio, tert-butylthio, n-pentylthio, iso-pentylthio, neo-pentylthio, tert-pentylthio, n-hexylthio, iso-hexylthio, etc.

The term $C_{1-n}$-alkylcarbonyl denotes a $C_{1-n}$-alkyl-C(=O)— group, wherein $C_{1-n}$-alkyl is defined as above. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably, the term $C_{3-7}$-cycloalkyl includes saturated monocyclic groups.

The term $C_{5-n}$-cycloalkenyl denotes a monounsaturated mono-, bi-, tri- or spirocarbocyclic group with 5 to n C atoms. Examples of such groups include cyclopentenyl, cyclohexenyl, cycloheptenyl, cyclooctenyl, cyclononenyl, etc.

The term $C_{3-n}$-cycloalkylcarbonyl denotes a $C_{3-n}$-cycloalkyl-C(=O) group, wherein $C_{3-n}$-cycloalkyl is defined as above.

The term aryl denotes a carbocyclic, aromatic ring system, such as for example phenyl, biphenyl, naphthyl, anthracenyl, phenanthrenyl, fluorenyl, indenyl, pentalenyl, azulenyl, biphenylenyl, etc. A particularly preferred meaning of "aryl" is phenyl.

The term cyclo-$C_{3-7}$-alkyleneimino denotes a 4- to 7-membered ring which has 3 to 7 methylene units as well as an imino group, the bond to the rest of the molecule being made via the imino group.

The term cyclo-$C_{3-7}$-alkyleneimino-carbonyl denotes a cyclo-$C_{3-7}$-alkyleneimino ring as defined hereinbefore which is linked to a carbonyl group via the imino group.

The term heteroaryl used in this application denotes a heterocyclic, aromatic ring system which comprises in addition to at least one C atom one or more heteroatoms selected from N, O and/or S. Examples of such groups are furanyl, thiophenyl, pyrrolyl, oxazolyl, thiazolyl, imidazolyl, isoxazolyl, isothiazolyl, 1,2,3-triazolyl, 1,3,5-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl(thianaphthenyl), indazolyl, benzimidazolyl, benzthiazolyl, benzisothiazolyl, benzoxazolyl, benzisoxazolyl, purinyl, quinazolinyl, quinozilinyl, quinolinyl, isoquinolinyl, quinoxalinyl, naphthyridinyl, pteridinyl, carbazolyl, azepinyl, diazepinyl, acridinyl, etc. The term heteroaryl also comprises the partially hydrogenated heterocyclic, aromatic ring systems, particularly those listed above. Examples of such partially hydrogenated ring systems are 2,3-dihydrobenzofuranyl, pyrolinyl, pyrazolinyl, indolinyl, oxazolidinyl, oxazolinyl, oxazepinyl, etc. Particularly preferably, heteroaryl denotes a heteroaromatic mono- or bicyclic ring system.

Terms such as aryl-$C_{1-n}$-alkyl, heteroaryl-$C_{1-n}$-alkyl, etc. refer to $C_{1-n}$-alkyl, as defined above, which is substituted with an aryl or heteroaryl group.

Many of the terms given above may be used repeatedly in the definition of a formula or group and in each case have one of the meanings given above, independently of one another.

The term "unsaturated carbocyclic group" or "unsaturated heterocyclic group", as used particularly in the definition of the group Cy, comprises, in addition to the totally unsaturated groups, the corresponding, only partially unsaturated groups, particularly the mono- and diunsaturated groups.

The term "optionally substituted" used in this application indicates that the group thus designated is either unsubstituted or mono- or polysubstituted by the substituents specified. If the group in question is polysubstituted, the substituents may be identical or different.

The H atom of any carboxy group present or an H atom (imino or amino group) bonded to an N atom may in each case be replaced by a group which can be cleaved in vivo. By a group which can be cleaved in vivo from an N atom is meant for example a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_eCO$—O—$(R_fCR_g)$—O—CO group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_eCO$—O—$(R_fCR_g)$—O group wherein $R_e$ to $R_g$ are as hereinbefore defined, while additionally the phthalimido group is a possibility for an amino group, and the above-mentioned ester groups may also be used as groups which can be converted into a carboxy group in vivo.

The residues and substituents described above may be mono- or polysubstituted by fluorine as described. Preferred fluorinated alkyl groups are fluoromethyl, difluoromethyl and trifluoromethyl. Preferred fluorinated alkoxy groups are fluoromethoxy, difluoromethoxy and trifluoromethoxy. Preferred fluorinated alkylsulphinyl and alkylsulphonyl groups are trifluoromethylsulphinyl and trifluoromethylsulphonyl.

The compounds of general formula I according to the invention may have acid groups, predominantly carboxyl groups, and/or basic groups such as e.g. amino functions. Compounds of general formula I may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alkaline earth metal hydroxides or carbonates, zinc or ammonium hydroxides or organic amines such as e.g. diethylamine, triethylamine, triethanolamine inter alia.

The compounds according to the invention may be obtained using methods of synthesis which are known in principle. Preferably the compounds are obtained by the methods of preparation according to the invention, which are described more fully hereinafter.

The two reaction plans A and B which follow illustrate the synthesis of the compounds A.5 and B.5 according to the invention, wherein $R^1$, $R^2$, X, Y, Z, W, A and B have one of the meanings described hereinbefore. In reaction plan A the group Y denotes an aryl or heteroaryl group, whereas in reaction plan B the group A denotes an aryl or heteroaryl group. Hal denotes chlorine, bromine or iodine, particularly bromine or iodine, particularly preferably iodine.

According to reaction plan A the halogen compound A.1 is reacted with the alkyne compound A.2 in a molar ratio of about 1.5:1 to 1:1.5 under a protective gas atmosphere in the presence of a suitable palladium catalyst, a suitable base and copper(I)iodide in a suitable solvent.

A preferred amount of copper(I)iodide is in the range from 1 to 15 mol %, particularly from 5 to 10 mol % based on the educt A.1. Suitable palladium catalysts are for example $Pd(PPh_3)_4$, $Pd_2(dba)_3$, $Pd(OAc)_2$, $Pd(PPh_3)_2Cl_2$, $Pd(CH_3CN)_2Cl_2$, $Pd(dppf)Cl_2$. The palladium catalyst is preferably used in an amount of from 1 to 15 mol %, particularly 5 to 10 mol % based on the educt A.1.

Suitable bases are particularly amines, such as for example triethylamine or ethyldiisopropylamine, as well as $Cs_2CO_3$. The base is preferably used in at least equimolar amounts based on the educt A.1, in excess or as the solvent as well. Other suitable solvents are dimethylformamide or ethers, such as for example tetrahydrofuran, including the mixtures thereof. The reaction is carried out over a period of about 2 to 24 hours in a temperature range from about 20 to 90° C.

The alkyne compound A.3 obtained is reacted directly or after previous purification with methanesulphonic acid chloride to form the methanesulphonate derivative A.4. The reaction conditions required are known as such to the skilled man. Advantageous solvents are halogenated hydrocarbons, such as for example dichloromethane. Suitable reaction temperatures are normally in the range from 0 to 30° C.

The reaction solution containing the methanesulphonate derivative A.4, or the purified methanesulphonate derivative A.4, dissolved in a suitable solvent, is reacted with an amine H—$NR^1R^2$ to obtain the end product A.5 and then optionally purified. If the amine H—$NR^1R^2$ has another primary or secondary amine function, this is advantageously protected beforehand by a protective group which can be cleaved again after the reaction has ended, using methods known from the literature. The product thus obtained may for example be converted into the salt form by reaction with a corresponding acid. A preferred molar ratio of the derivative A.4 to the amine compound is in the range from 1.5:1 to 1:1.5. Suitable solvents are dimethylformamide or ether, such as for example tetrahydrofuran, including the mixtures thereof.

The reaction to obtain the product A.5 is advantageously carried out in a temperature range of about 20 to 90° C.

Reaction plan A:

HO-X-Y-Hal   +   H—C≡C—W-A-B
  (A.1)               (A.2)

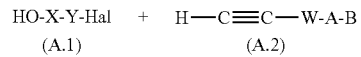

HO-X-Y—C≡C—W-A-B
       (A.3)

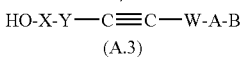 MsCl

MsO-X-Y—C≡C—W-A-B
       (A.4)

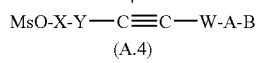 $HNR^1R^2$ $R^1R^2N$-X-Y—C≡C—W-A-B
       (A.5)

According to reaction plan B the halogen compound B.2 is reacted with the alkyne compound B.1 in a molar ratio of about 1.5:1 to 1:1.5 under a protective gas atmosphere in the presence of a suitable palladium catalyst, a suitable base and copper(I)iodide in a suitable solvent. Details of suitable reaction conditions, including catalysts, bases and solvents, may be found in the description of reaction plan A.

The alkyne compound B.3 obtained is reacted with methanesulphonic acid chloride directly or after previous purification, to form the methanesulphonate derivative B.4. The reaction conditions required can again be found in the description relating to Reaction plan A.

The reaction solution containing the methanesulphonate derivative B.4, or the purified methanesulphonate derivative B.4, dissolved in a suitable solvent, is reacted with an amine H—NR¹R² to obtain the end product B.5 and then optionally purified. Once again, the remarks relating to Reaction plan A apply.

Reaction plan B:

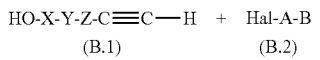

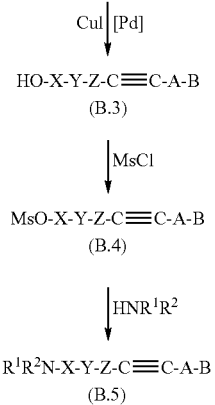

According to the additional reaction plan C the halogen compound C.1 is reacted directly with the alkyne compound C.2 in a molar ratio of about 1.5:1 to 1:1.5 under a protective gas atmosphere in the presence of a suitable palladium catalyst, a suitable base and copper(I)iodide in a suitable solvent to obtain the product C.3. Details of suitable reaction conditions, including catalysts, bases and solvents, may be found in the description of reaction plan A.

Reaction plan C:

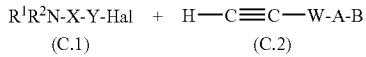

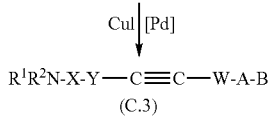

An alternative method of synthesis is shown in reaction plan D. According to this the halogen compound D.2 is reacted directly with the alkyne compound D.1 in a molar ratio of about 1.5:1 to 1:1.5 under a protective gas atmosphere in the presence of a suitable palladium catalyst, a suitable base and copper(I)iodide in a suitable solvent to form the product D.3. Once again, details of suitable reaction conditions, including catalysts, bases and solvents, may be found in the description of reaction plan A.

Reaction plan D:

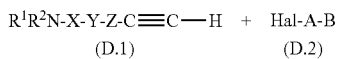

-continued
R¹R²N-X-Y-Z-C≡C-A-B
(D.3)

The reactions according to plans A, B, C and D may be carried out to particular advantage with the corresponding iodine compounds A.1, B.2, C.1 and D.2. In the event that Hal denotes bromine in compounds A.1, B.2, C.1 and D.2, it is advantageous to convert it into the corresponding iodine compound beforehand. A particularly advantageous process is the Aryl-Finkelstein reaction (Klapars, Artis; Buchwald, Stephen L. Copper-Catalyzed Halogen Exchange in Aryl Halides: An Aromatic Finkelstein Reaction. Journal of the American Chemical Society (2002), 124(50), 14844-14845). Thus for example the halogen compound A.1, B.2, C.1 bzw. D.2 may be reacted with sodium iodide in the presence of N,N'-dimethyl-ethylenediamine and copper(I)iodide in a suitable solvent to obtain the corresponding iodine compound. An advantageous molar ratio of the halogen compound to sodium iodide is 1:1.8 to 1:2.3. N,N'-dimethyl-ethylenediamine is advantageously used in a molar ratio of 10 to 30 mol % based on the halogen compound A.1, B.2, C.1 or D.2. Preferred amounts of copper(I)iodide are in the range from 5 to 20 mol % based on the halogen compound A.1, B.2, C.1 or D.2. A suitable solvent is 1,4-dioxane, for example. Suitable reaction temperatures are in the range from about 20 to 110° C. The reaction is substantially complete after 2 to 72 hours.

The compounds according to the invention may advantageously also be obtained using methods described in the following Examples, which may also be combined with methods known to the skilled man from the literature, for example.

Stereoisomeric compounds of formula (I) may be separated in principle by conventional methods. The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvents provided that they show sufficient differences in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. On the other hand, in the case of acidically bound hydrogen, the compound of formula (I) may also be converted by reaction with inorganic bases into physiologically and pharmacologically acceptable salts with alkali or alkaline earth metal cations as counter-ion. The acid addition salts may be prepared, for example, using hydrochloric acid, hydrobromic acid, sulphuric acid, phosphoric acid, methanesulphonic acid, ethanesulphonic acid, toluenesulphonic acid, benzenesulphonic acid, acetic acid, fumaric acid, succinic acid, lactic acid, citric acid, tartaric acid or maleic acid. Moreover, mixtures of the above mentioned acids may be used. To prepare the alkali and alkaline earth metal salts of the compound of formula (I) with acidically bound hydrogen the alkali and alkaline earth metal hydroxides and hydrides are preferably used, while the hydroxides and hydrides of the alkali metals, particularly sodium and potassium are preferred and sodium and potassium hydroxide are most preferred.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH-antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have an intracerebral transitivity, particularly brain accessibility.

Therefore, MCH antagonists which contain at least one compound according to the invention, are particularly suitable in mammals, such as for example rats, mice, guinea pigs, hares, dogs, cats, sheep, horses, pigs, cattle, monkeys and also humans, for the treatment and/or prevention of symptoms and/or diseases which are caused by MCH or are otherwise causally connected with MCH.

Diseases caused by MCH or otherwise causally connected with MCH are particularly metabolic disorders, such as for example obesity, and eating disorders, such as for example bulimia, including bulimia nervosa. The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity. This range of indications also includes cachexia, anorexia and hyperphagia.

Compounds according to the invention may, in particular, be suitable for reducing hunger, curbing appetite, controlling eating behaviour and/or promoting a feeling of satiety.

In addition, the diseases caused by MCH or otherwise causally connected with MCH also include hyperlipidaemia, cellulitis, fat accumulation, malignant mastocytosis, systemic mastocytosis, emotional disorders, affectivity disorders, depression, anxiety states, sleep disoreders, reproductive disorders, sexual disorders, memory disorders, epilepsy, forms of dementia and hormonal disorders.

Compounds according to the invention are also suitable as active substances for the prevention and/or treatment of other illnesses and/or disorders, particularly those which accompany obesity, such as, for example, diabetes, diabetes mellitus, especially type II diabetes, hyperglycaemia, particularly chronic hyperglycaemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis and gonitis.

MCH antagonists and formulations according to the invention may advantageously be used in combination with a dietary therapy, such as for example a dietary diabetes treatment, and exercise.

Another range of indications for which the compounds according to the invention are advantageously suitable is the prevention and/or treatment of urinary disorders, such as for example urinary incontinence, overactive bladder, urgency, nycturia and enuresis, while the overactive bladder and urgency may or may not be connected with benign prostatic hyperplasia.

The dosage required to achieve such an effect is conveniently, by intravenous or subcutaneous route, 0.001 to 30 mg/kg of body weight, preferably 0.01 to 5 mg/kg of body weight, and by oral or nasal route or by inhalation, 0.01 to 50 mg/kg of body weight, preferably 0.1 to 30 mg/kg of body weight, in each case once to three times a day.

For this purpose, the compounds of formula I prepared according to the invention may be formulated, optionally together with other active substances as described hereinafter, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, granules, solutions, emulsions, syrups, aerosols for inhalation, ointments or suppositories.

In addition to pharmaceutical compositions the invention also covers compositions containing at least one alkyne compound according to the invention and/or a salt according to the invention optionally together with one or more physiologically acceptable excipients. Such compositions may also be foods, for example, which may be solid or liquid, in which the compound according to the invention is incorporated.

For the above mentioned combinations it is possible to use as additional active substances particularly those which for example potentiate the therapeutic effect of an MCH antagonist according to the invention in terms of one of the indications mentioned above and/or which make it possible to reduce the dosage of an MCH antagonist according to the invention. Preferably one or more additional active substances are selected from among active substances for the treatment of diabetes,
    active substances for the treatment of diabetic complications,
    active substances for the treatment of obesity, preferably other than MCH antagonists, active substances for the treatment of high blood pressure,
active substances for the treatment of hyperlipidaemia, including arteriosclerosis,
active substances for the treatment of arthritis,
active substances for the treatment of anxiety states,
active substances for the treatment of depression.

The above mentioned categories of active substances will now be explained in more detail by means of examples.

Examples of active substances for the treatment of diabetes are insulin sensitisers, insulin secretion accelerators, biguanides, insulins, α-glucosidase inhibitors, β3 adreno-receptor agonists.

Insulin sensitisers include pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702, GW-1929.

Insulin secretion accelerators include sulphonylureas, such as for example tolbutamide, chloropropamide, tolzamide, acetohexamide, glyclopyramide and its ammonium salts, glibenclamide, gliclazide, glimepiride. Further examples of insulin secretion accelerators are repaglinide, nateglinide, mitiglinide (KAD-1229) and JTT-608.

Biguanides include metformin, buformin and phenformin.

Insulins include those obtained from animals, particularly cattle or pigs, semisynthetic human insulins which are synthesised enzymatically from insulin obtained from animals, human insulin obtained by genetic engineering, e.g. from *Escherichia coli* or yeasts. Moreover, the term insulin also includes insulin-zinc (containing 0.45 to 0.9 percent by weight of zinc) and protamine-insulin-zinc obtainable from zinc chloride, protamine sulphate and insulin. Insulation may also be obtained from insulin fragments or derivatives (for example INS-1, etc.).

Insulin may also include different kinds, e.g. with regard to the onset time and duration of effect ("ultra immediate action type", "immediate action type", "two phase type", "intermediate type", "prolonged action type", etc.), which are selected depending on the pathological condition of the patient.

α-Glucosidase inhibitors include acarbose, voglibose, miglitol, emiglitate.

β3 Adreno receptor agonists include AJ-9677, BMS-196085, SB-226552, AZ40140.

Active substances for the treatment of diabetes other than those mentioned above include ergoset, pramlintide, leptin, BAY-27-9955 as well as glycogen phosphorylase inhibitors, sorbitol dehydrogenase inhibitors, protein tyrosine phosphatase 1B inhibitors, dipeptidyl protease inhibitors, glipazid, glyburide.

Active substances for the treatment of diabetic complications include for example aldose reductase inhibitors, glycation inhibitors and protein kinase C inhibitors.

Aldose reductase inhibitors are for example tolrestat, epalrestat, imirestat, zenarestat, SNK-860, zopolrestat, ARI-50i, AS-3201.

An example of a glycation inhibitor is pimagedine.

Protein Kinase C inhibitors are for example NGF, LY-333531.

Active substances other than those mentioned above for the treatment of diabetic complications include alprostadil, thiapride hydrochloride, cilostazol, mexiletine hydrochloride, ethyl eicosapentate, memantine, pimagedine (ALT-711).

Active substances for the treatment of obesity, preferably other than MCH antagonists, include lipase inhibitors and anorectics.

A preferred example of a lipase inhibitor is orlistat.

Examples of preferred anorectics are phentermine, mazindol, dexfenfluramine, fluoxetine, sibutramine, baiamine, (S)-sibutramine, SR-141716, NGD-95-1.

Active substances other than those mentioned above for the treatment of obesity include lipstatin.

Moreover for the purposes of this application the active substance group of anti-obesity active substances also includes the anorectics, of which the β3 agonists, thyromimetic active substances and NPY antagonists should be emphasised. The scope of the anti-obesity or anorectic active substances which are preferred here is indicated by the following additional list, by way of example: phenylpropanolamine, ephedrine, pseudoephedrine, phentermine, a cholecystokinin-A (hereinafter referred to as CCK-A) agonist, a monoamine reuptake inhibitor (such as for example sibutramine), a sympathomimetic active substance, a serotonergic active substance (such as for example dexfenfluramine or fenfluramine), a dopamine antagonist (such as for example bromocriptine), a melanocyte-stimulating hormone receptor agonist or mimetic, an analogue of melanocyte-stimulating hormone, a cannabinoid receptor antagonist, an MCH antagonist, the OB protein (hereinafter referred to as leptin), a leptin analogue, a leptin receptor agonist, a galanine antagonist, a GI lipase inhibitor or reducer (such as for example orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as for example exendin and ciliary neurotrophic factors, such as for example axokine.

Active substances for the treatment of high blood pressure include inhibitors of angiotensin converting enzyme, calcium antagonists, potassium channel openers and angiotensin II antagonists.

Inhibitors of angiotensin converting enzyme include captopril, enalapril, alacepril, delapril (hydrochloride), lisinopril, imidapril, benazepril, cilazapril, temocapril, trandolapril, manidipine (hydrochloride).

Examples of calcium antagonists are nifedipine, amlodipine, efonidipine, nicardipine.

Potassium channel openers include levcromakalim, L-27152, AL0671, NIP-121.

Angiotensin II antagonists include telmisartan, losartan, candesartan cilexetil, valsartan, irbesartan, CS-866, E4177.

Active substances for the treatment of hyperlipidaemia, including arteriosclerosis, include HMG-CoA reductase inhibitors, fibrate compounds.

HMG-CoA reductase inhibitors include pravastatin, simvastatin, lovastatin, atorvastatin, fluvastatin, lipantil, cerivastatin, itavastatin, ZD-4522 and the salts thereof.

Fibrate compounds include bezafibrate, clinofibrate, clofibrate and simfibrate.

Active substances for the treatment of arthritis include ibuprofen.

Active substances for the treatment of anxiety states include chlordiazepoxide, diazepam, oxazolam, medazepam, cloxazolam, bromazepam, lorazepam, alprazolam, fludiazepam.

Active substances for the treatment of depression include fluoxetine, fluvoxamine, imipramine, paroxetine, sertraline.

The dosage for these active substances is conveniently 1/5 of the lowest normal recommended dose up to 1/1 of the normal recommended dose.

In another embodiment the invention also relates to the use of at least one alkyne compound according to the invention and/or a salt according to the invention for influencing the eating behaviour of a mammal. This use is based particularly on the fact that compounds according to the invention may be suitable for reducing hunger, curbing appetite, controlling eating behaviour and/or promoting a feeling of satiety. The eating behaviour is advantageously influenced in such a way as to reduce food intake. Therefore, the compounds according to the invention are advantageously used for reducing body weight. A further use according to the invention is the prevention of increases in body weight, for example in people who have previously taken steps to reduce their weight and are then interested in maintaining their reduced body weight. According to this embodiment it is preferably a non-therapeutic use. Such a non-therapeutic use may be a cosmetic use, for example for altering the outer appearance, or an application for improving the general feeling of wellbeing. The compounds according to the invention are preferably used in a non-therapeutic capacity for mammals, particularly humans, who have no diagnosed disorders of eating behaviour, no diagnosed obesity, bulimia, diabetes and/or no diagnosed urinary problems, particularly urinary incontinence. Preferably the compounds according to the invention are suitable for non-therapeutic use in humans whose body mass index (BMI=body mass index), which is defined as the body weight measured in kilograms divided by the height (in meters) squared, is less than 30, particularly less than 25.

The Examples that follow are intended to illustrate the invention:

Preliminary Remarks:

As a rule, IR, $^1$H-NMR and/or mass spectra have been obtained for the compounds prepared. Unless otherwise stated the $R_f$-values are determined using ready-made silica gel 60 TLC plates $F_{254}$ (E. Merck, Darmstadt, Item no. 1.05714) without chamber saturation. The $R_f$-values obtained under the name Alox are determined using ready-made aluminium oxide 60 $F_{254}$ TLC plates (E. Merck, Darmstadt, Item no. 1.05713) without chamber saturation. The ratios given for the eluants relate to units by volume of the solvent in question. The units by volume for $NH_3$ relate to a concentrated solution of $NH_3$ in water. Silica gel made by Millipore (MATREX™, 35-70 my) is used for chromatographic purification. Alox (E. Merck, Darmstadt, aluminium oxide 90 standardised, 63-200 μm, Item no. 1.01097.9050) is used for chromatographic purification. The HPLC data given are measured under the following parameters:

Analytical columns: Zorbax column (Agilent Technologies), SB (Stable Bond)—C18; 3.5 μm; 4.6×75 mm; column temperature: 30° C.; flow: 0.8 mL/min; injection volume: 5 μL; detection at 254 nm (methods A and B)

Symmetry 300 (Waters), 3.5 μm; 4.6×75 mm; column temperature: 30° C.; flow: 0.8 mL/min; injection volume: 5 μL; detection at 254 nm (method C)

method A: water:acetonitrile:formic acid 9:1:0.01 to 1:9:0.01 over 9 min method B: water:acetonitrile:formic acid 9:1:0.01 to 1:9:0.01 over 4 min, then 6 min 1:9:0.01 method C: water:acetonitrile:formic acid 9:1:0.01 to 1:9:0.01 over 4 min, then 6 min 1:9:0.01

Preparative column: Zorbax column (Agilent Technologies), SB (Stable Bond)—C18; 3.5 μm; 30×100 mm; column temperature: ambient temperature; flow: 30 mL/min; detection at 254 nm.

In preparative HPLC purifications, as a rule, the same gradients are used as were used to raise the analytical HPLC data.

The products are collected under mass control, the fractions containing product are combined and freeze-dried.

If there is no specific information as to the configuration, it is not clear whether there are pure enantiomers or whether partial or even total racemisation has taken place.

The following abbreviations are used above and hereinafter:

CDI carbonyldiimidazole
cyc cyclohexane
DCM dichloromethane
DMF dimethylformamide
DMSO dimethylsulphoxide
dppf 1,1'-bis(diphenylphosphino)ferrocene
EtOAc ethyl acetate
EtOH ethanol
Fp melting point
i.vac. in vacuo
MeOH methanol
PE petroleum ether
PPh$_3$ triphenylphosphane
RT ambient temperature
TBAF tetrabutylammoniumfluoride trihydrate
THF tetrahydrofuran General Experimental Method I (Sonogashira Couplings)

Under an argon atmosphere, a suitable palladium catalyst (e.g. Pd(PPh$_3$)$_4$ (5 mol %), Pd(PPh$_3$)$_2$Cl$_2$ (5 mol %), Pd(CH$_3$CN)Cl$_2$ (5 mol %) or Pd(dppf)Cl$_2$ (5 or 10 mol %)), a suitable base (e.g. caesium carbonate (1.5 eq) or triethylamine (1.5 eq.)) and CuI (5 or 10 mol %) are added successively to a solution of the aryl or heteroaryl iodide or bromide (1.0 eq) and the alkyne (1.05 eq) in THF or DMF. The reaction solution is stirred at RT to 90° C. for between 2-24 h, filtered and the solvent is eliminated i.vac. Further purification is carried out by column chromatography or by purification using HPLC-MS.

General Experimental Method II (Bromine-Iodine Exchange)

NaI (2.0 eq), N,N'-dimethyl-ethylenediamine (0.2 eq.) and CuI (0.1 eq.) are added successively to a solution of the aryl or heteroaryl bromide (1.0 eq.) in 1,4-dioxane under argon. The reaction is stirred for 2-72 h at RT to 110° C. and then diluted with NH$_3$. The aqueous phase is extracted with DCM, the organic phase is dried over MgSO$_4$ and the solvent is eliminated i.vac. If necessary further purification is carried out by column chromatography.

Example 1

Diethyl-(2-{4-[5-(4-methoxy-phenyl)-pyridin-2-ylethynyl]-phenoxy}-ethyl)-amine

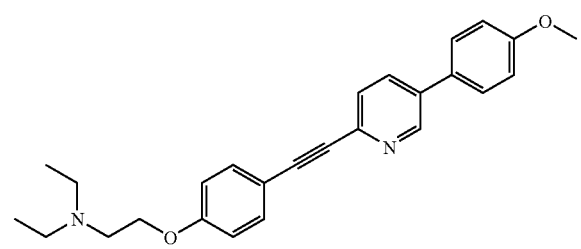

1a

[2-(4-bromo-phenoxy)-ethyl]-diethyl-amine

A suspension of 31.4 g (178 mmol) 4-bromophenol, 30.6 g (178 mmol) (2-chloro-ethyl)-diethyl-amine (used as the hydrochloride) and 61.5 g (445 mmol) $K_2CO_3$ in 300 mL DMF is heated to 80° C. for 8 h. The solvent is evaporated down i.vac., the residue combined with water, the aqueous phase exhaustively extracted with EtOAc, the combined organic phases washed with water again and dried over $MgSO_4$. After the desiccant and solvent have been eliminated the residue is purified by chromatography (silica gel, EtOAc/MeOH/$NH_3$ 90:10:1).

Yield: 28.0 g (58% of theory)
$C_{12}H_{18}BrNO$ (M=272.187)
Calc.: molpeak $(M+H)^+$: 272/274 Found: molpeak $(M+H)^+$: 272/274
$R_f$ value: 0.25 (silica gel, EtOAc/MeOH/$NH_3$ 90:10:1)

1b diethyl-[2-(4-trimethylsilanylethynyl-phenoxy)-ethyl]-amine

Under a nitrogen atmosphere a mixture of 5.44 g (20 mmol) [2-(4-bromo-phenoxy)-ethyl]-diethyl-amine, 3.11 mL (22 mmol) ethynyl-trimethyl-silane, 462 mg (0.4 mmol) tetrakis-triphenylphosphane-palladium, 76 mg (0.4 mmol) CuI in 50 mL piperidine is heated to 70° C. for 21 h. The solvent is distilled off i.vac., the residue is taken up in water, exhaustively extracted with EtOAc and dried over $Na_2SO_4$. After the desiccant and solvent have been eliminated the residue is purified on silica gel (EtOAc/MeOH/$NH_3$ 95:5:0.5).

Yield: 1.4 g (24% of theory)
$C_{17}H_{27}NOSi$ (M=289.497)
Calc.: molpeak $(M+H)^+$: 290 Found: molpeak $(M+H)^+$: 290
$R_f$ value: 0.67 (silica gel, EtOAc/MeOH/$NH_3$ 95:5:0.5)

1c diethyl-[2-(4-ethynyl-phenoxy)-ethyl]-amine

Under a nitrogen atmosphere a solution of 1.4 g (4.8 mmol) diethyl-[2-(4-trimethylsilanylethynyl-phenoxy)-ethyl]-amine in 50 mL THF is combined with 1.68 g (5.3 mmol) TBAF and stirred overnight at RT. The solvent is distilled off i.vac., the residue is taken up in water, exhaustively extracted with EtOAc and dried over $Na_2SO_4$. After the desiccant and solvent have been eliminated the residue is purified on silica gel (EtOAc/MeOH 95:5).

Yield: 0.5 g (47% of theory)
$C_{14}H_{19}NO$ (M=217.314)
Calc.: molpeak $(M+H)^+$: 218 Found: molpeak $(M+H)^+$: 218
$R_f$ value: 0.46 (silica gel, EtOAc/MeOH/$NH_3$ 95:5:0.5)

1d

{2-[4-(5-bromo-pyridin-2-ylethynyl)-phenoxy]-ethyl}-diethyl-amine

A mixture of 500 mg (2.30 mmol) diethyl-[2-(4-ethynyl-phenoxy)-ethyl]-amine, 545 mg (2.30 mmol) 2,5-dibromopyridine, 161 mg (0.23 mmol) tetrakis-triphenylphosphane-palladium, 13 mg (0.07 mmol) CuI, 2 mL ethyldiisopropylamine and 2 mL diisopropylamine in 50 mL DMF is heated for 20 h at 100° C. under a nitrogen atmosphere. The solvent is distilled off i.vac., the residue is taken up in water, exhaustively extracted with EtOAc and dried over $Na_2SO_4$. After the desiccant and solvent have been eliminated the residue is purified on silica gel (EtOAc/MeOH/$NH_3$ 95:5:0.5).

Yield: 200 mg (23% of theory)
$C_{19}H_{21}BrN_2O$ (M=373.296)
Calc.: molpeak $(M+H)^+$: 373/375 Found: molpeak $(M+H)^+$: 373/375
$R_f$ value: 0.50 (silica gel, EtOAc/MeOH/$NH_3$ 90:10:1)

1e diethyl-(2-{4-[5-(4-methoxy-phenyl)-pyridin-2-yl-ethynyl]-phenoxy}-ethyl)-amine A mixture of 200 mg (0.54 mmol) {2-[4-(5-bromo-pyridin-2-ylethynyl)-phenoxy]-ethyl}-diethyl-amine, 163 mg (1.07 mmol) 4-methoxy-phenylboric acid, 31 mg (0.03 mmol) tetrakis-triphenylphosphane-palladium and 0.27 mL of a 2 M aqueous $Na_2CO_3$ solution in 5 mL 1,4-dioxane is heated for 20 h at 110° C. under a nitrogen atmosphere. The solvent is distilled off i.vac., the residue is taken up in water, exhaustively extracted with EtOAc and dried over $Na_2SO_4$. After the desiccant and solvent have been eliminated the residue is purified on silica gel (EtOAc/MeOH/$NH_3$ 95:5:0.5). The product fractions are evaporated down, the residue is triturated with diethyl ether, suction filtered and washed with diisopropylether.

Yield: 30 mg (14% of theory)
$C_{26}H_{28}N_2O_2$ (M=400.525)
Calc.: molpeak $(M+H)^+$: 401 Found: molpeak $(M+H)^+$: 401
$R_f$ value: 0.46 (silica gel, EtOAc/MeOH/$NH_3$ 95:5:0.5)

Example 1.1 diethyl-(2-{4-[5-(2-methoxy-phenyl)-pyridin-2-yl-ethynyl]-phenoxy}-ethyl)-amine

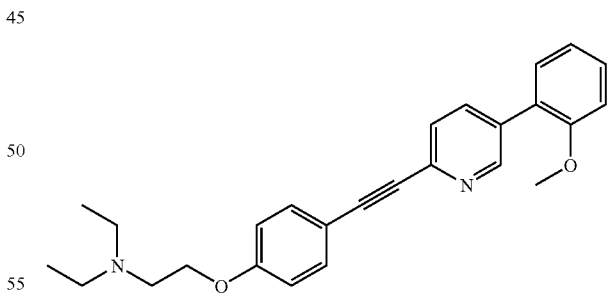

The product is obtained analogously to Example 1e from 200 mg (0.54 mmol) {2-[4-(5-bromo-pyridin-2-ylethynyl)-phenoxy]-ethyl}-diethyl-amine and 163 mg (1.07 mmol) 2-methoxy-phenylboric acid.

Yield: 40 mg (14% of theory)
$C_{26}H_{28}N_2O_2$ (M=400.525)
Calc.: molpeak $(M+H)^+$: 401 Found: molpeak $(M+H)^+$: 401
$R_f$ value: 0.23 (silica gel, EtOAc/MeOH/$NH_3$ 95:5:0.5)

Example 1.2

(2-{4-[5-(4-ethoxy-phenyl)-pyridin-2-ylethynyl]-phenoxy}-ethyl)-diethyl-amine

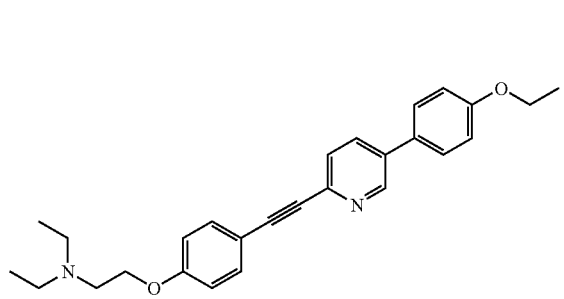 [SMILES: CCOc1ccc(-c2ccc(C#Cc3ccc(OCCN(CC)CC)cc3)nc2)cc1]

The product is obtained analogously to Example 1e from 200 mg (0.54 mmol) {2-[4-(5-bromo-pyridin-2-ylethynyl)-phenoxy]-ethyl}-diethyl-amine and 178 mg (1.07 mmol) 4-ethoxy-phenylboric acid.

Yield: 83 mg (37% of theory)

$C_{27}H_{30}N_2O_2$ (M=414.552)

Calc.: molpeak $(M+H)^+$: 414 Found: molpeak $(M+H)^+$: 414

$R_f$ value: 0.26 (silica gel, EtOAc/MeOH/NH$_3$ 95:5:0.5)

Example 1.3

(2-{4-[5-(3,4-difluoro-phenyl)-pyridin-2-ylethynyl]-phenoxy}-ethyl)-diethyl-amine

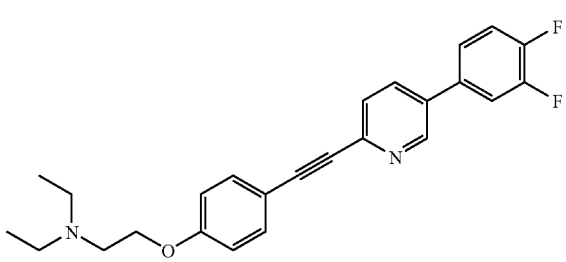 [SMILES: CCN(CC)CCOc1ccc(C#Cc2ccc(-c3ccc(F)c(F)c3)cn2)cc1]

The product is obtained analogously to Example 1e from 200 mg (0.54 mmol) {2-[4-(5-bromo-pyridin-2-ylethynyl)-phenoxy]-ethyl}-diethyl-amine and 169 mg (1.07 mmol) 3,4-difluoro-phenylboric acid.

Yield: 35 mg (16% of theory)

$C_{25}H_{24}F_2N_2O$ (M=406.480)

Calc.: molpeak $(M+H)^+$: 407 Found: molpeak $(M+H)^+$: 407

$R_f$ value: 0.34 (silica gel, EtOAc/MeOH/NH$_3$ 95:5:0.5)

Example 1.4

(2-{4-[5-(4-chloro-phenyl)-pyridin-2-ylethynyl]-phenoxy}-ethyl)-diethyl-amine

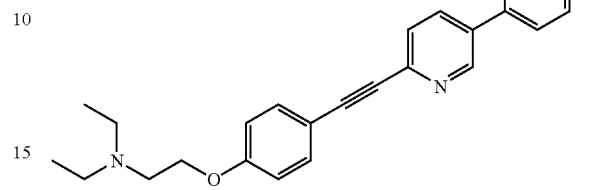

The product is obtained analogously to Example 1e from 200 mg (0.54 mmol) {2-[4-(5-bromo-pyridin-2-ylethynyl)-phenoxy]-ethyl}-diethyl-amine and 167 mg (1.07 mmol) 4-chloro-phenylboric acid.

Yield: 51 mg (24% of theory)

$C_{25}H_{25}ClN_2O$ (M=404.944)

Calc.: molpeak $(M+H)^+$: 405/407 Found: molpeak $(M+H)^+$: 405/407

$R_f$ value: 0.26 (silica gel, EtOAc/MeOH/NH$_3$ 95:5:0.5)

Example 1.5 diethyl-(2-{4-[5-(4-methoxy-phenyl)-pyrimidine-2-ylethynyl]-phenoxy}-ethyl)-amine

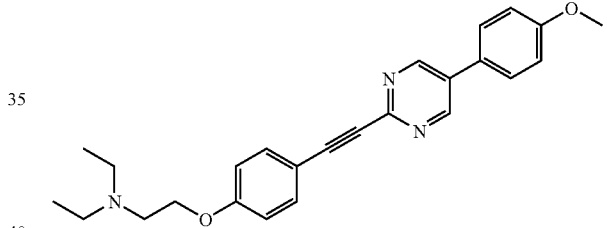

The product is obtained analogously to Example 1d from 434 mg (2.0 mmol) diethyl-[2-(4-ethynyl-phenoxy)-ethyl]-amine and 441 mg (2.0 mmol) 2-chloro-5-(4-methoxy-phenyl)-pyrimidine.

Yield: 100 mg (13% of theory)

$C_{25}H_{27}N_3O_2$ (M=401.513)

Calc.: molpeak $(M+H)^+$: 402 Found: molpeak $(M+H)^+$: 402

$R_f$ value: 0.65 (silica gel, EtOAc/MeOH/NH$_3$ 90:10:1)

Example 1.6

5-(4-chloro-phenyl)-2-[4-(2-pyrrolidin-1-yl-ethoxy)-phenylethynyl]-pyridine

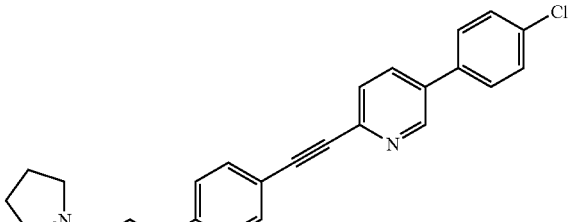

1.6a

1-[2-(4-iodo-phenoxy)-ethyl]-pyrrolidine

A suspension of 22 g (100 mmol) 4-iodophenol, 17 g (100 mmol) 1-(2-chloro-ethyl)-pyrrolidine (used as the hydrochloride) and 55.3 g (400 mmol) $K_2CO_3$ in 400 mL DMF is stirred for 48 h at RT. The solvent is evaporated down i.vac., the residue is combined with water, the aqueous phase exhaustively extracted with EtOAc, the combined organic phases are washed with saturated, aqueous NaCl solution and dried over $Na_2SO_4$. After the desiccant and solvent have been eliminated the residue is purified on silica gel (EtOAc/MeOH/$NH_3$ 85:15:1.5).

Yield: 18.0 g (57% of theory)
$C_{12}H_{16}INO$ (M=317.172)
Calc.: molpeak $(M+H)^+$: 318 Found: molpeak $(M+H)^+$: 318
$R_f$ value: 0.59 (silica gel, EtOAc/MeOH/$NH_3$ 80:20:2)

1.6b

1-[2-(4-trimethylsilanylethynyl-phenoxy)-ethyl]-pyrrolidine

Under a nitrogen atmosphere 7.0 mL (49.5 mmol) ethynyl-trimethyl-silane is slowly added to a mixture of 14.3 g (45 mmol) 1-[2-(4-iodo-phenoxy)-ethyl]-pyrrolidine, 1.04 g (0.9 mmol) tetrakis-triphenylphosphane-palladium and 171 mg (0.4 mmol) CuI in 140 mL piperidine (exothermic reaction) and stirred for 30 minutes. The solvent is distilled off i.vac., the residue is taken up in water, exhaustively extracted with EtOAc and dried over $Na_2SO_4$. After the desiccant and solvent have been eliminated the residue is purified on silica gel (EtOAc/MeOH/$NH_3$ 95:5:0.5).

Yield: 12.8 g (99% of theory)
$C_{17}H_{25}NOSi$ (M=287.481)
Calc.: molpeak $(M+H)^+$: 288 Found: molpeak $(M+H)^+$: 288
$R_f$ value: 0.42 (silica gel, EtOAc/MeOH/$NH_3$ 90:10:1)

1.6c

1-[2-(4-ethynyl-phenoxy)-ethyl]-pyrrolidine

Under a nitrogen atmosphere a solution of 12.8 g (44.5 mmol) 1-[2-(4-trimethylsilanylethynyl-phenoxy)-ethyl]-pyrrolidine in 200 mL THF is combined with 15.5 g (49.0 mmol) TBAF and stirred for 3 h at RT. The solvent is distilled off i.vac., the residue taken up in EtOAc, the organic phase is washed with saturated, aqueous NaCl solution and dried over $Na_2SO_4$. After the desiccant and solvent have been eliminated the product is further reacted without any purification.

Yield: 9.6 g (100% of theory)
$C_{14}H_{17}NO$ (M=215.298)
Calc.: molpeak $(M+H)^+$: 216 Found: molpeak $(M+H)^+$: 216
$R_f$ value: 0.76 (silica gel, EtOAc/MeOH/$NH_3$ 80:20:2)

1.6d

5-bromo-2-[4-(2-pyrrolidin-1-yl-ethoxy)-phenylethynyl]-pyridine

A mixture of 9.6 g (44.6 mmol) 1-[2-(4-ethynyl-phenoxy)-ethyl]-pyrrolidine, 10.6 g (44.6 mmol) 2,5-dibromopyridine, 626 mg (0.9 mmol) tetrakis-triphenylphosphane-palladium, 170 mg (0.9 mmol) CuCl and 12.6 mL diisopropylamine in 500 mL THF is heated for 3 h at 40° C. under an argon atmosphere. The solvent is distilled off i.vac., the residue is taken up in EtOAc, the organic phase is washed with water and saturated, aqueous NaCl solution and dried over $Na_2SO_4$. After the desiccant and solvent have been eliminated the residue is purified on silica gel (EtOAc/MeOH/$NH_3$ 90:10:1).

Yield: 8.9 g (54% of theory)
$C_{19}H_{19}BrN_2O$ (M=371.280)
Calc.: molpeak $(M+H)^+$: 371/373 Found: molpeak $(M+H)^+$: 371/373
$R_f$ value: 0.47 (silica gel, EtOAc/MeOH/$NH_3$ 90:10:1)

1.6e

5-(4-chloro-phenyl)-2-[4-(2-pyrrolidin-1-yl-ethoxy)-phenylethynyl]-pyridine A mixture of 2.97 g (8.0 mmol) 5-bromo-2-[4-(2-pyrrolidin-1-yl-ethoxy)-phenylethynyl]-pyridine, 2.50 g (16.0 mmol) 4-chloro-phenylboric acid, 462 mg (0.4 mmol) tetrakis-triphenylphosphane-palladium and 8.0 mL of a 2M aqueous $Na_2CO_3$ solution in 100 mL 1,4-dioxane is heated for 4 h at 100° C. under an argon atmosphere. The solvent is distilled off i.vac., the residue is stirred with water/EtOAc (1/1, v/v), suction filtered through a fibreglass filter, the organic phase is washed with saturated, aqueous NaCl solution and dried over $Na_2SO_4$. After the desiccant and solvent have been eliminated the residue is purified by chromatography (Alox, cyc/EtOAc 2:1). The product fractions are evaporated down, the residue is triturated with diethyl ether, suction filtered and washed with diethyl ether.

Yield: 1.95 g (60% of theory)
$C_{25}H_{23}ClN_2O$ (M=402.928)
Calc.: molpeak $(M+H)^+$: 403/405 Found: molpeak $(M+H)^+$: 403/405
$R_f$ value: 0.47 (Alox, cyc/EtOAc 2:1)

Example 1.7

5-(4-fluoro-phenyl)-2-[4-(2-pyrrolidin-1-yl-ethoxy)-phenylethynyl]-pyridine

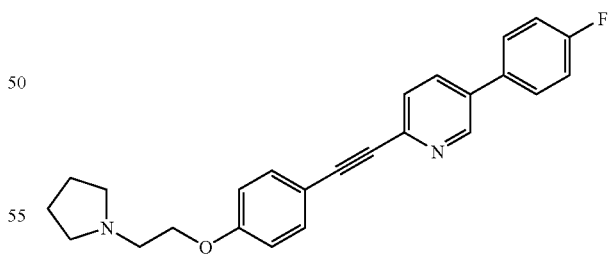

The product is obtained analogously to Example 1.6e from 297 mg (0.8 mmol) 5-bromo-2-[4-(2-pyrrolidin-1-yl-ethoxy)-phenylethynyl]-pyridine and 224 mg (1.6 mmol) 4-fluoro-phenylboric acid.

Yield: 37 mg (12% of theory)
$C_{25}H_{23}FN_2O$ (M=386.473)
Calc.: molpeak $(M+H)^+$: 387 Found: molpeak $(M+H)^+$: 387
$R_f$ value: 0.41 (Alox, cyc/EtOAc 2:1)

Example 1.8

5-(4-bromo-phenyl)-2-[4-(2-pyrrolidin-1-yl-ethoxy)-phenylethynyl]-pyridine

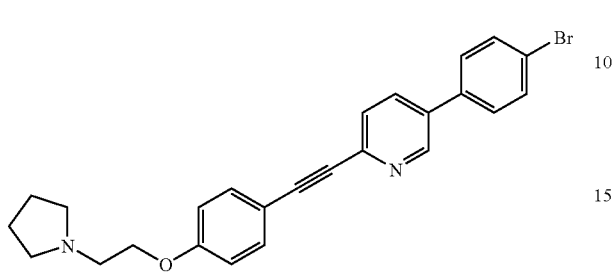

The product is obtained analogously to Example 1.6e from 297 mg (0.8 mmol) 5-bromo-2-[4-(2-pyrrolidin-1-yl-ethoxy)-phenylethynyl]-pyridine and 321 mg (1.6 mmol) 4-bromo-phenylboric acid. Purification is carried out using neutral Alox (Merck aluminium oxide 90 standardised, 63-200 my; cyc/EtOAc 4:1). The product thus obtained is recrystallised from EtOH.

Yield: 40 mg (11% of theory)

$C_{25}H_{23}BrN_2O$ (M=447.379)

Calc.: molpeak $(M+H)^+$: 447/449 Found: molpeak $(M+H)^+$: 447/449

$R_f$ value: 0.45 (Alox, cyc/EtOAc 2:1)

Example 1.9

2-[4-(2-pyrrolidin-1-yl-ethoxy)-phenylethynyl]-5-(4-trifluoromethoxy-phenyl)-pyridine

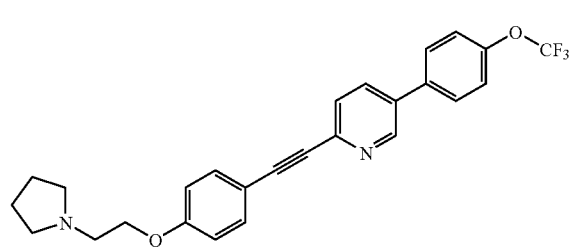 [SMILES: FC(F)(F)Oc1ccc(-c2ccc(C#Cc3ccc(OCCN4CCCC4)cc3)nc2)cc1]

The product is obtained analogously to Example 1.6e from 297 mg (0.8 mmol) 5-bromo-2-[4-(2-pyrrolidin-1-yl-ethoxy)-phenylethynyl]-pyridine and 329 mg (1.6 mmol) 4-trifluoromethoxy-phenylboric acid. Purification is carried out using neutral Alox (Merck aluminium oxide 90 standardised, 63-200 my; cyc/EtOAc 4:1). The product thus obtained is stirred with n-hexane and suction filtered.

Yield: 190 mg (53% of theory)

$C_{26}H_{23}F_3N_2O_2$ (M=452.481)

Calc.: molpeak $(M+H)^+$: 453 Found: molpeak $(M+H)^+$: 453

$R_f$ value: 0.46 (Alox, cyc/EtOAc 2:1)

Example 1.10

2-[4-(2-pyrrolidin-1-yl-ethoxy)-phenylethynyl]-5-(4-methoxy-phenyl)-pyridine

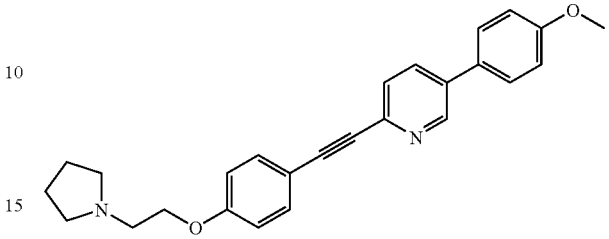

The product is obtained analogously to Example 1.9 from 297 mg (0.8 mmol) 5-bromo-2-[4-(2-pyrrolidin-1-yl-ethoxy)-phenylethynyl]-pyridine and 243 mg (1.6 mmol) 4-methoxy-phenylboric acid.

Yield: 115 mg (53% of theory)

$C_{26}H_{26}N_2O_2$ (M=398.509)

Calc.: molpeak $(M+H)^+$: 399 Found: molpeak $(M+H)^+$: 399

$R_f$ value: 0.30 (Alox, cyc/EtOAc 2:1)

Example 1.11

2-[4-(2-pyrrolidin-1-yl-ethoxy)-phenylethynyl]-5-(4-trifluoromethyl-phenyl)-pyridine

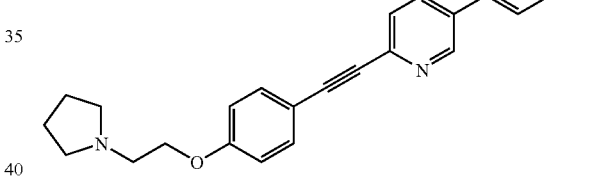

The product is obtained analogously to Example 1.9 from 297 mg (0.8 mmol) 5-bromo-2-[4-(2-pyrrolidin-1-yl-ethoxy)-phenylethynyl]-pyridine and 304 mg (1.6 mmol) 4-trifluoromethyl-phenylboric acid.

Yield: 150 mg (43% of theory)

$C_{26}H_{23}F_3N_2O$ (M=436.481)

Calc.: molpeak $(M+H)^+$: 437 Found: molpeak $(M+H)^+$: 437

$R_f$ value: 0.45 (Alox, cyc/EtOAc 2:1)

Example 2

5-(4-chloro-phenyl)-2-[4-(4-pyrrolidin-1-ylmethyl-phenyl)-but-1-ynyl]-pyridine

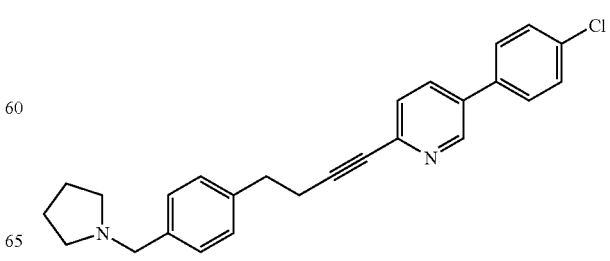

2a

1-(4-bromo-benzyl)-pyrrolidine

A solution of 12.5 g (50 mmol) 4-bromobenzylbromide is slowly added dropwise to a solution of 4.52 mL (55 mmol) pyrrolidine and 10.3 mL (60 mmol) ethyldiisopropylamine in 100 mL THF and stirred overnight at RT. The precipitate is filtered off and the solvent is eliminated i.vac. The product is obtained as a light-brown liquid which is further reacted without purification.

Yield: 9.0 g (75% of theory)
$C_{11}H_{14}BrN$ (M=240.145)
Calc.: molpeak $(M+H)^+$: 241/243 Found: molpeak $(M+H)^+$: 241/243
$R_f$ value: 0.74 (silica gel, EtOAc/MeOH/NH$_3$ 90:10:1)

2b

3-(4-pyrrolidin-1-ylmethyl-phenyl)-prop-2-yn-1-ol

A mixture of 4.8 g (20.0 mmol) 1-(4-bromo-benzyl)-pyrrolidine, 1.75 mL (30.0 mmol) propargylalcohol, 2.31 g (2.0 mmol) tetrakis-triphenylphosphane-palladium, 381 mg (2.0 mmol) CuI and 7.07 mL diisopropylamine in 100 mL acetonitrile is heated for 14 h at 60° C. under an argon atmosphere. The solvent is distilled off i.vac., the residue is taken up in water, exhaustively extracted with EtOAc and the organic phase is dried over $Na_2SO_4$. After the desiccant and solvent have been eliminated the residue is purified on silica gel (EtOAc/MeOH/NH$_3$ 95:5:0.5).

Yield: 1.55 g (36% of theory)
$C_{14}H_{17}NO$ (M=215.298)
Calc.: molpeak $(M+H)^+$: 216 Found: molpeak $(M+H)^+$: 216
$R_f$ value: 0.48 (silica gel, EtOAc/MeOH/NH$_3$ 90:10:1)

2c

3-(4-pyrrolidin-1-ylmethyl-phenyl)-propan-1-ol

A solution of 1.65 g (7.66 mmol) 3-(4-pyrrolidin-1-ylmethyl-phenyl)-prop-2-yn-1-ol in 20 mL EtOH is combined with 200 mg 10% Pd/C and hydrogenated in the autoclave at RT and 30 psi $H_2$ until the theoretical uptake of hydrogen is achieved. The catalyst is suction filtered, the filtrate concentrated by evaporation and the residue is purified on silica gel (EtOAc/MeOH/NH$_3$ 90:10:1).

Yield: 0.81 g (48% of theory)
$C_{14}H_{21}NO$ (M=219.330)
Calc.: molpeak $(M+H)^+$: 220 Found: molpeak $(M+H)^+$: 220
$R_f$ value: 0.2 (silica gel, EtOAc/MeOH/NH$_3$ 90:10:1)

2d

3-(4-pyrrolidin-1-ylmethyl-phenyl)-propionaldehyde 2.87 mL (35.56 mmol) pyridine and 2.11 g (4.98 mmol) Dess-Martin periodinane are added to a solution of 780 mg (3.56 mmol) 3-(4-pyrrolidin-1-ylmethyl-phenyl)-propan-1-ol in 30 mL DCM. The reaction mixture is stirred for 4 h at RT, then added to 100 mL saturated, aqueous NaHCO$_3$ solution, exhaustively extracted with tert-butylmethylether, the organic phase is washed with saturated, aqueous NaCl solution and dried over $Na_2SO_4$. After the desiccant and solvent have been eliminated the crude product is further reacted without purification.

Yield: 750 mg (97% of theory)

2e

1-(4-but-3-ynyl-benzyl)-pyrrolidine 815 mg (4.2 mmol) dimethyl (1-diazo-2-oxo-propyl)-phosphonate is added to a mixture of 760 mg (3.5 mmol) 3-(4-pyrrolidin-1-ylmethyl-phenyl)-propionaldehyde and 970 mg (7.0 mmol) $K_2CO_3$ in 100 mL dry MeOH under an argon atmosphere and stirred overnight at RT. The reaction mixture is diluted with diethyl ether, the organic phase is washed with saturated, aqueous NaHCO$_3$ solution and dried over $Na_2SO_4$. After the desiccant and solvent have been eliminated the residue is purified on silica gel (EtOAc/MeOH/NH$_3$ 95:5:0.5).

Yield: 200 mg (27% of theory)
$C_{15}H_{19}N$ (M=213.325)
Calc.: molpeak $(M+H)^+$: 214 Found: molpeak $(M+H)^+$: 214
$R_f$ value: 0.74 (silica gel, EtOAc/MeOH/NH$_3$ 95:5:0.5)

2f

5-bromo-2-[4-(4-pyrrolidin-1-ylmethyl-phenyl)-but-1-ynyl]-pyridine

A mixture of 200 mg (0.94 mmol) 1-(4-but-3-ynyl-benzyl)-pyrrolidine, 222 mg (0.94 mmol) 2,5-dibromopyridine, 13.2 mg (0.02 mmol) tetrakis-triphenylphosphane-palladium, 3.6 mg (0.02 mmol) CuI and 0.27 mL diisopropylamine in 10 mL THF is heated for 4 h at 40° C. under an argon atmosphere. The reaction mixture is diluted with water, exhaustively extracted with EtOAc, the organic phase is washed with saturated, aqueous NaCl solution and dried over $Na_2SO_4$. After the desiccant and solvent have been eliminated the residue is purified on silica gel (EtOAc/MeOH/NH$_3$ 95:5:0.5).

Yield: 110 mg (32% of theory)
$C_{20}H_{21}BrN_2$ (M=369.308)
Calc.: molpeak $(M+H)^+$: 369/371 Found: molpeak $(M+H)^+$: 369/371
$R_f$ value: 0.44 (silica gel, EtOAc/MeOH/NH$_3$ 95:5:0.5)

2g

5-(4-chloro-phenyl)-2-[4-(4-pyrrolidin-1-ylmethyl-phenyl)-but-1-ynyl]-pyridine A mixture of 100 mg (0.27 mmol) 5-bromo-2-[4-(4-pyrrolidin-1-ylmethyl-phenyl)-but-1-ynyl]-pyridine, 85 mg (0.54 mmol) 4-chloro-phenylboric acid, 15.7 mg (0.014 mmol) tetrakis-triphenylphosphane-palladium, 0.28 mL of a 2 M aqueous $Na_2CO_3$ solution in 10 mL 1,4-dioxane is heated for 8 h at 100° C. under an argon atmosphere. The solvent is distilled off i.vac., the residue is taken up in water, exhaustively extracted with EtOAc and dried over $Na_2SO_4$. After the desiccant and solvent have been eliminated the residue is purified over neutral Alox (ICN Alumina N+5% $H_2O$; cyc/EtOAc 7:3). The product fractions are evaporated down, the residue is triturated with PE and suction filtered.

Yield: 12 mg (11% of theory)
$C_{26}H_{25}ClN_2$ (M=400.956)
Calc.: molpeak $(M+H)^+$: 401/403 Found: molpeak $(M+H)^+$: 401/403
$R_f$ value: 0.41 (Alox, cyc/EtOAc 7:3)

Example 2.1

5-(4-chloro-phenyl)-2-[4-(4-piperidin-1-ylmethyl-phenyl)-but-1-ynyl]-pyridine

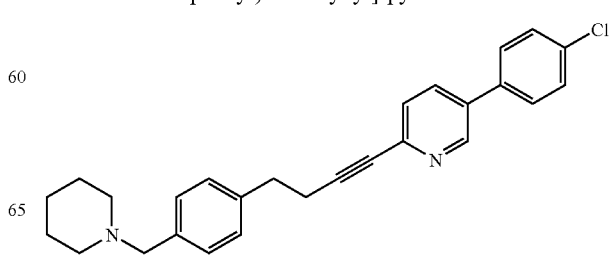

2.1a

3-(4-hydroxymethyl-phenyl)-propionaldehyde 10.5 mL (152.8 mmol) allylalcohol, 18.8 g (62.2 mmol) Tetrabutylammonium chloride monohydrate, 12.8 g (152.8 mmol) $NaHCO_3$ and 0.75 g (3.1 mmol) $Pd(OAc)_2$ is added to a solution of 15.0 g (62.2 mmol) 4-iodobenzylalcohol in 100 mL DMF at RT under an $N_2$ atmosphere and the reaction solution is heated to 60° C. for 3 h. The solvent is eliminated i.vac., the residue combined with 250 mL EtOAc and 80 mL water and suction filtered through a fibreglass filter. 80 mL NaCl solution are added to the filtrate, the phases are separated and the organic phase is dried over $MgSO_4$. After the desiccant and solvent have been eliminated the residue is purified by column chromatography on silica gel (gradient: cyc/EtOAc 3:1 after cyc/EtOAc 1:1).

Yield: 7.43 g (72.7% of theory)
$C_{10}H_{12}O_2$ (M=164.206)
Calc.: molpeak $(M+H-H_2O)^+$: 147 Found: molpeak $(M+H-H_2O)^+$: 147
HPLC retention time: 5.26 min (method A)

2.1b

(4-but-3-ynyl-phenyl)-methanol 8.5 g (61.5 mmol) $K_2CO_3$ are added to a solution of 5.0 g (30.4 mmol) 3-(4-hydroxymethyl-phenyl)-propionaldehyde in 100 mL MeOH and then a solution of 7.0 g (36.4 mmol) dimethyl (1-diazo-2-oxo-propyl)-phosphonate in 50 mL MeOH is added dropwise and stirred for 3 h at RT. The reaction mixture is diluted with 200 mL EtOAc, washed with 80 mL saturated $NaHCO_3$ solution, the aqueous phase extracted with 100 mL EtOAc and the combined organic phases are dried over $Na_2SO_4$. After the desiccant and solvent have been eliminated the residue is purified by chromatography on silica gel (cyc/EtOAc 3:1).

Yield: 3.42 g (70.1% of theory)
$C_{11}H_{12}O$ (M=160.218)
Calc.: molpeak $(M+H-H_2O)^+$: 143 Found: molpeak $(M+H)^+$: $(M+H-H_2O)^+$: 143
$R_f$ value: 0.36 (silica gel, cyc/EtOAc 2:1)

2.1c

(4-{4-[5-(4-chloro-phenyl)-pyridin-2-yl]-but-3-ynyl}-phenyl)-methanol

Under a nitrogen atmosphere 76 mg (0.4 mmol) CuI and 281 mg (0.4 mmol) $Pd(PPh_3)_2Cl_2$ are added to a solution of 1.27 g (7.92 mmol) (4-but-3-ynyl-phenyl)-methanol and 2.5 g (7.92 mmol) 5-(4-chloro-phenyl)-2-iodo-pyridine in 40 mL triethylamine and 20 mL DMF and the reaction mixture is stirred for 2 h at 65° C. The solvent is eliminated in vacuo, the residue is dissolved in a little EtOAc and MeOH and purified by chromatography on silica gel (gradient: cyc/EtOAc 3:1 to cyc/EtOAc 1:1).

Yield: 1.48 g (53.6% of theory)
$C_{22}H_{18}ClNO$ (M=347.848)
Calc.: molpeak $(M+H)^+$: 348/350 Found: molpeak $(M+H)^+$: 348/350
$R_f$ value: 0.23 (silica gel, cyc/EtOAc 2:1)

2.1d

5-(4-chloro-phenyl)-2-[4-(4-piperidin-1-ylmethyl-phenyl)-but-1-ynyl]-pyridine 20 µL (0.26 mmol) methanesulphonic acid chloride and 45 µL (0.26 mmol) ethyldiisopropylamine are added to a solution, cooled to 0° C., of 75 mg (0.22 mmol) 4-{4-[5-(4-chloro-phenyl)-pyridin-2-yl]-but-3-ynyl}-phenyl)-methanol in 5 mL DCM and stirred at this temperature for 30 min. Then 108 µL (1.09 mmol) piperidine are added and the reaction mixture is stirred for 72 h at RT. The reaction solution is evaporated down i.vac. and the residue is purified by HPLC.

Yield: 9.3 mg (53.6% of theory)
$C_{27}H_{27}ClN_2$ (M=414.983)
Calc.: molpeak $(M+H)^+$: 415/417 Found: molpeak $(M+H)^+$: 415/417
HPLC retention time: 7.62 min (method A)

The following compounds are prepared as described in Example 2.1d:

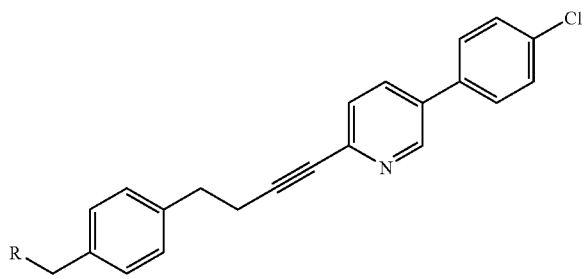

| Example | R | Yield (%) | empirical formula | mass spectrum | HPLC retention time in min (method) |
|---|---|---|---|---|---|
| 2.2 | 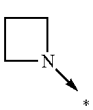 | 19.3 | $C_{25}H_{23}ClN_2$ | 387/389 [M + H]$^+$ | 7.04 (A) |

-continued
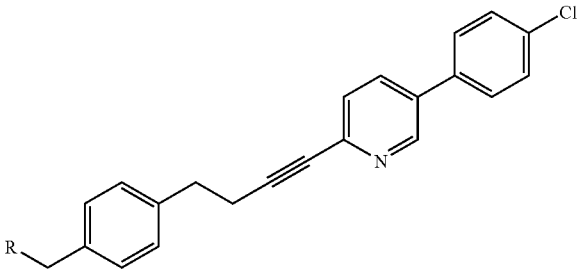
| Example | R | Yield (%) | empirical formula | mass spectrum | HPLC retention time in min (method) |
|---|---|---|---|---|---|
| 2.3 | 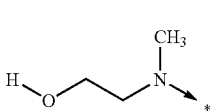 | 24.4 | $C_{31}H_{34}ClN_3$ | 484/486 $[M + H]^+$ | 5.96 (A) |
| 2.4 | 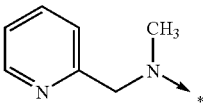 | 13.1 | $C_{25}H_{25}ClN_2O$ | 405/407 $[M + H]^+$ | 6.95 (A) |
| 2.5 | 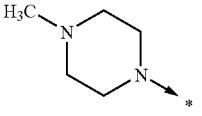 | 22.4 | $C_{29}H_{26}ClN_3$ | 452/454 $[M + H]^+$ | 7.71 (A) |
| 2.6 | 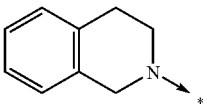 | 11.4 | $C_{27}H_{28}ClN_3$ | 430/432 $[M + H]^+$ | 6.87 (A) |
| 2.7 | 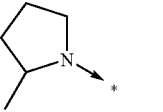 | 25.9 | $C_{31}H_{27}ClN_2$ | 463/465 $[M + H]^+$ | 8.26 (A) |
| 2.8 | 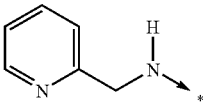 | 24.7 | $C_{27}H_{27}ClN_2$ | 415/417 $[M + H]^+$ | 7.53 (A) |
| 2.9 | 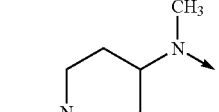 | 28.1 | $C_{28}H_{24}ClN_3$ | 438/440 $[M + H]^+$ | 7.47 (A) |
| 2.10 | 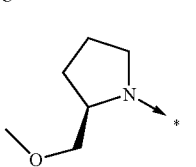 | 15.7 | $C_{29}H_{32}ClN_3$ | 458/460 $[M + H]^+$ | 5.82 (A) |
| 2.11 |  | 19.7 | $C_{28}H_{29}ClN_2O$ | 445/447 $[M + H]^+$ | 7.81 (A) |

-continued
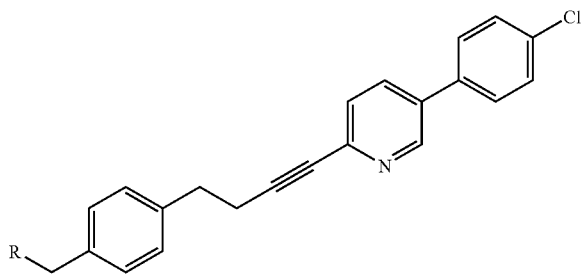
| Example | R | Yield (%) | empirical formula | mass spectrum | HPLC retention time in min (method) |
|---|---|---|---|---|---|
| 2.12 | | 10.1 | $C_{28}H_{29}ClN_3O_2$ | 445/447 $[M + H]^+$ | 7.83 (A) |
| 2.13 | | 21.4 | $C_{31}H_{34}ClN_3O_2$ | 516/518 $[M + H]^+$ | 8.18 (A) |
| 2.14 | | 25.1 | $C_{28}H_{27}ClN_2O_2$ | 459/461 $[M + H]^+$ | 7.56 (A) |
| 2.15 | | 23.8 | $C_{28}H_{29}ClN_2$ | 429/431 $[M + H]^+$ | 8.18 (A) |
Example 2.16
tert-butyl 4-[(4-{4-[5-(4-chloro-phenyl)-pyridin-2-yl]-but-3-ynyl}-benzyl)-methyl-amino]-piperidin-1-carboxylate
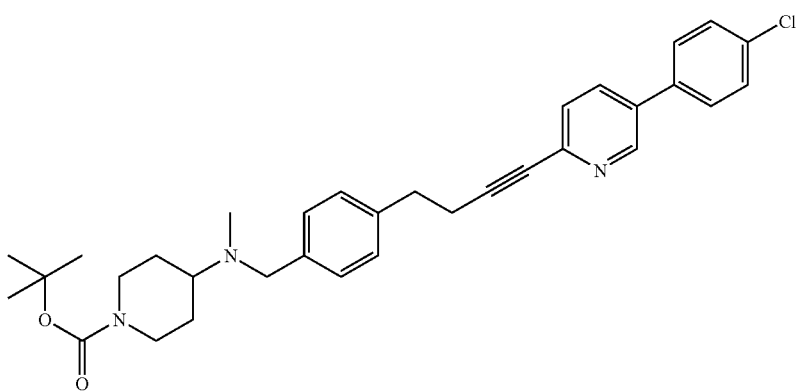 [SMILES: CN(Cc1ccc(CCC#Cc2ccc(-c3ccc(Cl)cc3)cn2)cc1)C1CCN(C(=O)OC(C)(C)C)CC1]

Prepared analogously to Example 2.1d from 75 mg (0.22 mmol) 4-{4-[5-(4-chlorophenyl)-pyridin-2-yl]-but-3-ynyl}-phenyl)-methanol and 20 µL (1.09 mmol) 4 tert-butyl-methylamino-piperidin-1-carboxylate, stirring for 7 days at RT. To complete the reaction the reaction sequence described is repeated again using the same amount of reagents and after 24 h reaction the mixture is worked up.

Yield: 8.5 mg (7.2% of theory)
$C_{33}H_{38}ClN_3O_2$ (M=544.143)
Calc.: molpeak (M+H)$^+$: 544/546 Found: molpeak (M+H)$^+$: 544/546
HPLC retention time: 8.46 min (method A)

Example 2.17

(4-{4-[5-(4-chloro-phenyl)-pyridin-2-yl]-but-3-ynyl}-benzyl)-methyl-piperidin-4-yl-amine

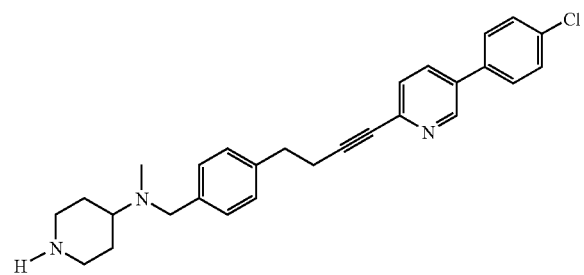 [SMILES: CN(Cc1ccc(CCC#Cc2ccc(-c3ccc(Cl)cc3)cn2)cc1)C1CCNCC1]

0.5 mL trifluoroacetic acid are added to a solution of 35 mg (0.06 mmol) tert-butyl4-[(4-{4-[5-(4-chloro-phenyl)-pyridin-2-yl]-but-3-ynyl}-benzyl)-methyl-amino]-piperidin-1-carboxylate in 3 mL DCM and the reaction mixture is stirred for 3 h at RT. The mixture is evaporated down i. vac., the residue is combined with 10 mL NaHCO$_3$ solution, extracted with 20 mL DCM and the organic phase is dried over Na$_2$SO$_4$. After the desiccant and solvent have been eliminated the desired product is obtained.

Yield: 8.0 mg (28.2% of theory)
$C_{28}H_{30}ClN_3$ (M=444.024)
Calc.: molpeak (M+H)$^+$: 444/446 Found: molpeak (M+H)$^+$: 444/446
HPLC retention time: 5.83 min (method A)

Example 2.18

1-(4-{4-[5-(4-chloro-phenyl)-pyridin-2-yl]-but-3-ynyl}-benzyl)-pyrrolidin-3-ylamine

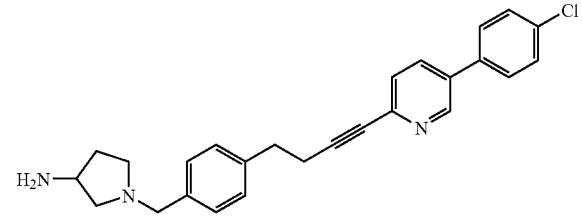 [SMILES: NC1CCN(Cc2ccc(CCC#Cc3ccc(-c4ccc(Cl)cc4)cn3)cc2)C1]

Prepared analogously to Example 2.17 from 17 mg (0.03 mmol) tert-butyl [1-(4-{4-[5-(4-chloro-phenyl)-pyridin-2-yl]-but-3-ynyl}-benzyl)-pyrrolidin-3-yl]-carbaminate (Example 2.13).

Yield: 12.0 mg (87.4% of theory)
$C_{26}H_{26}ClN_3$ (M=415.970)
Calc.: molpeak (M+H)$^+$: 416/418 Found: molpeak (M+H)$^+$: 416/418
HPLC retention time: 5.83 min (method A)

Example 2.19

1-(4-{4-[5-(4-chloro-phenyl)-pyridin-2-yl]-but-3-ynyl}-benzyl)-pyrrolidine-2-carboxylic acid

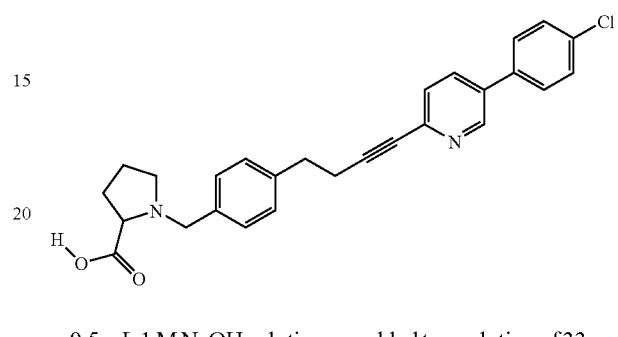

0.5 mL 1 M NaOH solution are added to a solution of 33 mg (0.07 mmol) methyl 1-(4-{4-[5-(4-chloro-phenyl)-pyridin-2-yl]-but-3-ynyl}-benzyl)-pyrrolidine-2-carboxylate (Example 2.14) in 5 mL MeOH and the reaction mixture is stirred for 4 h at RT. The mixture is evaporated down i. vac., combined with 5 mL water, extracted with 10 mL EtOAc and the aqueous phase is saturated with NaCl, during which time the product is precipitated. It is evaporated down again i. vac., the residue is combined with EtOH, filtered and the solvent is eliminated.

Yield: 30.0 mg (93.6% of theory)
$C_{27}H_{25}ClN_2O_2$ (M=444.966)
Calc.: molpeak (M+H)$^+$: 445/447 Found: molpeak (M+H)$^+$: 445/447
HPLC retention time: 7.28 min (method A)

Example 2.20

5-(2,4-dichloro-phenyl)-2-[4-(4-pyrrolidin-1-ylmethyl-phenyl)-but-1-ynyl]-pyridine

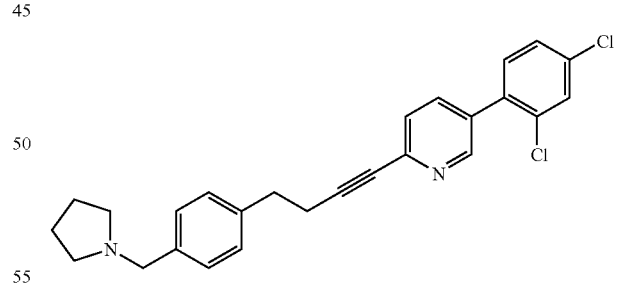

2.20a

{4-[4-(5-bromo-pyridin-2-yl)-but-3-ynyl]-phenyl}-methanol

Under an N$_2$ atmosphere 130 mg (0.67 mmol) CuI and 300 mg (0.42 mmol) Pd(PPh$_3$)$_2$Cl$_2$ are added to a solution of 2.0 g (12.48 mmol) (4-but-3-ynyl-phenyl)-methanol and 3.2 g (13.1 mmol) 2,5-dibromopyridine in 80 mL triethylamine and the reaction mixture is stirred for 1.5 h at 50° C. The solvent is eliminated in vacuo, the residue dissolved in a little DCM and purified by chromatography on silica gel (gradient: cyc/EtOAc 4:1 to cyc/EtOAc 3:1).

Yield: 2.76 g (66.6% of theory)
$C_{16}H_{14}BrNO$ (M=316.20)
Calc.: molpeak $(M+H)^+$: 316/318 Found: molpeak $(M+H)^+$: 316/318
$R_f$ value: 0.28 (silica gel, cyc/EtOAc 2:1)

2.20b 5-bromo-2-[4-(4-pyrrolidin-1-ylmethyl-phenyl)-but-1-ynyl]-pyridine 0.24 mL (3.04 mmol) methanesulphonic acid chloride are added to a solution, cooled to 0° C., of 800 mg (2.53 mmol) {4-[4-(5-bromo-pyridin-2-yl)-but-3-ynyl]-phenyl}-methanol in 17 mL DCM and then a solution of 0.52 mL ethyldiisopropylamine in 3 mL DCM is added dropwise. The mixture is stirred for a further 30 min at 0° C., 0.51 mL (6.08 mmol) pyrrolidine is added, the reaction mixture is heated to RT and kept at this temperature for 5 h. To complete the reaction another 0.26 mL (3 mmol) pyrrolidine are added and stirred for 1 h at RT. The mixture is evaporated down i. vac., combined with 10 mL water and 20 ml EtOAc, acidified with 1 M HCl and the organic phase is separated off. The aqueous phase is made alkaline with 2 M $Na_2CO_3$ solution, extracted with 20 mL EtOAc, the organic phase is separated off and dried over $Na_2SO_4$. After the desiccant and solvent have been eliminated the desired product is obtained.

Yield: 630.0 mg (67.4% of theory)
$C_{20}H_{21}BrN_2$ (M=369.308)
Calc.: molpeak $(M+H)^+$: 369/371 Found: molpeak $(M+H)^+$: 369/371
HPLC retention time: 6.08 min (method A)

2.20c 5-(2,4-dichloro-phenyl)-2-[4-(4-pyrrolidin-1-ylmethyl-phenyl)-but-1-ynyl]-pyridine 10 mg (0.01 mmol) tetrakis-triphenylphosphane-palladium are added to a suspension of 60 mg (0.16 mmol) 5-bromo-2-[4-(4-pyrrolidin-1-ylmethyl-phenyl)-but-1-ynyl]-pyridine and 63 mg (0.32 mmol) 2,4-dichlorophenylboric acid in 4 mL 1,4-dioxane and 1 mL 2 M $Na_2CO_3$ solution and the reaction mixture is stirred for 1 h at 110° C. The mixture is evaporated down i. vac. and the residue is extracted twice with in each case 15 mL EtOH. The solvent is removed and the residue is purified by HPLC.

Yield: 22.7 mg (32.2% of theory)
$C_{26}H_{24}Cl_2N_2$ (M=435.401)
Calc.: molpeak $(M+H)^+$: 435/437/439 Found: molpeak $(M+H)^+$: 435/437/439
HPLC retention time: 5.53 min (method C)

The following compounds are prepared as described in Example 2.20c:

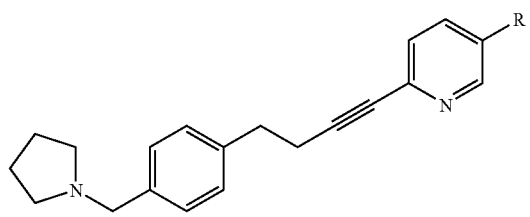

| Example | R | Yield (%) | empirical formula | mass spectrum | HPLC retention time in min (method) |
|---|---|---|---|---|---|
| 2.21 | 4-Br-phenyl | 13.0 | $C_{26}H_{25}BrN_2$ | 445/447 $[M+H]^+$ | 5.53 (C) |
| 2.22 | 2-OMe-phenyl | 41.4 | $C_{27}H_{28}N_2O$ | 397 $[M+H]^+$ | 3.39 (C) |
| 2.23 | 3,4-diCl-phenyl | 30.8 | $C_{26}H_{24}Cl_2N_2$ | 435/437/439 $[M+H]^+$ | 3.70 (A) |
| 2.24 | 3,4-diF-phenyl | 21.8 | $C_{26}H_{24}F_2N_2$ | 403 $[M+H]^+$ | 7.21 (A) |

-continued

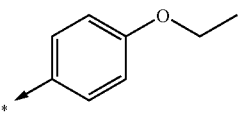

| Example | R | Yield (%) | empirical formula | mass spectrum | HPLC retention time in min (method) |
|---|---|---|---|---|---|
| 2.25 | (4-ethoxyphenyl) | 7.5 | $C_{28}H_{30}N_2O$ | 411 [M + H]$^+$ | 7.30 (A) |

Example 2.26

5-(4-methoxy-phenyl)-2-[4-(4-pyrrolidin-1-ylm-ethyl-phenyl)-but-1-ynyl]-pyridine

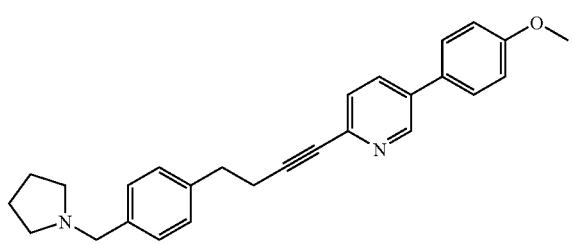 [SMILES: COc1ccc(-c2ccc(C#CCCc3ccc(CN4CCCC4)cc3)nc2)cc1]

Prepared analogously to Example 2.20c, after the reaction has ended the reaction mixture is combined with 10 mL water and 20 mL EtOAc, filtered through a fibreglass filter, the organic phase is separated off and dried over $Na_2SO_4$. The solvent is removed and the residue is purified by HPLC.

Yield: 17.4 mg (23.1% of theory)
$C_{27}H_{28}N_2O_2$ (M=396.537)
Calc.: molpeak (M+H)$^+$: 397 Found: molpeak (M+H)$^+$: 397
HPLC retention time: 8.15 min (method A)

Example 2.27

4-(4-{4-[5-(4-chloro-phenyl)-pyridin-2-yl]-but-3-ynyl}-benzyl)-morpholine

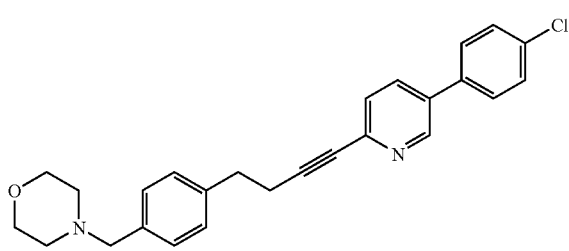 [SMILES: Clc1ccc(-c2ccc(C#CCCc3ccc(CN4CCOCC4)cc3)nc2)cc1]

2.27a

4-{4-[4-(5-bromo-pyridin-2-yl)-but-3-ynyl]-benzyl}-morpholine

36 µL (0.46 mmol) methanesulphonic acid chloride are added to a solution, cooled to 0° C., of 120 mg (0.38 mmol) {4-[4-(5-bromo-pyridin-2-yl)-but-3-ynyl]-phenyl}-methanol (Example 2.20a) in 5 mL DCM. A solution of 78 µL (0.46 mmol) ethyldiisopropylamine in 1 mL DCM is slowly added dropwise, the mixture is stirred for a further 30 min at 0° C., then 80 µL (0.92 mmol) of morpholine are added, the mixture is allowed to come up to RT and kept at RT for 2 h. The mixture is evaporated down i. vac., the residue is combined with 20 mL EtOAc and 10 mL water, acidified with 1 M HCl and the phases are separated. The aqueous phase is combined with 2 M $Na_2CO_3$ solution, extracted with 20 mL EtOAc and the organic phase is dried over $Na_2SO_4$. After the desiccant and solvent have been eliminated the product is obtained.

Yield: 146 mg (100% of theory)
$C_{20}H_{21}BrN_2O$ (M=385.307)
Calc.: molpeak (M+H)$^+$: 385/387 Found: molpeak (M+H)$^+$: 385/387
HPLC retention time: 5.92 min (method A)

2.27b 4-(4-{4-[5-(4-chloro-phenyl)-pyridin-2-yl]-but-3-ynyl}-benzyl)-morpholine Prepared analogously to Example 2.20c from 90 mg (0.23 mmol) 4-{4-[4-(5-bromo-pyridin-2-yl)-but-3-ynyl]-benzyl}-morpholine and 73 mg (0.47 mmol) 4-chlorophenylboric acid.

Yield: 17.5 mg (17.9% of theory)
$C_{26}H_{25}ClN_2O$ (M=416.955)
Calc.: molpeak (M+H)$^+$: 417/419 Found: molpeak (M+H)$^+$: 417/419
HPLC retention time: 7.51 min (method A)

Example 2.28

(4-{4-[5-(4-chloro-phenyl)-pyridin-2-yl]-but-3-ynyl}-benzyl)-cyclopropylmethyl-amine

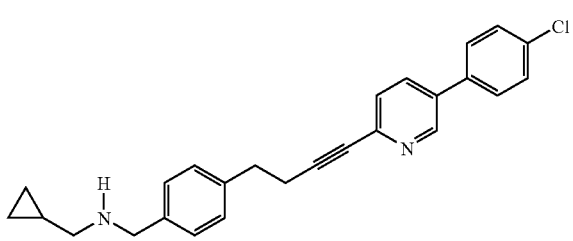 [SMILES: Clc1ccc(-c2ccc(C#CCCc3ccc(CNCC4CC4)cc3)nc2)cc1]

2.28a (4-{4-[4-(5-bromo-pyridin-2-yl)-but-3-ynyl]-benzyl)-cyclopropylmethyl-amine 36 μL (0.46 mmol) methanesulphonic acid chloride are added to a solution, cooled to 0° C., of 120 mg (0.38 mmol) {4-[4-(5-bromo-pyridin-2-yl)-but-3-ynyl]-phenyl}-methanol (Example 2.20a) in 5 mL DCM. A solution of 78 μL (0.46 mmol) ethyldiisopropylamine in 1 mL DCM is slowly added dropwise, stirred for a further 30 min at 0° C., then 70 μL (0.92 mmol) C-cyclopropyl-methylamine are added, the reaction mixture is allowed to come up to RT and kept at RT for 21 h. To complete the reaction another 78 μL C-cyclopropyl-methylamine are added and stirred for another 5.5 h at RT. The reaction mixture is evaporated down i.vac. and the residue purified by chromatography on silica gel (gradient: cyc/EtOAc 2:1 to cyc/EtOAc 1:1).

Yield: 70.0 mg (49.9% of theory)

$C_{20}H_{21}BrN_2$ (M=369.308)

Calc.: molpeak (M+H)$^+$: 369/371 Found: molpeak (M+H)$^+$: 369/371

HPLC retention time: 6.55 min (method A)

2.28b (4-{4-[5-(4-chloro-phenyl)-pyridin-2-yl]-but-3-ynyl}-benzyl)-cyclopropylmethyl-amine Prepared analogously to Example 2.20c from 65 mg (0.18 mmol) (4-{4-[4-(5-bromo-pyridin-2-yl)-but-3-ynyl]-benzyl)-cyclopropylmethyl-amine and 55 mg (0.35 mmol)) 4-chloro-phenylboric acid.

Yield: 15.4 mg (21.8% of theory)

$C_{26}H_{25}ClN_2$ (M=400.956)

Calc.: molpeak (M+H)$^+$: 401/403 Found: molpeak (M+H)$^+$: 401/403

HPLC retention time: 7.63 min (method A)

Example 2.29

3-(4-chloro-phenyl)-6-[4-(4-pyrrolidin-1-ylmethyl-phenyl)-but-1-ynyl]-pyridazine

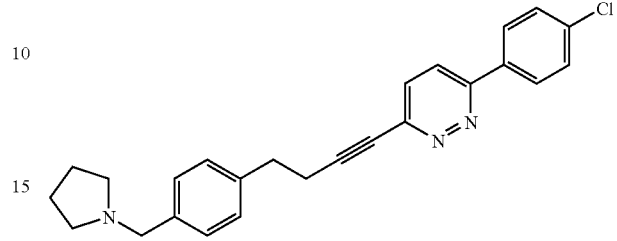

2.29a 3-chloro-6-(4-chloro-phenyl)-pyridazine

Under an argon atmosphere a solution of 1.08 g (7.05 mmol) 3,6-dichloro-pyridazin, 10 mL 2 M Na$_2$CO$_3$ solution and 80 mg (0.14 mmol) chlorine(di-2-norbornylphosphino)(2'-dimethylamino-1-1'-biphenyl-2-yl)palladium(II) in 150 mL 1,4-dioxane is heated to 110° C. At this temperature a solution of 1.13 g (7.05 mmol) 4-chlorophenyl-boric acid in 50 mL 1,4-dioxane is added dropwise within 2 h and the reaction mixture is heated for another hour. After cooling it is combined with 100 mL water, extracted with 100 mL EtOAc and the organic phase is dried over Na$_2$SO$_4$. After the desiccant and solvent have been eliminated the residue is purified by chromatography (silica gel, cyc/EtOAc 8:2).

Yield: 567 mg (35.7% of theory)

$C_{10}H_6Cl_2N_2$ (M=225.079)

Calc.: molpeak (M+H)$^+$: 225/227 Found: molpeak (M+H)$^+$: 225/227

R$_f$ value: 0.29 (silica gel, cyc/EtOAc 8:2)

2.29b 3-(4-chloro-phenyl)-6-[4-(4-pyrrolidin-1-ylmethyl-phenyl)-but-1-ynyl]-pyridazin Under an argon atmosphere 0.1 mL (0.72 mmol) triethylamine, 3 mg (0.02 mmol) CuI and 8 mg (0.01 mmol) bis-triphenylphosphane-palladium(II)-chloride are added to a solution of 77 mg (0.34 mmol) 3-chloro-6-(4-chloro-phenyl)-pyridazine and 73 mg (0.34 mmol) 1-(4-but-3-ynyl-benzyl)-pyrrolidine (Example 2e) in 4 mL DMF and the reaction mixture is stirred for 20 min at 100° C. and at 300 W in the microwave. The reaction mixture is combined with 10 mL water, extracted with 10 mL EtOAc and the organic phase is washed with water and dried over Na$_2$SO$_4$. After the desiccant and solvent have been eliminated the residue is purified by chromatography (silica gel, EtOAc/MeOH/NH$_3$ 90:10:1).

Yield: 6 mg (4.4% of theory)

$C_{25}H_{24}BrN_3$ (M=401.943)

Calc.: molpeak (M+H)$^+$: 402/404 Found: molpeak (M+H)$^+$: 402/404

R$_f$ value: 0.66 (silica gel, EtOAc/MeOH/NH$_3$ 90:10:1)

Example 2.30

5-(4-chloro-phenyl)-2-[4-(4-pyrrolidin-1-ylmethyl-phenyl)-but-1-ynyl]-nicotinonitrile

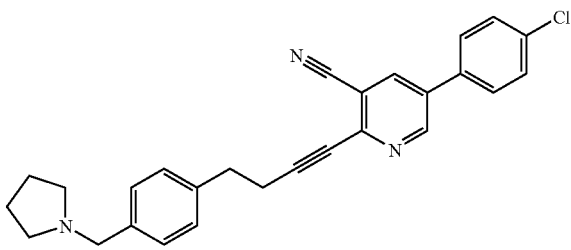 [SMILES: N#Cc1cc(-c2ccc(Cl)cc2)cnc1C#CCCc1ccc(CN2CCCC2)cc1]

Under an argon atmosphere 1.9 mg (0.1 mmol) CuI and 7 mg (0.1 mmol) Pd(PPh$_3$)$_2$Cl$_2$ are added to a solution of 50 mg (0.2 mmol) 2-chloro-5-(4-chloro-phenyl)-nicotinonitrile and 43 mg (0.2 mmol) 1-(4-but-3-ynyl-benzyl)-pyrrolidine in 2 mL DMF and 5 mL (20 mmol) triethylamine and the reaction mixture is stirred for 18 h at 50° C. The mixture is evaporated down i. vac., the residue is taken up in water, extracted exhaustively with EtOAc and the organic phase is dried over Na$_2$SO$_4$. After the desiccant and solvent have been eliminated the residue is is purified by HPLC.

Yield: 6.5 mg (7.6% of theory)
C$_{27}$H$_{24}$BrN$_3$ (M=425.965)
Calc.: molpeak (M+H)$^+$: 425 Found: molpeak (M+H)$^+$: 425
HPLC retention time: 6.80 min (method A)

Example 3.1

5-(4-chloro-phenyl)-2-[3-chloro-4-(2-pyrrolidin-1-yl-ethoxy)-phenylethynyl]-pyridine

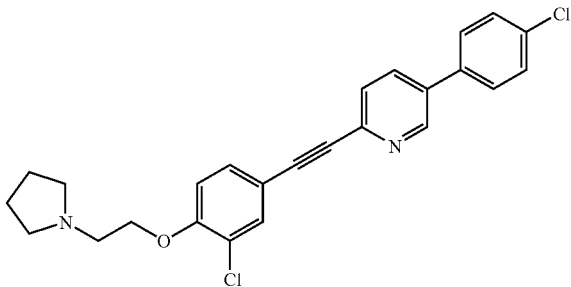 [SMILES: Clc1ccc(-c2ccc(C#Cc3ccc(OCCN4CCCC4)c(Cl)c3)nc2)cc1]

3.1a 5-(4-chloro-phenyl)-pyridin-2-ylamine 300 mL (600 mmol) of a 2 M Na$_2$CO$_3$ solution and 3.45 g (3.0 mmol) tetrakis-triphenylphosphane-palladium are added successively to a solution of 53.5 g (300 mmol) 2-amino-5-bromopyridine and 50.0 g (313 mmol) 4-chlorophenylboric acid in 1.0 L 1,4-dioxane and 250 mL methanol under argon. The reaction mixture is stirred for 2.5 h at 110° C. The solvent is eliminated i.vac., the residue is taken up in EtOAc and water. The organic phase is dried over Na$_2$SO$_4$ and the solvent is eliminated i.vac. Further purification is carried out by column chromatography on silica gel (gradient: DCM to DCM/MeOH 20:1).

Yield: 47 g (76.5% of theory)
C$_{11}$H$_9$ClN$_2$ (M=204.661)
Calc.: molpeak (M+H)$^+$: 205/207 Found: molpeak (M+H)$^+$: 205/207
HPLC retention time: 5.15 min (method A)

3.1b 5-(4-chloro-phenyl)-2-iodo-pyridine 40.5 mL (33 mmol) tert-butylnitrite and 54 g (210 mmol) iodine are added to a solution of 38 g (190 mmol) 5-(4-chloro-phenyl)-pyridin-2-ylamine in 400 mL carbon tetrachloride in a flask protected from light and the mixture is stirred for 72 h at RT. A further 40.5 mL (33 mmol) tert-butylnitrite, 54 g (210 mmol) iodine and 100 mL DCM are added. The reaction solution is stirred for a further 24 h at RT. The solvent is eliminated i.vac. and the residue taken up in 125 mL EtOAc and 50 mL water. The aqueous phase is extracted once with EtOAc. The organic phase is dried over Na$_2$SO$_4$ and stirred for one night over activated charcoal. After filtration the solvent is eliminated i.vac. Further purification is carried out by column chromatography on silica gel (PE/EtOAc 9:1).

Yield: 35 g (58.4% of theory)
C$_{11}$H$_7$ClIN (M=315.543)
Calc.: molpeak (M+H)$^+$: 316/318 Found: molpeak (M+H)$^+$: 316/318
R$_f$ value: 0.87 (silica gel, PE/EtOAc 6:4)

3.1c 5-(4-chloro-phenyl)-2-trimethylsilanylethynyl-pyridine 34.9 mL (250 mmol) triethylamine and 20.8 mL (150.0 mmol) ethynyl-trimethyl-silane are added successively to a solution of 34 g (110 mmol) 5-(4-chloro-phenyl)-2-iodo-pyridine in 300 mL acetonitrile and 150 mL THF under an argon atmosphere. Then 803 mg (1.10 mmol) Pd(dppf)Cl$_2$ and 209 mg (1.10 mmol) CuI are added. The reaction solution is stirred overnight at RT. The solvent is eliminated i.vac. and further purification is carried out by column chromatography on silica gel (PE/EtOAc 8:2).

Yield: 15.3 g (48.7% of theory)
C$_{16}$H$_{16}$ClNSi (M=285.852)
Calc.: molpeak (M+H)$^+$: 286/288 Found: molpeak (M+H)$^+$: 286/288
HPLC retention time: 7.10 min (method A)

3.1d 5-(4-chloro-phenyl)-2-ethynyl-pyridine

Under an argon atmosphere 6.6 g (21.0 mmol) TBAF are added to a solution of 5.8 g (20.3 mmol) 5-(4-chloro-phenyl)-2-trimethylsilanylethynyl-pyridine in 200 mL DCM at 0° C. The reaction solution is stirred for 3 h, while the reaction temperature slowly rises to RT. It is added to 50 mL water and the organic phase is extracted four times with 50 mL water, dried over MgSO$_4$ and filtered over activated charcoal. The solvent is eliminated i.vac. and further purification is carried out by column chromatography on silica gel (PE/EtOAc 1:1).

Yield: 3.9 g (90.0% of theory)

$C_{13}H_8ClN$ (M=213.668)
Calc.: molpeak (M+H)$^+$: 214/216 Found: molpeak (M+H)$^+$: 214/216
R$_f$ value: 0.87 (silica gel, cyc/EtOAc 8:2)

3.1e

1-[2-(4-bromo-2-chloro-phenoxy)-ethyl]-pyrrolidine 415 mg (3.00 mmol) K$_2$CO$_3$ and 170 mg (1.00 mmol) N-(2-chloroethyl)-pyrrolidine-hydrochloride is added to a solution of 207 mg (1.00 mmol) 4-bromo-2-chloro-phenol in 5 mL DMF and the mixture is stirred for 24 h at RT. The reaction mixture is diluted with 50 mL EtOAc, extracted once with 30 mL water and twice with 30 mL semisaturated NaHCO$_3$ solution. The organic phase is dried over MgSO$_4$ and the solvent is eliminated i.vac. Further purification is carried out by column chromatography on silica gel (gradient: DCM to DCM/MeOH 9:1).
Yield: 100 mg (32.8% of theory)
$C_{12}H_{15}BrClNO$ (M=304.616)
Calc.: molpeak (M+H)$^+$: 304/306/308 Found: molpeak (M+H)$^+$: 304/306/308
HPLC retention time: 5.59 min (method A)

3.1f 5-(4-chloro-phenyl)-2-[3-chloro-4-(2-pyrrolidin-1-yl-ethoxy)-phenylethynyl]-pyridine Under an argon atmosphere 0.14 mL (1.00 mmol) triethylamine, 11 mg (0.02 mmol) Pd(PPh$_3$)$_2$Cl$_2$ and 2.9 mg (0.015 mmol) CuI are added successively to a solution of 71 mg (0.33 mmol) 5-(4-chloro-phenyl)-2-ethynyl-pyridine and 100 mg (0.33 mmol) 1-[2-(4-bromo-2-chloro-phenoxy)-ethyl]-pyrrolidine in 3.0 mL DMF. The mixture is stirred for 10 min at 100° C. and at 200 Watt in the microwave. The reaction solution is diluted with 30 mL EtOAc, washed twice with semisaturated NaCl solution and the organic phase is dried over MgSO$_4$. The solvent is eliminated i.vac. and further purification is carried out by column chromatography with HPLC-MS.
Yield: 12 mg (8.3% of theory)
$C_{25}H_{22}Cl_2N_2O$ (M=437.373)
Calc.: molpeak (M+H)$^+$: 437/439/441 Found: molpeak (M+H)$^+$: 437/439/441
R$_f$ value: 0.28 (silica gel, DCM/MeOH 9:1)

Example 3.2

5-(4-chloro-phenyl)-2-[3,5-dimethyl-4-(2-pyrrolidin-1-yl-ethoxy)-phenylethynyl]-pyridine

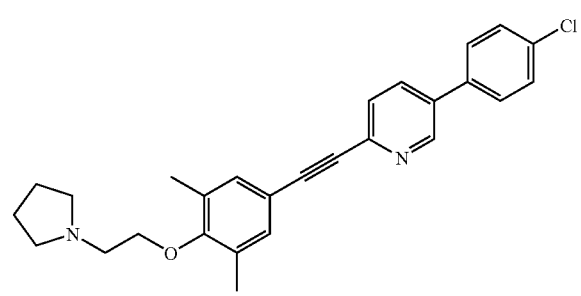 [SMILES: Cc1cc(C#Cc2ccc(-c3ccc(Cl)cc3)cn2)cc(C)c1OCCN1CCCC1]

3.2a

1-[2-(4-bromo-2,6-dimethyl-phenoxy)-ethyl]-pyrrolidine

The product is obtained analogously to Example 3.1e from 201 mg (1.00 mmol) 4-bromo-2,6-dimethyl-phenol and 170 mg (1.00 mmol) N-(2-chloroethyl)-pyrrolidine-hydrochloride.
Yield: 200 mg (67.1% of theory)
$C_{14}H_{20}BrNO$ (M=298.226)
Calc.: molpeak (M+H)$^+$: 298/300 Found: molpeak (M+H)$^+$: 298/300
HPLC retention time: 5.76 min (method A)

3.2b 5-(4-chloro-phenyl)-2-[3,5-dimethyl-4-(2-pyrrolidin-1-yl-ethoxy)-phenylethynyl]-pyridine The product is obtained analogously to Example 3.1f from 200 mg (0.67 mmol) 1-[2-(4-bromo-2,6-dimethyl-phenoxy)-ethyl]-pyrrolidine and 143 mg (0.67 mmol) 5-(4-chloro-phenyl)-2-ethynyl-pyridine.
Yield: 5 mg (1.7% of theory)
$C_{27}H_{27}ClN_2O$ (M=430.982)
Calc.: molpeak (M+H)$^+$: 431/433 Found: molpeak (M+H)$^+$: 431/433
R$_f$ value: 0.29 (silica gel, DCM/MeOH 9:1)

Example 3.3

5-(4-chloro-phenyl)-2-[3-fluoro-4-(2-pyrrolidin-1-yl-ethoxy)-phenylethynyl]-pyridine

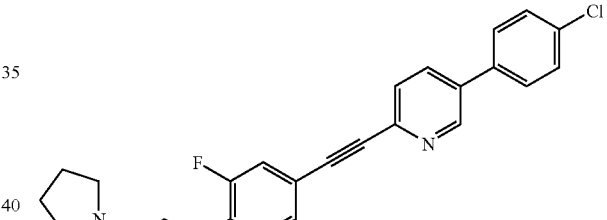

3.3a

1-[2-(4-bromo-2-fluoro-phenoxy)-ethyl]-pyrrolidine

The product is obtained analogously to Example 3.1e (acetonitrile instead of DMF) from 0.57 mL (5.24 mmol) 4-bromo-2-fluoro-phenol and 1.02 g (6.00 mmol) N-(2-chloroethyl)-pyrrolidine-hydrochloride.
Yield: 1.16 g (76.6% of theory)
$C_{12}H_{15}BrFNO$ (M=288.162)
Calc.: molpeak (M+H)$^+$: 288/290 Found: molpeak (M+H)$^+$: 288/290
R$_f$ value: 0.21 (silica gel, EtOAc/MeOH 9:1).

3.3b

1-[2-(2-fluoro-4-iodo-phenoxy)-ethyl]-pyrrolidine

Prepared according to general working method II from 1-[2-(4-bromo-2-fluoro-phenoxy)-ethyl]-pyrrolidine (1.10 g, 3.82 mmol).
Yield: 1.13 g (88.3% of theory)
$C_{12}H_{15}FINO$ (M=335.162)
Calc.: molpeak (M+H)$^+$: 336 Found: molpeak (M+H)$^+$: 336
HPLC retention time: 4.79 min (method A)

3.3c 5-(4-chloro-phenyl)-2-[3-fluoro-4-(2-pyrrolidin-1-yl-ethoxy)-phenylethynyl]-pyridine Prepared according to general working method I from 1-[2-(2-fluoro-4-iodo-phenoxy)-ethyl]-pyrrolidine (300 mg, 0.90 mmol) and 5-(4-chloro-phenyl)-2-ethynyl-pyridine (201 mg, 0.94 mmol).

Yield: 150 mg (39.8% of theory)
$C_{25}H_{22}ClFN_2O$ (M=420.918)
Calc.: molpeak $(M+H)^+$: 421/423 Found: molpeak $(M+H)^+$: 421/423
HPLC retention time: 7.18 min (method A)

Example 3.4 methyl 5-[5-(4-chloro-phenyl)-pyridin-2-ylethynyl]-2-(2-pyrrolidin-1-yl-ethoxy)-benzoate

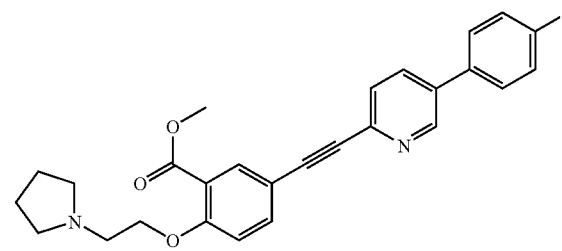

3.4a methyl 5-iodo-2-(2-pyrrolidin-1-yl-ethoxy)-benzoate

The product is obtained analogously to Example 3.1.e (acetonitrile instead of F) from 10.0 g (36.0 mmol) methyl 5-iodo-salicylate and 6.12 g (36.0 mmol) N-(2-chloroethyl)-pyrrolidine-hydrochloride.

Yield: 12.0 g (88.8% of theory)
$C_{14}H_{18}INO_3$ (M=375.209)
Calc.: molpeak $(M+H)^+$: 376 Found: molpeak $(M+H)^+$: 376
$R_f$ value: 0.40 (silica gel, DCM/MeOH/NH$_3$ 9:1:0.1)

3.4b methyl 5-[5-(4-chloro-phenyl)-pyridin-2-ylethynyl]-2-(2-pyrrolidin-1-yl-ethoxy)-benzoate Prepared according to general working method I from methyl 5-iodo-2-(2-pyrrolidin-1-yl-ethoxy)-benzoate (3.0 g, 8.0 mmol) and 5-(4-chloro-phenyl)-2-ethynyl-pyridine (1.76 g, 8.24 mmol).

Yield: 1.02 g (26.9% of theory)
$C_{27}H_{25}ClN_2O_3$ (M=460.965)
Calc.: molpeak $(M+H)^+$: 461/463 Found: molpeak $(M+H)^+$: 461/463
HPLC retention time: 7.49 min (method A)

Example 3.5

5-(4-chloro-phenyl)-2-[3-methoxy-4-(2-pyrrolidin-1-yl-ethoxy)-phenylethynyl]-pyridine

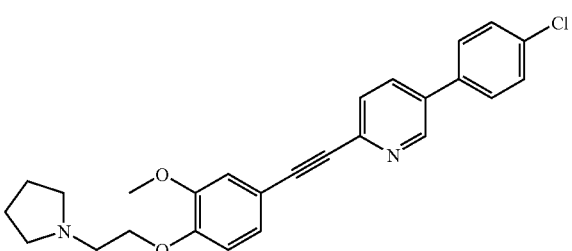

3.5a

1-[2-(4-bromo-2-methoxy-phenoxy)-ethyl]-pyrrolidine

The product is obtained analogously to Example 3.1e (acetonitrile instead of DMF) from 6.0 g (29.6 mmol) 4-bromo-2-methoxy-phenol and 5.63 g (33.1 mmol) N-(2-chloroethyl)-pyrrolidine-hydrochloride.

Yield: 3.96 g (44.6% of theory)
$C_{13}H_{18}BrNO_2$ (M=300.198)
Calc.: molpeak $(M+H)^+$: 300/302 Found: molpeak $(M+H)^+$: 300/302
HPLC retention time: 4.67 min (method A)

3.5b

1-[2-(4-iodo-2-methoxy-phenoxy)-ethyl]-pyrrolidine

Prepared according to general working method II from 1-[2-(4-bromo-2-methoxy-phenoxy)-ethyl]-pyrrolidine (3.90 g, 13.0 mmol).

Yield: 4.19 g (92.9% of theory)
$C_{13}H_{18}INO_2$ (M=347.198)
Calc.: molpeak $(M+H)^+$: 348 Found: molpeak $(M+H)^+$: 348
HPLC retention time: 4.65 min (method A)

3.5c 5-(4-chloro-phenyl)-2-[3-methoxy-4-(2-pyrrolidin-1-yl-ethoxy)-phenylethynyl]-pyridine Prepared according to general working method I from 1-[2-(4-iodo-2-methoxy-phenoxy)-ethyl]-pyrrolidine (300 mg, 0.86 mmol) and 5-(4-chloro-phenyl)-2-ethynyl-pyridine (194 mg, 0.91 mmol).

Yield: 106 mg (28.3% of theory)
$C_{26}H_{25}ClN_2O_2$ (M=432.954)
Calc.: molpeak $(M+H)^+$: 433/435 Found: molpeak $(M+H)^+$: 433/435
HPLC retention time: 7.44 min (method A)

Example 3.6

5-(4-chloro-phenyl)-2-[4-(2-pyrrolidin-1-yl-ethoxy)-3-trifluoromethoxy-phenylethynyl]-pyridine

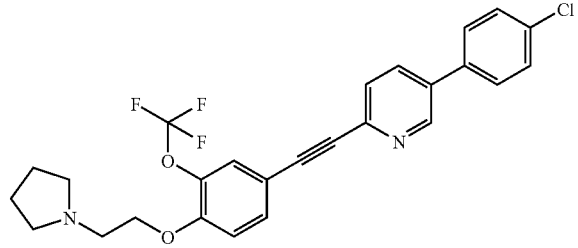 [SMILES: FC(F)(F)Oc1cc(C#Cc2ccc(-c3ccc(Cl)cc3)cn2)ccc1OCCN1CCCC1]

3.6a 4-bromo-2-trifluoromethoxy-phenol 1.55 mL (30.3 mmol) bromine in 50 mL DCM is added dropwise to a solution of 5.0 g (28.1 mmol) 2-trifluoromethoxy-phenol in 70 mL DCM at −78° C. The reaction solution is heated to RT and stirred for a further 48 h. Then 70 mL Na$_2$SO$_3$ solution are added and the mixture is stirred until the orange colour has disappeared. The solution is diluted with DCM, the organic phase is washed with NaCl solution, dried over MgSO$_4$ and the solvent is eliminated i.vac. The purification is carried out by column chromatography on silica gel (gradient: PE to PE:EtOAc 4:1).

Yield: 5.36 g (74.3% of theory)
C$_7$H$_4$BrF$_3$O$_2$ (M=257.008)
Calc.: molpeak (M−H)$^−$: 255/257 Found: molpeak (M−H)$^−$: 255/257
HPLC retention time: 8.18 min (method A)

3.6b

1-[2-(4-bromo-2-trifluoromethoxy-phenoxy)-ethyl]-pyrrolidine

The product is obtained analogously to Example 3.1e (acetonitrile instead of DMF) from 2.0 g (7.78 mmol) 4-bromo-2-trifluoromethoxy-phenol and 1.53 g (33.1 mmol) N-(2-chloroethyl)-pyrrolidine-hydrochloride.

Yield: 0.49 g (17.8% of theory)
C$_{13}$H$_{15}$BrF$_3$NO$_2$ (M=354.169)
Calc.: molpeak (M+H)$^+$: 354/356 Found: molpeak (M+H)$^+$: 354/356
HPLC retention time: 5.82 min (method A)

3.6c

1-[2-(4-iodo-2-trifluoromethoxy-phenoxy)-ethyl]-pyrrolidine

Prepared according to general working method 11 from 1-[2-(4-bromo-2-trifluoromethoxy-phenoxy)-ethyl]-pyrrolidine (476 mg, 1.34 mmol).

Yield: 540 mg (100.0% of theory)
C$_{13}$H$_{15}$F$_3$INO$_2$ (M=401.170)
Calc.: molpeak (M+H)$^+$: 402 Found: molpeak (M+H)$^+$: 402
HPLC retention time: 6.07 min (method A)

3.6d 5-(4-chloro-phenyl)-2-[4-(2-pyrrolidin-1-yl-ethoxy)-3-trifluoromethoxy-phenylethynyl]-pyridine Prepared according to general working method I from 1-[2-(4-iodo-2-trifluoromethoxy-phenoxy)-ethyl]-pyrrolidine (250 mg, 0.62 mmol) and 5-(4-chloro-phenyl)-2-ethynyl-pyridine (140 mg, 0.65 mmol).

Yield: 116 mg (38.5% of theory)
C$_{26}$H$_{22}$ClF$_3$N$_2$O$_2$ (M=486.926)
Calc.: molpeak (M+H)$^+$: 487/489 Found: molpeak (M+H)$^+$: 487/489
HPLC retention time: 8.09 min (method A)

Example 3.7

2-[3-bromo-4-(2-pyrrolidin-1-yl-ethoxy)-phenylethynyl]-5-(4-chloro-phenyl)-pyridine

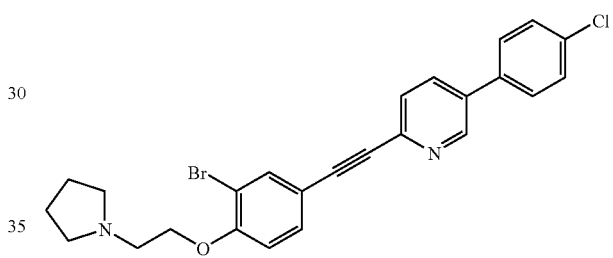

3.7a 2-bromo-4-iodo-phenol 1.55 mL (30.3 mmol) bromine in 15 mL EtOAc is added dropwise to a solution of 4.0 g (18.2 mmol) 4-iodo-phenol in 35 mL EtOAc at RT. The reaction solution is stirred for 2 h at RT. Then 75 mL Na$_2$SO$_3$ solution is added and stirred until the orange colour has disappeared. The solution is diluted with DCM, the organic phase washed with NaCl solution, dried over MgSO$_4$ and the solvent is eliminated i.vac. A 3.4:1.4:1.0 mixture of 2-bromo-4-iodo-phenol:2,4-dibromo-phenol:4-bromo-phenol is obtained, which is further reacted without any more purification.

Yield of 2-bromo-4-iodo-phenol: 2.60 g (47.9% of theory)
C$_6$H$_4$BrIO (M=298.907)
Calc.: molpeak (M−H)$^−$: 297/299 Found: molpeak (M−H)$^−$: 297/299
R$_f$ value: 0.40 (silica gel, EtOAc/MeOH 9:1)

3.7b

1-[2-(2-bromo-4-iodo-phenoxy)-ethyl]-pyrrolidine

The product is obtained analogously to Example 3.1e from 1.0 g (1.15 mmol, 59%) 2-bromo-4-iodo-phenol and 626 mg (3.68 mmol) N-(2-chloroethyl)-pyrrolidine-hydrochloride. A 4.7:1.0:1.0 mixture of 1-[2-(2-bromo-4-iodo-phenoxy)-ethyl]-pyrrolidine:1- [2-(2,4-dibromo-phenoxy)-ethyl]-pyrrolidine:1-[2-(2-bromo-phenoxy)-ethyl]-pyrrolidine is obtained, which is further reacted without any more purification.

Yield 1-[2-(2-bromo-4-iodo-phenoxy)-ethyl]-pyrrolidine: 0.37 g (47.7% of theory)

$C_{12}H_{15}BrINO$ (M=396.068)

Calc.: molpeak (M+H)$^+$: 397/399 Found: molpeak (M+H)$^+$: 397/399

$R_f$ value: 0.25 (silica gel, EtOAc/MeOH 9:1)

3.7c

2-[3-bromo-4-(2-pyrrolidin-1-yl-ethoxy)-phenylethynyl]-5-(4-chloro-phenyl)-pyridine Prepared according to general working method I from 1-[2-(2-bromo-4-iodo-phenoxy)-ethyl]-pyrrolidine (278 mg, 0.34 mmol, 70%) and 5-(4-chloro-phenyl)-2-ethynyl-pyridine (110 mg, 0.52 mmol).

Yield: 152 mg (64.3% of theory)

$C_{25}H_{22}BrClN_2O$ (M=481.824)

Calc.: molpeak (M+H)$^+$: 481/483/485 Found: molpeak (M+H)$^+$: 481/483/485

$R_f$ value: 0.25 (silica gel, DCM/MeOH/NH$_3$ 9:1:0.1)

Example 3.8

5-(4-chloro-phenyl)-2-[4-(2-pyrrolidin-1-yl-ethoxy)-3-trifluoromethyl-phenylethynyl]-pyridine

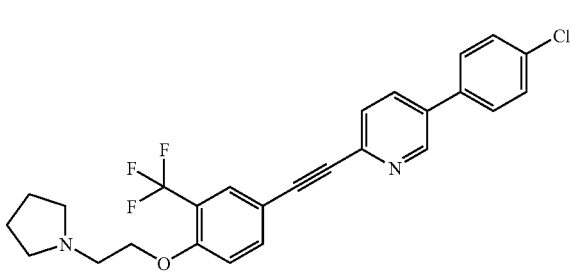 [SMILES: FC(F)(F)c1cc(C#Cc2ccc(-c3ccc(Cl)cc3)cn2)ccc1OCCN1CCCC1]

3.8a 4-bromo-2-trifluoromethyl-phenol

A solution of 3.0 g (11.8 mmol) 4-bromo-1-methoxy-2-trifluoromethyl-benzene in 20 mL 1 M HBr in glacial acetic acid is stirred for 60 h at 90° C. The reaction solution is diluted with 300 mL water, adjusted to pH 7 with K$_2$CO$_3$. The aqueous phase is extracted with EtOAc, the combined organic extracts are with washed 40 mL quarter-saturated NaHCO$_3$ solution and dried over MgSO$_4$. The solvent is eliminated i.vac. and the product is further reacted without any more purification.

Yield: 1.20 g (42.3% of theory)

$C_7H_4BrF_3O$ (M=241.009)

Calc.: molpeak (M−H)$^-$: 239/241 Found: molpeak (M−H)$^-$: 239/241

HPLC retention time: 8.37 min (method A)

3.8b

1-[2-(4-bromo-2-trifluoromethyl-phenoxy)-ethyl]-pyrrolidine

The product is obtained analogously to Example 3.1e from 1.20 g (4.98 mmol) 4-bromo-2-trifluoromethyl-phenol and 850 mg (5.00 mmol) N-(2-chloroethyl)-pyrrolidine-hydrochloride.

Yield: 400 mg (23.8% of theory)

$C_{13}H_{15}BrF_3NO$ (M=338.170)

Calc.: molpeak (M+H)$^+$: 338/340 Found: molpeak (M+H)$^+$: 338/340

HPLC retention time: 5.91 min (method A)

3.8c

1-[2-(4-iodo-2-trifluoromethyl-phenoxy)-ethyl]-pyrrolidine

Prepared according to general working method II from 1-[2-(4-bromo-2-trifluoromethyl-phenoxy)-ethyl]-pyrrolidine (400 mg, 1.18 mmol).

Yield: 350 mg (76.8% of theory)

$C_{13}H_{15}F_3INO$ (M=385.170)

Calc.: molpeak (M+H)$^+$: 386 Found: molpeak (M+H)$^+$: 386

HPLC retention time: 6.01 min (method A)

3.8d 5-(4-chloro-phenyl)-2-[4-(2-pyrrolidin-1-yl-ethoxy)-3-trifluoromethyl-phenylethynyl]-pyridine Prepared according to general working method I from 1-[2-(4-iodo-2-trifluoromethyl-phenoxy)-ethyl]-pyrrolidine (180 mg, 0.47 mmol) and 5-(4-chloro-phenyl)-2-ethynyl-pyridine (83 mg, 0.39 mmol).

Yield: 35 mg (19.1% of theory)

$C_{26}H_{22}ClF_3N_2O$ (M=470.926)

Calc.: molpeak (M+H)$^+$: 471/473 Found: molpeak (M+H)$^+$: 471/473

HPLC retention time: 8.23 min (method A)

Example 3.9

5-(4-chloro-phenyl)-2-[2-methyl-4-(2-pyrrolidin-1-yl-ethoxy)-phenylethynyl]-pyridine

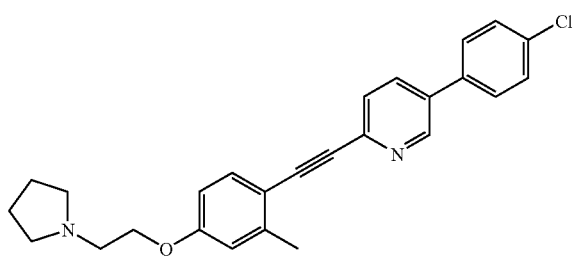

3.9a

1-[2-(4-bromo-3-methyl-phenoxy)-ethyl]-pyrrolidine

The product is obtained analogously to Example 3.1e (acetonitrile instead of DMF) from 1.0 g (5.35 mmol) 4-bromo-3-methyl-phenol and 909 mg (5.35 mmol) N-(2-chloroethyl)-pyrrolidine-hydrochloride.

Yield: 1.20 g (79.0% of theory)
$C_{13}H_{18}BrNO$ (M=284.199)
Calc.: molpeak $(M+H)^+$: 284/286 Found: molpeak $(M+H)^+$: 284/286
HPLC retention time: 3.64 min (method B)

3.9b 5-(4-chloro-phenyl)-2-[2-methyl-4-(2-pyrrolidin-1-yl-ethoxy)-phenylethynyl]-pyridine 0.13 mL (1.00 mmol) triethylamine, 22 mg (0.02 mmol) tetrakis-triphenylphosphane-palladium and 3.7 mg (0.02 mmol) CuI are added successively to a solution of 80 mg (0.37 mmol) 5-(4-chloro-phenyl)-2-ethynyl-pyridine and 106 mg (0.37 mmol) 1-[2-(4-bromo-3-methyl-phenoxy)-ethyl]-pyrrolidine in 3.0 mL DMF in an argon atmosphere. The mixture is stirred for 15 min at 100° C. and at 200 Watt in the microwave. The reaction solution is diluted with 30 mL EtOAc, washed with semisaturated $NaHCO_3$ solution and the organic phase is dried over $MgSO_4$. The solvent is eliminated i.vac. and the residue is triturated with tert-butylmethylether. The solvent is eliminated i.vac. and further purified by HPLC-MS.

Yield: 5.0 mg (3.2% of theory)
$C_{26}H_{25}ClN_2O$ (M=416.955)
Calc.: molpeak $(M+H)^+$: 417/419 Found: molpeak $(M+H)^+$: 417/419
$R_f$ value: 0.38 (silica gel, DCM/MeOH/$NH_3$ 9:1:0.1)

Example 3.10

5-(4-chloro-phenyl)-2-[2-chloro-4-(2-pyrrolidin-1-yl-ethoxy)-phenylethynyl]-pyridine

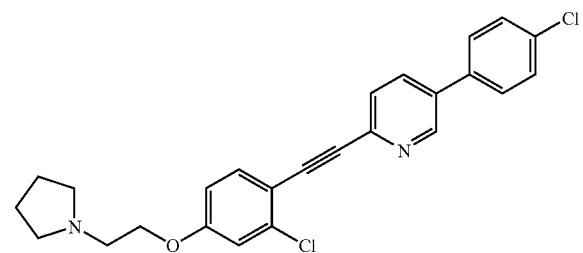

3.10a

1-[2-(4-bromo-3-chloro-phenoxy)-ethyl]-pyrrolidine

The product is obtained analogously to Example 3.1e (acetonitrile instead of DMF) from 820 mg (4.82 mmol) 4-bromo-3-chloro-phenol and 1.0 g (4.82 mmol) N-(2-chloroethyl)-pyrrolidine-hydrochloride.

Yield: 1.20 g (81.7% of theory)
$C_{12}H_{15}BrClNO$ (M=304.616)
Calc.: molpeak $(M+H)^+$: 304/306/308 Found: molpeak $(M+H)^+$: 304/306/308
HPLC retention time: 3.69 min (method B)

3.10b 5-(4-chloro-phenyl)-2-[2-chloro-4-(2-pyrrolidin-1-yl-ethoxy)-phenylethynyl]-pyridine Under an argon atmosphere 0.13 mL (1.00 mmol) triethylamine, 22 mg (0.02 mmol) tetrakis-triphenylphosphane-palladium and 3.7 mg (0.02 mmol) CuI are added successively to a solution of 80 mg (0.37 mmol) 5-(4-chloro-phenyl)-2-ethynyl-pyridine and 114 mg (0.37 mmol) 1-[2-(4-bromo-3-chloro-phenoxy)-ethyl]-pyrrolidine in 3.0 mL DMF. The mixture is stirred for 15 min at 100° C. and at 200 W in the microwave. The reaction solution is diluted with 40 mL EtOAc, washed twice with semisaturated $NaHCO_3$ solution and the organic phase is dried over $MgSO_4$. The solvent is eliminated i.vac. and the residue is triturated with tert-butylmethylether. The solvent is eliminated i.vac. and further purification is carried out by column chromatography with HPLC-MS.

Yield: 12.0 mg (7.3% of theory)
$C_{25}H_{22}Cl_2N_2O$ (M=437.373)
Calc.: molpeak $(M+H)^+$: 437/439/441 Found: molpeak $(M+H)^+$: 437/439/441
HPLC retention time: 4.91 min (method B)

Example 3.11

5-(4-chloro-phenyl)-2-[3-(2-pyrrolidin-1-yl-ethoxy)-phenylethynyl]-pyridine

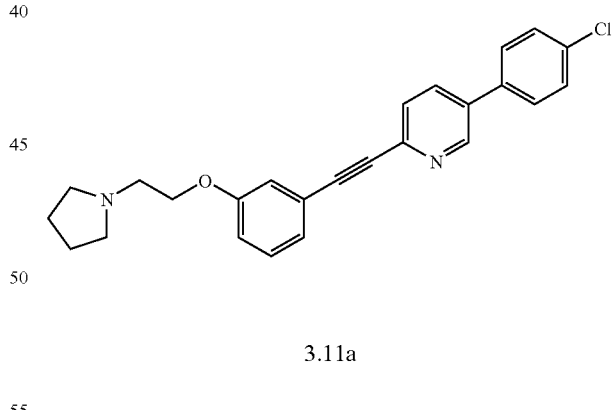

3.11a

1-[2-(3-iodo-phenoxy)-ethyl]-pyrrolidine

The product is obtained analogously to Example 3.1e (acetonitrile instead of DMF) from 1.06 g (4.82 mmol) 3-iodo-phenol and 820 mg (4.82 mmol) N-(2-chloroethyl)-pyrrolidine-hydrochloride.

Yield: 1.20 g (78.5% of theory)
$C_{12}H_{16}INO$ (M=317.172)
Calc.: molpeak $(M+H)^+$: 318 Found: molpeak $(M+H)^+$: 318
HPLC retention time: 5.01 min (method A)

3.11b

5-(4-chloro-phenyl)-2-[3-(2-pyrrolidin-1-yl-ethoxy)-phenylethynyl]-pyridine

Prepared according to general working method I from 1-[2-(3-iodo-phenoxy)-ethyl]-pyrrolidine (119 mg, 0.37 mmol) and 5-(4-chloro-phenyl)-2-ethynyl-pyridine (80 mg, 0.37 mmol).

Yield: 14 mg (9.3% of theory)

$C_{25}H_{23}ClN_2O$ (M=402.928)

Calc.: molpeak $(M+H)^+$: 403/405 Found: molpeak $(M+H)^+$: 403/405

HPLC retention time: 4.07 min (method A)

Example 3.12

5-(4-chloro-phenyl)-2-[3-(3-pyrrolidin-1-yl-propoxy)-phenylethynyl]-pyridine

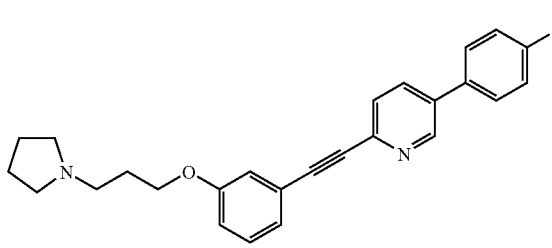

3.12a

1-[3-(3-iodo-phenoxy)-propyl]-pyrrolidine

The product is obtained analogously to Example 3.1e (acetonitrile instead of DMF) from 2.7 g (12.2 mmol) 3-iodo-phenol and 1.80 mg (12.2 mmol) N-(3-chloropropyl)-pyrrolidine.

Yield: 3.60 g (89.2% of theory)

$C_{13}H_{18}INO$ (M=331.199)

Calc.: molpeak $(M+H)^+$: 332 Found: molpeak $(M+H)^+$: 332

HPLC retention time: 5.42 min (method A)

3.12b

5-(4-chloro-phenyl)-2-[3-(3-pyrrolidin-1-yl-propoxy)-phenylethynyl]-pyridine Prepared according to general working method I from 1-[3-(3-iodo-phenoxy)-propyl]-pyrrolidine (124 mg, 0.37 mmol) and 5-(4-chloro-phenyl)-2-ethynyl-pyridine (80 mg, 0.37 mmol).

Yield: 54 mg (34.6% of theory)

$C_{26}H_{25}ClN_2O$ (M=416.955)

Calc.: molpeak $(M+H)^+$: 416/418 Found: molpeak $(M+H)^+$: 416/418

HPLC retention time: 4.99 min (method B)

Example 3.13

5-(4-chloro-phenyl)-2-[3-nitro-4-(2-pyrrolidin-1-yl-ethoxy)-phenylethynyl]-pyridine

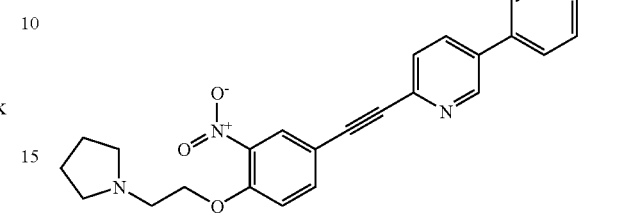

3.13a

1-[2-(4-bromo-2-nitro-phenoxy)-ethyl]-pyrrolidine

The product is obtained analogously to Example 3.1e (acetonitrile instead of DMF) from 10.5 g (48.2 mmol) 4-bromo-3-nitro-phenol and 8.2 mg (48.2 mmol) N-(2-chloroethyl)-pyrrolidine-hydrochloride.

Yield: 1.0 g (6.6% of theory)

$C_{12}H_{15}BrN_2O_3$ (M=315.17)

Calc.: molpeak $(M+H)^+$: 315/317 Found: molpeak $(M+H)^+$: 315/317

$R_f$ value: 0.30 (silica gel, DCM/MeOH/NH$_3$ 9:1:0.1)

3.13b

1-[2-(4-iodo-2-nitro-phenoxy)-ethyl]-pyrrolidine

Prepared according to general working method II from 1-[2-(4-bromo-2-nitro-phenoxy)-ethyl]-pyrrolidine (1.0 g, 2.22 mmol).

Yield: 600 mg (74.6% of theory)

$C_{12}H_{15}IN_2O_3$ (M=362.17)

Calc.: molpeak $(M+H)^+$: 363 Found: molpeak $(M+H)^+$: 363

$R_f$ value: 0.35 (silica gel, DCM/MeOH/NH$_3$ 9:1:0.1)

3.13c

5-(4-chloro-phenyl)-2-[3-nitro-4-(2-pyrrolidin-1-yl-ethoxy)-phenylethynyl]-pyridine Prepared according to general working method I from 1-[2-(4-iodo-2-nitro-phenoxy)-ethyl]-pyrrolidine (600 mg, 1.66 mmol) and 5-(4-chloro-phenyl)-2-ethynyl-pyridine (363 mg, 1.70 mmol).

Yield: 100 mg (13.1% of theory)

$C_{25}H_{22}ClN_3O_3$ (M=447.93)

Calc.: molpeak $(M+H)^+$: 448/450 Found: molpeak $(M+H)^+$: 448/450

$R_f$ value: 0.35 (silica gel, DCM/MeOH/NH$_3$ 9:1:0.1)

Example 3.14 methyl 5-[5-(4-chloro-phenyl)-pyridin-2-ylethynyl]-3-methyl-2-(2-pyrrolidin-1-yl-ethoxy)-benzoate

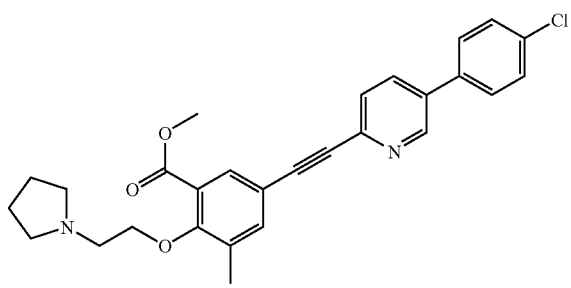 [SMILES: COC(=O)c1cc(C#Cc2ccc(-c3ccc(Cl)cc3)cn2)cc(C)c1OCCN1CCCC1]

3.14a 2-hydroxy-5-iodo-3-methyl-benzoic acid 14.9 mL (24.1 mmol) sodium hypochlorite solution (10 percent by weight in water) is added dropwise to a solution of 4.0 g (24.1 mmol) methyl 2-hydroxy-3-methyl-benzoate, 3.6 g (24.1 mmol) NaI, 0.96 g (24.1 mmol) NaOH in 100 mL MeOH at −5° C. over 40 min. The reaction is stirred for 30 min at −5° C. and 5 days at RT. The solvent is eliminated i.vac. and the residue is taken up in 80 mL water and 50 mL DCM. After the organic phase has been saturated with NaCl it is extracted twice with DCM. The combined organic extracts are filtered and the solvent is eliminated i.vac. The product is further reacted without any more purification.

Yield: 7.25 g (108% of theory)
$C_8H_7IO_3$ (M=278.048)
Calc.: molpeak $(M+H)^+$: 279 Found: molpeak $(M+H)^+$: 279
HPLC retention time: 8.41 min (method A)

3.14b methyl 2-hydroxy-5-iodo-3-methyl-benzoate

A solution of 2.0 g (7.19 mmol) 2-hydroxy-5-iodo-3-methyl-benzoic acid in 5.0 mL thionyl chloride (69.0 mmol) is stirred for 20 min at 80° C. Thionyl chloride is eliminated i.vac. and the residue is combined with 20 mL MeOH and stirred for 20 min at RT. The product is precipitated out of the reaction. MeOH is eliminated i.vac. down to 5 mL and the residue is suction filtered. The product is further reacted without any more purification.

Yield: 1.14 g (54.3% of theory)
$C_9H_9IO_3$ (M=292.075)
Calc.: molpeak $(M-H)^-$: 291 Found: molpeak $(M-H)^-$: 291
$R_f$ value: 0.96 (silica gel, EtOAc)

3.14c methyl 5-iodo-3-methyl-2-(2-pyrrolidin-1-yl-ethoxy)-benzoate

The product is obtained analogously to Example 3.1e from 1.1 g (3.77 mmol) methyl 2-hydroxy-5-iodo-3-methyl-benzoate and 641 mg (3.77 mmol) N-(2-chloroethyl)-pyrrolidine-hydrochloride.

Yield: 347 mg (23.7% of theory)
$C_{15}H_{20}INO_3$ (M=389.236)
Calc.: molpeak $(M+H)^+$: 390 Found: molpeak $(M+H)^+$: 390
HPLC retention time: 6.20 min (method A)

3.14d methyl 5-[5-(4-chloro-phenyl)-pyridin-2-ylethynyl]-3-methyl-2-(2-pyrrolidin-1-yl-ethoxy)-benzoate Prepared according to general working method I from methyl 5-iodo-3-methyl-2-(2-pyrrolidin-1-yl-ethoxy)-benzoate (150 mg, 0.39 mmol) and 5-(4-chloro-phenyl)-2-ethynyl-pyridine (112 mg, 0.53 mmol).

Yield: 31 mg (17.1% of theory)
$C_{28}H_{27}ClN_2O_3$ (M=474.992)
Calc.: molpeak $(M+H)^+$: 475/477 Found: molpeak $(M+H)^+$: 475/477
HPLC retention time: 8.11 min (method A)

Example 3.15

5-(4-chloro-phenyl)-2-[2-(2-pyrrolidin-1-yl-ethoxy)-pyridin-5-yl-ethynyl]-pyridine

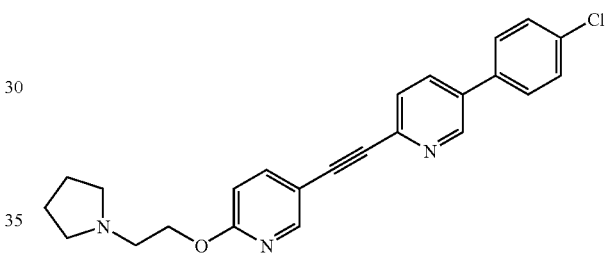

3.15a 5-bromo-2-(2-pyrrolidin-1-yl-ethoxy)-pyridine 280 mg (7.00 mmol, 60%) NaH are added to a solution of 0.76 mL (6.14 mmol) N-(2-hydroxyethyl)pyrrolidine in 20 mL DMF at RT. The reaction solution is stirred for 45 min at RT and then 1.35 g (5.53 mmol) 2,5-dibromopyridine are added. The solution is stirred for 16 h at 70° C. and the solvent is eliminated i.vac. The residue is taken up in 100 mL EtOAc and 50 mL water and the organic phase is extracted with 40 mL saturated NaCl solution. The organic phase is dried over $Na_2SO_4$ and the solvent is eliminated i.vac. Further purification is carried out by column chromatography on silica gel (gradient: cyc/EtOAc 1:1 to EtOAc).

Yield: 926 mg (61.8% of theory)
$C_{11}H_{15}BrN_2O$ (M=271.159)
Calc.: molpeak $(M+H)^+$: 271/273 Found: molpeak $(M+H)^+$: 271/273
$R_f$ value: 0.05 (silica gel, cyc/EtOAc 2:1)

3.15b 5-(4-chloro-phenyl)-2-[2-(2-pyrrolidin-1-yl-ethoxy)-pyridin-5-yl-ethynyl]-pyridine Prepared according to general working method I from 5-bromo-2-(2-pyrrolidin-1-yl-ethoxy)-pyridine (90 mg, 0.33 mmol) and 5-(4-chloro-phenyl)-2-ethynyl-pyridine (80 mg, 0.37 mmol).

Yield: 19 mg (13.8% of theory)
$C_{24}H_{22}ClN_3O$ (M=403.915)
Calc.: molpeak $(M+H)^+$: 404/406 Found: molpeak $(M+H)^+$: 404/406
$R_f$ value: 0.38 (silica gel, DCM/MeOH/NH$_3$ 9:1:0.1)

Example 3.16

5-[5-(4-chloro-phenyl)-pyridin-2-ylethynyl]-2-(2-pyrrolidin-1-yl-ethoxy)-pyrimidine

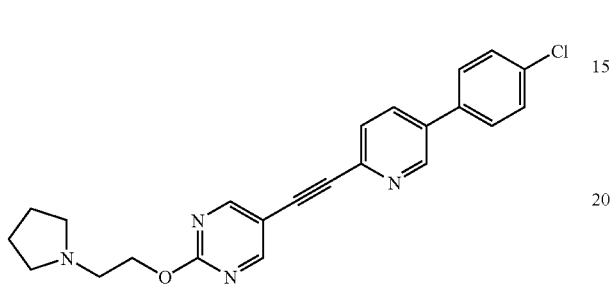

3.16a 5-bromo-2-(2-pyrrolidin-1-yl-ethoxy)-pyrimidine 50 mg (1.15 mmol, 60%) NaH are added to a solution of 0.17 mL (1.38 mmol) N-(2-hydroxyethyl)pyrrolidine in 10 mL THF at RT. The reaction solution is stirred for 15 min at RT and then 200 mg (1.03 mmol) 5-bromo-2-chloropyrimidine are added. The solution is stirred for 16 h at RT. 10 mL water are added and the aqueous phase is extracted with 20 mL EtOAc. The organic phase is dried over Na$_2$SO$_4$ and the solvent is eliminated i.vac. Further purification is carried out by column chromatography on silica gel (DCM/MeOH/NH$_3$ 9:1:0.1).

Yield: 200 mg (71.1% of theory)
$C_{10}H_{14}BrN_3O$ (M=272.147)
Calc.: molpeak $(M+H)^+$: 272/274 Found: molpeak $(M+H)^+$: 272/274
$R_f$ value: 0.47 (silica gel, DCM/MeOH/NH$_3$ 9:1:0.1)

3.16b

5-[5-(4-chloro-phenyl)-pyridin-2-ylethynyl]-2-(2-pyrrolidin-1-yl-ethoxy)-pyrimidine Under an argon atmosphere 0.11 mL (0.79 mmol) triethylamine, 7 mg (0.01 mmol) tetrakis-triphenylphosphane-palladium and 1.3 mg (0.01 mmol) CuI are added successively to a solution of 56 mg (0.26 mmol) 5-(4-chloro-phenyl)-2-ethynyl-pyridine and 71 mg (0.26 mmol) 5-bromo-2-(2-pyrrolidin-1-yl-ethoxy)-pyrimidine in 3.0 mL DMF. The mixture is stirred for 20 min at 100° C. and at 300 Watt in the microwave. The reaction solution is diluted with 10 mL water and the aqueous phase is extracted with 20 mL EtOAc. The organic phase is extracted with saturated NaCl solution and dried over Na$_2$SO$_4$. The solvent is eliminated i.vac. and further purification is carried out by column chromatography with HPLC-MS.

Yield: 7 mg (6.6% of theory)
$C_{23}H_{21}ClN_4O$ (M=404.903)
Calc.: molpeak $(M+H)^+$: 405/407 Found: molpeak $(M+H)^+$: 405/407
$R_f$ value: 0.39 (silica gel, DCM/MeOH/NH$_3$ 9:1:0.1)

Example 3.17

3-[5-(4-chloro-phenyl)-pyridin-2-ylethynyl]-6-(2-pyrrolidin-1-yl-ethoxy)-pyridazine

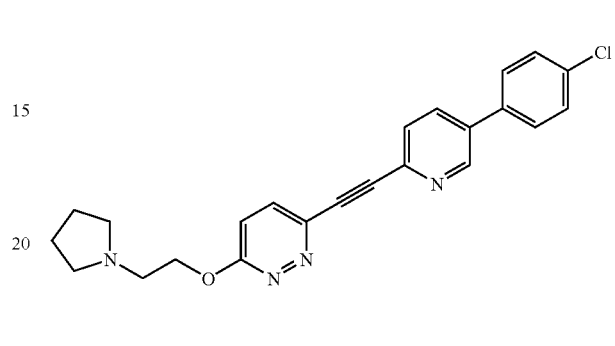

3.17a 3-chloro-6-(2-pyrrolidin-1-yl-ethoxy)-pyridazine 175 mg (4.01 mmol, 55%) NaH are added to a solution of 0.50 mL (4.04 mmol) N-(2-hydroxyethyl)pyrrolidine in 50 mL THF at 0° C. The reaction solution is stirred for 60 min and heated to RT. 500 mg (3.26 mmol) 3,6-dichloro-pyridazine are added. The solution is stirred for 5 h at RT. 50 mL water are added and the aqueous phase is extracted with 100 mL EtOAc. The organic phase is extracted once with saturated NaCl solution and dried over Na$_2$SO$_4$. The solvent is eliminated i.vac. and further purification is carried out by column chromatography on silica gel (gradient: EtOAc to EtOAc/MeOH/NH$_3$ 9:1:0.1).

Yield: 652 mg (87.9% of theory)
$C_{10}H_{14}ClN_3O$ (M=227.696)
Calc.: molpeak $(M+H)^+$: 228/230 Found: molpeak $(M+H)^+$: 228/230
$R_f$ value: 0.45 (silica gel, EtOAc/MeOH/NH$_3$ 9:1:0.1)

3.17b

3-[5-(4-chloro-phenyl)-pyridin-2-ylethynyl]-6-(2-pyrrolidin-1-yl-ethoxy)-pyridazine Under an argon atmosphere 0.11 mL (0.79 mmol) triethylamine, 4 mg (0.01 mmol) chlorine(di-2-norbornylphosphino)(2'-dimethylamino-1-1'-biphenyl-2-yl)palladium(II) and 1.2 mg (0.01 mmol) CuI are added successively to a solution of 57 mg (0.27 mmol) 5-(4-chloro-phenyl)-2-ethynyl-pyridine and 61 mg (0.26 mmol) 3-chloro-6-(2-pyrrolidin-1-yl-ethoxy)-pyridazine in 3.0 mL DMF. The mixture is stirred for 20 min at 100° C. and 300 Watt in the microwave. The reaction solution is diluted with 10 mL water and the aqueous phase is extracted with 20 mL EtOAc. The organic phase is extracted with saturated NaCl solution and dried over Na$_2$SO$_4$. The solvent is eliminated i.vac. and further purification is carried out by column chromatography with HPLC-MS.

Yield: 3 mg (2.9% of theory)
$C_{23}H_{21}ClN_4O$ (M=404.903)
Calc.: molpeak $(M+H)^+$: 405/407 Found: molpeak $(M+H)^+$: 405/407
HPLC retention time: 6.39 min (method A)

Example 3.18

5-(4-chloro-phenyl)-2-[4-(1-ethyl-piperidin-3-yloxy)-phenylethynyl]-pyridine

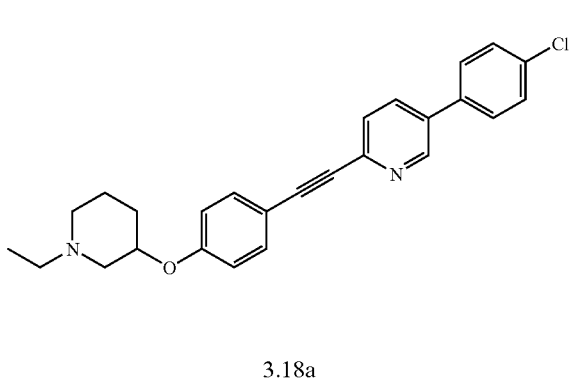

3.18a 3-(4-bromo-phenoxy)-1-ethyl-piperidine 652 mg (2.00 mmol) caesium carbonate, 36 mg (0.20 mmol) 1,10-phenanthroline and 19 mg (0.10 mmol) CuI are added to a solution of 289 mg (1.00 mmol) 1-bromo-4-iodo-benzene and 0.27 mL (2.00 mmol) N-ethyl-3-hydroxypiperidine in 1.0 mL toluene. The reaction mixture is stirred for 36 h at 110° C. and then combined with 10 mL water and 10 mL EtOAc. After filtration the aqueous phase is extracted with 10 mL EtOAc and the combined organic extracts are washed with saturated NaCl solution and dried over $Na_2SO_4$. The solvent is eliminated i.vac. and further purification is carried out by column chromatography on silica gel (EtOAc).
Yield: 100 mg (35.2% of theory)
$C_{13}H_{18}BrNO$ (M=284.199)
Calc.: molpeak $(M+H)^+$: 284/286 Found: molpeak $(M+H)^+$: 284/286
$R_f$ value: 0.50 (silica gel, EtOAc)

3.18b 5-(4-chloro-phenyl)-2-[4-(1-ethyl-piperidin-3-yloxy)-phenylethynyl]-pyridine Prepared according to general working method I from 3-(4-bromo-phenoxy)-1-ethyl-piperidine (90 mg, 0.32 mmol) and 5-(4-chloro-phenyl)-2-ethynyl-pyridine (68 mg, 0.32 mmol).
Yield: 24 mg (18.1% of theory)
$C_{26}H_{25}ClN_2O$ (M=416.955)
Calc.: molpeak $(M+H)^+$: 417/419 Found: molpeak $(M+H)^+$: 417/419
$R_f$ value: 0.69 (silica gel, EtOAc/MeOH/$NH_3$ 9:1:0.1)

Example 3.19

(S)-3-{4-[5-(4-chloro-phenyl)-pyridin-2-ylethynyl]-phenoxy}-1-aza-bicyclo[2.2.2]octane 3.19a (S)-3-(4-bromo-phenoxy)-1-aza-bicyclo[2.2.2]octane The product is obtained analogously to Example 3.18a from 577 mg (2.00 mmol) 1-bromo-4-iodobenzene and 254 mg (2.00 mmol) (S)-(+)-3-hydroxyquinuclidine.
Yield: 170 mg (30.1% of theory)
$C_{13}H_{16}BrNO$ (M=282.183)
Calc.: molpeak $(M+H)^+$: 282/284 Found: molpeak $(M+H)^+$: 282/284
$R_f$ value: 0.28 (silica gel, EtOAc/MeOH/$NH_3$ 9:1:0.1)

3.19b (S)-3-{4-[5-(4-chloro-phenyl)-pyridin-2-ylethynyl]-phenoxy}-1-aza-bicyclo[2.2.2]octane Prepared according to general working method I from (S)-3-(4-bromo-phenoxy)-1-aza-bicyclo[2.2.2]octane (170 mg, 0.62 mmol) and 5-(4-chloro-phenyl)-2-ethynyl-pyridine (100 mg, 0.47 mmol).
Yield: 3.4 mg (1.8% of theory)
$C_{26}H_{23}ClN_2O$ (M=414.939)
Calc.: molpeak $(M+H)^+$: 415/417 Found: molpeak $(M+H)^+$: 415/417
$R_f$ value: 0.11 (silica gel, EtOAc/MeOH/$NH_3$ 9:1:0.1)

Example 3.20

(2-{4-[5-(4-chloro-phenyl)-pyridin-2-ylethynyl]-phenoxy}-ethyl)-pyridin-4-yl-amine

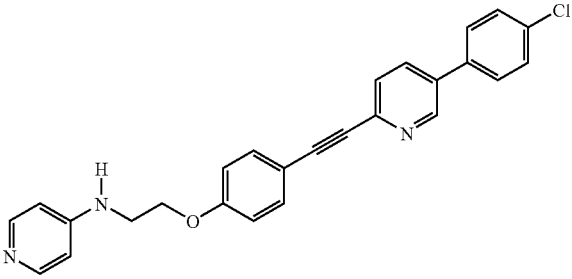 [SMILES: Clc1ccc(-c2ccc(C#Cc3ccc(OCCNc4ccncc4)cc3)nc2)cc1]

3.20a tert-butyl pyridin-4-yl-[2-(tetrahydro-pyran-2-yloxy)-ethyl]-carbaminate 309 mg (7.72 mmol, 60%) NaH is added to a solution of 1.50 g (7.72 mmol) tert-butyl pyridin-4-yl-carbaminate in 80 mL DMF at 0° C. The reaction is stirred for 1 h and at the same time heated to RT. 2.09 g (10.00 mmol) 2-(2-bromoethoxy) tetrahydro-2H-pyrane in 20 mL DMF is added within 10 min. The reaction mixture is stirred for 16 h at RT and combined with 50 mL water and 100 mL EtOAc. The organic phase is dried over $Na_2SO_4$ and the solvent is eliminated i.vac. Further purification is carried out by column chromatography on silica gel (cyc/EtOAc 7:3).

Yield: 1.08 g (43.4% of theory)
$C_{17}H_{26}BrN_2O_4$ (M=322.408)
$R_f$ value: 0.25 (silica gel, EtOAc/cyc 8:2)

3.20b 2-(pyridin-4-ylamino)-ethanol

Trifluoroacetic acid is added to a solution of 1.08 g (3.35 mmol) tert-butyl pyridin-4-yl-[2-(tetrahydro-pyran-2-yloxy)-ethyl]-carbaminate in DCM at 0° C., heated to RT and stirred for 16 h. The reaction mixture is cooled to 0° C. and made alkaline with saturated $K_2CO_3$ solution. The aqueous phase is extracted with 50 mL EtOAc, the organic phase is dried over $Na_2SO_4$ and the solvent is eliminated i.vac. Further purification is carried out by column chromatography on silica gel (EtOAc/MeOH/$NH_3$ 9:1:0.1).

Yield: 120 mg (25.9% of theory)
$C_7H_{10}N_2O$ (M=138.171)
Calc.: molpeak $(M+H)^+$: 139 Found: molpeak $(M+H)^+$: 139
$R_f$ value: 0.18 (silica gel, EtOAc/MeOH/$NH_3$ 9:1:0.1)

3.20c

[2-(4-bromo-phenoxy)-ethyl]-pyridin-4-yl-amine

The product is obtained analogously to Example 3.18a from 251 mg (0.87 mmol) 1-bromo-4-iodobenzene and 120 mg (0.86 mmol) 2-(pyridin-4-ylamino)-ethanol.

Yield: 90 mg (35.4% of theory)
$C_{13}H_{13}BrN_2O$ (M=293.165)
Calc.: molpeak $(M+H)^+$: 293/295 Found: molpeak $(M+H)^+$: 293/295
$R_f$ value: 0.50 (silica gel, EtOAc/MeOH/$NH_3$ 9:1:0.1)

3.20d

[2-(4-iodo-phenoxy)-ethyl]-pyridin-4-yl-amine

Prepared according to general working method II from [2-(4-bromo-phenoxy)-ethyl]-pyridin-4-yl-amine (90 mg, 0.31 mmol).

Yield: 95 mg (91.0% of theory)
$C_{13}H_{13}IN_2O$ (M=340.166)
HPLC retention time: 5.86 min (method A)

3.20e (2-{4-[5-(4-chloro-phenyl)-pyridin-2-ylethynyl]-phenoxy}-ethyl)-pyridin-4-yl-amine Prepared according to general working method I from [2-(4-iodo-phenoxy)-ethyl]-pyridin-4-yl-amine (95 mg, 0.28 mmol) and 5-(4-chloro-phenyl)-2-ethynyl-pyridine (70 mg, 0.33 mmol).

Yield: 30 mg (25.2% of theory)
$C_{26}H_{20}ClN_3O$ (M=425.922)
Calc.: molpeak $(M+H)^+$: 426/428 Found: molpeak $(M+H)^+$: 426/428
$R_f$ value: 0.38 (silica gel, EtOAc/MeOH/$NH_3$ 9:1:0.1)

Example 3.21

5-(4-chloro-phenyl)-2-{4-[2-(2,2,6,6-tetramethyl-piperidin-1-yl)-ethoxy]-phenylethynyl}-pyridine

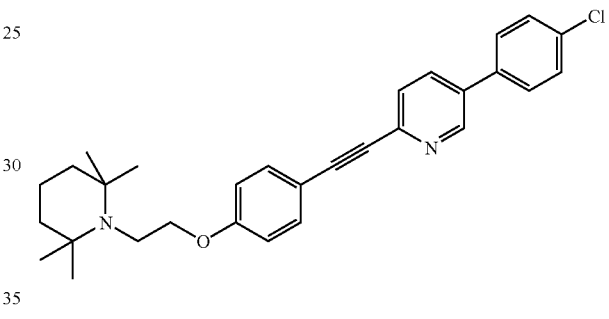

3.21a

1-[2-(4-iodo-phenoxy)-ethyl]-2,2,6,6-tetramethyl-piperidine

The product is obtained analogously to EXAMPLE 3.1e from 500 mg (2.27 mmol) 4-iodo-phenol and 500 mg (2.08 mmol) 1-(2-chloro-ethyl)-2,2,6,6-tetramethyl-piperidine.

Yield: 673 mg (83.5% of theory)
$C_{17}H_{26}INO$ (M=387.307)
Calc.: molpeak $(M+H)^+$: 388 Found: molpeak $(M+H)^+$: 388
$R_f$ value: 0.79 (silica gel, cyc/EtOAc 4:1)

3.21b 5-(4-chloro-phenyl)-2-{4-[2-(2,2,6,6-tetramethyl-piperidin-1-yl)-ethoxy]-phenylethynyl}-pyridine Prepared according to general working method I from 1-[2-(4-iodo-phenoxy)-ethyl]-2,2,6,6-tetramethyl-piperidine (260 mg, 0.67 mmol) and 5-(4-chloro-phenyl)-2-ethynyl-pyridine (155 mg, 0.73 mmol).

Yield: 31 mg (9.8% of theory)
$C_{30}H_{33}ClN_2O$ (M=473.063)
Calc.: molpeak $(M+H)^+$: 473/475 Found: molpeak $(M+H)^+$: 473/475
$R_f$ value: 0.21 (silica gel, cyc/EtOAc 3:1)

Example 3.22

5-(4-chloro-phenyl)-2-[4-(3-pyrrolidin-1-yl-propyl)-phenylethynyl]-pyridine

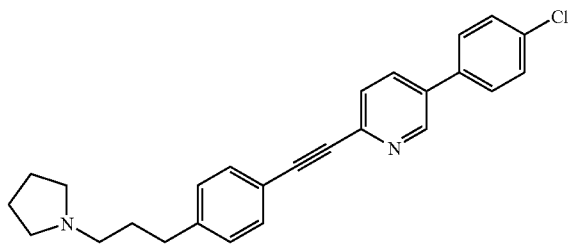 [SMILES: Clc1ccc(-c2ccc(C#Cc3ccc(CCCN4CCCC4)cc3)nc2)cc1]

3.22a 3-(4-bromo-phenyl)-propionaldehyde 210 mg (0.86 mmol) Pd(OAc)$_2$, 5.23 g (17.32 mmol) tetra-n-butylammonium chloride and 3.6 g NaHCO$_3$ are added to a solution of 5.0 g (17.32 mmol) 4-bromo-iodo-benzene and 3.0 mL (43.67 mmol) allylalcohol in 30 mL DMF. The reaction solution is stirred for 2 h at 60° C. and diluted with 50 mL water. The aqueous phase is extracted with 50 mL EtOAc and the combined organic extracts are washed with 50 mL saturated NaCl solution. The organic phase is dried over Na$_2$SO$_4$ and the solvent is eliminated i.vac. Further purification is carried out by column chromatography on silica gel (cyc/EtOAc 3:1).

Yield: 2.48 g (67.2% of theory)
C$_9$H$_9$BrO (M=213.075)
Calc.: molpeak (M−H)$^-$: 211/213 Found: molpeak (M−H)$^-$: 211/213
R$_f$ value: 0.43 (silica gel, cyc/EtOAc 4:1)

3.22b

1-[3-(4-bromo-phenyl)-propyl]-pyrrolidine

A solution of 1.03 g (4.82 mmol) 3-(4-bromo-phenyl)-propionaldehyde and 0.41 mL (4.82 mmol) pyrrolidine in 50 mL MeOH is adjusted to pH 4-5 with glacial acetic acid. Then 400 mg (6.05 mmol) NaBH$_3$CN are added batchwise and the reaction is stirred for 3 days at RT. The reaction solution is diluted with 30 mL water and the aqueous phase is extracted with 50 mL EtOAc. The organic phase is dried over Na$_2$SO$_4$ and the solvent is eliminated i.vac. Further purification is carried out by column chromatography on silica gel (EtOAc/MeOH/NH$_3$ 9:1:0.1).

Yield: 1.06 g (82.1% of theory)
C$_{13}$H$_{18}$BrN (M=268.199)
Calc.: molpeak (M+H)$^+$: 268/270 Found: molpeak (M+H)$^+$: 268/270
R$_f$ value: 0.50 (silica gel, EtOAc/MeOH/NH$_3$ 9:1:0.1)

3.22c 5-(4-chloro-phenyl)-2-[4-(3-pyrrolidin-1-yl-propyl)-phenylethynyl]-pyridine The product is obtained analogously to Example 3.16b (Pd(PPh$_3$)$_2$Cl$_2$ instead of tetrakis-triphenylphosphane-palladium) from 72 mg (0.27 mmol) 1-[3-(4-bromo-phenyl)-propyl]-pyrrolidine and 57 mg (0.27 mmol) 5-(4-chloro-phenyl)-2-ethynyl-pyridine.

Yield: 10 mg (9.6% of theory)
C$_{26}$H$_{25}$ClN$_2$ (M=400.956)
Calc.: molpeak (M+H)$^+$: 401/403 Found: molpeak (M+H)$^+$: 401/403
HPLC retention time: 6.94 min (method A)

Example 3.23

5-(4-chloro-phenyl)-2-[4-(2-pyrrolidin-1-yl-ethyl)-phenylethynyl]-pyridine

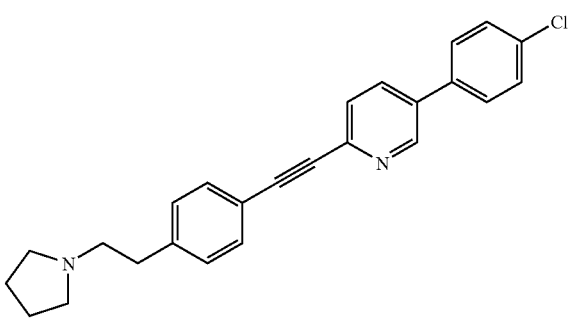 [SMILES: Clc1ccc(-c2ccc(C#Cc3ccc(CCN4CCCC4)cc3)nc2)cc1]

3.23a

1-[2-(4-bromo-phenyl)-ethyl]-pyrrolidine 0.51 mL (4.23 mmol) 1,4-dibromobutane in 20 mL acetonitrile is added slowly to a solution of 1.0 g (4.23 mmol) 4-bromo-phenethylamine hydrochloride, 1.8 g (13.0 mmol) K$_2$CO$_3$ and 200 mg (1.20 mmol) KI in 100 mL acetonitrile at 75° C. and the reaction mixture is stirred for a further 4 h at 75° C. The reaction solution is diluted with 100 mL water and the aqueous phase is extracted with 100 mL EtOAc. The combined organic extracts are washed with saturated NaCl solution, the organic phase is dried over Na$_2$SO$_4$ and the solvent is eliminated i.vac. Further purification is carried out by column chromatography on silica gel (EtOAc/MeOH/NH$_3$ 9:1:0.1).

Yield: 540 mg (50.2% of theory)
C$_{12}$H$_{16}$BrN (M=254.172)
Calc.: molpeak (M+H)$^+$: 254/256 Found: molpeak (M+H)$^+$: 254/256
R$_f$ value: 0.54 (silica gel, EtOAc/MeOH/NH$_3$ 9:1:0.1)

3.23b 5-(4-chloro-phenyl)-2-[4-(2-pyrrolidin-1-yl-ethyl)-phenylethynyl]-pyridine The product is obtained analogously to Example 3.16b from 60 mg (0.23 mmol) 1-[2-(4-bromo-phenyl)-ethyl]-pyrrolidine and 50 mg (0.23 mmol) 5-(4-chloro-phenyl)-2-ethynyl-pyridine.

Yield: 8 mg (8.7% of theory)
C$_{25}$H$_{23}$ClN$_2$ (M=386.928)
Calc.: molpeak (M+H)$^+$: 387/389 Found: molpeak (M+H)$^+$: 387/389
HPLC retention time: 6.45 min (method A)

Example 3.24

1-{5-[5-(4-chloro-phenyl)-pyridin-2-ylethynyl]-pyridin-2-yl}-4-methyl-[1,4]diazepan

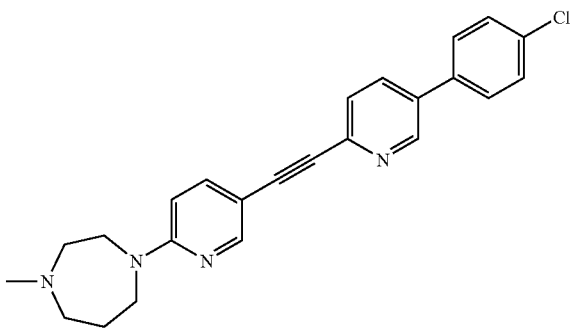 [SMILES: CN1CCCN(c2ccc(C#Cc3ccc(-c4ccc(Cl)cc4)cn3)cn2)CC1]

3.24a 1-(5-bromo-pyridin-2-yl)-4-methyl-[1,4]diazepan 1.5 g (5.29 mmol) 5-bromo-2-iodobenzene and 1.5 mL (11.7 mmol) 1-methylhomopiperazine are heated to 170° C. for 1.5 h. After the reaction mixture has cooled 40 mL semi-saturated $NaHCO_3$ solution and 100 mL EtOAc are added. The organic phase is dried over $Na_2SO_4$ and the solvent is eliminated i.vac. Further purification is carried out by column chromatography on silica gel (EtOAc/MeOH/$NH_3$ 85:15:1).

Yield: 1.10 g (77.1% of theory)
$C_{11}H_{16}BrN_3$ (M=270.174)
Calc.: molpeak (M+H)$^+$: 270/272 Found: molpeak (M+H)$^+$: 270/272
$R_f$ value: 0.57 (silica gel, EtOAc/MeOH/$NH_3$ 8:2:0.2)

3.24b 1-(5-iodo-pyridin-2-yl)-4-methyl-[1,4]diazepan

Prepared according to general working method II from 1-(5-bromo-pyridin-2-yl)-4-methyl-[1,4]diazepan (472 mg, 1.75 mmol).

Yield: 546 mg (98.5% of theory)
$C_{11}H_{16}IN_3$ (M=317.175)
HPLC retention time: 4.56 min (method A)

3.24c

1-{5-[5-(4-chloro-phenyl)-pyridin-2-ylethynyl]-pyridin-2-yl}-4-methyl-[1,4]diazepan Prepared according to general working method I from 1-(5-iodo-pyridin-2-yl)-4-methyl-[1,4]diazepan (237 mg, 0.75 mmol) and 5-(4-chloro-phenyl)-2-ethynyl-pyridine (161 mg, 0.75 mmol).

Yield: 54 mg (17.9% of theory)
$C_{24}H_{23}ClN_4$ (M=402.931)
Calc.: molpeak (M+H)$^+$: 403/405 Found: molpeak (M+H)$^+$: 403/405
HPLC retention time: 6.79 min (method A)

Example 3.25

1-{5-[5-(4-chloro-phenyl)-pyridin-2-ylethynyl]-pyridin-2-yl}-4-methyl-piperazine

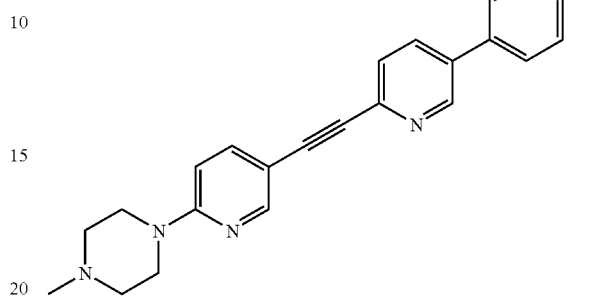

3.25a 1-(5-bromo-pyridin-2-yl)-4-methyl-piperazine

The product is obtained analogously to Example 3.24a is from 1.5 g (5.28 mmol) 5-bromo-2-iodopyridine and 1.3 mL (11.7 mmol) N-methylpiperazine.

Yield: 1.15 g (85.1% of theory)
$C_{10}H_{14}BrN_3$ (M=256.147)
Calc.: molpeak (M+H)$^+$: 256/258 Found: molpeak (M+H)$^+$: 256/258
$R_f$ value: 0.50 (silica gel, EtOAc/MeOH/$NH_3$ 9:1:0.1)

3.25b 1-(5-iodo-pyridin-2-yl)-4-methyl-piperazine

Prepared according to general working method II from 1-(5-bromo-pyridin-2-yl)-4-methyl-piperazine (500 mg, 1.95 mmol).

Yield: 532 mg (89.9% of theory)
$C_{10}H_{14}IN_3$ (M=303.148)
HPLC retention time: 4.59 min (method A)

3.25c

1-{5-[5-(4-chloro-phenyl)-pyridin-2-ylethynyl]-pyridin-2-yl}-4-methyl-piperazine Prepared according to general working method I from 1-(5-iodo-pyridin-2-yl)-4-methyl-piperazine (235 mg, 0.78 mmol) and 5-(4-chloro-phenyl)-2-ethynyl-pyridine (167 mg, 0.78 mmol).

Yield: 15 mg (5.0% of theory)
$C_{23}H_{21}ClN_4$ (M=388.904)
Calc.: molpeak (M+H)$^+$: 389/391 Found: molpeak (M+H)$^+$: 389/391
HPLC retention time: 6.79 min (method A)

Example 3.26

(1S,4S)-2-{5-[5-(4-chloro-phenyl)-pyridin-2-ylethynyl]-pyridin-2-yl}-6-methyl-2,6-diaza-bicyclo[2.2.1]heptane

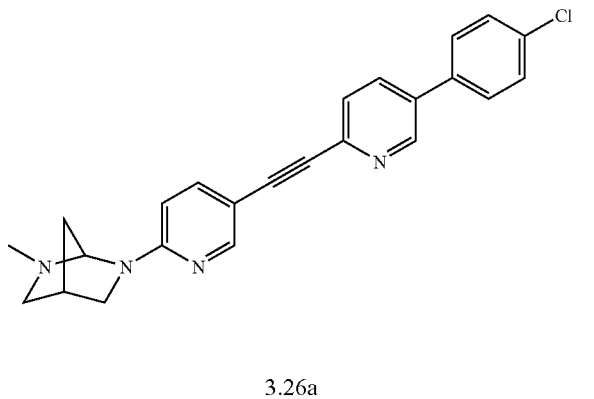

3.26a (1S,4S)-2-(5-bromo-pyridin-2-yl)-6-methyl-2,6-diaza-bicyclo[2.2.1]heptane

A solution of 300 mg (1.10 mmol) (1S,4S)-2-methyl-2,5-diazabicylo[2.2.1]heptane dihydrobromide, 0.75 mL (4.40 mmol) ethyldiisopropylamine and 270 mg (1.11 mmol) 2,5-dibromopyridine in 1.5 mL n-butanol are stirred for 18 h at 115° C. The solvent is eliminated i.vac., the residue is combined with 10 mL EtOAc and acidified with 1 M HCl. The aqueous phase is twice made alkaline with 2 M $K_2CO_3$ solution and extracted with 30 mL EtOAc. The combined organic extracts are dried over $Na_2SO_4$ and the solvent is eliminated i.vac.

Yield: 70 mg (23.8% of theory)
$C_{11}H_{14}BrN_3$ (M=268.158)
HPLC retention time: 4.07 min (method A)
$R_f$ value: 0.05 (silica gel, EtOAc/MeOH/$NH_3$ 9:1:0.1)

3.26b (1S,4S)-2-(5-iodo-pyridin-2-yl)-6-methyl-2,6-diaza-bicyclo[2.2.1]heptane

Prepared according to general working method II from (1S,4S)-2-(5-bromo-pyridin-2-yl)-6-methyl-2,6-diaza-bicyclo[2.2.1]heptane (70 mg, 0.26 mmol).

Yield: 45 mg (54.7% of theory)
$C_{11}H_{14}IN_3$ (M=315.159)
HPLC retention time: 4.18 min (method A)
$R_f$ value: 0.06 (silica gel, EtOAc/MeOH/$NH_3$ 9:1:0.1)

3.26c (1S,4S)-2-{5-[5-(4-chloro-phenyl)-pyridin-2-ylethynyl]-pyridin-2-yl}-6-methyl-2,6-diaza-bicyclo[2.2.1]heptane Prepared according to general working method I from (1S,4S)-2-(5-iodo-pyridin-2-yl)-6-methyl-2,6-diaza-bicyclo[2.2.1]heptane (45 mg, 0.14 mmol) and 5-(4-chloro-phenyl)-2-ethynyl-pyridine (51 mg, 0.24 mmol).

Yield: 6 mg (10.3% of theory)
$C_{24}H_{21}ClN_4$ (M=400.915)
Calc.: molpeak $(M+H)^+$: 401/403 Found: molpeak $(M+H)^+$: 401/403
HPLC retention time: 6.44 min (method A)

Example 3.27

{5-[5-(4-chloro-phenyl)-pyridin-2-ylethynyl]-pyridin-2-yl}-methyl-(2-pyrrolidin-1-yl-ethyl)-amine

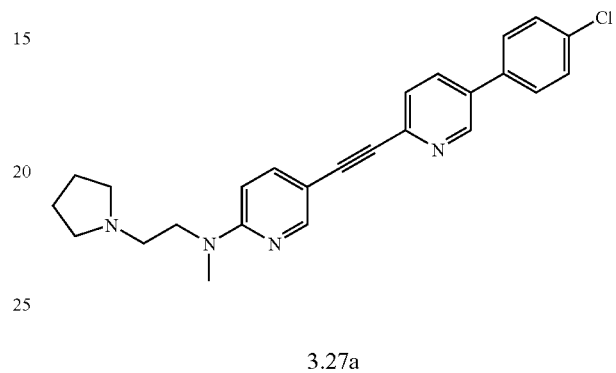

3.27a (5-bromo-pyridin-2-yl)-methyl-(2-pyrrolidin-1-yl-ethyl)-amine

The product is obtained analogously to Example 3.24a (reaction time 2.5 h) from 11.5 g (40.5 mmol) 5-bromo-2-iodopyridine and 6.3 mL (11.7 mmol) methyl-(2-pyrrolidin-1-yl-ethyl)-amine.

Yield: 4.0 g (34.8% of theory)
$C_{12}H_{18}BrN_3$ (M=284.201)
Calc.: molpeak $(M+H)^+$: 284/286 Found: molpeak $(M+H)^+$: 284/286
$R_f$ value: 0.37 (silica gel, DCM/MeOH/$NH_3$ 9:1:0.1)
HPLC retention time: 5.09 min (method A)

3.27b (5-iodo-pyridin-2-yl)-methyl-(2-pyrrolidin-1-yl-ethyl)-amine

Prepared according to general working method II from (5-bromo-pyridin-2-yl)-methyl-(2-pyrrolidin-1-yl-ethyl)-amine (1.1 g, 3.87 mmol).

Yield: 1.0 g (81.1% of theory)
$C_{12}H_{18}IN_3$ (M=331.202)
Calc.: molpeak $(M+H)^+$: 332 Found: molpeak $(M+H)^+$: 332
HPLC retention time: 5.19 min (method A)

3.27c

{5-[5-(4-chloro-phenyl)-pyridin-2-ylethynyl]-pyridin-2-yl}-methyl-(2-pyrrolidin-1-yl-ethyl)-amine Prepared according to general working method I from (5-iodo-pyridin-2-yl)-methyl-(2-pyrrolidin-1-yl-ethyl)-amine (100 mg, 0.30 mmol) and 5-(4-chloro-phenyl)-2-ethynyl-pyridine (65 mg, 0.30 mmol).

Yield: 43 mg (34.2% of theory)
$C_{25}H_{25}ClN_4$ (M=416.958)

Calc.: molpeak (M+H)⁺: 417/419 Found: molpeak (M+H)⁺: 417/419

R_f value: 0.25 (Alox, cyc/EtOAc 2:1).

HPLC retention time: 7.57 min (method A)

Example 3.28

(1-{5-[5-(4-chloro-phenyl)-pyridin-2-ylethynyl]-pyridin-2-yl}-pyrrolidin-3-yl)-dimethyl-amine

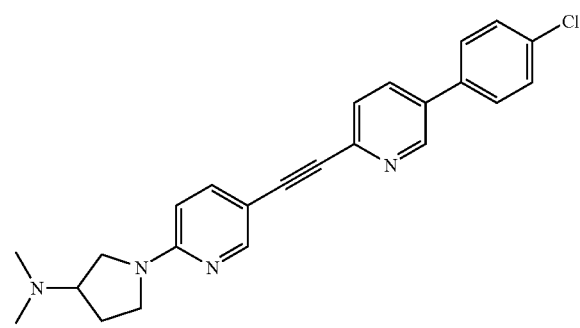 [SMILES: CN(C)C1CCN(c2ccc(C#Cc3ccc(-c4ccc(Cl)cc4)cn3)cn2)C1]

3.28a

[1-(5-bromo-pyridin-2-yl)-pyrrolidin-3-yl]-dimethyl-amine

A solution of 215 mg (0.88 mmol) 2,5-dibromobenzene, 100 mg (0.88 mmol) 3-(dimethylamino)-pyrrolidine and 0.60 mL (3.51 mmol) ethyldiisopropylamine in 0.5 mL n-butanol is stirred for 30 min in the microwave at 150° C. The solvent is eliminated i.vac. and the residue is taken up in 20 mL EtOAc and 10 mL water. The aqueous phase is acidified with 1 M HCl. The phases are separated and then the aqueous phase is made alkaline with 2 M $Na_2CO_3$ solution and extracted with 40 mL EtOAc. The organic phase is dried over $Na_2SO_4$ and the solvent is eliminated i.vac.

Yield: 179 mg (75.6% of theory)

$C_{11}H_{16}BrN_3$ (M=270.174)

Calc.: molpeak (M+H)⁺: 270/272 Found: molpeak (M+H)⁺: 270/272

R_f value: 0.30 (silica gel, EtOAc/MeOH/NH₃ 9:1:0.1)

3.28b

[1-(5-iodo-pyridin-2-yl)-pyrrolidin-3-yl]-dimethyl-amine

Prepared according to general working method II from [1-(5-bromo-pyridin-2-yl)-pyrrolidin-3-yl]-dimethyl-amine (160 mg, 0.59 mmol).

Yield: 168 mg (89.5% of theory)

$C_{11}H_{16}IN_3$ (M=317.175)

Calc.: molpeak (M+H)⁺: 318 Found: molpeak (M+H)⁺: 318

HPLC retention time: 3.56 min (method A)

3.28c (1-{5-[5-(4-chloro-phenyl)-pyridin-2-ylethynyl]-pyridin-2-yl}-pyrrolidin-3-yl)-dimethyl-amine Prepared according to general working method I from [1-(5-iodo-pyridin-2-yl)-pyrrolidin-3-yl]-dimethyl-amine (160 mg, 0.50 mmol) and 5-(4-chloro-phenyl)-2-ethynyl-pyridine (108 mg, 0.50 mmol).

Yield: 8 mg (3.9% of theory)

$C_{24}H_{23}ClN_4$ (M=402.931)

Calc.: molpeak (M+H)⁺: 403/405 Found: molpeak (M+H)⁺: 403/405

HPLC retention time: 6.37 min (method A)

Example 3.29

{5-[5-(4-chloro-phenyl)-pyridin-2-ylethynyl]-pyridin-2-yl}-(2-pyrrolidin-1-yl-ethyl)-amine

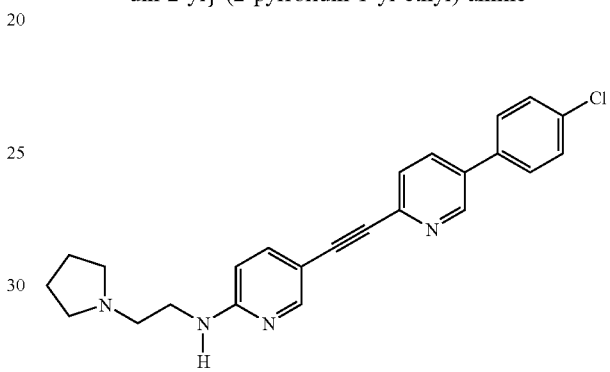

3.29a (5-bromo-pyridin-2-yl)-(2-pyrrolidin-1-yl-ethyl)-amine 13.8 g (100.0 mmol) $K_2CO_3$, 79 mg (0.12 mmol) 2,2'-bis(diphenylphosphino)-1,1'-binaphthyl and 28 mg (0.12 mmol) Pd(OAc)₂ are added successively to a solution of 1.5 g (6.33 mmol) 2,5-dibromopyridine and 0.98 mL (7.60 mmol) 1-(2-aminoethyl)-pyrrolidine in 60 mL toluene. The reaction is refluxed for 40 h. The solvent is eliminated i.vac. and the residue is taken up in 150 mL EtOAc and 100 mL water. The organic phase is dried over $Na_2SO_4$ and the solvent is eliminated i.vac. Purification is carried out by column chromatography on silica gel (gradient: EtOAc/MeOH/NH₃ 19:1:0.1 to EtOAc/MeOH/NH₃ 9:1:0.1).

Yield: 145 mg (8.5% of theory)

$C_{11}H_{16}BrN_3$ (M=270.174)

Calc.: molpeak (M+H)⁺: 270/272 Found: molpeak (M+H)⁺: 270/272

R_f value: 0.05 (silica gel, EtOAc/MeOH/NH₃ 9:1:0.1)

3.29b

{5-[5-(4-chloro-phenyl)-pyridin-2-ylethynyl]-pyridin-2-yl}-(2-pyrrolidin-1-yl-ethyl)-amine The product is obtained analogously to Example 3.16b is from 90 mg (0.33 mmol) (5-bromo-pyridin-2-yl)-(2-pyrrolidin-1-yl-ethyl)-amine and 88 mg (0.41 mmol) 5-(4-chlorophenyl)-2-ethynyl-pyridine.

Yield: 4 mg (5.8% of theory)

$C_{24}H_{23}ClN_4$ (M=402.931)
Calc.: molpeak $(M+H)^+$: 403/405 Found: molpeak $(M+H)^+$: 403/405
HPLC retention time: 6.71 min (method A)

Example 3.30

N-{5-[5-(4-chloro-phenyl)-pyridin-2-ylethynyl]-pyridin-2-yl}-N-(2-pyrrolidin-1-yl-ethyl)-acetamide

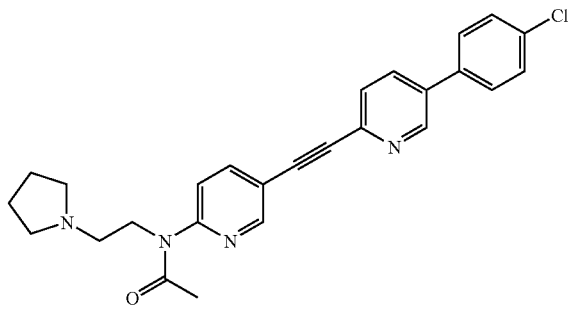 [SMILES: CC(=O)N(CCN1CCCC1)c1ccc(C#Cc2ccc(-c3ccc(Cl)cc3)cn2)cn1]

45 µL (0.48 mmol) acetic anhydride is added to a solution of 89 mg (0.22 mmol) {5-[5-(4-chloro-phenyl)-pyridin-2-ylethynyl]-pyridin-2-yl}-(2-pyrrolidin-1-yl-ethyl)-amine in 2 mL DCM. The reaction solution is stirred for 16 h at RT. The solvent is eliminated i.vac. and further purification is carried out by HPLC-MS.
Yield: 62 mg (63.0% of theory)
$C_{26}H_{25}ClN_4O$ (M=444.968)
Calc.: molpeak $(M+H)^+$: 445/447 Found: molpeak $(M+H)^+$: 445/447
$R_f$ value: 0.38 (Alox, cyc/EtOAc 1:1).

Example 3.31

{5-[5-(4-chloro-phenyl)-pyridin-2-ylethynyl]-pyridin-2-yl}-(2-piperidin-1-yl-ethyl)-amine

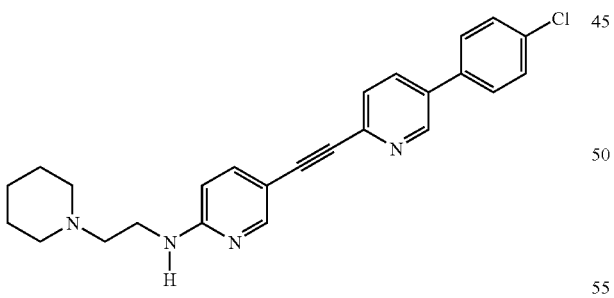

3.31a (5-bromo-pyridin-2-yl)-(2-piperidin-1-yl-ethyl)-amine 800 mg (3.38 mmol) 2,5-dibrombenzene and 1.0 g (7.80 mmol) N-(2-aminoethyl)piperidine are heated to 170° C. for 45 min. After the reaction mixture has cooled 80 mL EtOAc are added and filtered. The filtrate is washed twice with 40 mL saturated $NaHCO_3$ solution and dried over $MgSO_4$. After the desiccant and solvent have been eliminated the residue is purified by chromatography (silica gel, EtOAc/MeOH/$NH_3$ 85:15:2).
Yield: 720 mg (75.0% of theory)
$C_{12}H_{18}BrN_3$ (M=284.201)
Calc.: molpeak $(M+H)^+$: 284/286 Found: molpeak $(M+H)^+$: 284/286
$R_f$ value: 0.30 (silica gel, EtOAc/MeOH/$NH_3$ 9:1:0.1)

3.31b (5-iodo-pyridin-2-yl)-(2-piperidin-1-yl-ethyl)-amine

Prepared according to general working method II from (5-bromo-pyridin-2-yl)-(2-piperidin-1-yl-ethyl)-amine (720 mg, 2.53 mmol).
Yield: 750 mg (89.4% of theory)
$C_{12}H_{18}IN_3$ (M=331.202)
Calc.: molpeak $(M+H)^+$: 332 Found: molpeak $(M+H)^+$: 332
HPLC retention time: 4.32 min (method A)

3.31c

{5-[5-(4-chloro-phenyl)-pyridin-2-ylethynyl]-pyridin-2-yl}-(2-piperidin-1-yl-ethyl)-amine Prepared according to general working method I from (5-iodo-pyridin-2-yl)-(2-piperidin-1-yl-ethyl)-amine (397 mg, 1.20 mmol) and 5-(4-chloro-phenyl)-2-ethynyl-pyridine (256 mg, 1.20 mmol).
Yield: 230 mg (46.0% of theory)
$C_{25}H_{25}ClN_4$ (M=416.958)
Calc.: molpeak $(M+H)^+$: 417/419 Found: molpeak $(M+H)^+$: 417/419
$R_f$ value: 0.55 (silica gel, EtOAc/MeOH/$NH_3$ 9:1:0.1)
HPLC retention time: 7.26 min (method A)

Example 3.32

5'-[5-(4-chloro-phenyl)-pyridin-2-ylethynyl]-3-pyrrolidin-1-yl-3,4,5,6-tetrahydro-2H-[1,2']bipyridinyl

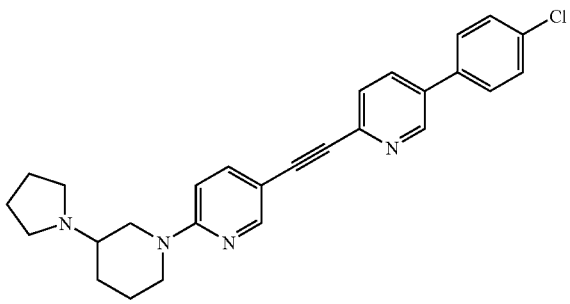 [SMILES: Clc1ccc(-c2ccc(C#Cc3ccc(N4CCCC(N5CCCC5)C4)nc3)nc2)cc1]

3.32a

5'-bromo-3-pyrrolidin-1-yl-3,4,5,6-tetrahydro-2H-[1,2']bipyridinyl

The product is obtained analogously to Example 3.31a (reaction time: 35 min at 160° C.) from 2.37 g (10.0 mmol) 2,5-dibromopyridine and 1.6 g (10.4 mmol) 3-pyrrolidin-1-yl-piperidine.

Yield: 700 mg (21.8% of theory)
$C_{14}H_{20}BrN_3$ (M=310.240)
Calc.: molpeak $(M+H)^+$: 310/312 Found: molpeak $(M+H)^+$: 310/312
HPLC retention time: 5.06 min (method B)

3.32b

5'-iodo-3-pyrrolidin-1-yl-3,4,5,6-tetrahydro-2H-[1,2']bipyridinyl

Prepared according to general working method II from 5'-bromo-3-pyrrolidin-1-yl-3,4,5,6-tetrahydro-2H-[1,2']bipyridinyl (700 mg, 2.26 mmol).
Yield: 700 mg (86.9% of theory)
$C_{14}H_{20}IN_3$ (M=357.240)
Calc.: molpeak $(M+H)^+$: 358 Found: molpeak $(M+H)^+$: 358
HPLC retention time: 5.20 min (method A)

3.32c

5'-[5-(4-chloro-phenyl)-pyridin-2-ylethynyl]-3-pyrrolidin-1-yl-3,4,5,6-tetrahydro-2H-[1,2']bipyridinyl Prepared according to general working method I from 5'-iodo-3-pyrrolidin-1-yl-3,4,5,6-tetrahydro-2H-[1,2']bipyridinyl (179 mg, 0.50 mmol) and 5-(4-chloro-phenyl)-2-ethynyl-pyridine (107 mg, 0.50 mmol).
Yield: 120 mg (54.2% of theory)
$C_{27}H_{27}ClN_4$ (M=442.996)
Calc.: molpeak $(M+H)^+$: 443/445 Found: molpeak $(M+H)^+$: 443/445
$R_f$ value: 0.38 (silica gel, DCM/MeOH/$NH_3$ 9:1:0.1)
HPLC retention time: 7.40 min (method A)

Example 3.33

1'-{5-[5-(4-chloro-phenyl)-pyridin-2-ylethynyl]-pyridin-2-yl}-[1,3']bipyrrolidinyl

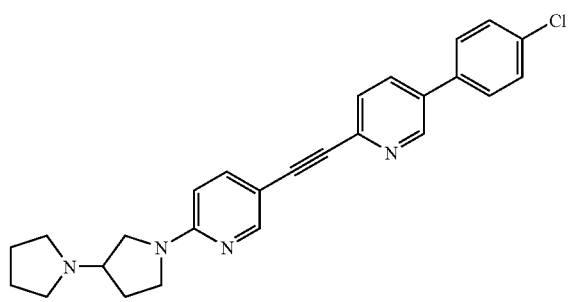 [SMILES: Clc1ccc(-c2ccc(C#Cc3ccc(N4CCC(N5CCCC5)C4)nc3)nc2)cc1]

3.33a

1'-benzyl-[1,3']bipyrrolidinyl 3.82 g (18.0 mmol) $NaBH(OAc)_3$ are added to a solution of 1.23 mL (15.0 mmol) pyrrolidine and 2.41 mL (15.0 mmol) N-benzylpyrrolidinone in 100 mL THF and acidified with 2 mL acetic acid. The reaction is stirred overnight at RT. The reaction solution is combined with 200 mL saturated $NaHCO_3$ solution and extracted twice with 200 mL EtOAc. The organic phase is dried over $MgSO_4$ and the solvent is eliminated i.vac. The purification is carried out by column chromatography on silica gel (EtOAc/MeOH/$NH_3$ 8:2:0.2).
Yield: 1.80 g (52.1% of theory)
$C_{15}H_{22}N_2$ (M=230.356)
Calc.: molpeak $(M+H)^+$: 231 Found: molpeak $(M+H)^+$: 231
$R_f$ value: 0.05 (silica gel, EtOAc/MeOH/$NH_3$ 9:1:0.1)

3.33b

[1,3']bipyrrolidinyl 180 mg 10% Pd/C are added to a solution of 1.80 g (7.42 mmol) 1'-benzyl-[1,3']bipyrrolidinyl in 80 mL MeOH. The reaction solution is stirred for 5 h at RT and at 3 bar $H_2$. Another 180 mg 10% Pd/C are added and after 4 h 100 mg palladium hydroxide are added. The reaction is stirred for a further 6 h at RT and at 3 bar $H_2$. The catalyst is suction filtered and the solvent is eliminated i.vac.
Yield: 900 mg (86.5% of theory)
$C_8H_{16}N_2$ (M=140.230)
$R_f$ value: 0.05 (silica gel, EtOAc/MeOH/$NH_3$ 8:2:0.2)

3.33c

1'-(5-bromo-pyridin-2-yl)-[1,3']bipyrrolidinyl

The product is obtained analogously to Example 3.31a (reaction time: 60 min at 170° C.) from 1.52 g (6.40 mmol) 2,5-dibromopyridine and 0.90 g (6.42 mmol) [1,3']bipyrrolidinyl.
Yield: 700 mg (36.8% of theory)
$C_{13}H_{18}BrN_3$ (M=296.213)
Calc.: molpeak $(M+H)^+$: 296/298 Found: molpeak $(M+H)^+$: 296/298
$R_f$ value: 0.42 (silica gel, EtOAc/MeOH/$NH_3$ 9:1:0.1)

3.33d

1'-(5-iodo-pyridin-2-yl)-[1,3']bipyrrolidinyl

Prepared according to general working method II from 1'-(5-bromo-pyridin-2-yl)-[1,3']bipyrrolidinyl (700 mg, 2.36 mmol).
Yield: 650 mg (80.1% of theory)
$C_{13}H_{18}IN_3$ (M=343.213)
Calc.: molpeak $(M+H)^+$: 344 Found: molpeak $(M+H)^+$: 344
HPLC retention time: 3.95 min (method A)

3.33e

1'-{5-[5-(4-chloro-phenyl)-pyridin-2-ylethynyl]-pyridin-2-yl}-[1,3']bipyrrolidinyl Prepared according to general working method I from 1'-(5-iodo-pyridin-2-yl)-[1,3']bipyrrolidinyl (172 mg, 0.50 mmol) and 5-(4-chloro-phenyl)-2-ethynyl-pyridine (107 mg, 0.50 mmol).
Yield: 65 mg (30.3% of theory)
$C_{26}H_{25}ClN_4$ (M=428.969)
Calc.: molpeak $(M+H)^+$: 429/431 Found: molpeak $(M+H)^+$: 429/431
$R_f$ value: 0.50 (silica gel, EtOAc/MeOH/$NH_3$ 9:1:0.1)
HPLC retention time: 6.71 min (method A)

Example 3.34

{5-[5-(4-chloro-phenyl)-pyridin-2-ylethynyl]-pyridin-2-yl}-(2-pyrrolidin-1-yl-propyl)-amine

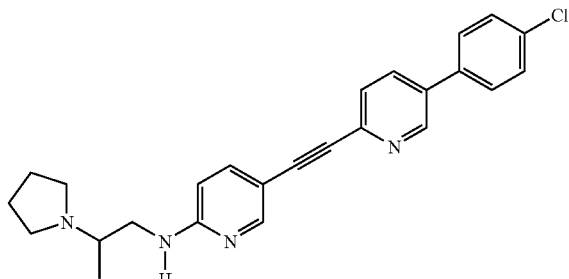

3.34a

N-(5-bromo-pyridin-2-yl)-2-chloro-propionamide 2.14 mL (22.0 mmol) 2-chloropropionic acid chloride in 5 mL DCM is added dropwise to a solution of 3.46 g (20.0 mmol) 2-amino-5-bromopyridine and 6.12 mL (44.0 mmol) triethylamine in 80 mL DCM at 0° C. The ice bath is removed and the reaction solution is stirred for a further 1.5 h at RT. Another 0.40 mL (4.12 mmol) 2-chloropropionic acid chloride is added and the solution is stirred for a further hour at RT. The reaction mixture is combined with 80 mL water, washed once with 80 mL saturated NaCl solution and dried over MgSO$_4$. The solvent is eliminated i.vac. and the residue is triturated with a little EtOAc, suction filtered and dried.

Yield: 3.50 g (66.4% of theory)
$C_8H_8BrClN_2O$ (M=263.523)
Calc.: molpeak (M+H)$^+$: 263/265/267 Found: molpeak (M+H)$^+$: 263/265/267
R$_f$ value: 0.85 (silica gel, PE/EtOAc 6:4)

3.34b

N-(5-bromo-pyridin-2-yl)-2-pyrrolidin-1-yl-propionamide 4.01 g (29.0 mmol) K$_2$CO$_3$ and 1.19 mL (14.5 mmol) pyrrolidine are added successively to a solution of 3.5 g (13.3 mmol) N-(5-bromo-pyridin-2-yl)-2-chloro-propionamide in 50 mL DMF. The reaction is stirred for 3 days at RT and combined with 150 mL water. The aqueous phase is extracted twice with EtOAc and the organic phase is dried over MgSO$_4$. After the desiccant and solvent have been eliminated the residue is purified by chromatography (silica gel, gradient: PE/EtOAc 4:6 after EtOAc).

Yield: 1.80 g (45.4% of theory)
$C_{12}H_{16}BrN_3O_3$ (M=298.185)
Calc.: molpeak (M+H)$^+$: 298/300 Found: molpeak (M+H)$^+$: 298/300
HPLC retention time: 4.21 min (method A)

3.34c (5-bromo-pyridin-2-yl)-(2-pyrrolidin-1-yl-propyl)-amine

Under a nitrogen atmosphere 6.00 mL (6.00 mmol) 1 M lithium aluminium hydride solution in THF are added to a solution, cooled to 0° C., of 1.8 g (6.04 mmol) N-(5-bromo-pyridin-2-yl)-2-pyrrolidin-1-yl-propionamide in 30 mL THF, in such a way that the internal temperature does not exceed 4° C. The reaction solution is stirred for a further 20 min at 0° C. EtOAc is carefully added, the aluminium complex is decomposed with 0.2 mL water, then with 0.2 mL 15% sodium hydroxide solution solution and finally with 0.6 mL water. The precipitate formed is suction filtered and the filtrate is diluted with 50 mL EtOAc. The organic phase is washed with 30 mL saturated NaHCO$_3$ solution and dried over MgSO$_4$. The solvent is eliminated i.vac. and further purification is carried out by column chromatography on silica gel (EtOAc/MeOH/NH$_3$ 9:1:0.1).

Yield: 700 mg (40.8% of theory)
$C_{12}H_{18}BrN_3$ (M=284.201)
Calc.: molpeak (M+H)$^+$: 284/286 Found: molpeak (M+H)$^+$: 284/286
R$_f$ value: 0.32 (silica gel, EtOAc/MeOH/NH$_3$ 9:1:0.1)
HPLC retention time: 4.63 min (method A)

3.34d (5-iodo-pyridin-2-yl)-(2-pyrrolidin-1-yl-propyl)-amine

Prepared according to general working method II from (5-bromo-pyridin-2-yl)-(2-pyrrolidin-1-yl-propyl)-amine (600 mg, 2.11 mmol).

Yield: 560 mg (80.1% of theory)

3.34e

{5-[5-(4-chloro-phenyl)-pyridin-2-ylethynyl]-pyridin-2-yl}-(2-pyrrolidin-1-yl-propyl)-amine Prepared according to general working method I from (5-iodo-pyridin-2-yl)-(2-pyrrolidin-1-yl-propyl)-amine (250 mg, 0.76 mmol) and 5-(4-chloro-phenyl)-2-ethynyl-pyridine (165 mg, 0.77 mmol).

Yield: 95 mg (29.5% of theory)
$C_{25}H_{25}ClN_4$ (M=416.958)
Calc.: molpeak (M+H)$^+$: 417/419 Found: molpeak (M+H)$^+$: 417/419
HPLC retention time: 7.19 min (method A)

Example 3.35

N-{4-[5-(4-chloro-phenyl)-pyridin-2-ylethynyl]-phenyl}-2-pyrrolidin-1-yl-propionamide

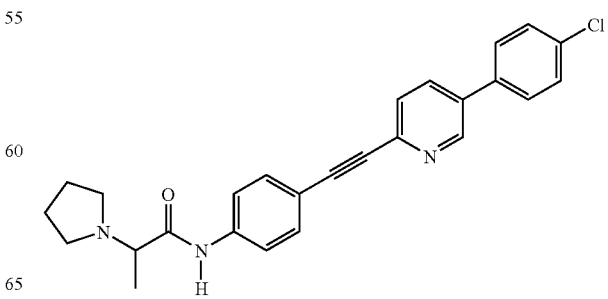

3.35a

4-[5-(4-chloro-phenyl)-pyridin-2-ylethynyl]-phenylamine

Prepared according to general working method I from 4-iodoaniline (732 mg, 3.28 mmol) and 5-(4-chloro-phenyl)-2-ethynyl-pyridine (700 mg, 3.28 mmol).

Yield: 440 mg (44.1% of theory)
$C_{19}H_{13}ClN_2$ (M=304.782)
Calc.: molpeak (M+H)$^+$: 305/307 Found: molpeak (M+H)$^+$: 305/307
HPLC retention time: 5.70 min (method A)

3.35b

N-{4-[5-(4-chloro-phenyl)-pyridin-2-ylethynyl]-phenyl}-2-pyrrolidin-1-yl-propionamide 0.18 mL (1.31 mmol) triethylamine and 269 mg (0.84 mmol) TBTU are added successively to a solution of 100 mg (0.70 mmol) 2-pyrrolidin-1-yl-propionic acid in 10 mL THF. The solution is stirred for 1 h at RT and then 200 mg (0.66 mmol) 4-[5-(4-chloro-phenyl)-pyridin-2-ylethynyl]-phenylamine are added. The reaction solution is stirred overnight at RT. The reaction is incomplete. Therefore 100 mg (0.70 mmol) 2-pyrrolidin-1-yl-propionic acid in 10 mL THF is added to the reaction mixture (activated for 1 h by stirring with 0.18 mL (1.31 mmol) triethylamine and 269 mg (0.84 mmol) TBTU). The reaction solution is stirred for a further 16 h and diluted with NaHCO$_3$ solution. The aqueous phase is extracted with EtOAc and the organic phase is dried over MgSO$_4$. The solvent is eliminated i.vac. and further purification is carried out by column chromatography on silica gel (EtOAc/MeOH/NH$_3$ 8:2:0.2).

Yield: 40 mg (14.2% of theory)
$C_{26}H_{24}ClN_3O$ (M=429.954)
Calc.: molpeak (M+H)$^+$: 430/432 Found: molpeak (M+H)$^+$: 430/432
HPLC retention time: 7.29 min (method A)

Example 3.36

N-{4-[5-(4-chloro-phenyl)-pyridin-2-ylethynyl]-phenyl}-2-pyrrolidin-1-yl-acetamide

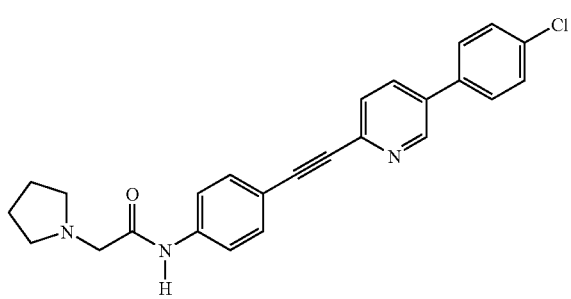 [SMILES: O=C(CN1CCCC1)Nc1ccc(C#Cc2ccc(-c3ccc(Cl)cc3)cn2)cc1]

The product is obtained analogously to Example 3.35b from 200 mg (0.66 mmol) 4-[5-(4-chloro-phenyl)-pyridin-2-ylethynyl]-phenylamine and 100 mg (0.77 mmol) pyrrolidin-1-yl-acetic acid. Yield: 5 mg (1.8% of theory)
$C_{25}H_{22}ClN_3O$ (M=415.927)
Calc.: molpeak (M+H)$^+$: 416/418 Found: molpeak (M+H)$^+$: 416/418
HPLC retention time: 6.75 min (method B)

Example 3.37

5-[5-(4-chloro-phenyl)-pyridin-2-ylethynyl]-1-(2-pyrrolidin-1-yl-ethyl)-1,3-dihydro-benzimidazol-2-one

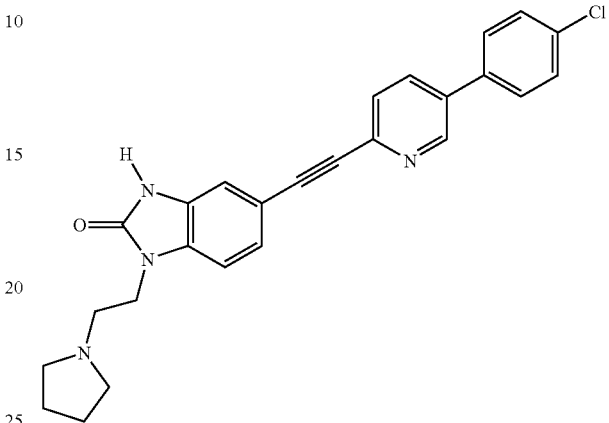

3.37a (4-bromo-2-nitro-phenyl)-(2-pyrrolidin-1-yl-ethyl)-amine 4.42 g (32.0 mmol) K$_2$CO$_3$ are added to a solution of 5.00 g (22.7 mmol) 2-bromo-5-fluoronitrobenzene and 2.59 g (22.7 mmol) 1-(2-amino)-pyrrolidine in 20 mL acetonitrile. The reaction solution is stirred overnight at RT. The solution is filtered and the solvent is eliminated i.vac. The purification is carried out by column chromatography on silica gel (gradient: DCM to DCM/MeOH 9:1).

Yield: 5.90 g (82.6% of theory)
$C_{12}H_{16}BrN_3O_2$ (M=314.184)
Calc.: molpeak (M+H)$^+$: 314/316 Found: molpeak (M+H)$^+$: 314/316
R$_f$ value: 0.40 (silica gel, DCM/MeOH 9:1)

3.37b 4-bromo-N$^1$-(2-pyrrolidin-1-yl-ethyl)-benzene-1,2-diamine 100 mg Raney Nickel are added to a solution of 1.00 g (3.18 mmol) (4-bromo-2-nitro-phenyl)-(2-pyrrolidin-1-yl-ethyl)-amine in 100 mL MeOH. The reaction solution is stirred for 15 min at 3 bar H$_2$ and RT. After filtration the solvent is eliminated i.vac. and the product is further reacted without purification.

Yield: 850 mg (94.0% of theory)
$C_{12}H_{18}BrN_3$ (M=284.201)
Calc.: molpeak (M+H)$^+$: 284/286 Found: molpeak (M+H)$^+$: 284/286
HPLC retention time: 4.56 min (method A)

3.37c

5-bromo-1-(2-pyrrolidin-1-yl-ethyl)-1,3-dihydro-benzimidazol-2-one

600 mg (3.70 mmol) CDI are added to a solution of 853 mg (3.00 mmol) 4-bromo-N[1]-(2-pyrrolidin-1-yl-ethyl)-benzene-1,2-diamine in 20 mL THF at RT. The reaction solution is heated to 40° C. and stirred for 30 min at this temperature. A further 600 mg (3.70 mmol) CDI are added and the reaction is stirred for a further 30 min at 40° C. The solution is diluted with semisaturated NaHCO$_3$ solution and the aqueous phase is extracted twice with EtOAc. The organic phase is dried over MgSO$_4$ and the solvent is eliminated i.vac. The residue is triturated with acetonitrile, the precipitate is filtered and dried in the air.
Yield: 500 mg (53.7% of theory)
$C_{13}H_{16}BrN_3O$ (M=310.196)
Calc.: molpeak (M+H)$^+$: 310/312 Found: molpeak (M+H)$^+$: 310/312
HPLC retention time: 4.30 min (method A)

3.37d

5-iodo-1-(2-pyrrolidin-1-yl-ethyl)-1,3-dihydro-benzimidazol-2-one

Prepared according to general working method II from 5-bromo-1-(2-pyrrolidin-1-yl-ethyl)-1,3-dihydro-benzimidazol-2-one (150 mg, 0.48 mmol).
Yield: 140 mg (81.0% of theory)
$C_{13}H_{16}IN_3O$ (M=357.196)
Calc.: molpeak (M+H)$^+$: 358 Found: molpeak (M+H)$^+$: 358
HPLC retention time: 4.53 min (method A)

3.37e

5-[5-(4-chloro-phenyl)-pyridin-2-ylethynyl]-1-(2-pyrrolidin-1-yl-ethyl)-1,3-dihydro-benzimidazol-2-one

Prepared according to general working method I from 5-iodo-1-(2-pyrrolidin-1-yl-ethyl)-1,3-dihydro-benzimidazol-2-one (140 mg, 0.39 mmol) and 5-(4-chloro-phenyl)-2-ethynyl-pyridine (83 mg, 0.39 mmol).
Yield: 7 mg (3.7% of theory)
$C_{26}H_{23}ClN_4O$ (M=442.952)
Calc.: molpeak (M+H)$^+$: 443/445 Found: molpeak (M+H)$^+$: 443/445
HPLC retention time: 6.78 min (method A)

Example 3.38

5-[5-(4-chloro-phenyl)-pyridin-2-ylethynyl]-3-methyl-1-(2-pyrrolidin-1-yl-ethyl)-1,3-dihydro-benzoimidazol-2-one

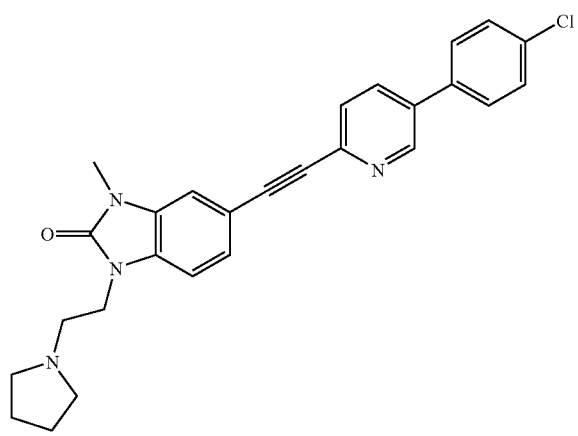 [SMILES: Cn1c(=O)n(CCN2CCCC2)c2ccc(C#Cc3ccc(-c4ccc(Cl)cc4)cn3)cc21]

3.38a

5-bromo-3-methyl-1-(2-pyrrolidin-1-yl-ethyl)-1,3-dihydro-benzimidazol-2-one

73 mg (0.65 mmol) potassium-tert-butoxide are added to a solution of 200 mg (0.65 mmol) 5-bromo-1-(2-pyrrolidin-1-yl-ethyl)-1,3-dihydro-benzimidazol-2-one in 4 mL DMSO at RT. The reaction solution is stirred for 30 min and then 40 µL (0.65 mmol) iodomethane are added and stirred for a further 30 min. The mixture is combined with semisaturated NaHCO$_3$ solution and the aqueous phase is extracted twice with 30 mL EtOAc. The organic phase is dried over MgSO$_4$ and the solvent is eliminated i.vac.
Yield: 180 mg (86.1% of theory)
$C_{14}H_{18}BrN_3O$ (M=324.223)
Calc.: molpeak (M+H)$^+$: 324/326 Found: molpeak (M+H)$^+$: 324/326
HPLC retention time: 4.69 min (method B)

3.38b

5-iodo-3-methyl-1-(2-pyrrolidin-1-yl-ethyl)-1,3-dihydro-benzimidazol-2-one

Prepared according to general working method II from 5-bromo-3-methyl-1-(2-pyrrolidin-1-yl-ethyl)-1,3-dihydro-benzimidazol-2-one (160 mg, 0.49 mmol).
Yield: 120 mg (65.6% of theory)
$C_{14}H_{18}IN_3O$ (M=371.223)
Calc.: molpeak (M+H)$^+$: 372 Found: molpeak (M+H)$^+$: 372
HPLC retention time: 5.02 min (method A)

3.38c

5-[5-(4-chloro-phenyl)-pyridin-2-ylethynyl]-3-methyl-1-(2-pyrrolidin-1-yl-ethyl)-1,3-dihydro-benzimidazol-2-one

Prepared according to general working method I from 5-iodo-3-methyl-1-(2-pyrrolidin-1-yl-ethyl)-1,3-dihydro-benzimidazol-2-one (120 mg, 0.32 mmol) and 5-(4-chloro-phenyl)-2-ethynyl-pyridine (68 mg, 0.32 mmol).
Yield: 15 mg (9.8% of theory)
$C_{27}H_{25}ClN_4O$ (M=456.980)
Calc.: molpeak (M+H)$^+$: 457/459 Found: molpeak (M+H)$^+$: 457/459
HPLC retention time: 7.11 min (method A)

Example 3.39

6-[5-(4-chloro-phenyl)-pyridin-2-ylethynyl]-3-(2-pyrrolidin-1-yl-ethyl)-3H-imidazo[4,5-b]pyridine

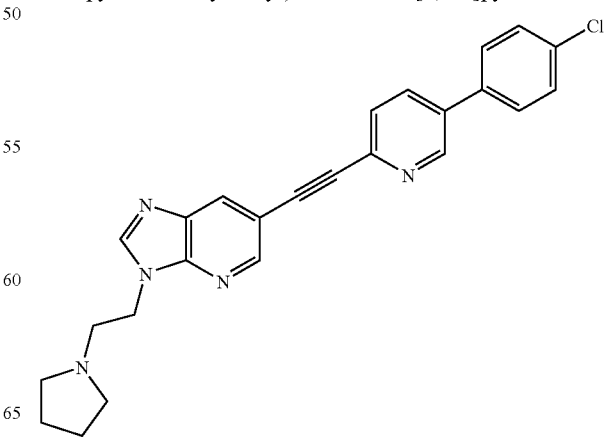

3.39a (5-bromo-3-nitro-pyridin-2-yl)-(2-pyrrolidin-1-yl-ethyl)-amine 0.86 mL (5.05 mmol) ethyldiiopropylamine are added to a solution of 600 mg (2.53 mmol) 5-bromo-2-chloro-3-nitro-pyridine and 0.32 mL (2.53 mmol) 1-(2-aminoethyl)-pyrrolidine in 3 mL n-butanol. The reaction is heated to 50° C. and stirred for one hour at this temperature. The solvent is eliminated i.vac. and the residue is combined with 40 mL water and acidified with 1 M HCl. The aqueous phase is extracted with 20 mL EtOAc and the aqueous phase is then made alkaline with saturated $K_2CO_3$ solution. The aqueous phase is extracted with 40 mL EtOAc. The organic phase is dried over $Na_2SO_4$ and the solvent is eliminated i.vac.

Yield: 692 mg (86.9% of theory)
$C_{11}H_{15}BrN_4O_2$ (M=315.172)
Calc.: molpeak (M+H)$^+$: 315/317 Found: molpeak (M+H)$^+$: 315/317
HPLC retention time: 5.00 min (method A)
$R_f$ value: 0.08 (silica gel, cyc/EtOAc 2:1)

3.39b 5-bromo-$N^2$-(2-pyrrolidin-1-yl-ethyl)-pyridine-2,3-diamine 2.44 g (10.8 mmol) Zinn(II)chloride dihydrate and 2.20 g (26.2 mmol) $NaHCO_3$ are added to a solution of 680 mg (2.16 mmol) (5-bromo-3-nitro-pyridin-2-yl)-(2-pyrrolidin-1-yl-ethyl)-amine in 40 mL EtOAc at RT. The reaction is refluxed for 1.5 h and then diluted with 20 mL water. The aqueous phase is acidified with 1 M HCl and separated off from the organic phase. The aqueous phase is made alkaline with saturated $K_2CO_3$ solution and extracted twice with 40 mL EtOAc. The organic phase is dried over $Na_2SO_4$ and the solvent is eliminated i.vac.

Yield: 479 mg (77.8% of theory)
$C_{11}H_{17}BrN_4$ (M=285.189)
Calc.: molpeak (M+H)$^+$: 285/287 Found: molpeak (M+H)$^+$: 285/287
HPLC retention time: 3.9 min (method A)

3.39c 6-bromo-3-(2-pyrrolidin-1-yl-ethyl)-3H-imidazo[4,5-b]pyridine

A solution of 470 mg (1.65 mmol) 5-bromo-$N^2$-(2-pyrrolidin-1-yl-ethyl)-pyridine-2,3-diamine in 10 mL formic acid is refluxed for 1.5 h. The mixture is made alkaline with saturated $K_2CO_3$ solution and extracted with 40 mL EtOAc. The organic phase is dried over $Na_2SO_4$ and the solvent is eliminated i.vac.

Yield: 466 mg (95.8% of theory)
$C_{12}H_{15}BrN_4$ (M=295.184)
Calc.: molpeak (M+H)$^+$: 295/297 Found: molpeak (M+H)$^+$: 295/297
HPLC retention time: 4.0 min (method A)

3.39d 6-iodo-3-(2-pyrrolidin-1-yl-ethyl)-3H-imidazo[4,5-b]pyridine

Prepared according to general working method II from 6-bromo-3-(2-pyrrolidin-1-yl-ethyl)-3H-imidazo[4,5-b]pyridine (450 mg, 1.52 mmol).

Yield: 510 mg (97.8% of theory)
$C_{12}H_{15}IN_4$ (M=342.185)
Calc.: molpeak (M+H)$^+$: 343 Found: molpeak (M+H)$^+$: 343
HPLC retention time: 4.08 min (method A)
$R_f$ value: 0.09 (silica gel, EtOAc/MeOH/$NH_3$ 9:1:0.1)

3.39e

6-[5-(4-chloro-phenyl)-pyridin-2-ylethynyl]-3-(2-pyrrolidin-1-yl-ethyl)-3H-imidazo[4,5-b]pyridine Prepared according to general working method I from 6-iodo-3-(2-pyrrolidin-1-yl-ethyl)-3H-imidazo[4,5-b]pyridine (300 mg, 0.88 mmol) and 5-(4-chloro-phenyl)-2-ethynyl-pyridine (187 mg, 0.88 mmol).

Yield: 67 mg (17.9% of theory)
$C_{25}H_{22}ClN_5$ (M=427.941)
Calc.: molpeak (M+H)$^+$: 428/430 Found: molpeak (M+H)$^+$: 428/430
$R_f$ value: 0.41 (silica gel, DCM/MeOH/$NH_3$ 9:1:0.1)
HPLC retention time: 6.52 min (method A)

Example 3.40

5-[5-(4-chloro-phenyl)-pyridin-2-ylethynyl]-2-pyrrolidin-1-ylmethyl-1H-benzimidazole

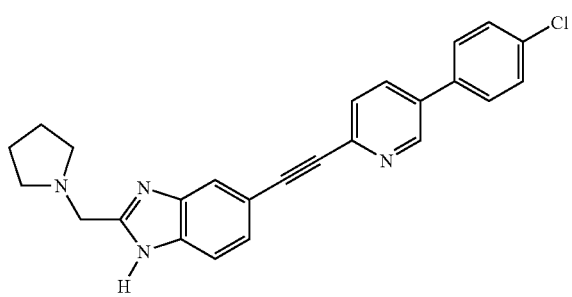 [SMILES: Clc1ccc(-c2ccc(C#Cc3ccc4[nH]c(CN5CCCC5)nc4c3)nc2)cc1]

3.40a (5-nitro-1H-benzimidazol-2-yl)-methanol 6.2 g (81.5 mmol) glycolic acid is added to a solution of 6.24 g (40.8 mmol) 4-nitro-o-phenylenediamine in 80 mL semiconcentrated HCl. The reaction solution is refluxed for 4 h and the solvent is eliminated i.vac. The residue is taken up in water and made basic with 2 N NaOH. The product precipitates out and is stirred for another 1 hour in the ice bath. The precipitate is suction filtered and washed successively with water and PE. The product is dried at 40° C. This still contains 40% 4-nitro-o-phenylenediamine. It is again taken up in semiconcentrated HCl and after the addition of 6.5 mL glycolic acid (57% in water) it is refluxed for 3 h and heated for a further 12 h at 80° C. The solvent is eliminated i.vac. and the residue is dissolved in water and made alkaline with 6 N NaOH, during which time the product is precipitated. The precipitate is suction filtered and washed successively with water and PE. The product is dried in the circulating air dryer at 50° C.

Yield: 6.40 g (81.3% of theory)
$C_8H_7N_3O_3$ (M=193.163)

Calc.: molpeak (M+H)⁺: 194 Found: molpeak (M+H)⁺: 194

R_f value: 0.13 (silica gel, DCM/MeOH/NH₃ 9:1:0.1)

3.40b 2-chloromethyl-5-nitro-1H-benzimidazole 20 mL (275 mmol) thionyl chloride are added slowly to a solution of 6.4 g (33.1 mmol) (5-nitro-1H-benzimidazol-2-yl)-methanol in 100 mL DCM at 10° C. The reaction is stirred for 1 h at RT and the solvent is eliminated i.vac. The residue is triturated with DCM, suction filtered, washed with DCM and ether and dried in the circulating air dryer at 35° C.

Yield: 7.01 g (100% of theory)
$C_8H_6ClN_3O_3$ (M=211.609)
Calc.: molpeak (M+H)⁺: 212/214 Found: molpeak (M+H)⁺: 212/214
HPLC retention time: 4.1 min (method B)

3.40c 5-nitro-2-pyrrolidin-1-ylmethyl-1H-benzimidazole 9.47 mL (113 mmol) pyrrolidine are added to a solution of 6.00 g (28.4 mmol) 2-chloromethyl-5-nitro-1H-benzimidazole in 100 mL DCM. The reaction is stirred overnight at RT. The reaction solution is washed four times with water. The organic phase is dried over MgSO₄ and the solvent is eliminated i.vac.

Yield: 5.50 g (78.8% of theory)
$C_{12}H_{14}N_4O_2$ (M=246.271)
Calc.: molpeak (M+H)⁺: 247 Found: molpeak (M+H)⁺: 247
R_f value: 0.22 (silica gel, EtOAc/MeOH 9:1)

3.40d 2-pyrrolidin-1-ylmethyl-1H-benzimidazol-5-ylamine 1.00 g Raney nickel is added to a solution of 5.50 g (22.3 mmol) 5-nitro-2-pyrrolidin-1-ylmethyl-1H-benzimidazole in 50 mL MeOH. The reaction solution is stirred for 30 h at 3 bar H₂ and RT. After filtration the solvent is eliminated i.vac. and further purification is carried out by column chromatography on silica gel (EtOAc/MeOH/NH₃ 8:2:0.2).

Yield: 3.10 g (64.2% of theory)
$C_{12}H_{16}N_4$ (M=216.288)
Calc.: molpeak (M+H)⁺: 217 Found: molpeak (M+H)⁺: 217

3.40e 5-bromo-2-pyrrolidin-1-ylmethyl-1H-benzimidazole 3.10 g (14.3 mmol) 2-pyrrolidin-1-ylmethyl-1H-benzimidazol-5-ylamine is suspended in 32.2 mL 48% hydrobromic acid and 32.2 mL water and the solution is cooled to 0° C. 2.5 M sodium nitrite solution (1.68 g in 9.7 mL water) is slowly added dropwise, so that the internal temperature does not exceed 5° C. The reaction is stirred for 10 min at 0° C. and then 3.50 g (24.37 mmol) CuBr in 11.3 mL 48% hydrobromic acid is added dropwise. The reaction is heated to 60° C. and stirred for one hour at this temperature. The solvent is eliminated i.vac. and the residue triturated with isopropanol. The precipitate is suction filtered and washed with isopropanol. The purification is carried out by column chromatography on silica gel (MeOH/NH₃ 9:1).

Yield: 2.20 g (54.8% of theory)
$C_{12}H_{14}BrN_3$ (M=280.169)
Calc.: molpeak (M+H)⁺: 280/282 Found: molpeak (M+H)⁺: 280/282
HPLC retention time: 4.47 min (method A)

3.40f 5-iodo-2-pyrrolidin-1-ylmethyl-1H-benzimidazole

Prepared according to general working method II from 5-bromo-2-pyrrolidin-1-ylmethyl-1H-benzimidazole (700 mg, 2.50 mmol).

Yield: 200 mg (24.5% of theory)
$C_{12}H_{14}IN_3$ (M=327.170)
Calc.: molpeak (M+H)⁺: 328 Found: molpeak (M+H)⁺: 328
HPLC retention time: 4.55 min (method A)

3.40g

5-[5-(4-chloro-phenyl)-pyridin-2-ylethynyl]-2-pyrrolidin-1-ylmethyl-1H-benzimidazole Prepared according to general working method I from 5-iodo-2-pyrrolidin-1-ylmethyl-1H-benzimidazole (200 mg, 0.61 mmol) and 5-(4-chloro-phenyl)-2-ethynyl-pyridine (131 mg, 0.61 mmol).

Yield: 5 mg (2.0% of theory)
$C_{25}H_{21}ClN_4$ (M=412.926)
Calc.: molpeak (M−H)⁻: 411/413 Found: molpeak (M−H)⁻: 411/413
HPLC retention time: 3.94 min (method A)

Example 3.41

5-[5-(4-chloro-phenyl)-pyridin-2-ylethynyl]-1-(2-pyrrolidin-1-yl-ethyl)-1H-benzimidazole

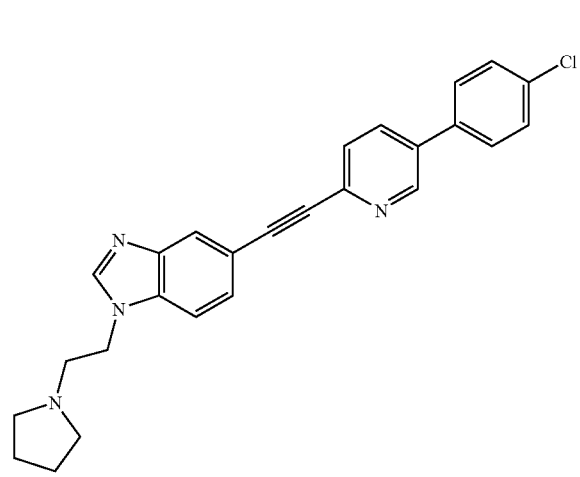 [SMILES: Clc1ccc(-c2ccc(C#Cc3ccc4c(c3)ncn4CCN3CCCC3)nc2)cc1]

3.41a 5-bromo-1-(2-pyrrolidin-1-yl-ethyl)-1H-benzimidazole

A solution of 904 mg (3.18 mmol) 4-bromo-N¹-(2-pyrrolidin-1-yl-ethyl)-benzene-1,2-diamine in 5 mL formic acid is refluxed for 1.5 h. It is made alkaline with semisaturated NaHCO$_3$ solution and extracted twice with 70 mL EtOAc. The organic phase is dried over MgSO$_4$ and the solvent is eliminated i.vac.

Yield: 750 mg (80.2% of theory)
C$_{13}$H$_{16}$BrN$_3$ (M=294.197)
Calc.: molpeak (M+H)$^+$: 294/296 Found: molpeak (M+H)$^+$: 294/296
HPLC retention time: 3.78 min (method A)

3.41b 5-iodo-1-(2-pyrrolidin-1-yl-ethyl)-1H-benzimidazole

Prepared according to general working method II from 5-bromo-1-(2-pyrrolidin-1-yl-ethyl)-1H-benzimidazole (750 mg, 2.55 mmol).

Yield: 680 mg (78.2% of theory)
C$_{13}$H$_{16}$IN$_3$ (M=341.197)
Calc.: molpeak (M+H)$^+$: 342 Found: molpeak (M+H)$^+$: 342
HPLC retention time: 4.04 min (method A)

3.41c

5-[5-(4-chloro-phenyl)-pyridin-2-ylethynyl]-1-(2-pyrrolidin-1-yl-ethyl)-1H-benzimidazole Prepared according to general working method I from 5-iodo-1-(2-pyrrolidin-1-yl-ethyl)-1H-benzimidazole (150 mg, 0.44 mmol) and 5-(4-chloro-phenyl)-2-ethynyl-pyridine (94 mg, 0.44 mmol).

Yield: 26 mg (13.7% of theory)
C$_{26}$H$_{23}$ClN$_4$ (M=426.953)
Calc.: molpeak (M+H)$^+$: 427/429 Found: molpeak (M+H)$^+$: 427/429
HPLC retention time: 6.51 min (method A)

Example 3.42

2-[5-(4-chloro-phenyl)-pyridin-2-ylethynyl]-1-methyl-5-pyrrolidin-1-ylmethyl-1H-benzimidazole

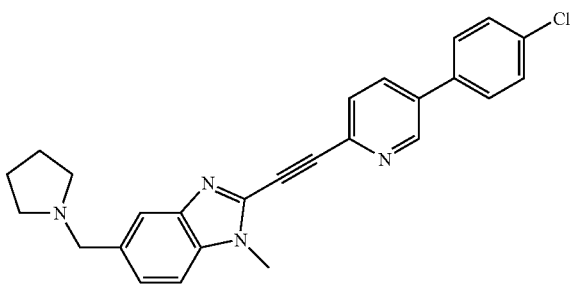 [SMILES: Cn1c(C#Cc2ccc(-c3ccc(Cl)cc3)cn2)nc2cc(CN3CCCC3)ccc21]

3.42a methyl-(2-nitro-4-pyrrolidin-1-ylmethyl-phenyl)-amine 5.55 g (78.0 mmol) pyrrolidine are added to a solution of 4.70 g (26.1 mmol) 4-methylamino-3-nitro-benzaldehyde in 100 mL THF and the reaction mixture is acidified with glacial acetic acid. 6.36 g (30.0 mmol) NaBH(OAc)$_3$ are added and the reaction mixture is stirred overnight at RT. The mixture is combined with saturated NaHCO$_3$ solution and the aqueous phase is extracted twice with EtOAc. The combined organic extracts are washed with 200 mL semisaturated NaHCO$_3$ solution and dried over MgSO$_4$. The solvent is eliminated i.vac. and further purification is carried out by column chromatography on silica gel (gradient: DCM to DCM/MeOH 9:1).

Yield: 2.00 g (32.6% of theory)
C$_{12}$H$_{17}$N$_3$O$_2$ (M=235.288)
Calc.: molpeak (M+H)$^+$: 236 Found: molpeak (M+H)$^+$: 236
R$_f$ value: 0.15 (silica gel, DCM/MeOH 9:1)

3.42b

N$^1$-methyl-4-pyrrolidin-1-ylmethyl-benzene-1,2-diamine 4.85 g (21.5 mmol) tin(II)chloride dihydrate and 4.45 g (53.0 mmol) NaHCO$_3$ are added to a solution of 1.00 g (4.25 mmol) methyl-(2-nitro-4-pyrrolidin-1-ylmethyl-phenyl)-amine in 60 mL EtOAc at RT. The reaction is refluxed for 2 h and then diluted with 100 mL 1 M KHSO$_4$ solution and some water. The mixture is filtered. The aqueous phase is combined with K$_2$CO$_3$ and extracted twice with 80 mL EtOAc. The organic phase is dried over MgSO$_4$ and the solvent is eliminated i.vac.

Yield: 850 mg (97.4% of theory)
C$_{12}$H$_{19}$N$_3$ (M=205.305)
Calc.: molpeak (M+H)$^+$: 206 Found: molpeak (M+H)$^+$: 206
R$_f$ value: 0.15 (silica gel, DCM/MeOH/NH$_3$ 9:1:0.1)

3.42c 1-methyl-5-pyrrolidin-1-ylmethyl-1H-benzimidazole

A solution of 850 mg (4.14 mmol) N$^1$-methyl-4-pyrrolidin-1-ylmethyl-benzene-1,2-diamine in 4 mL formic acid is refluxed for 1.5 h. It is made alkaline with 250 mL semisaturated NaHCO$_3$ solution and extracted twice with 70 mL EtOAc. The organic phase is dried over MgSO$_4$ and the solvent is eliminated i.vac.

Yield: 650 mg (72.9% of theory)
C$_{13}$H$_{17}$N$_3$ (M=215.301)
Calc.: molpeak (M+H)$^+$: 216 Found: molpeak (M+H)$^+$: 216
R$_f$ value: 0.25 (silica gel, DCM/MeOH/NH$_3$ 9:1:0.1)

3.42d 2-iodo-1-methyl-5-pyrrolidin-1-ylmethyl-1H-benzimidazole 0.80 mL (1.28 mmol) 1.6 M n-butyllithium solution in hexane are added to a solution, cooled to −75° C., of 250 mg (1.16 mmol) 1-methyl-5-pyrrolidin-1-ylmethyl-1H-benzimidazole in 8 mL THF. The reaction mixture is stirred for 10 min at this temperature and then 288 mg (1.28 mmol) N-iodosuccinimide in 5 mL THF are added. The cooling bath is removed and the reaction stirred for 1 h at RT. 12 mL 0.1 M HCl are added and the aqueous phase is extracted with EtOAc. The organic phase is dried over MgSO$_4$ and the solvent is eliminated i.vac. The purification is carried out by column chromatography on silica gel (gradient: DCM to DCM/MeOH/NH$_3$ 9:1:0.1).

Yield: 140 mg (22.2% of theory)
$C_{13}H_{16}IN_3$ (M=341.197)
Calc.: molpeak (M+H)$^+$: 342 Found: molpeak (M+H)$^+$: 342
$R_f$ value: 0.20 (silica gel, DCM/MeOH/NH$_3$ 9:1:0.1)
HPLC retention time: 3.89 min (method A)

3.42e

2-[5-(4-chloro-phenyl)-pyridin-2-ylethynyl]-1-methyl-5-pyrrolidin-1-ylmethyl-1H-benzimidazole Prepared according to general working method I from 2-iodo-1-methyl-5-pyrrolidin-1-ylmethyl-1H-benzimidazole (100 mg, 0.29 mmol) and 5-(4-chloro-phenyl)-2-ethynyl-pyridine (68 mg, 0.32 mmol).
Yield: 9 mg (7.2% of theory)
$C_{26}H_{23}ClN_4$ (M=426.953)
Calc.: molpeak (M+H)$^+$: 427/429 Found: molpeak (M+H)$^+$: 427/429
$R_f$ value: 0.20 (silica gel, DCM/MeOH/NH$_3$ 9:1:0.1)
HPLC retention time: 6.69 min (method A)

Example 3.43

5-(4-chloro-phenyl)-2-[2-fluoro-4-(2-pyrrolidin-1-yl-ethoxy)-phenylethynyl]-pyridine

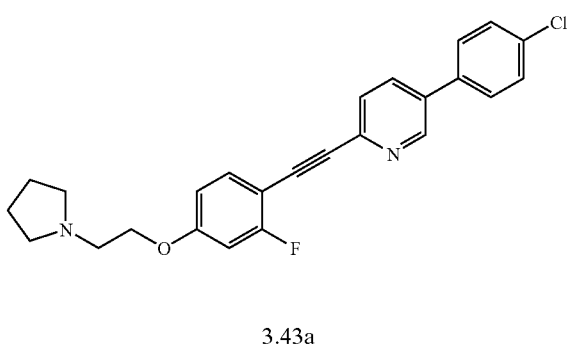

3.43a

1-[2-(3-fluoro-4-iodo-phenoxy)-ethyl]-pyrrolidine

The product is obtained analogously to Example 3.1e from 13.6 g (57.0 mmol) 3-fluoro-4-iodo-phenol and 9.69 g (57.0 mmol) N-(2-chloroethyl)-pyrrolidine hydrochloride.
Yield: 17.1 g (89.6% of theory)
$C_{12}H_{15}FINO$ (M=335.162)
Calc.: molpeak (M+H)$^+$: 336 Found: molpeak (M+H)$^+$: 336
$R_f$ value: 0.57 (silica gel, EtOAc/MeOH/NH$_3$ 95:5:0.5).

3.43b 5-(4-chloro-phenyl)-2-[2-fluoro-4-(2-pyrrolidin-1-yl-ethoxy)-phenylethynyl]-pyridine Prepared according to general working method I from 1-[2-(3-fluoro-4-iodo-phenoxy)-ethyl]-pyrrolidine (500 mg, 0.75 mmol) and 5-(4-chloro-phenyl)-2-ethynyl-pyridine (159 mg, 0.75 mmol).
Yield: 48 mg (15.4% of theory)
$C_{25}H_{22}ClFN_2O$ (M=420.918)

Calc.: molpeak (M+H)$^+$: 421/423 Found: molpeak (M+H)$^+$: 421/423
$R_f$ value: 0.65 (silica gel, EtOAc/MeOH/NH$_3$ 9:1:0.1)
HPLC retention time: 7.74 min (method A)

Example 3.44

5-[5-(4-chloro-phenyl)-pyridin-2-ylethynyl]-8-(2-pyrrolidin-1-yl-ethoxy)-quinoline

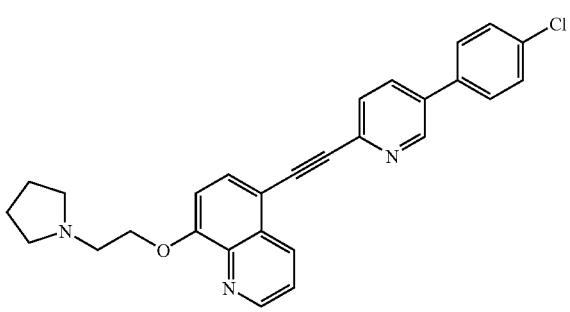 [SMILES: Clc1ccc(-c2ccc(C#Cc3ccc(OCCN4CCCC4)c4ncccc34)nc2)cc1]

3.44a 5-iodo-8-(2-pyrrolidin-1-yl-ethoxy)-quinoline

The product is obtained analogously to Example 3.1e from 700 mg (2.58 mmol) 5-iodo-quinolin-8-ol and 450 mg (2.59 mmol) N-(2-chloroethyl)-pyrrolidine hydrochloride.
Yield: 829 mg (87.2% of theory)
$C_{15}H_{17}IN_2O$ (M=368.220)
Calc.: molpeak (M+H)$^+$: 369 Found: molpeak (M+H)$^+$: 369
HPLC retention time: 5.56 min (method B)

3.44b

5-[5-(4-chloro-phenyl)-pyridin-2-ylethynyl]-8-(2-pyrrolidin-1-yl-ethoxy)-quinoline Prepared according to general working method I from 5-iodo-8-(2-pyrrolidin-1-yl-ethoxy)-quinoline (200 mg, 0.54 mmol) and 5-(4-chloro-phenyl)-2-ethynyl-pyridine (116 mg, 0.54 mmol).
Yield: 23 mg (9.4% of theory)
$C_{28}H_{24}ClN_3O$ (M=453.976)
Calc.: molpeak (M+H)$^+$: 454/456 Found: molpeak (M+H)$^+$: 454/456
HPLC retention time: 7.40 min (method A)

Example 3.45

6-[5-(4-chloro-phenyl)-pyridin-2-ylethynyl]-2-pyrrolidin-1-ylmethyl-quinoline

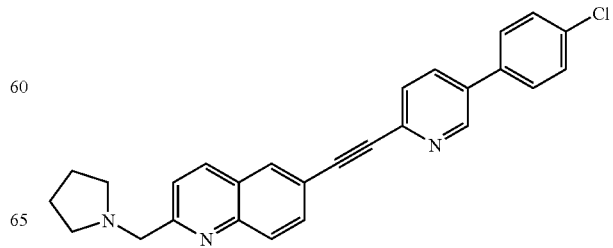

3.45a

6-bromo-2-brom0methyl-quinoline 148 mg (1.00 mmol) α,α-azoisobutyronitrile and 8.01 g (45.0 mmol) N-bromosuccinimide are added successively to a solution of 10.0 g (45.0 mmol) 6-bromo-2-methyl-quinoline in 60 mL carbon tetrachloride. The reaction mixture is refluxed for 8 h. It is filtered and the filtrate is washed twice with water. The organic phase is dried over MgSO$_4$ and the solvent is eliminated i.vac. The purification is carried out by column chromatography on silica gel (PE/EtOAc 4:1).

Yield: 5.10 g (37.7% of theory)
$C_{10}H_7Br_2N$ (M=300.982)
Calc.: molpeak (M+H)$^+$: 300/302/304 Found: molpeak (M+H)$^+$: 300/302/304
HPLC retention time: 5.75 min (method B)

3.45b

6-bromo-2-pyrrolidin-1-ylmethyl-quinoline 4.60 g (15.28 mmol) 6-bromo-2-bromomethyl-quinoline are added to a solution of 1.40 mL (16.8 mmol) pyrrolidine and 6.34 g (45.9 mmol) K$_2$CO$_3$ in 50 mL acetonitrile. The reaction is stirred overnight at RT and then the inorganic salts are filtered off. The organic phase is washed with water and the aqueous phase is extracted with EtOAc. The combined organic extracts are dried over MgSO$_4$ and the solvent is eliminated i.vac.

Yield: 4.45 g (100% of theory)
$C_{14}H_{15}BrN_2$ (M=291.193)
Calc.: molpeak (M+H)$^+$: 291/293 Found: molpeak (M+H)$^+$: 291/293
R$_f$ value: 0.27 (silica gel, DCM/MeOH 9:1)

3.45c

6-iodo-2-pyrrolidin-1-ylmethyl-quinoline

Prepared according to general working method II from 6-bromo-2-pyrrolidin-1-ylmethyl-quinoline (500 mg, 1.72 mmol).

Yield: 400 mg (59.9% of theory)
$C_{14}H_{15}IN_2$ (M=338.193)
Calc.: molpeak (M+H)$^+$: 339 Found: molpeak (M+H)$^+$: 339
HPLC retention time: 5.16 min (method A)

3.45d

6-[5-(4-chloro-phenyl)-pyridin-2-ylethynyl]-2-pyrrolidin-1-ylmethyl-quinoline Prepared according to general working method I from 6-iodo-2-pyrrolidin-1-ylmethyl-quinoline (151 mg, 0.45 mmol) and 5-(4-chloro-phenyl)-2-ethynyl-pyridine (80 mg, 0.37 mmol).

Yield: 18 mg (11.4% of theory)
$C_{27}H_{22}ClN_3$ (M=423.949)
Calc.: molpeak (M+H)$^+$: 424/426 Found: molpeak (M+H)$^+$: 424/426
HPLC retention time: 4.78 min (method B)

Example 3.46

6-[5-(4-chloro-phenyl)-pyridin-2-ylethynyl]-2-pyrrolidin-1-ylmethyl-1,2,3,4-tetrahydro-quinoline

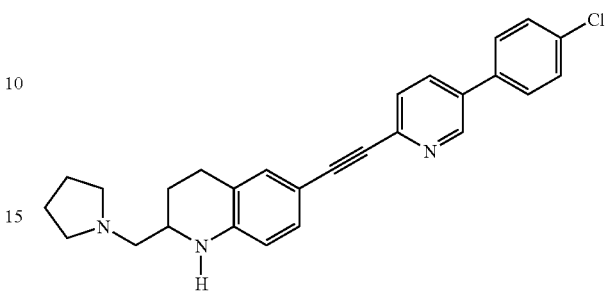

3.46a

6-bromo-2-pyrrolidin-1-ylmethyl-1,2,3,4-tetrahydro-quinoline

Under an argon atmosphere 0.69 mL (6.87 mmol) borane-pyridine complex are added to a solution of 500 mg (1.72 mmol) 6-bromo-2-pyrrolidin-1-ylmethyl-quinoline (see 3.45b) in 10 mL acetic acid at RT. The mixture is stirred for 7 h at RT, again combined with 0.35 mL (3.46 mmol) borane-pyridine complex and stirred for another hour at RT. It is cooled to 0° C. and the solution is made basic with 8% NaOH solution. The aqueous phase is extracted with EtOAc and the solvent is eliminated i.vac. The residue is taken up with water and acidified with 12% HCl. The aqueous phase is extracted with EtOAc and then made basic with 20% NaOH solution while cooling with ice. The aqueous phase is extracted with EtOAc. The organic phase is dried over MgSO$_4$ and the solvent is eliminated i.vac.

Yield: 420 mg (82.9% of theory)
$C_{14}H_{19}BrN_2$ (M=295.25)
Calc.: molpeak (M+H)$^+$: 295/297 Found: molpeak (M+H)$^+$: 295/297
HPLC retention time: 5.01 min (method B)

3.46b

6-iodo-2-pyrrolidin-1-ylmethyl-1,2,3,4-tetrahydro-quinoline

Prepared according to general working method II from 6-bromo-2-pyrrolidin-1-ylmethyl-1,2,3,4-tetrahydro-quinoline (280 mg, 0.95 mmol).

Yield: 260 mg (80.1% of theory)
$C_{14}H_{19}IN_2$ (M=342.225)
Calc.: molpeak (M+H)$^+$: 343 Found: molpeak (M+H)$^+$: 343
HPLC retention time: 5.34 min (method A)

3.46c

6-[5-(4-chloro-phenyl)-pyridin-2-ylethynyl]-2-pyrrolidin-1-ylmethyl-1,2,3,4-tetrahydro-quinoline Prepared according to general working method I from 6-iodo-2-pyrrolidin-1-ylmethyl-1,2,3,4-tetrahydro-quinoline (260 mg, 0.76 mmol) and 5-(4-chloro-phenyl)-2-ethynyl-pyridine (162 mg, 0.76 mmol).

Yield: 72 mg (22.1% of theory)
$C_{27}H_{26}ClN_3$ (M=427.981)
Calc.: molpeak (M+H)$^+$: 428 Found: molpeak (M+H)$^+$: 428
HPLC retention time: 4.66 min (method B)

Example 3.47

5-(4-chloro-phenyl)-2-(6-pyrrolidin-1-ylmethyl-naphthalen-2-ylethynyl)-pyridine

3.47a (6-iodo-naphthalen-2-yl)-methanol

Prepared according to general working method II from (6-bromo-naphthalen-2-yl)-methanol (500 mg, 2.11 mmol).
Yield: 450 mg (75.1% of theory)
$C_{11}H_9IO$ (M=284.10)
Calc.: molpeak (M+H)$^+$: 284 Found: molpeak (M+H)$^+$: 284
HPLC retention time: 8.30 min (method A)

3.47b

{6-[5-(4-chloro-phenyl)-pyridin-2-ylethynyl]-naphthalen-2-yl}-methanol

Prepared according to general working method I from (6-iodo-naphthalen-2-yl)-methanol (450 mg, 1.58 mmol) and 5-(4-chloro-phenyl)-2-ethynyl-pyridine (342 mg, 1.60 mmol).
Yield: 250 mg (42.8% of theory)
$C_{24}H_{16}ClNO$ (M=369.85)
Calc.: molpeak (M+H)$^+$: 370/372 Found: molpeak (M+H)$^+$: 370/372
$R_f$ value: 0.25 (silica gel, DCM/MeOH 19:1)

3.47c 5-(4-chloro-phenyl)-2-(6-pyrrolidin-1-ylmethyl-naphthalen-2-ylethynyl)-pyridine 58 μL (0.80 mmol) thionyl chloride are added at 0° C. to a solution of 148 mg (0.40 mmol) {6-[5-(4-chloro-phenyl)-pyridin-2-ylethynyl]-naphthalen-2-yl}-methanol in 5 mL DCM. The solution is heated to RT and stirred for 1 h at this temperature. The reaction mixture is diluted with 30 mL DCM, combined with ice water, made alkaline with saturated NaHCO$_3$ solution and the organic phase is washed with water. The organic phase is dried over MgSO$_4$ and filtered. 0.10 mL (1.20 mmol) pyrrolidine are added to the filtrate, which is stirred for 2 h at RT and for 1 h at 40° C. The solvent is eliminated i.vac. and the purification is carried out by column chromatography on silica gel (gradient: DCM to DCM/MeOH/NH$_3$ 5:1:0.1).
Yield: 40 mg (23.6% of theory)
$C_{28}H_{23}ClN_2$ (M=422.96)
Calc.: molpeak (M+H)$^+$: 423/425 Found: molpeak (M+H)$^+$: 423/425
$R_f$ value: 0.10 (silica gel, DCM/MeOH/NH$_3$ 19:1:0.1)

Example 3.48

5-[5-(4-chloro-phenyl)-pyridin-2-ylethynyl]-1-(2-pyrrolidin-1-yl-ethyl)-2,3-dihydro-1H-indole

3.48a 5-bromo-1-(2-pyrrolidin-1-yl-ethyl)-2,3-dihydro-1H-indole

Under a nitrogen atmosphere 700 mg (3.46 mmol) 5-bromoindoline are added to a solution of 722 mg (4.16 mmol) N-(2-chloroethyl)-pyrrolidine hydrochloride and 1.19 mL (6.93 mmol) ethyldiisopropylamine in 10 mL DMF. The reaction solution is stirred for 21 h at RT and again combined with N-(2-chloroethyl)-pyrrolidine hydrochloride. The reaction solution is heated to 70° C. and stirred for 4 h at this temperature. The solvent is eliminated i.vac. and the residue taken up in 50 mL semisaturated NaCl solution and 50 mL EtOAc. The aqueous phase is extracted twice with 50 mL DCM, the combined organic extracts are dried over Na$_2$SO$_4$ and the solvent is eliminated i.vac.
Yield: 226 mg (22.1% of theory)
$C_{14}H_{19}BrN_2$ (M=295.225)
Calc.: molpeak (M+H)$^+$: 295/297 Found: molpeak (M+H)$^+$: 295/297
HPLC retention time: 5.93 min (method A)

3.48b 5-iodo-1-(2-pyrrolidin-1-yl-ethyl)-2,3-dihydro-1H-indole

Prepared according to general working method II from 5-bromo-1-(2-pyrrolidin-1-yl-ethyl)-2,3-dihydro-1H-indole (226 mg, 0.77 mmol).
Yield: 142 mg (54.2% of theory)
$C_{14}H_{19}IN_2$ (M=342.225)
HPLC retention time: 6.10 min (method A)

3.48c

5-[5-(4-chloro-phenyl)-pyridin-2-ylethynyl]-1-(2-pyrrolidin-1-yl-ethyl)-2,3-dihydro-1H-indole Prepared according to general working method I from 5-iodo-1-(2-pyrrolidin-1-yl-ethyl)-2,3-dihydro-1H-indole (142 mg, 0.42 mmol) and 5-(4-chloro-phenyl)-2-ethynyl-pyridine (89 mg, 0.42 mmol).

Yield: 39 mg (22.1% of theory)
$C_{27}H_{26}ClN_3$ (M=427.981)
Calc.: molpeak $(M+H)^+$: 428/430 Found: molpeak $(M+H)^+$: 428/430
$R_f$ value: 0.55 (Alox, cyc/EtOAc 2:1)
HPLC retention time: 7.98 min (method A)

Example 3.49

5-(4-chloro-phenyl)-2-[4-(1-methyl-2-piperidin-1-yl-ethoxy)-phenylethynyl]-pyridine

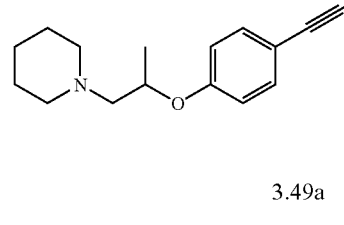

3.49a

1-[2-(4-iodo-phenoxy)-propyl]-piperidine 1.54 g (7.00 mmol) iodobenzene and 2.75 g (10.5 mmol) triphenylphosphane are added successively to a solution of 1.00 g (6.98 mmol) 1-piperidin-1-yl-propan-2-ol in 20 mL DCM. 2.19 mL (10.5 mmol, 95%) diisopropyl azodicarboxylate is added dropwise at RT and the reaction is stirred for 2 h at RT. It is diluted with water, the organic phase is washed with water and dried over $MgSO_4$. After the desiccant and solvent have been eliminated the residue is purified by chromatography (silica gel, DCM/MeOH 9:1). The oily residue is triturated with diisopropylether, filtered off from the insoluble residue and the filtrate is evaporated to dryness i.vac.

Yield: 500 mg (20.7% of theory)
$C_{14}H_{20}INO$ (M=345.226)
Calc.: molpeak $(M+H)^+$: 346 Found: molpeak $(M+H)^+$: 346
$R_f$ value: 0.32 (silica gel, DCM/MeOH 9:1)

3.49b 5-(4-chloro-phenyl)-2-[4-(1-methyl-2-piperidin-1-yl-ethoxy)-phenylethynyl]-pyridine Prepared according to general working method I from 1-[2-(4-iodo-phenoxy)-propyl]-piperidine (173 mg, 0.50 mmol) and 5-(4-chloro-phenyl)-2-ethynyl-pyridine (107 mg, 0.50 mmol).

Yield: 80 mg (37.1% of theory)
$C_{27}H_{27}ClN_2O$ (M=430.982)
Calc.: molpeak $(M+H)^+$: 431/433 Found: molpeak $(M+H)^+$: 431/433
$R_f$ value: 0.25 (silica gel, EtOAc/MeOH 9:1)
HPLC retention time: 5.03 min (method A)

Example 3.50

5-(4-chloro-phenyl)-2-[4-(3-piperidin-1-yl-pyrrolidin-1-yl)-phenylethynyl]-pyridine

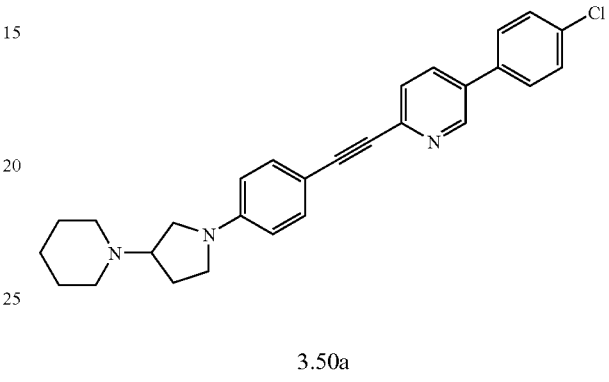

3.50a 1-(1-benzyl-pyrrolidin-3-yl)-piperidine 12.7 g (60.0 mmol) $NaBH(OAc)_3$ and 2.3 mL acetic acid are added to a solution of 4.94 mL (50.0 mmol) piperidine and 8.03 mL (50.0 mmol) N-benzylpyrrolidinone in 200 mL THF. The reaction is stirred overnight at RT. The reaction solution is combined with 200 mL saturated $NaHCO_3$ solution and extracted twice with 200 mL EtOAc. The organic phase is dried over $MgSO_4$ and the solvent is eliminated i.vac. The purification is carried out by column chromatography on silica gel (EtOAc/MeOH/$NH_3$ 8:2:0.2).

Yield: 5.50 g (45.0% of theory)
$C_{16}H_{24}N_2$ (M=244.383)
Calc.: molpeak $(M+H)^+$: 245 Found: molpeak $(M+H)^+$: 245
$R_f$ value: 0.25 (silica gel, EtOAc/MeOH/$NH_3$ 9:1:0.1)

3.50b 1-pyrrolidin-3-yl-piperidine 550 mg 10% Pd/C are added to a solution of 5.50 g (22.5 mmol) 1-(1-benzyl-pyrrolidin-3-yl)-piperidine in 200 mL MeOH. The reaction solution is stirred for 5 h at RT and 3 bar $H_2$. 550 mg palladiumhydroxide are added and the reaction is stirred for a further 6 h at RT and 3 bar $H_2$. The catalyst is suction filtered and the solvent is eliminated i.vac.

Yield: 900 mg (86.5% of theory)
$C_9H_{18}N_2$ (M=154.257)
Calc.: molpeak $(M+H)^+$: 155 Found: molpeak $(M+H)^+$: 155
$R_f$ value: 0.05 (silica gel, EtOAc/MeOH/$NH_3$ 8:2:0.2)

3.50c

1-[1-(4-bromo-phenyl)-pyrrolidin-3-yl]-piperidin 283 mg (1.00 mmol) 4-bromo-iodobenzene, 10 mg (0.05 mmol) CuI, 124 mg (2.00 mmol) ethyleneglycol and 424 mg (2.00 mmol) potassium phosphate are added to a reaction vessel, which is evacuated and rinsed with argon several times. Then 154 mg (1.00 mmol) 1-pyrrolidin-3-yl-piperidine in 1 mL isopropanol are added and the reaction is shaken for 15 h at 80° C. The reaction solution is diluted with EtOAc and extracted twice with 5% ammonia solution. The organic phase is dried over $MgSO_4$ and the solvent is eliminated i.vac.

Yield: 230 mg (74.4% of theory)
$C_{15}H_{21}BrN_2$ (M=309.252)
Calc.: molpeak $(M+H)^+$: 309/311 Found: molpeak $(M+H)^+$: 309/311
$R_f$ value: 0.73 (silica gel, DCM/MeOH/$NH_3$ 9:1:0.1)

3.50d

1-[1-(4-iodo-phenyl)-pyrrolidin-3-yl]-piperidine

Prepared according to general working method II from 1-[1-(4-bromo-phenyl)-pyrrolidin-3-yl]-piperidine (200 mg, 0.65 mmol).

Yield: 120 mg (52.1% of theory)
$C_{15}H_{21}IN_2$ (M=356.252)
Calc.: molpeak $(M+H)^+$: 357 Found: molpeak $(M+H)^+$: 357
HPLC retention time: 6.13 min (method A)

3.50e 5-(4-chloro-phenyl)-2-[4-(3-piperidin-1-yl-pyrrolidin-1-yl)-phenylethynyl]-pyridine Prepared according to general working method I from 1-[1-(4-iodo-phenyl)-pyrrolidin-3-yl]-piperidine (120 mg, 0.34 mmol) and 5-(4-chloro-phenyl)-2-ethynyl-pyridine (73 mg, 0.34 mmol).

Yield: 75 mg (50.4% of theory)
$C_{28}H_{28}ClN_3$ (M=442.008)
Calc.: molpeak $(M+H)^+$: 442/444 Found: molpeak $(M+H)^+$: 442/444
$R_f$ value: 0.30 (silica gel, DCM/MeOH/$NH_3$ 9:1:0.1)
HPLC retention time: 4.94 min (method B)

Example 3.51

5-(4-chloro-phenyl)-2-[5-(2-pyrrolidin-1-yl-ethoxy)-pyridin-2-yl-ethynyl]-pyridine

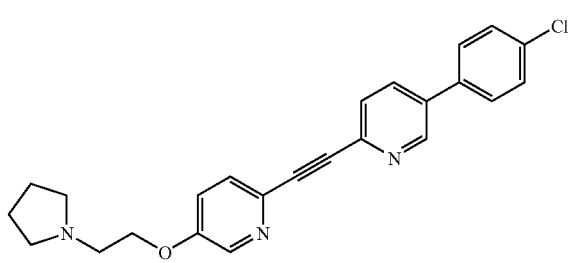 [SMILES: Clc1ccc(-c2ccc(C#Cc3ccc(OCCN4CCCC4)cn3)nc2)cc1]

3.51a 2-bromo-5-(2-pyrrolidin-1-yl-ethoxy)-pyridine

The product is obtained analogously to Example 3.1 e (1:1 mixture of acetone:acetonitrile instead of DMF) from 3.90 g (22.4 mmol) 6-bromo-pyridin-3-ol and 4.25 g (25.0 mmol) N-(2-chloroethyl)-pyrrolidine hydrochloride.

Yield: 4.70 g (69.3% of theory)
$C_{11}H_{15}BrN_2O$ (M=271.159)
Calc.: molpeak $(M+H)^+$: 271/273 Found: molpeak $(M+H)^+$: 271/273
$R_f$ value: 0.27 (silica gel, EtOAc/MeOH/$NH_3$ 9:1:0.1)

3.51b 5-(4-chloro-phenyl)-2-[5-(2-pyrrolidin-1-yl-ethoxy)-pyridin-2-yl-ethynyl]-pyridine Prepared according to general working method I from 2-bromo-5-(2-pyrrolidin-1-yl-ethoxy)-pyridine (271 mg, 0.50 mmol) and 5-(4-chloro-phenyl)-2-ethynyl-pyridine (106 mg, 0.50 mmol).

Yield: 22 mg (10.9% of theory)
$C_{24}H_{22}ClN_3O$ (M=403.915)
Calc.: molpeak $(M+H)^+$: 404/406 Found: molpeak $(M+H)^+$: 404/406
$R_f$ value: 0.20 (silica gel, EtOAc/MeOH/$NH_3$ 9:1:0.1)

Example 3.52

5-[5-(4-chloro-phenyl)-pyridin-2-ylethynyl]-2-(2-pyrrolidin-1-yl-ethoxy)-benzonitrile

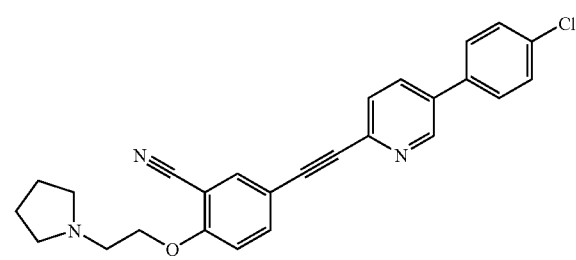 [SMILES: N#Cc1cc(C#Cc2ccc(-c3ccc(Cl)cc3)cn2)ccc1OCCN1CCCC1]

3.52a 5-bromo-2-(2-pyrrolidin-1-yl-ethoxy)-benzonitrile

The product is obtained analogously to Example 3.1e (acetonitrile instead of DMF) from 2.00 g (10.1 mmol) 5-bromo-2-hydroxy-benzonitrile and 2.00 g (11.8 mmol) N-(2-chloroethyl)-pyrrolidine hydrochloride.

Yield: 1.32 g (44.3% of theory)
$C_{13}H_{15}BrN_2O$ (M=295.181)
Calc.: molpeak $(M+H)^+$: 295/297 Found: molpeak $(M+H)^+$: 295/297
HPLC retention time: 4.91 min (method A)

3.52b 5-iodo-2-(2-pyrrolidin-1-yl-ethoxy)-benzonitrile

Prepared according to general working method II from 5-bromo-2-(2-pyrrolidin-1-yl-ethoxy)-benzonitrile (350 mg, 1.19 mmol).

Yield: 324 mg (79.8% of theory)
$C_{13}H_{15}IN_2O$ (M=342.182)
Calc.: molpeak $(M+H)^+$: 343 Found: molpeak $(M+H)^+$: 343
HPLC retention time: 5.14 min (method A)

3.52c

5-[5-(4-chloro-phenyl)-pyridin-2-ylethynyl]-2-(2-pyrrolidin-1-yl-ethoxy)-benzonitrile Prepared according to general working method I from 5-iodo-2-(2-pyrrolidin-1-yl-ethoxy)-benzonitrile (300 mg, 0.88 mmol) and 5-(4-chloro-phenyl)-2-ethynyl-pyridine (206 mg, 0.97 mmol).

Yield: 76 mg (20.3% of theory)

$C_{26}H_{22}ClN_3O$ (M=427.938)

Calc.: molpeak $(M+H)^+$: 428/430 Found: molpeak $(M+H)^+$: 428/430

HPLC retention time: 7.31 min (method A)

Example 3.53

5-(4-chloro-phenyl)-2-[2-(4-methyl-piperidin-1-ylmethyl)-benzofuran-5-ylethynyl]-pyridine

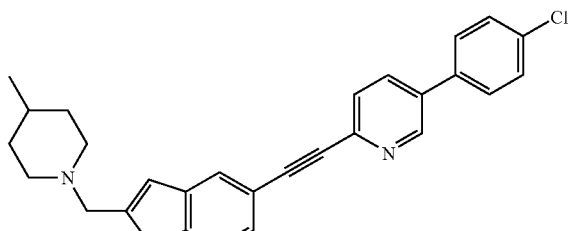

3.53a ethyl 5-bromo-benzofuran-2-carboxylate 13.8 g (100 mmol) $Na_2CO_3$ are added to a solution of 4.02 g (20.0 mmol) 5-bromo-salicylaldehyde and 2.26 mL (20.0 mmol, 98%) ethyl bromoacetate in 50 mL DMF. The reaction mixture is heated to 80° C. and stirred for 2 h at this temperature. It is diluted with 200 mL water, the aqueous phase is extracted three times with 100 mL tert-butylmethylether and the combined organic extracts are washed twice with 50 mL water. The organic phase is dried over $MgSO_4$, filtered through activated charcoal and the solvent is eliminated i.vac.

Yield: 3.80 g (70.6% of theory)

$C_{11}H_9BrO_3$ (M=269.097)

Calc.: molpeak $(M+H)^+$: 269/271 Found: molpeak $(M+H)^+$: 269/271

$R_f$ value: 0.75 (silica gel, PE/EtOAc 8:2)

3.53b

(5-bromo-benzofuran-2-yl)-methanol 7.0 mL (7.00 mmol) 1 M lithium aluminium hydride solution in THF is slowly added dropwise at −5° C. to a solution of 3.70 g (13.8 mmol) ethyl 5-bromo-benzofuran-2-carboxylate in 50 mL THF. The reaction solution is heated to RT and then cooled again to 10° C. Another 0.7 mL (0.70 mmol) 1 M lithium aluminium hydride solution in THF are added dropwise and the reaction is stirred for 1 h at RT. 1.0 mL water, 1.0 mL 15% NaOH and finally 3.0 mL water are added successively to the reaction mixture and the insoluble precipitate is filtered off. The organic phase is dried over $MgSO_4$, filtered through activated charcoal and the solvent is eliminated i.vac.

Yield: 2.10 g (67.3% of theory)

$C_9H_7BrO_2$ (M=227.059)

Calc.: molpeak $(M)^+$: 226/228 Found: molpeak $(M)^+$: 226/228

$R_f$ value: 0.15 (silica gel, PE/EtOAc 8:2)

3.53c

(5-iodo-benzofuran-2-yl)-methanol

Prepared according to general working method II from (5-bromo-benzofuran-2-yl)-methanol (2.10 g, 9.25 mmol).

Yield: 2.53 g (100% of theory)

$C_9H_7IO_2$ (M=274.059)

Calc.: molpeak $(M)^+$: 274 Found: molpeak $(M)^+$: 274

$R_f$ value: 0.26 (silica gel, PE/EtOAc 8:2)

3.53d

{5-[5-(4-chloro-phenyl)-pyridin-2-ylethynyl]-benzofuran-2-yl}-methanol

Prepared according to general working method I from (5-iodo-benzofuran-2-yl)-methanol (685 mg, 2.50 mmol) and 5-(4-chloro-phenyl)-2-ethynyl-pyridine (534 mg, 2.50 mmol).

Yield: 400 mg (44.5% of theory)

$C_{22}H_{14}ClNO_2$ (M=359.815)

Calc.: molpeak $(M+H)^+$: 360/362 Found: molpeak $(M+H)^+$: 360/362

$R_f$ value: 0.58 (silica gel, DCM/MeOH/$NH_3$ 9:1:0.1)

3.53e

5-(4-chloro-phenyl)-2-[2-(4-methyl-piperidin-1-ylmethyl)-benzofuran-5-ylethynyl]-pyridine 32 μL (0.40 mmol) methanesulphonic acid chloride are added to a solution of 100 mg (0.28 mmol) {5-[5-(4-chloro-phenyl)-pyridin-2-ylethynyl]-benzofuran-2-yl}-methanol and 69 μL (0.50 mmol) triethylamine in 5 mL DCM at 0° C. and the reaction is stirred for 1 h at this temperature. Another 70 μL (0.89 mmol) methanesulphonic acid chloride are added and the reaction is stirred overnight at RT. Then 0.24 ml (2.00 mmol) 4-methylpiperidine is added and the reaction is stirred for 2 hours at RT. The reaction solution is diluted with water and the aqueous phase extracted twice with DCM. The organic phase is dried over $MgSO_4$ and the solvent is eliminated i.vac. The purification is carried out by column chromatography on silica gel (DCM/methanol 9:1).

Yield: 10 mg (8.1% of theory)

$C_{28}H_{25}ClN_2O$ (M=440.977)

Calc.: molpeak $(M+H)^+$: 441/443 Found: molpeak $(M+H)^+$: 441/443

$R_f$ value: 0.27 (silica gel, DCM/MeOH 9:1)

Example 3.54

{4-[5-(4-chloro-phenyl)-pyridin-2-ylethynyl]-phenyl}-(2-pyrrolidin-1-yl-ethyl)-amine

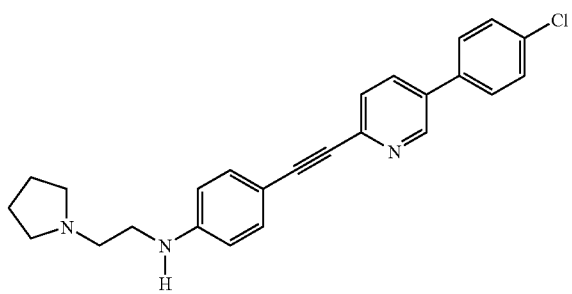 [SMILES: Clc1ccc(-c2ccc(C#Cc3ccc(NCCN4CCCC4)cc3)nc2)cc1]

3.54a 2-chloro-N-(4-iodo-phenyl)-acetamide 2.0 mL (25.1 mmol) chloro-acetylchloride in 5 mL DCM are added to a solution of 5.00 g (22.83 mmol) 4-iodo-phenylamine and 7.0 mL (50.2 mmol) triethylamine in 100 mL DCM at 0° C. The ice bath is removed and the reaction is stirred for a further 1.5 h at RT. The reaction solution is diluted with 80 mL water and the organic phase is washed with saturated NaCl solution. The organic phase is dried over $MgSO_4$ and the solvent is eliminated i.vac. The residue is triturated with EtOAc, suction filtered and dried in the air.

Yield: 2.25 g (33.4% of theory)
$C_8H_7ClINO$ (M=295.508)
Calc.: molpeak $(M+H)^+$: 296/298 Found: molpeak $(M+H)^+$: 296/298
HPLC retention time: 7.91 min (method A)

3.54b

N-(4-iodo-phenyl)-2-pyrrolidin-1-yl-acetamide 1.53 mL (18.6 mmol) pyrrolidine are added to a solution of 2.20 g (7.45 mmol) 2-chloro-N-(4-iodo-phenyl)-acetamide in 50 mL DCM. The reaction solution is stirred overnight at RT. The mixture is filtered, the filtrate dried over $MgSO_4$ and the solvent is eliminated i.vac.

Yield: 1.65 g (67.1% of theory)
$C_{12}H_{15}IN_2O$ (M=330.171)
Calc.: molpeak $(M+H)^+$: 331 Found: molpeak $(M+H)^+$: 331
HPLC retention time: 5.10 min (method A)

3.54c (4-iodo-phenyl)-(2-pyrrolidin-1-yl-ethyl)-amine 2.25 mL (2.25 mmol) 1 M lithium aluminium hydride solution are added to a solution of 500 mg (1.51 mmol) N-(4-iodo-phenyl)-2-pyrrolidin-1-yl-acetamide in 10 mL THF at 0° C. and the reaction is stirred for 20 min at this temperature. EtOAc is added and then 85 µL water, 85 µL 15% NaOH solution and finally 256 µL water are added. The precipitate is removed by suction filtering and the filtrate is diluted with 50 mL EtOAc. The organic phase is washed with 30 mL saturated $NaHCO_3$ solution. The organic phase is dried over $MgSO_4$ and the solvent is eliminated i.vac.

Yield: 450 mg (94.0% of theory)
$C_{12}H_{17}IN_2$ (M=316.187)
Calc.: molpeak $(M+H)^+$: 317 Found: molpeak $(M+H)^+$: 317
$R_f$ value: 0.17 (silica gel, DCM/MeOH/$NH_3$ 9:1:0.1)

3.54d

{4-[5-(4-chloro-phenyl)-pyridin-2-ylethynyl]-phenyl}-(2-pyrrolidin-1-yl-ethyl)-amine Prepared according to general working method I from (4-iodo-phenyl)-(2-pyrrolidin-1-yl-ethyl)-amine (450 mg, 1.42 mmol) and 5-(4-chloro-phenyl)-2-ethynyl-pyridine (450 mg, 2.11 mmol).

Yield: 98 mg (17.1% of theory)
$C_{25}H_{24}ClN_3$ (M=401.943)
Calc.: molpeak $(M+H)^+$: 402/404 Found: molpeak $(M+H)^+$: 402/404
HPLC retention time: 7.08 min (method A)

Example 3.55

5-[5-(4-chloro-phenyl)-pyridin-2-ylethynyl]-2-(2-pyrrolidin-1-yl-ethoxy)-benzaldehyde

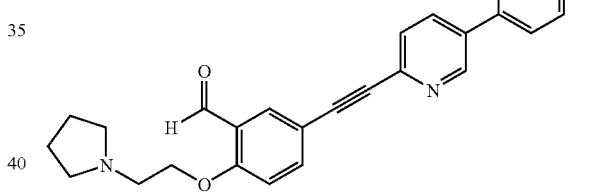

3.55a 5-iodo-2-(2-pyrrolidin-1-yl-ethoxy)-benzaldehyde

The product is obtained analogously to Example 3.1e (acetonitrile instead of DMF) from 8.93 g (36.0 mmol) 2-hydroxy-5-iodo-benzaldehyde and 7.14 g (42.0 mmol) N-(2-chloroethyl)-pyrrolidine hydrochloride.

Yield: 4.80 g (38.6% of theory)
$C_{13}H_{16}INO_2$ (M=345.182)
Calc.: molpeak $(M+H)^+$: 346 Found: molpeak $(M+H)^+$: 346
HPLC retention time: 5.27 min (method A)

3.55b

5-[5-(4-chloro-phenyl)-pyridin-2-ylethynyl]-2-(2-pyrrolidin-1-yl-ethoxy)-benzaldehyde Prepared according to general working method I from 5-iodo-2-(2-pyrrolidin-1-yl-ethoxy)-benzaldehyde (1.50 g, 4.35 mmol) and 5-(4-chloro-phenyl)-2-ethynyl-pyridine (214 mg, 5.00 mmol).

Yield: 320 mg (17.1% of theory)

$C_{26}H_{23}ClN_2O_2$ (M=430.938)
Calc.: molpeak (M+H)$^+$: 431/433 Found: molpeak (M+H)$^+$: 431/433
HPLC retention time: 7.31 min (method A)

Example 3.56

5-[5-(4-chloro-phenyl)-pyridin-2-ylethynyl]-2-(2-pyrrolidin-1-yl-ethoxy)-benzaldehyde-oxime

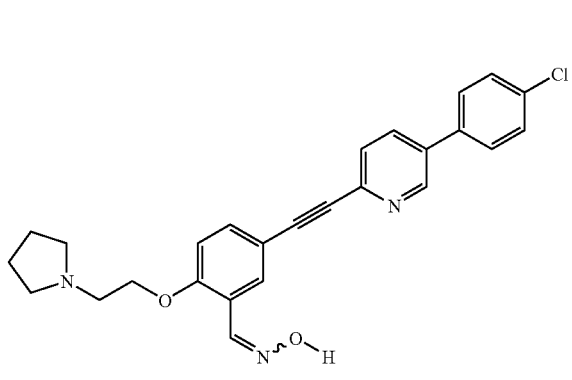 [SMILES: ON=Cc1cc(C#Cc2ccc(-c3ccc(Cl)cc3)cn2)ccc1OCCN1CCCC1]

27 mg (0.38 mmol) hydroxylamine and 53 μL (0.38 mmol) triethylamine are added to a solution of 200 mg (0.35 mmol) 5-[5-(4-chloro-phenyl)-pyridin-2-ylethynyl]-2-(2-pyrrolidin-1-yl-ethoxy)-benzaldehyde (Example 3.55b) in 2 mL of a 1:1 mixture of acetonitrile and MeOH. The reaction solution is heated to 85° C. After the reaction is complete the mixture is diluted with water and saturated NaHCO$_3$ solution and the organic phase is extracted with DCM. The organic phase is dried over MgSO$_4$ and the solvent is eliminated i.vac. The purification is carried out by column chromatography using HPLC-MS.
Yield: 5 mg (3.2% of theory)
$C_{26}H_{24}ClN_3O_2$ (M=445.953)
Calc.: molpeak (M+H)$^+$: 446/448 Found: molpeak (M+H)$^+$: 446/448
HPLC retention time: 5.25 min (method A)

Example 3.57

5-[5-(4-chloro-phenyl)-pyridin-2-ylethynyl]-2-(2-pyrrolidin-1-yl-ethoxy)-benzaldehyde O-methyl-oxime

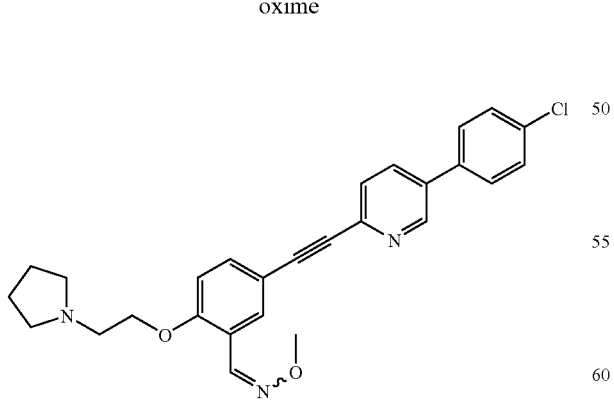

The product is obtained analogously to Example 3.56a from 250 mg (0.44 mmol) 5-[5-(4-chloro-phenyl)-pyridin-2-ylethynyl]-2-(2-pyrrolidin-1-yl-ethoxy)-benzaldehyde (Example 3.55b) and 50 mg (0.60 mmol) O-methyl-hydroxylamine.

Yield: 40 mg (20.1% of theory)
$C_{27}H_{26}ClN_3O_2$ (M=459.980)
Calc.: molpeak (M+H)$^+$: 460/462 Found: molpeak (M+H)$^+$: 460/462
HPLC retention time: 8.11 min (method A)

Example 3.58

5-(4-chloro-phenyl)-2-[3-ethynyl-4-(2-pyrrolidin-1-yl-ethoxy)-phenylethynyl]-pyridine

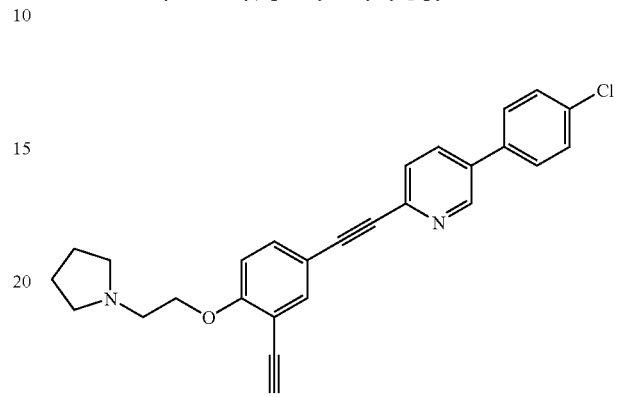

152 mg (0.79 mmol) dimethyl (1-diazo-2-oxo-propyl)-phosphate in 2 mL MeOH are added to a solution of 300 mg (0.66 mmol) 5-[5-(4-chloro-phenyl)-pyridin-2-ylethynyl]-2-(2-pyrrolidin-1-yl-ethoxy)-benzaldehyde (Example 3.55b) and 183 mg (1.32 mmol) K$_2$CO$_3$ in 9 mL MeOH. The reaction solution is stirred for for 3 h at RT and diluted with 20 mL DCM. The organic phase is extracted twice with saturated NaHCO$_3$ solution. The organic phase is dried over MgSO$_4$ and the solvent is eliminated i.vac. The purification is carried out by HPLC-MS.
Yield: 104 mg (37.0% of theory)
$C_{27}H_{23}ClN_2O$ (M=426.950)
Calc.: molpeak (M+H)$^+$: 427/429 Found: molpeak (M+H)$^+$: 427/429
HPLC retention time: 7.69 min (method A)

Example 3.59

2-pyrrolidin-1-yl-ethyl 5-[5-(4-chloro-phenyl)-pyridin-2-ylethynyl]-2,3-dihydro-indole-1-carboxylate

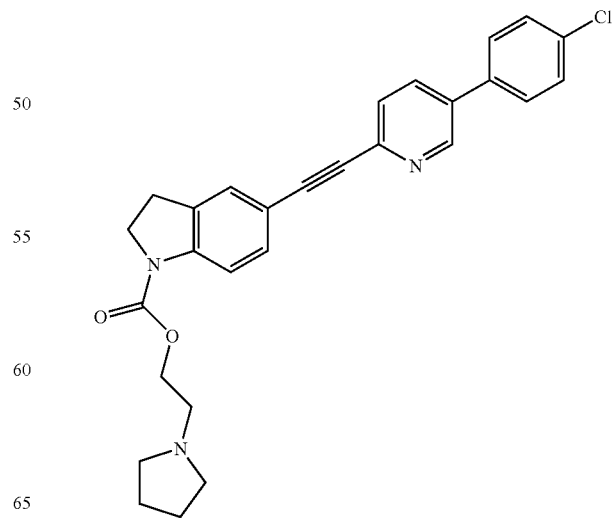

3.59a

2-pyrrolidin-1-yl-ethyl 5-bromo-2,3-dihydro-indole-1-carboxylate 1.00 g (4.95 mmol) 5-bromoindoline is added to a solution of 868 mg (5.00 mmol) N-(2-chloroethyl)-pyrrolidine hydrochloride and 1.70 g (12.2 mmol) $K_2CO_3$ in 15 mL DMF. The reaction solution is stirred for 4 h at 70° C. and more N-(2-chloroethyl)-pyrrolidine hydrochloride is added. The reaction solution is stirred for a further 3 h at 70° C. and then diluted with 25 mL water. The aqueous phase is extracted twice with 30 mL EtOAc. The organic phase is washed with saturated NaCl solution, dried over $Na_2SO_4$ and the solvent is eliminated i.vac. The purification is carried out by column chromatography on silica gel (gradient: EtOAc/MeOH 9:1 to EtOAc/MeOH 4:1).

Yield: 687 mg (47.0% of theory)
$C_{15}H_{19}BrN_2O_2$ (M=339.235)
Calc.: molpeak $(M+H)^+$: 339/341 Found: molpeak $(M+H)^+$: 339/341
$R_f$ value: 0.62 (silica gel, EtOAc/MeOH/$NH_3$ 9:1:0.1)

3.59b

2-pyrrolidin-1-yl-ethyl 5-iodo-2,3-dihydro-indole-1-carboxylate

Prepared according to general working method II from 2-pyrrolidin-1-yl-ethyl 5-bromo-2,3-dihydro-indole-1-carboxylate (700 mg, 2.37 mmol).

Yield: 590 mg (64.4% of theory)
$C_{15}H_{19}IN_2O_2$ (M=386.235)
Calc.: molpeak $(M+H)^+$: 387 Found: molpeak $(M+H)^+$: 387
$R_f$ value: 0.37 (silica gel, EtOAc/MeOH/$NH_3$ 9:1:0.1)

3.59c

2-pyrrolidin-1-yl-ethyl 5-[5-(4-chloro-phenyl)-pyridin-2-ylethynyl]-2,3-dihydro-indole-1-carboxylate Prepared according to general working method I from 2-pyrrolidin-1-yl-ethyl 5-iodo-2,3-dihydro-indole-1-carboxylate (120 mg, 0.31 mmol) and 5-(4-chloro-phenyl)-2-ethynyl-pyridine (80 mg, 0.37 mmol).

Yield: 48 mg (32.8% of theory)
$C_{28}H_{26}ClN_3O_2$ (M=471.991)
Calc.: molpeak $(M+H)^+$: 472/474 Found: molpeak $(M+H)^+$: 472/474
HPLC retention time: 7.66 min (method A)

Example 3.60

3-[5-(4-chloro-phenyl)-pyridin-2-ylethynyl]-6,7,8,9-tetrahydro-5H-10-thia-7-aza-benzo[a]azulene

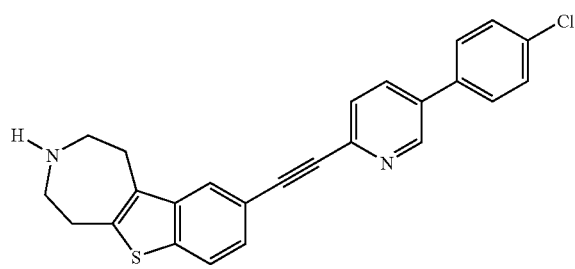 [SMILES: Clc1ccc(-c2ccc(C#Cc3ccc4sc5c(c4c3)CCNCC5)nc2)cc1]

3.60a ethyl 4-bromo-5-oxo-azepan-1-carboxylate 79.9 g (500 mmol) bromine are added to a solution of 92.7 g (500 mmol) ethyl 4-oxo-azepan-1-carboxylate in 350 mL chloroform and the reaction is stirred overnight. The reaction solution is washed three times with saturated $NaHCO_3$ solution, the organic phase is dried over $Na_2SO_4$ and the solvent is eliminated i.vac. The product is further reacted without purification.

Yield: 118 g (89.3% of theory)
$C_9H_{14}BrNO_3$ (M=264.135)

3.60b ethyl 4-(4-bromo-phenylsulphanyl)-5-oxo-azepan-1-carboxylate 60.5 g (320 mmol) 4-bromothiophenol in 300 mL chloroform are added to a solution of 84.5 g (320 mmol) ethyl 4-bromo-5-oxo-azepan-1-carboxylate and 32.4 g (320 mmol) triethylamine in 80 mL chloroform over 45 min, so that the internal temperature does not exceed 40° C. The reaction solution is stirred for 1.5 h at RT. The reaction mixture is washed twice with dilute ammonia solution and twice with water. The organic phase is dried over $Na_2SO_4$ and $K_2CO_3$ and the solvent is eliminated i.vac. The purification is carried out by repeated column chromatography on silica gel.

Yield: 44.4 g (37.2% of theory)
$C_{15}H_{18}BrNO_3S$ (M=372.30)
$R_f$ value: 0.33 (silica gel, chloroform/acetone 19:1)

3.60c ethyl 3-bromo-5,6,8,9-tetrahydro-10-thia-7-aza-benzo[a]azulen-7-carboxylate A solution of 44.3 g (119 mmol) ethyl 4-(4-bromo-phenyl-sulphanyl)-5-oxo-azepan-1-carboxylate in 443 g polyphosphoric acid is heated to 80° C. for 45 min and then diluted with 1000 mL water. The aqueous phase is extracted three times with chloroform. The organic phase is washed with water, dried over $Na_2SO_4$ and the solvent is eliminated i.vac. The purification is carried out by repeated column chromatography on silica gel (chloroform/EtOAc 19:1) and by recrystallisation from MeOH/acetone.

Yield: 22.4 g (52.8% of theory)
$C_{15}H_{16}BrNO_2S$ (M=354.28)
melting point: 109° C.

3.60d

3-bromo-6,7,8,9-tetrahydro-5H-10-thia-7-aza-benzo[a]azulene 30.0 g (53.5 mmol) KOH in 700 mL EtOH are added to a solution of 19.0 g (53.5 mmol) ethyl 3-bromo-5,6,8,9-tetrahydro-10-thia-7-aza-benzo[a]azulen-7-carboxylate. EtOH is distilled off at normal pressure and the residue is taken up in water. The solution is acidified with HCl. Then it is made basic with NaOH and the aqueous phase is extracted four times with chloroform. The organic phase is dried over $Na_2SO_4$ and $K_2CO_3$ and the solvent is eliminated i.vac. The purification is carried out by repeated column chromatography on silica gel.

Yield: 12.6 g (83.0% of theory)
$C_{12}H_{12}BrNS$ (M=282.22)
melting point: 89° C.

3.60e

3-iodo-6,7,8,9-tetrahydro-5H-10-thia-7-aza-benzo[a]azulene

Prepared according to general working method II from 3-bromo-6,7,8,9-tetrahydro-5H-10-thia-7-aza-benzo[a]azulene (1.80 g, 6.38 mmol).

Yield: 1.80 g (85.7% of theory)
$C_{12}H_{12}INS$ (M=329.205)
Calc.: molpeak $(M+H)^+$: 330 Found: molpeak $(M+H)^+$: 330
HPLC retention time: 5.45 min (method A)

3.60f

3-[5-(4-chloro-phenyl)-pyridin-2-ylethynyl]-6,7,8,9-tetrahydro-5H-10-thia-7-aza-benzo[a]azulene Prepared according to general working method I from 3-iodo-6,7,8,9-tetrahydro-5H-10-thia-7-aza-benzo[a]azulene (770 mg, 2.34 mmol) and 5-(4-chloro-phenyl)-2-ethynyl-pyridine (500 mg, 2.34 mmol).

Yield: 350 mg (36.0% of theory)
$C_{25}H_{19}ClN_2S$ (M=414.961)
Calc.: molpeak $(M+H)^+$: 415/417 Found: molpeak $(M+H)^+$: 415/417
HPLC retention time: 7.41 min (method A)

Example 3.61

3-[5-(4-chloro-phenyl)-pyridin-2-ylethynyl]-7-methyl-6,7,8,9-tetrahydro-5H-10-thia-7-aza-benzo[a]azulene

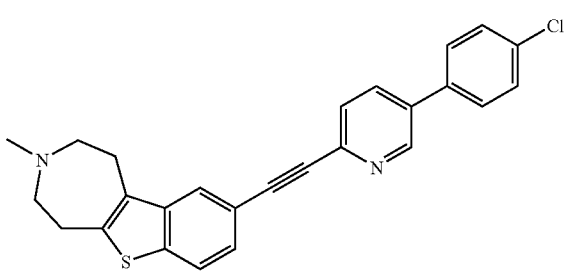 [SMILES: CN1CCc2sc3ccc(C#Cc4ccc(-c5ccc(Cl)cc5)cn4)cc3c2CC1]

0.18 mL (2.41 mmol) 37% formalin solution in water are added to a solution of 100 mg (0.24 mmol) 3-[5-(4-chloro-phenyl)-pyridin-2-ylethynyl]-6,7,8,9-tetrahydro-5H-10-thia-7-aza-benzo[a]azulene (see 3.60f) in 5 mL acetonitrile. Then 60 mg (0.96 mmol) $NaBH_3CN$ and 56 µL (0.96 mmol) acetic acid are added and the reaction mixture is stirred overnight. The solution is combined with 2 M NaOH and extracted with EtOAc. The organic phase is dried over $MgSO_4$ and the solvent is eliminated i.vac. The purification is carried out by column chromatography by HPLC-MS.

Yield: 3 mg (2.9% of theory)
$C_{26}H_{21}ClN_2S$ (M=428.988)
Calc.: molpeak $(M+H)^+$: 429/431 Found: molpeak $(M+H)^+$: 429/431
HPLC retention time: 4.97 min (method B)

Example 3.62

5-[5-(4-chloro-phenyl)-pyridin-2-ylethynyl]-1-(2-pyrrolidin-1-yl-ethyl)-1H-indazole

3.62a

5-nitro-1-(2-pyrrolidin-1-yl-ethyl)-1H-indazole and 5-nitro-2-(2-pyrrolidin-1-yl-ethyl)-2H-indazole 10.5 g (62.0 mmol) 1-(2-chloroethyl)-pyrrolidine hydrochloride and 12.9 g (93.0 mmol) $K_2CO_3$ are added successively to a solution of 5.00 g (31.0 mmol) 5-nitroindazole in 100 mL acetonitrile. The reaction solution is stirred for 2 h at RT and refluxed for a further 5 h. After the solution has cooled the insoluble salts are filtered off and the solvent is eliminated i.vac. The residue is taken up in EtOAc and water. The organic phase is dried over $MgSO_4$ and the solvent is eliminated i.vac. A 4:1 mixture of 5-nitro-1-(2-pyrrolidin-1-yl-ethyl)-1H-indazole and 5-nitro-2-(2-pyrrolidin-1-yl-ethyl)-2H-indazole is obtained. The purification is carried out by column chromatography on Alox (PE/EtOAc 3:2).

5-nitro-1-(2-pyrrolidin-1-yl-ethyl)-1H-indazole
Yield: 4.00 g (49.6% of theory)
$C_{13}H_{16}N_4O_2$ (M=260.298)
Calc.: molpeak $(M+H)^+$: 261 Found: molpeak $(M+H)^+$: 261
$R_f$ value: 0.78 (Alox, PE/EtOAc 1:1)

5-nitro-2-(2-pyrrolidin-1-yl-ethyl)-2H-indazole
Yield: 1.00 g (12.4% of theory)
$C_{13}H_{16}N_4O_2$ (M=260.298)
Calc.: molpeak $(M+H)^+$: 261 Found: molpeak $(M+H)^+$: 261
$R_f$ value: 0.61 (Alox, PE/EtOAc 1:1)

3.62b

1-(2-pyrrolidin-1-yl-ethyl)-1H-indazol-5-ylamine 0.50 g Raney nickel are added to a solution of 3.50 g (13.4 mmol) 5-nitro-1-(2-pyrrolidin-1-yl-ethyl)-1H-indazole in 50 mL EtOAc and the reaction mixture is stirred for 20 h at RT at 1.4 bar $H_2$. After filtration the solvent is eliminated i.vac. The product is further reacted without any more purification.

Yield: 2.90 g (93.6% of theory)

$C_{13}H_{18}N_4$ (M=230.315)

Calc.: molpeak (M+H)$^+$: 231 Found: molpeak (M+H)$^+$: 231

3.62c 5-bromo-1-(2-pyrrolidin-1-yl-ethyl)-1H-indazole 1.00 g (4.34 mmol) 1-(2-pyrrolidin-1-yl-ethyl)-1H-indazol-5-ylamine is dissolved in 9.76 mL 48% hydrobromic acid and 9.76 mL water and the solution is cooled to 0° C. 2.5 M sodium nitrite solution (300 mg in 1.74 mL water) is slowly added dropwise. The reaction is stirred for 10 min at 0° C. and then a solution of 935 mg (6.51 mmol) CuBr in 3.42 mL 48% hydrobromic acid is added dropwise. The reaction is heated to 60° C. and stirred for one hour at this temperature. The mixture is diluted with water and the aqueous phase is extracted with EtOAc. The organic phase is discarded and the aqueous phase is made alkaline with saturated NaHCO$_3$ solution. The aqueous phase is extracted with EtOAc and the organic phase is washed with water. The organic phase is dried over MgSO$_4$ and the solvent is eliminated i.vac.

Yield: 500 mg (39.1% of theory)

$C_{13}H_{16}BrN_3$ (M=294.197)

Calc.: molpeak (M+H)$^+$: 294/296 Found: molpeak (M+H)$^+$: 294/296

R$_f$ value: 0.59 (silica gel, EtOAc/MeOH/NH$_3$ 9:1:0.1)

3.62d 5-iodo-1-(2-pyrrolidin-1-yl-ethyl)-1H-indazole

Prepared according to general working method II from 5-bromo-1-(2-pyrrolidin-1-yl-ethyl)-1H-indazole (500 mg, 1.70 mmol).

Yield: 230 mg (39.7% of theory)

$C_{13}H_{16}IN_3$ (M=341.197)

Calc.: molpeak (M+H)$^+$: 342 Found: molpeak (M+H)$^+$: 342

R$_f$ value: 0.55 (silica gel, DCM/MeOH 4:1)

3.62e

5-[5-(4-chloro-phenyl)-pyridin-2-ylethynyl]-1-(2-pyrrolidin-1-yl-ethyl)-1H-indazole hydriodide Prepared according to general working method I from 5-iodo-1-(2-pyrrolidin-1-yl-ethyl)-1H-indazole (230 mg, 0.67 mmol) and 5-(4-chloro-phenyl)-2-ethynyl-pyridine (144 mg, 0.67 mmol).

Yield: 90 mg (24.1% of theory)

$C_{26}H_{23}ClN_4$*HI (M=554.865)

Calc.: molpeak (M+H)$^+$: 427/429 Found: molpeak (M+H)$^+$: 427/429

HPLC retention time: 4.59 min (method B)

Example 3.63

5-[5-(4-chloro-phenyl)-pyridin-2-ylethynyl]-2-(2-pyrrolidin-1-yl-ethyl)-2H-indazole

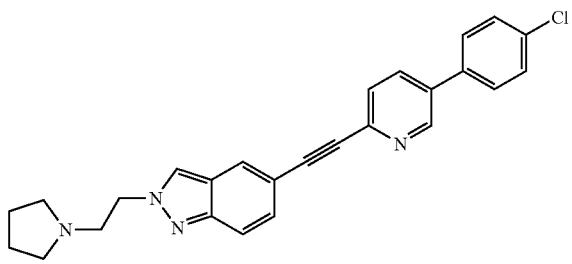 [SMILES: Clc1ccc(-c2ccc(C#Cc3ccc4nn(CCN5CCCC5)cc4c3)nc2)cc1]

3.63a 2-(2-pyrrolidin-1-yl-ethyl)-2H-indazol-5-ylamine

The product is obtained analogously to Example 3.62b from 1.0 g (3.84 mmol) 5-nitro-2-(2-pyrrolidin-1-yl-ethyl)-2H-indazole (see 3.62a).

Yield: 840 mg (94.9% of theory)

$C_{13}H_{18}N_4$ (M=230.315)

Calc.: molpeak (M+H)$^+$: 231 Found: molpeak (M+H)$^+$: 231

3.63b 5-bromo-2-(2-pyrrolidin-1-yl-ethyl)-2H-indazole

The product is obtained analogously to Example 3.62c from 840 mg (3.65 mmol) 2-(2-pyrrolidin-1-yl-ethyl)-2H-indazol-5-ylamine.

Yield: 440 mg (41.0% of theory)

$C_{13}H_{16}BrN_3$ (M=294.197)

Calc.: molpeak (M+H)$^+$: 294/296 Found: molpeak (M+H)$^+$: 294/296

HPLC retention time: 5.04 min (method A)

3.63c 5-iodo-2-(2-pyrrolidin-1-yl-ethyl)-2H-indazole

Prepared according to general working method II from 5-bromo-2-(2-pyrrolidin-1-yl-ethyl)-2H-indazole (440 mg, 1.50 mmol).

Yield: 170 mg (33.3% of theory)

$C_{13}H_{16}IN_3$ (M=341.197)

Calc.: molpeak (M+H)$^+$: 342 Found: molpeak (M+H)$^+$: 342

R$_f$ value: 0.40 (silica gel, DCM/MeOH 4:1)

3.63d

5-[5-(4-chloro-phenyl)-pyridin-2-ylethynyl]-2-(2-pyrrolidin-1-yl-ethyl)-2H-indazole Prepared according to general working method I from 5-iodo-2-(2-pyrrolidin-1-yl-ethyl)-2H-indazole (170 mg, 0.50 mmol) and 5-(4-chloro-phenyl)-2-ethynyl-pyridine (106 mg, 0.50 mmol).

Yield: 100 mg (42.3% of theory)

$C_{26}H_{23}ClN_4$ (M=426.953)

Calc.: molpeak (M+H)$^+$: 427/429 Found: molpeak (M+H)$^+$: 427/429

HPLC retention time: 4.61 min (method B)

Example 3.64

3-(4-chloro-phenyl)-6-[4-(2-pyrrolidin-1-yl-ethoxy)-phenylethynyl]-pyridazine

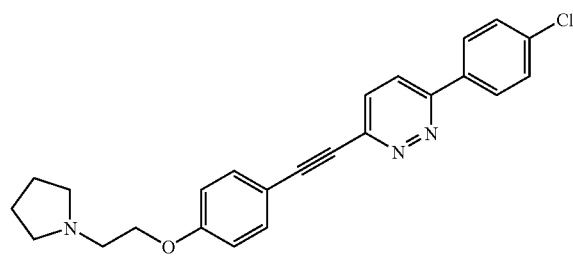 [SMILES: Clc1ccc(-c2ccc(C#Cc3ccc(OCCN4CCCC4)cc3)nn2)cc1]

3.64a 3-chloro-6-(4-chloro-phenyl)-pyridazine

Under an argon atmosphere a solution of 11.3 g (70.5 mmol) 4-chlorophenylboric acid in 50 mL 1,4-dioxane is added to a solution of 10.8 g (70.5 mmol) 3,6-dichloropyridazine, 10 mL (20 mmol) of a 2 M $Na_2CO_3$ solution and 600 mg (0.73 mmol) Pd(dppf)$Cl_2$ in 150 mL 1,4-dioxane at 110° C. over 2 h. The reaction mixture is stirred for 1 h at 110° C. 100 mL water are added and the aqueous phase is extracted with 100 mL EtOAc. The organic phase is dried over $Na_2SO_4$ and the solvent is eliminated i.vac. Purification is carried out by column chromatography on silica gel (cyc/EtOAc 4:1).

Yield: 8.00 g (50.4% of theory)

$C_{10}H_6Cl_2N_2$ (M=225.079)

Calc.: molpeak (M+H)$^+$: 225/227/229 Found: molpeak (M+H)$^+$: 225/227/229

HPLC retention time: 5.20 min (method A)

3.64b 3-(4-chloro-phenyl)-6-trimethylsilanylethynyl-pyridazine

Under an argon atmosphere 3.48 mL (25.0 mmol) triethylamine and 2.08 mL (15.0 mmol) ethynyl-trimethyl-silane are added successively to a solution of 2.25 g (10.0 mmol) 3-chloro-6-(4-chloro-phenyl)-pyridazine in 50 mL acetonitrile and 20 mL THF. Then 292 mg (0.40 mmol) Pd(dppf)$Cl_2$ and 76 mg (0.40 mmol) CuI are added. The reaction solution is stirred overnight at RT. The solvent is eliminated i.vac. and further purification is carried out by column chromatography on silica gel (PE/EtOAc 1:1).

Yield: 1.00 g (34.9% of theory)

$C_{15}H_{15}ClN_2Si$ (M=286.839)

Calc.: molpeak (M+H)$^+$: 287/289 Found: molpeak (M+H)$^+$: 287/289

$R_f$-value: 0.45 (silica gel, DCM)

3.64c 3-(4-chloro-phenyl)-6-ethynyl-pyridazine 1.10 g (3.49 mmol) TBAF are added at 0° C. to a solution of 1.00 g (3.49 mmol) 3-(4-chloro-phenyl)-6-trimethylsilanylethynyl-pyridazine in 10 mL DCM. The ice bath is removed and the reaction solution is stirred for 30 min. Water is added and the aqueous phase is extracted with EtOAc. The organic phase is dried over $MgSO_4$ and the solvent is eliminated i.vac. The product is reacted without any further purification.

Yield: 700 mg (93.5% of theory)

$C_{12}H_7ClN_2$ (M=214.656)

Calc.: molpeak (M+H)$^+$: 215/217 Found: molpeak (M+H)$^+$: 215/217

HPLC retention time: 5.16 min (method B)

3.64d 3-(4-chloro-phenyl)-6-[4-(2-pyrrolidin-1-yl-ethoxy)-phenylethynyl]-pyridazine Prepared according to general working method I from 1-[2-(4-iodo-phenoxy)-ethyl]-pyrrolidine (200 mg, 0.63 mmol) and 3-(4-chloro-phenyl)-6-ethynyl-pyridazine (135 mg, 0.63 mmol).

Yield: 15 mg (5.9% of theory)

$C_{24}H_{22}ClN_3O$ (M=403.915)

Calc.: molpeak (M+H)$^+$: 404/406 Found: molpeak (M+H)$^+$: 404/406

HPLC retention time: 5.01 min (method A)

Example 3.65

5-(4-chloro-phenyl)-3-fluoro-2-{4-[2-(4-methyl-piperidin-1-yl)-ethoxy]-phenylethynyl}-pyridine

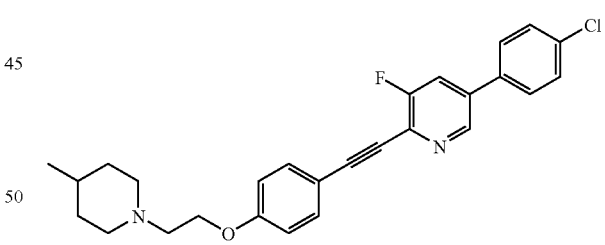

3.65a

1-[2-(4-iodo-phenoxy)-ethyl]-4-methyl-piperidine

The product is obtained analogously to Example 3.1e from 5.72 g (26.0 mmol) 4-iodo-phenol and 4.20 g (26.0 mmol) 1-(2-chloro-ethyl)-4-methyl-piperidine.

Yield: 2.60 g (29.0% of theory)

$C_{14}H_{20}INO$ (M=345.226)

Calc.: molpeak (M+H)$^+$: 346 Found: molpeak (M+H)$^+$: 346

HPLC retention time: 5.70 min (method A)

3.65b

5-(4-chloro-phenyl)-3-nitro-pyridin-2-ol 23.5 g (150 mmol) 4-chlorophenyl-boric acid are added under argon to a solution of 22.1 g (101 mmol) 5-bromo-3-nitro-pyridin-2-ol, 200 mL (400 mmol) of a 2 M $Na_2CO_3$ solution and 731 mg (1.00 mmol) $Pd(dppf)Cl_2$ in 400 mL acetone and 80 mL water. The reaction mixture is stirred for 18 h at 60° C. Acetone is eliminated i.vac. and the residue is adjusted to pH 7 with 160 mL 1 M citric acid. The aqueous phase is extracted three times with EtOAc and once with MeOH. The organic phase is dried over $MgSO_4$ and the solvent is eliminated i.vac. The residue is triturated with EtOAc.

Yield: 9.70 g (22.0% of theory)

$C_{11}H_7ClN_2O_3$ (M=250.643)

Calc.: molpeak $(M-H)^-$: 249/251 Found: molpeak $(M-H)^-$: 249/251

HPLC retention time: 6.83 min (method A)

3.65c

2-bromo-5-(4-chloro-phenyl)-3-nitro-pyridine 13.2 g (93.0 mmol) phosphorus pentoxide are added to a solution of 9.70 g (38.7 mmol) 5-(4-chloro-phenyl)-3-nitro-pyridin-2-ol and 14.5 mmol (45.0 mmol) tetrabutylammonium bromide in 100 mL toluene. The reaction mixture is stirred for 1.5 h at 95° C. After cooling the toluene phase is decanted off and the residue is twice combined with toluene and decanted off. The combined organic phases are washed with saturated $NaHCO_3$ solution. The organic phase is dried over $MgSO_4$ and the solvent is eliminated i.vac. The product is further reacted without any more purification.

Yield: 4.90 g (40.4% of theory)

$C_{11}H_6BrClN_2O_2$ (M=313.540)

Calc.: molpeak $(M+H)^+$: 313/315/317 Found: molpeak $(M+H)^+$: 313/315/317

HPLC retention time: 6.01 min (method B)

3.65d

2-bromo-5-(4-chloro-phenyl)-pyridin-3-ylamine

A solution of 5.60 g (17.9 mmol) 2-bromo-5-(4-chloro-phenyl)-3-nitro-pyridine, 20.3 g (90.0 mmol) tin(II)-chloride and 18.9 g (225 mmol) $NaHCO_3$ in 300 mL EtOAc is refluxed for 30 h. After filtration the solvent is eliminated i.vac. The residue is triturated with DCM and after filtration the filter residue is dried in the air.

Yield: 3.50 g (69.1% of theory)

$C_{11}H_8BrClN_2$ (M=283.557)

Calc.: molpeak $(M+H)^+$: 283/285/287 Found: molpeak $(M+H)^+$: 283/285/287

HPLC retention time: 5.45 min (method B)

3.65e

2-bromo-5-(4-chloro-phenyl)-3-fluoro-pyridine 243 mg (3.53 mmol) sodium nitrite in 0.5 mL water are added dropwise at −5° C. to a solution of 1.00 g (3.53 mmol) 2-bromo-5-(4-chloro-phenyl)-pyridin-3-ylamine in 2 mL water and 2.04 mL concentrated HCl. Then at 0° C. 1.56 mL (10.6 mmol) 60% hexafluorophosphoric acid in water are added and the reaction is stirred for a further hour at 0° C. The diazonium salt is suction filtered, washed with cold water, isopropanol and ether and dried overnight in the desiccator at RT and 7 mbar. This is then added batchwise at 90° C. to 50 mL PE (boiling point 100-140° C.). After the reaction solution has cooled the mixture is made alkaline with saturated $Na_2CO_3$ solution. The aqueous phase is extracted with EtOAc and the organic phase is washed successively with saturated $Na_2CO_3$ solution and water. The organic phase is dried over $MgSO_4$ and the solvent is eliminated i.vac.

The purification is carried out by column chromatography on silica gel (PE).

Yield: 460 mg (45.5% of theory)

$C_{11}H_6BrClFN$ (M=286.533)

Calc.: molpeak $(M+H)^+$: 286/288/290 Found: molpeak $(M+H)^+$: 286/288/290

HPLC retention time: 6.24 min (method B)

3.65f

5-(4-chloro-phenyl)-3-fluoro-2-trimethylsilanylethynyl-pyridine

The product is obtained analogously to Example 3.64b from 460 mg (1.61 mmol) 2-bromo-5-(4-chloro-phenyl)-3-fluoro-pyridine and 0.33 mL (2.41 mmol) ethynyl-trimethyl-silane.

Yield: 490 mg (100% of theory)

$C_{16}H_{15}ClFNSi$ (M=303.842)

Calc.: molpeak $(M+H)^+$: 304/306 Found: molpeak $(M+H)^+$: 304/306

3.65g

5-(4-chloro-phenyl)-2-ethynyl-3-fluoro-pyridine

The product is obtained analogously to Example 3.64c from 490 mg (1.61 mmol) 5-(4-chloro-phenyl)-3-fluoro-2-trimethylsilanylethynyl-pyridine.

Yield: 300 mg (57.4% of theory)

$C_{13}H_7ClFN$ (M=231.659)

Calc.: molpeak $(M+H)^+$: 232/234 Found: molpeak $(M+H)^+$: 232/234

3.65h

5-(4-chloro-phenyl)-3-fluoro-2-{4-[2-(4-methyl-piperidin-1-yl)-ethoxy]-phenylethynyl}-pyridine Prepared according to general working method I from 1-[2-(4-iodo-phenoxy)-ethyl]-4-methyl-piperidine (164 mg, 0.48 mmol) and 5-(4-chloro-phenyl)-2-ethynyl-3-fluoro-pyridine (110 mg, 0.48 mmol).

Yield: 14 mg (6.6% of theory)

$C_{27}H_{26}ClFN_2O$ (M=448.972)

Calc.: molpeak $(M+H)^+$: 449/451 Found: molpeak $(M+H)^+$: 449/451

HPLC retention time: 5.16 min (method B)

Example 3.66

6-[5-(4-chloro-phenyl)-pyridin-2-ylethynyl]-1-methanesulphonyl-2-pyrrolidin-1-ylmethyl-1,2,3,4-tetrahydro-quinoline

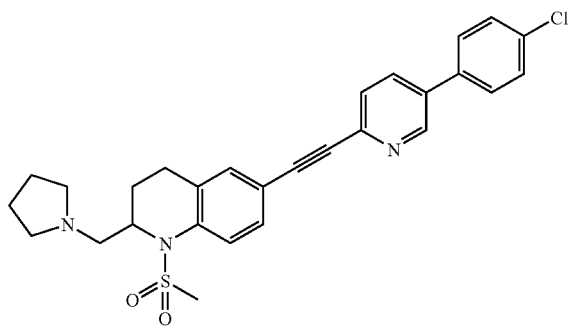 [SMILES: CS(=O)(=O)N1c2ccc(C#Cc3ccc(-c4ccc(Cl)cc4)cn3)cc2CCC1CN1CCCC1]

0.13 mL (0.93 mmol) triethylamine and 36 µL (0.47 mmol) methanesulphonic acid chloride are added successively at 0° C. to a solution of 200 mg (0.47 mmol) 6-[5-(4-chloro-phenyl)-pyridin-2-ylethynyl]-2-pyrrolidin-1-yl methyl-1,2,3,4-tetrahydro-quinoline (see Example 3.46) in 5 mL DCM. The reaction mixture is heated to RT and stirred for a further hour at this temperature. Another 36 µL (0.47 mmol) methanesulphonic acid chloride are added and the mixture is stirred for a further hour at RT. The reaction mixture is poured onto water and exhaustively extracted with DCM. The organic phase is dried over MgSO$_4$ and the solvent is eliminated i.vac. The purification is carried out by column chromatography using HPLC-MS.

Yield: 9 mg (3.8% of theory)

$C_{28}H_{28}ClN_3O_2S$ (M=506.071)

Calc.: molpeak (M+H)$^+$: 506/508 Found: molpeak (M+H)$^+$: 506/508

HPLC retention time: 5.26 min (column from method A; isocratic: 30% acetonitrile)

Example 3.67

1-{6-[5-(4-chloro-phenyl)-pyridin-2-ylethynyl]-2-pyrrolidin-1-ylmethyl-3,4-dihydro-2H-quinolin-1-yl}-ethanone

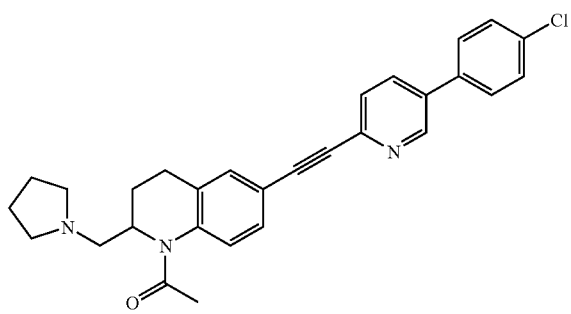 [SMILES: CC(=O)N1c2ccc(C#Cc3ccc(-c4ccc(Cl)cc4)cn3)cc2CCC1CN1CCCC1]

74 µL (0.77 mmol) acetic anhydride are added to a solution of 220 mg (0.51 mmol) 6-[5-(4-chloro-phenyl)-pyridin-2-ylethynyl]-2-pyrrolidin-1-ylmethyl-1,2,3,4-tetrahydro-quinoline (see Example 3.46) in 5 mL DCM and the mixture is stirred for 2 h at RT. Another 0.37 mL (3.85 mmol) acetic anhydride are added and the reaction is stirred for a further 4 days at RT. The solvent is eliminated i.vac. The purification is carried out by column chromatography using HPLC-MS.

Yield: 105 mg (43.5% of theory)

$C_{29}H_{28}ClN_3O$ (M=470.019)

Calc.: molpeak (M+H)$^+$: 470/472 Found: molpeak (M+H)$^+$: 470/472

HPLC retention time: 7.08 min (method A)

Example 3.68

5-(4-chloro-phenyl)-2-[3-pyridin-2-yl-4-(2-pyrrolidin-1-yl-ethoxy)-phenylethynyl]-pyridine

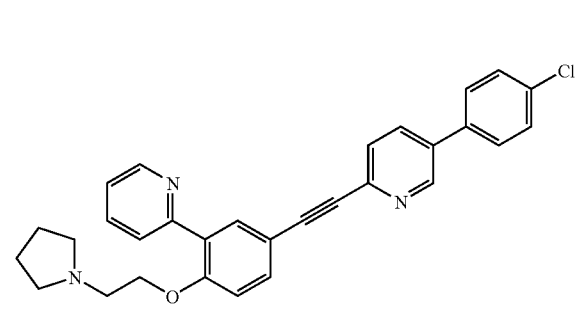 [SMILES: Clc1ccc(-c2ccc(C#Cc3ccc(OCCN4CCCC4)c(-c4ccccn4)c3)nc2)cc1]

30 mg (0.24 mmol) pyridine-3-boric acid are added to a solution of 115 mg (0.24 mmol) 2-[3-bromo-4-(2-pyrrolidin-1-yl-ethoxy)-phenylethynyl]-5-(4-chloro-phenyl)-pyridine (see Example 3.7), 0.5 mL (1.00 mmol) of a 2 M Na$_2$CO$_3$ solution and 15 mg (0.24 mmol) tetrakis-triphenylphosphane-palladium in 1 mL 1,4-dioxane and 0.3 mL methanol. The reaction mixture is refluxed for 6 h. After filtration the solvent is eliminated i.vac. The purification is carried out by column chromatography on silica gel (gradient: DCM to DCM/MeOH/NH$_3$ 1:1:0.1).

Yield: 1.8 mg (1.6% of theory)

$C_{30}H_{26}ClN_3O$ (M=480.01)

Calc.: molpeak (M−H)$^-$: 480/482 Found: molpeak (M−H)$^-$: 480/482

HPLC retention time: 6.50 min (method A)

Example 3.69

5-(4-chloro-phenyl)-2-{4-[2-(4-methyl-piperidin-1-yl)-ethoxy]-naphthyl-1-ylethynyl}-pyridine

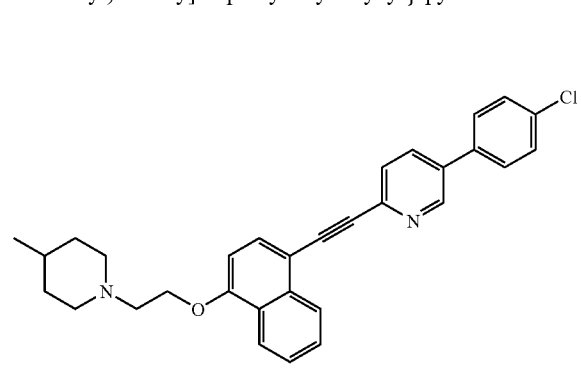

3.69a

1-[2-(4-bromo-naphthyl-1-yloxy)-ethyl]-4-methyl-piperidin

The product is obtained analogously to Example 3.1e from 1.0 g (5.35 mmol) 4-bromo-naphthyl-1-ol and 323 mg (2.00 mmol) 1-(2-chloro-ethyl)-4-methyl-piperidine.

Yield: 530 mg (97.0% of theory)
$C_{18}H_{22}BrNO$ (M=348.286)
Calc.: molpeak $(M+H)^+$: 348/350 Found: molpeak $(M+H)^+$: 348/350
HPLC retention time: 7.10 min (method A)

3.69b

1-[2-(4-iodo-naphthyl-1-yloxy)-ethyl]-4-methyl-piperidine

Prepared according to general working method II from 1-[2-(4-bromo-naphthyl-1-yloxy)-ethyl]-4-methyl-piperidine (530 mg, 1.52 mmol).

Yield: 500 mg (83.1% of theory)
$C_{18}H_{22}INO$ (M=395.287)
Calc.: molpeak $(M+H)^+$: 396 Found: molpeak $(M+H)^+$: 396
HPLC retention time: 6.74 min (method A)

3.69c

5-(4-chloro-phenyl)-2-{4-[2-(4-methyl-piperidin-1-yl)-ethoxy]-naphthyl-1-ylethynyl}-pyridine Prepared according to general working method I from 1-[2-(4-iodo-naphthyl-1-yloxy)-ethyl]-4-methyl-piperidine (277 mg, 0.70 mmol) and 5-(4-chloro-phenyl)-2-ethynyl-pyridine (150 mg, 0.70 mmol).

Yield: 66 mg (19.6% of theory)
$C_{31}H_{29}ClN_2O$ (M=481.043)
Calc.: molpeak $(M+H)^+$: 481/483 Found: molpeak $(M+H)^+$: 481/483
$R_f$ value: 0.60 (silica gel, EtOAc/MeOH/$NH_3$ 95:5:0.5)

Example 3.70

2-{4-[2-(4-methyl-piperidin-1-yl)-ethoxy]-phenyl-ethynyl}-5-phenyl-pyridine

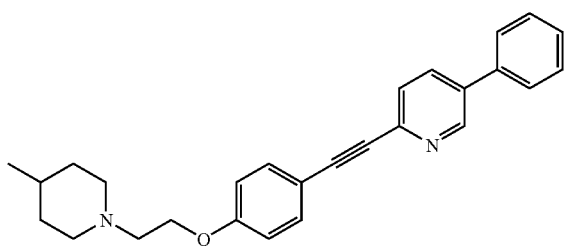 [SMILES: CC1CCN(CCOc2ccc(C#Cc3ccc(-c4ccccc4)cn3)cc2)CC1]

3.70a

5-bromo-2-{4-[2-(4-methyl-piperidin-1-yl)-ethoxy]-phenylethynyl}-pyridine

Prepared according to general working method I from 1-[2-(4-iodo-phenoxy)-ethyl]-4-methyl-piperidine (345 mg, 1.00 mmol) and 5-bromo-2-ethynyl-pyridine (83 mg, 0.39 mmol).

Yield: 100 mg (25.0% of theory)
$C_{21}H_{23}BrN_2O$ (M=399.334)
Calc.: molpeak $(M+H)^+$: 399/401 Found: molpeak $(M+H)^+$: 399/401
$R_f$ value: 0.83 (silica gel, DCM/MeOH/$NH_3$ 95:5:0.5)

3.70.b

2-{4-[2-(4-methyl-piperidin-1-yl)-ethoxy]-phenyl-ethynyl}-5-phenyl-pyridine

Under an argon atmosphere 30 mg (0.25 mmol) phenylboric acid are added to a solution of 100 mg (0.25 mmol) 5-bromo-2-{4-[2-(4-methyl-piperidin-1-yl)-ethoxy]-phenylethynyl}-pyridine, 0.25 mL (0.50 mmol) of a 2 M $Na_2CO_3$ solution and 4 mg (0.01 mmol) Pd(dppf)$Cl_2$ in 5 mL 1,4-dioxane and 2 mL MeOH. The reaction mixture is stirred for 3 days at 90° C. The reaction mixture is diluted with EtOAc and the organic phase is washed with 40 mL water and finally with saturated NaCl solution. The organic phase is dried over $MgSO_4$ and the solvent is eliminated i.vac. The purification is carried out using HPLC-MS and by column chromatography on silica gel (gradient: DCM/MeOH/NH3 95:5:0.5 to DCM/MeOH/$NH_3$ 9:1:0.1).

Yield: 27 mg (27.2% of theory)
$C_{27}H_{28}N_2O$ (M=396.537)
Calc.: molpeak $(M+H)^+$: 397 Found: molpeak $(M+H)^+$: 397
HPLC retention time: 7.61 min (method A)

Example 3.71

5-(4-chloro-phenyl)-2-{4-[2-(4-methyl-piperidin-1-yl)-propoxy]-phenylethynyl}-pyridine

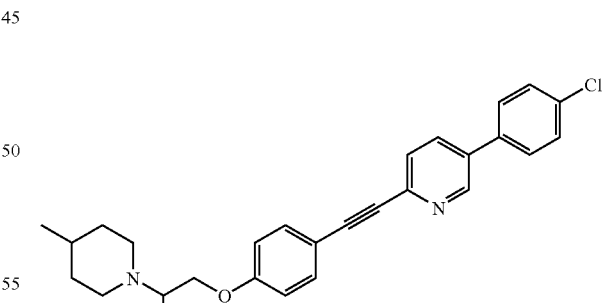

3.71a

1-(4-iodo-phenoxy)-propan-2-ol

The product is obtained analogously to Example 3.1e from 1.39 g (10.0 mmol) 1-bromo-2-propanol and 2.20 g (10.0 mmol) 4-iodophenol.

Yield: 2.00 g (71.9% of theory)

C₉H₁₁IO₂ (M=278.091)

Calc.: molpeak (M+Na)⁺: 301 Found: molpeak (M+Na)⁺: 301

R$_f$ value: 0.20 (silica gel, PE/EtOAc 4:1)

3.71b

1-{4-[5-(4-chloro-phenyl)-pyridin-2-ylethynyl]-phenoxy}-propan-2-ol

Prepared according to general working method I from 1-(4-iodo-phenoxy)-propan-2-ol (2.00 g, 7.19 mmol) and 5-(4-chloro-phenyl)-2-ethynyl-pyridine (1.54 g, 7.20 mmol).

Yield: 1.50 g (57.3% of theory)

C₂₂H₁₈ClNO₂ (M=363.847)

Calc.: molpeak (M+H)⁺: 364/366 Found: molpeak (M+H)⁺: 364/366

R$_f$ value: 0.25 (silica gel, PE/EtOAc/DCM 1:1:8)

3.71c

2-{4-[5-(4-chloro-phenyl)-pyridin-2-ylethynyl]-phenoxy}-1-methyl-ethyl methanesulphonate 0.35 mL (4.50 mmol) methanesulphonic acid chloride are added at RT to a solution of 1.50 g (4.12 mmol) 1-{4-[5-(4-chloro-phenyl)-pyridin-2-ylethynyl]-phenoxy}-propan-2-ol and 1.14 mL (8.20 mmol) triethylamine in 80 mL THF and the reaction is stirred for 3 h at this temperature. The solvent is eliminated i.vac. and the residue is combined with 40 mL tert-butylmethylether and 60 mL water. The precipitate is suction filtered and further purification is carried out by column chromatography on silica gel (EtOAc).

Yield: 1.00 g (54.9% of theory)

C₂₃H₂₀ClNO₄S (M=441.937)

Calc.: molpeak (M+H)⁺: 442/444 Found: molpeak (M+H)⁺: 442/444

R$_f$ value: 0.78 (silica gel, PE/EtOAc/DCM 1:1:8)

3.71d 5-(4-chloro-phenyl)-2-{4-[2-(4-methyl-piperidin-1-yl)-propoxy]-phenylethynyl}-pyridine 0.21 mL (1.80 mmol) 4-methylpiperidine are added to a solution of 133 mg (0.30 mmol) 2-{4-[5-(4-chloro-phenyl)-pyridin-2-ylethynyl]-phenoxy}-1-methyl-ethyl methanesulphonate in 2 mL DMF and the mixture is stirred for 16 h at 60° C. and 6 h at 80° C. The solvent is eliminated i.vac., the residue is triturated with isopropanol, suction filtered and dried at 30° C. in the circulating air dryer.

Yield: 65 mg (48.7% of theory)

C₂₈H₂₉ClN₂O (M=445.009)

Calc.: molpeak (M+H)⁺: 445/447 Found: molpeak (M+H)⁺: 445/447

HPLC retention time: 5.37 min (method B)

Example 3.72

(1-{5-[5-(4-chloro-phenyl)-pyridin-2-ylethynyl]-pyridin-2-yl}-pyrrolidin-3-yl)-4-methylpiperidine

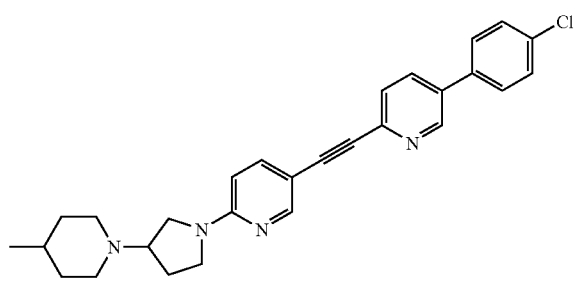 [SMILES: CC1CCN(C2CCN(c3ccc(C#Cc4ccc(-c5ccc(Cl)cc5)cn4)cn3)C2)CC1]

3.72a (R)-1-(5-bromo-pyridin-2-yl)-pyrrolidin-3-ol

The product is obtained analogously to Example 3.31a (reaction time: 60 min at 140° C.) from 2.72 g (11.5 mmol) 2,5-dibromopyridine and 1.00 g (11.5 mmol) (R)-3-pyrrolidinole.

Yield: 1.20 g (43.0% of theory)

C₉H₁₁BrN₂O (M=243.105)

Calc.: molpeak (M+H)⁺: 242/244 Found: molpeak (M+H)⁺: 242/244

HPLC retention time: 3.43 min (method A)

3.72b (R)-1-(5-iodo-pyridin-2-yl)-pyrrolidin-3-ol

Prepared according to general working method II from (R)-1-(5-bromo-pyridin-2-yl)-pyrrolidin-3-ol (1.20 g, 4.94 mmol).

Yield: 1.30 g (90.8% of theory)

C₉H₁₁N₂O (M=290.105)

Calc.: molpeak (M+H)⁺: 291 Found: molpeak (M+H)⁺: 291

HPLC retention time: 3.48 min (method A)

3.72c (R)-1-{5-[5-(4-chloro-phenyl)-pyridin-2-ylethynyl]-pyridin-2-yl}-pyrrolidin-3-ol Prepared according to general working method I from (R)-1-(5-iodo-pyridin-2-yl)-pyrrolidin-3-ol (1.30 g, 4.48 mmol) and 5-(4-chloro-phenyl)-2-ethynyl-pyridine (957 mg, 4.48 mmol).

Yield: 1.36 g (80.7% of theory)

C₂₂H₁₈ClN₃O (M=375.861)

Calc.: molpeak (M+H)⁺: 376/378 Found: molpeak (M+H)⁺: 376/378

HPLC retention time: 6.76 min (method A)

3.72d

1-{5-[5-(4-chloro-phenyl)-pyridin-2-ylethynyl]-pyridin-2-yl}-pyrrolidin-3-one 0.43 mL (5.32 mmol) pyridine and 2.26 g (0.80 mmol, 15 percent by weight) Dess-Martin-periodinane in DCM are added to a solution of 200 mg (0.53 mmol) (R)-1-{5-[5-(4-chloro-phenyl)-pyridin-2-ylethynyl]-pyridin-2-yl}-pyrrolidin-3-ol in 10 mL DCM. The reaction mixture is stirred for 3 h at RT and added to a solution of semisaturated NaHCO$_3$ solution and tert-butylmethylether. The aqueous phase is extracted twice with EtOAc. The organic phase is dried over MgSO$_4$ and the solvent is eliminated i.vac. The product is further reacted without purification.

Yield: 100 mg (35.2% of theory)
$C_{22}H_{16}ClN_3O$ (M=373.845)
Calc.: molpeak (M+H)$^+$: 374/376 Found: molpeak (M+H)$^+$: 374/376

3.72e (1-{5-[5-(4-chloro-phenyl)-pyridin-2-ylethynyl]-pyridin-2-yl}-pyrrolidin-3-yl)-4-methylpiperidine 48 mg (0.22 mmol) NaBH(OAc)$_3$ and 27 µL (0.47 mmol) acetic acid are added to a solution of 100 mg (0.19 mmol, 70% purity) 1-{5-[5-(4-chloro-phenyl)-pyridin-2-ylethynyl]-pyridin-2-yl}-pyrrolidin-3-one and 22 µL 4-methylpiperidine (0.19 mmol) in 5 mL THF. The reaction mixture is stirred overnight and combined with saturated NaHCO$_3$ solution. The organic phase is extracted twice with EtOAc. The organic phase is dried over MgSO$_4$ and the solvent is eliminated i.vac. Further purification is carried out by column chromatography using HPLC-MS.

Yield: 11 mg (12.9% of theory)
$C_{28}H_{29}ClN_4$ (M=457.023)
Calc.: molpeak (M+H)$^+$: 457/459 Found: molpeak (M+H)$^+$: 457/459
HPLC retention time: 5.19 min (method A)

Example 3.73

5-(4-chloro-phenyl)-2-[4-(3-pyrrolidin-1-yl-prop-1-ynyl)-phenylethynyl]-pyridine

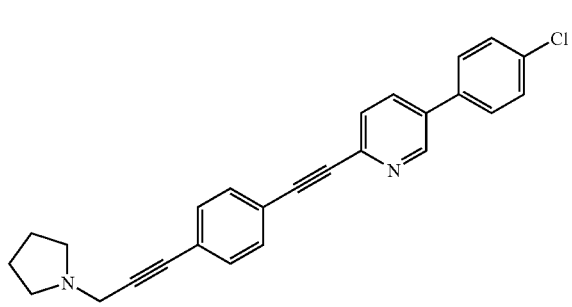 [SMILES: Clc1ccc(-c2ccc(C#Cc3ccc(C#CCN4CCCC4)cc3)nc2)cc1]

3.73a

1-[3-(4-bromo-phenyl)-prop-2-ynyl]-pyrrolidine

Prepared according to general working method I from 4-bromo-iodobenzene (10.9 g, 38.5 mmol) and 1-prop-2-ynyl-pyrrolidine (4.20 g, 71% purity, 27.3 mmol).

Yield: 6.40 g (88.7% of theory)
$C_{13}H_{14}BrN$ (M=264.167)
Calc.: molpeak (M+H)$^+$: 264/266 Found: molpeak (M+H)$^+$: 264/266

3.73b

1-[3-(4-iodo-phenyl)-prop-2-ynyl]-pyrrolidine

Prepared according to general working method II from 1-[3-(4-bromo-phenyl)-prop-2-ynyl]-pyrrolidine (3.2 g, 12.1 mmol).

Yield: 230 mg (4.6% of theory)
$C_{13}H_{14}IN$ (M=311.168)
Calc.: molpeak (M+H)$^+$: 312 Found: molpeak (M+H)$^+$: 312

3.73c 5-(4-chloro-phenyl)-2-[4-(3-pyrrolidin-1-yl-prop-1-ynyl)-phenylethynyl]-pyridine Prepared according to general working method I from 1-[3-(4-iodo-phenyl)-prop-2-ynyl]-pyrrolidine (230 mg, 75%, 0.55 mmol) and 5-(4-chloro-phenyl)-2-ethynyl-pyridine (118 mg, 0.55 mmol).

Yield: 96 mg (43.7% of theory)
$C_{26}H_{21}ClN_2$ (M=396.924)
Calc.: molpeak (M+H)$^+$: 397/399 Found: molpeak (M+H)$^+$: 397/399
HPLC retention time: 5.03 min (method B)

Example 3.74

6-[5-(4-chloro-phenyl)-pyridin-2-ylethynyl]-1-methyl-2-pyrrolidin-1-ylmethyl-1,2,3,4-tetrahydro-quinoline

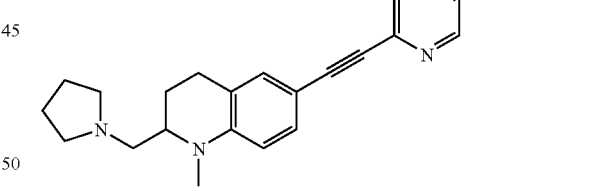

37 mg (1.23 mmol) paraformaldehyde in 1.8 mL THF are added to a solution of 350 mg (0.82 mmol) 6-[5-(4-chloro-phenyl)-pyridin-2-ylethynyl]-2-pyrrolidin-1-ylmethyl-1,2,3,4-tetrahydro-quinoline (see Example 3.46) in 1.6 mL THF. 0.24 mL acetic acid and 1.2 mL THF are added to this mixture. Finally, 1.00 g (2.05 mmol) cyanoborohydride resin (macroporous polystyrene, load: 2.04 mmol/g) are added and the mixture is stirred for 16 h at RT. After filtration the filtrate is combined with 1.50 g (2.15 mmol) toluenesulphonic acid resin (macroporous polystyrene, load: 1.43 mmol/g), shaken for 30 min and suction filtered. The solvent is eliminated i.vac. and purification is carried out by column chromatography using HPLC-MS.

Yield: 33 mg (9.1% of theory)
$C_{28}H_{28}ClN_3$ (M=442.008)

Calc.: molpeak (M+H)+: 442/444 Found: molpeak (M+H)+: 442/444

HPLC retention time: 5.22 min (method B)

Example 4

5-(4-chloro-phenyl)-2-{4-[2-(2,5-dihydro-pyrrol-1-yl)-ethoxy]-phenylethynyl}-pyridine

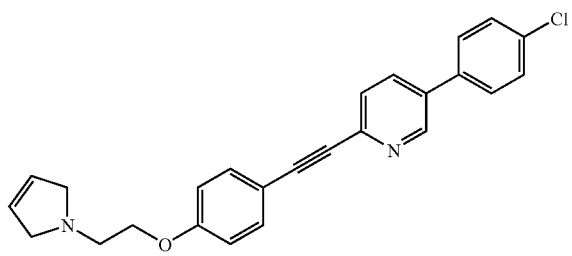 [SMILES: Clc1ccc(-c2ccc(C#Cc3ccc(OCCN4CC=CC4)cc3)nc2)cc1]

4a 2-(4-iodo-phenoxy)-ethanol

A suspension of 11 g (50 mmol) 4-iodophenol, 3.88 mL (55 mmol) 2-bromoethanol and 8.3 g (60 mmol) $K_2CO_3$ in 60 mL acetone is refluxed for 24 h. The solvent is eliminated i.vac., the residue is combined with water, exhaustively extracted with EtOAc and the organic phase is dried over $Na_2SO_4$. After the desiccant and solvent have been eliminated the residue is purified by chromatography on silica gel (cyc/EtOAc 7:3).

Yield: 2.9 g (22.0% of theory)
$C_8H_9IO_2$ (M=264.064)
Calc.: molpeak (M+H)+: 264 Found: molpeak (M+H)+: 264
$R_f$ value: 0.24 (silica gel, cyc/EtOAc 2:1)

4b

2-{4-[5-(4-chloro-phenyl)-pyridin-2-ylethynyl]-phenoxy}-ethanol

Under an argon atmosphere 253 mg (0.22 mmol) tetrakis-triphenylphosphane-palladium and 42 mg (0.22 mmol) CuI are added to a solution of 2.9 g (11 mmol) 2-(4-iodo-phenoxy)-ethanol and 2.35 g (11 mmol) 5-(4-chloro-phenyl)-2-ethynyl-pyridine in 50 mL piperidine and the reaction mixture is stirred for 30 min at RT. The solvent is eliminated i.vac., the residue is combined with water and stirred with EtOAc. The product precipitated is suction filtered and dried.

Yield: 2.1 g (54.7% of theory)
$C_{21}H_{16}ClNO_2$ (M=349.820)
Calc.: molpeak (M+H)+: 350 Found: molpeak (M+H)+: 350
$R_f$ value: 0.42 (silica gel, cyc/EtOAc 1:1)

4c 5-(4-chloro-phenyl)-2-{4-[2-(2,5-dihydro-pyrrol-1-yl)-ethoxy]-phenylethynyl}-pyridine 23 μL (0.29 mmol) methanesulphonic acid chloride are added dropwise to a solution, cooled to 0° C., of 85 mg (0.24 mmol) 2-{4-[5-(4-chloro-phenyl)-pyridin-2-ylethynyl]-phenoxy}-ethanol and 41 μL (0.29 mmol) triethylamine in 10 mL DCM and the reaction mixture is stirred for 1 h at this temperature. 46 μL (0.58 mmol) 2,5-dihydro-1H-pyrrole are added dropwise, the mixture is heated to RT and stirred overnight. 1 mL of DMF is added and the mixture is heated for 8 h to 70° C. The mixture is evaporated down i. vac., the residue is combined with water, extracted exhaustively with EtOAc and the organic phase is dried over $Na_2SO_4$. After the desiccant and solvent have been eliminated the residue is purified by chromatography on silica gel (EtOAc/MeOH/$NH_3$ 95:5:0.5).

Yield: 16 mg (16.4% of theory)
$C_{25}H_{21}ClN_2O$ (M=400.912)
Calc.: molpeak (M+H)+: 401/403 Found: molpeak (M+H)+: 401/403
$R_f$ value: 0.16 (silica gel, DCM/MeOH 95:5)

Example 4.1

5-(4-chloro-phenyl)-2-[4-(2-piperidin-1-yl-ethoxy)-phenylethynyl]-pyridine

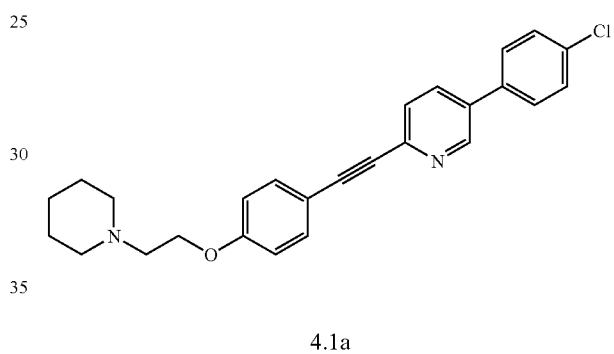

4.1a

2-{4-[5-(4-chloro-phenyl)-pyridin-2-ylethynyl]-phenoxy}-ethyl methanesulphonate 0.59 mL (7.55 mmol) methanesulphonic acid chloride are added dropwise to a solution, cooled to 0° C., of 2.2 g (6.29 mmol) 2-{4-[5-(4-chloro-phenyl)-pyridin-2-ylethynyl]-phenoxy}-ethanol and 1.74 mL (12.58 mmol) triethylamine in 25 mL THF. The reaction mixture is heated to RT and stirred for 2 h. To complete the reaction 5 mL pyridine are added and kept at RT for a further 18 h. The solvent is eliminated i.vac., the residue is combined with water and triturated with diethyl ether. The product precipitated is suction filtered and dried.

Yield: 2.4 g (89.2% of theory)
$C_{22}H_{18}ClNO_4S$ (M=427.910)
Calc.: molpeak (M+H)+: 428/430 Found: molpeak (M+H)+: 428/430
$R_f$ value: 0.42 (silica gel, cyc/EtOAc 1:1)

4.1b 5-(4-chloro-phenyl)-2-[4-(2-piperidin-1-yl-ethoxy)-phenylethynyl]-pyridine

99 μL (1.0 mmol) piperidine are added to a solution of 85.6 mg (0.2 mmol) of 2-{4-[5-(4-chloro-phenyl)-pyridin-2-ylethynyl]-phenoxy}-ethyl methanesulphonate in 2 mL DMF and the reaction mixture is stirred for 18 h at RT. The solvent is distilled off i.vac., the residue is stirred with 5 mL water and 40 mL DCM, the organic phase is separated off and dried with Na$_2$SO$_4$. After the desiccant and solvent have been eliminated the residue is triturated with 20 mL diethyl ether and suction filtered.

Yield: 62 mg (74.3% of theory)
C$_{26}$H$_{25}$ClN$_2$O (M=416.955)

Calc.: molpeak (M+H)$^+$: 417/419 Found: molpeak (M+H)$^+$: 417/419

HPLC retention time: 6.51 min (method A)

The following compounds are prepared as described in Example 4.1b:

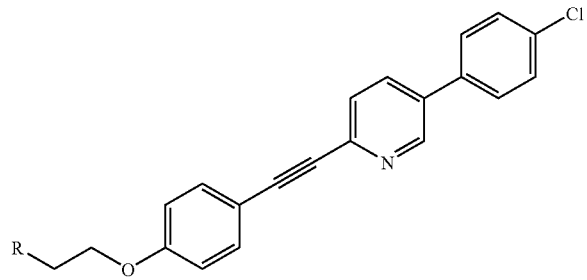

| Example | R | Yield (%) | empirical formula | mass spectrum | HPLC retention time in min (method) |
|---|---|---|---|---|---|
| 4.2 | azetidinyl | 48.9 | C$_{24}$H$_{21}$ClN$_2$O | 389/391 [M + H]$^+$ | 6.15 (A) |
| 4.3 | (pyridin-2-ylmethyl)(methyl)amino | 27.5 | C$_{28}$H$_{24}$ClN$_3$O | 454/456 [M + H]$^+$ | 7.25 (A) |
| 4.4 | (pyridin-2-ylmethyl)amino | 28.4 | C$_{27}$H$_{22}$ClN$_3$O | 440/442 [M + H]$^+$ | 7.46 (A) |
| 4.5 | 2-(methoxymethyl)pyrrolidinyl | 50.3 | C$_{27}$H$_{27}$ClN$_2$O$_2$ | 447/449 [M + H]$^+$ | 7.46 (A) |
| 4.6 | (1-methylpiperidin-4-yl)(methyl)amino | 27.2 | C$_{28}$H$_{30}$ClN$_3$O | 460/462 [M + H]$^+$ | 5.86 (A) |
| 4.7 | 1,2,3,4-tetrahydroisoquinolin-2-yl | 69.9 | C$_{30}$H$_{25}$ClN$_2$O | 465/467 [M + H]$^+$ | 7.98 (A) |
| 4.8 | (cyclopropylmethyl)amino | 55.8 | C$_{25}$H$_{23}$ClN$_2$O | 403/405 [M + H]$^+$ | 6.24 (A) |
| 4.9 | 4-(pyrrolidin-1-yl)piperidin-1-yl | 72.0 | C$_{30}$H$_{32}$ClN$_3$O | 486/488 [M + H]$^+$ | 5.54 (A) |

-continued

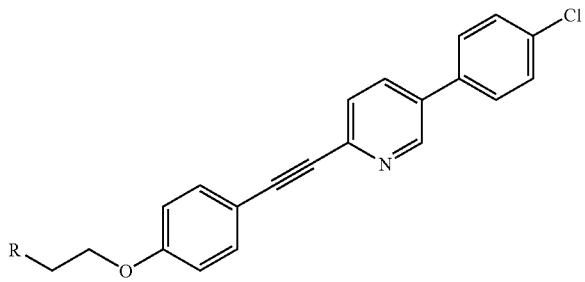

| Example | R | Yield (%) | empirical formula | mass spectrum | HPLC retention time in min (method) |
|---|---|---|---|---|---|
| 4.10 | morpholine-N-yl | 65.6 | C₂₅H₂₃ClN₂O₂ | 418/420 [M + H]⁺ | 6.38 (A) |
| 4.11 | 4-methylpiperazin-1-yl | 48.6 | C₂₆H₂₆ClN₃O | 432/434 [M + H]⁺ | 5.78 (A) |
| 4.12 | 2-(methoxymethyl)pyrrolidin-1-yl | 50.3 | C₂₇H₂₇ClN₂O₂ | 447/449 [M + H]⁺ | 0.80 (EtOAc/MeOH/NH₃ 90:10:1) |
| 4.13 | 4-(N-Boc-N-methylamino)piperidin-1-yl | 33.0 | C₃₂H₃₆ClN₃O₃ | 546/548 [M + H]⁺ | 0.75 (EtOAc/MeOH/NH₃ 90:10:1) |
| 4.14 | 2-methylpyrrolidin-1-yl | 54.0 | C₂₆H₂₅ClN₂O | 417/419 [M + H]⁺ | 0.78 (EtOAc/MeOH/NH₃ 90:10:1) |

The following compounds are prepared as described in Example 4.1b, while after the elimination of the solvent the reaction mixture is combined with 5 mL saturated NaHCO₃ solution, extracted with 40 mL DCM and after the organic phase has been removed it is dried with Na₂SO₄. After the desiccant and solvent have been eliminated the residue is purified by chromatography on silica gel.

| Example | R | Yield (%) | empirical formula | mass spectrum | HPLC retention time in min (method) |
|---|---|---|---|---|---|
| 4.15 | 3-(N-Boc-amino)pyrrolidin-1-yl | 57.9 | C₃₀H₃₂ClN₃O₃ | 518/520 [M + H]⁺ | 7.94 (A) |

-continued

| Example | R | Yield (%) | empirical formula | mass spectrum | HPLC retention time in min (method) |
|---|---|---|---|---|---|
| 4.16 | H-O-CH2-CH2-N(CH3)-* | 73.7 | $C_{24}H_{23}ClN_2O_2$ | 407/409 $[M+H]^+$ | 6.29 (A) |
| 4.17 | Ph-CH2-N(CH3)-* | 61.8 | $C_{29}H_{25}ClN_2O$ | 453/455 $[M+H]^+$ | 7.81 (A) |

3 eq. of the corresponding amine are added to a solution of 1 eq. 2-{4-[5-(4-chloro-phenyl)-pyridin-2-ylethynyl]-phenoxy}-ethyl methanesulphonate in DMF (2 mL/0.25 mmol) and the reaction mixture is stirred for 16-72 h at 60-70° C. The working up is done by 2 alternative methods:

Alternative A: The reaction mixture is purified directly by HPLC.

Alternative B: After the reaction mixture has cooled the precipitate formed is combined with 1.5 mL isopropanol, suction filtered, washed with a little isopropanol and dried overnight at 30° C. in the circulating air dryer.

The following compounds are obtained by this method:

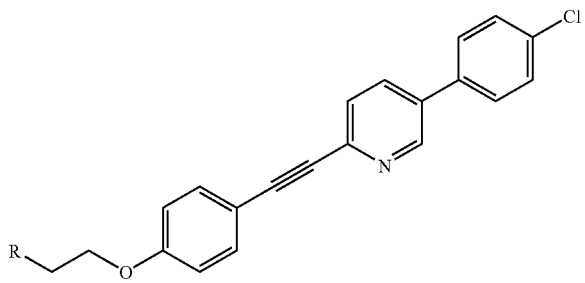

| Example | R | Yield (%) (variant) | empirical formula | mass spectrum | HPLC retention time in min (method) |
|---|---|---|---|---|---|
| 4.18 | Boc-N(CH3)-CH2-(4-piperidinyl)- | 53.6 (A) | $C_{33}H_{38}ClN_3O_3$ | 560/562 $[M+H]^+$ | 5.44 (B) |
| 4.19 | Boc-NH-(3-piperidinyl)-* | 37.6 (A) | $C_{31}H_{34}ClN_3O_3$ | 532/534 $[M+H]^+$ | 5.24 (B) |
| 4.20 | HO-CH2-(2-piperidinyl)-* | 42.1 (A) | $C_{27}H_{27}ClN_2O_2$ | 447/449 $[M+H]^+$ | 7.19 (A) |

-continued

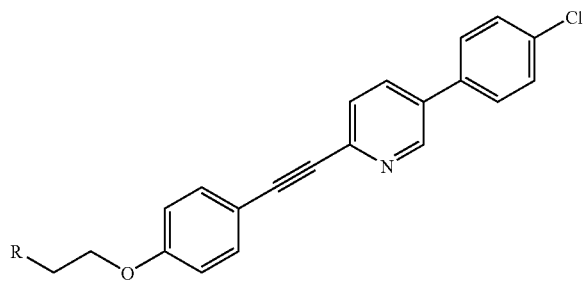

| Example | R | Yield (%) (variant) | empirical formula | mass spectrum | HPLC retention time in min (method) |
|---|---|---|---|---|---|
| 4.21 | (2-ethylpiperidinyl) | 41.3 (A) | $C_{28}H_{29}ClN_2O$ | 445/447 $[M+H]^+$ | 7.95 (A) |
| 4.22 | (4-hydroxy-4-methylpiperidinyl) | 40.3 (A) | $C_{27}H_{27}ClN_2O_2$ | 447/449 $[M+H]^+$ | 4.68 (B) |
| 4.23 | (N-methyl-N-acetyl-aminomethylpiperidinyl) | 69.3 (A) | $C_{30}H_{32}ClN_3O_2$ | 502/504 $[M+H]^+$ | 6.86 (A) |
| 4.24 | (2-hydroxymethylpyrrolidinyl) | 70.2 (A) | $C_{26}H_{25}ClN_2O_2$ | 433/435 $[M+H]^+$ | 4.68 (A) |
| 4.25 | (2,6-dimethylpiperidinyl) | 27.0 (A) | $C_{28}H_{29}ClN_2O$ | 445/447 $[M+H]^+$ | 5.30 (B) |
| 4.26 | (4-ethylpiperidinyl) | 23.4 (A) | $C_{28}H_{29}ClN_2O$ | 445/447 $[M+H]^+$ | 8.09 (A) |
| 4.27 | (4-hydroxymethylpiperidinyl) | 70.7 (A) | $C_{27}H_{27}ClN_2O_2$ | 447/449 $[M+H]^+$ | 6.79 (A) |
| 4.28 | (2,4,6-trimethylpiperidinyl) | 20.0 (B) | $C_{29}H_{31}ClN_2O$ | 459/461 $[M+H]^+$ | 5.49 (B) |

-continued

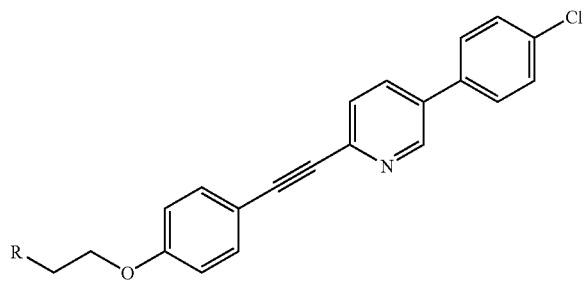

| Example | R | Yield (%) (variant) | empirical formula | mass spectrum | HPLC retention time in min (method) |
|---|---|---|---|---|---|
| 4.29 | (tert-butyl piperidine-piperidine group) | 66.6 (B) | $C_{36}H_{42}ClN_3O_3$ | 600/602 [M + H]$^+$ | 5.70 (B) |
| 4.30 | (diisopropylamino group) | 9.2 (A) | $C_{27}H_{29}ClN_2O$ | 433/435 [M + H]$^+$ | 5.20 (B) |
| 4.31 | (2-(dimethylaminoethyl)piperidine group) | 22.9 (A) | $C_{30}H_{34}ClN_3O$ | 488/490 [M + H]$^+$ | 5.60 (A) |
| 4.32 | (4-carbamoylpiperidine group) | 87.0 (B) | $C_{27}H_{26}ClN_3O_2$ | 460/462 [M + H]$^+$ | 0.12 (DCM/ MeOH/NH$_3$ 95:5:0.5) |
| 4.33 | (4-hydroxypiperidine group) | 48.0 (B) | $C_{26}H_{25}ClN_2O_2$ | 433/435 [M + H]$^+$ | 0.13 (DCM/ MeOH/NH$_3$ 95:5:0.5) |
| 4.34 | (4-methylpiperidine group) | 39.0 (B) | $C_{27}H_{27}ClN_2O$ | 431/433 [M + H]$^+$ | 0.28 (DCM/ MeOH/NH$_3$ 95:5:0.5) |
| 4.35 | (4-phenylpiperidine group) | 61.7 (B) | $C_{31}H_{29}ClN_2O$ | 493/495 [M + H]$^+$ | 0.35 (DCM/ MeOH/NH$_3$ 95:5:0.5) |
| 4.36 | (decahydroisoquinoline group) | 20.4 (B) | $C_{30}H_{31}ClN_2O$ | 471/473 [M + H]$^+$ | 0.25 (DCM/ MeOH/NH$_3$ 95:5:0.5) |

-continued

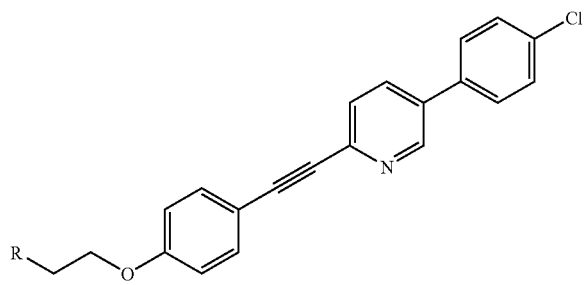

| Example | R | Yield (%) (variant) | empirical formula | mass spectrum | HPLC retention time in min (method) |
|---|---|---|---|---|---|
| 4.37 | (decahydroisoquinoline) | 75.6 (B) | C₃₀H₃₁ClN₂O | 471/473 [M + H]⁺ | 0.23 (DCM/MeOH/NH₃ 95:5:0.5) |
| 4.38 | (N,N-diethylcarboxamide piperidine) | 69.0 (B) | C₃₁H₃₄ClN₃O₂ | 516/518 [M + H]⁺ | 0.20 (DCM/MeOH/NH₃ 95:5:0.5) |
| 4.39 | (tetrahydropyridine) | 40.5 (B) | C₂₆H₂₃ClN₂O | 415/417 [M + H]⁺ | 0.22 (DCM/MeOH/NH₃ 95:5:0.5) |
| 4.40 | (thieno-azepine) | 63.5 (B) | C₂₉H₂₅ClN₂OS | 485/487 [M + H]⁺ | 0.18 (DCM/MeOH/NH₃ 95:5:0.5) |
| 4.41 | (4-(dimethylaminomethyl)piperidine) | 38.8 (B) | C₂₉H₃₂ClN₃O | 474/476 [M + H]⁺ | 0.09 (DCM/MeOH/NH₃ 95:5:0.5) |
| 4.42 | (decahydroquinoline) | 41.7 (B) | C₃₀H₃₁ClN₂O | 471/473 [M + H]⁺ | 0.30 (DCM/MeOH/NH₃ 95:5:0.5) |

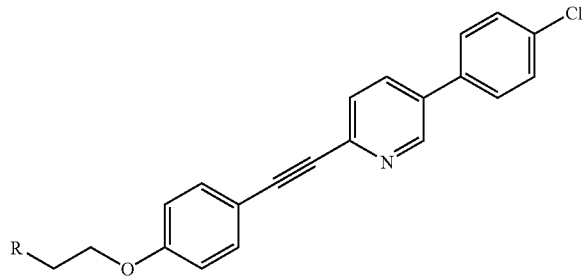

| Example | R | Yield (%) (variant) | empirical formula | mass spectrum | HPLC retention time in min (method) |
|---|---|---|---|---|---|
| 4.43 | (4-propylpiperidine) | 55.8 (B) | $C_{29}H_{31}ClN_2O$ | 459/461 [M + H]$^+$ | 0.23 (DCM/MeOH/NH$_3$ 95:5:0.5) |
| 4.44 | (3,5-dimethylpiperidine) | 29.7 (B) | $C_{28}H_{29}ClN_2O$ | 445/447 [M + H]$^+$ | 0.32 (DCM/MeOH/NH$_3$ 95:5:0.5) |

Example 4.45

1-(2-{4-[5-(4-chloro-phenyl)-pyridin-2-ylethynyl]-phenoxy}-ethyl)-[4,4']bipiperidine

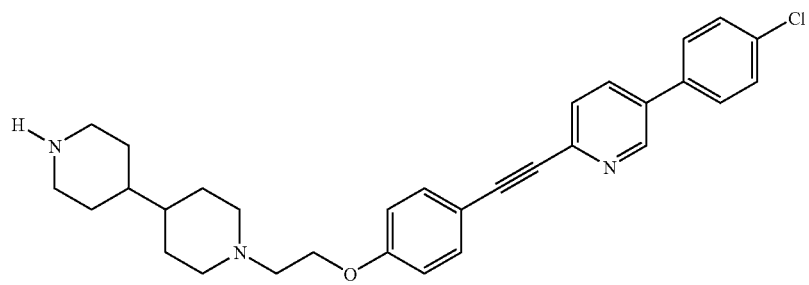 [SMILES: Clc1ccc(-c2ccc(C#Cc3ccc(OCCN4CCC(C5CCNCC5)CC4)cc3)nc2)cc1]

3 mL of a 5 N HCl solution in isopropanol are added to a solution of 200 mg (0.33 mmol) tert-butyl 1'-(2-{4-[5-(4-chloro-phenyl)-pyridin-2-ylethynyl]-phenoxy}-ethyl)-[4,4']bipiperidinyl-1-carboxylate (Example 4.29) in 5 mL DCM and the reaction mixture is stirred for 4 h at RT. It is diluted with 30 mL DCM, neutralised with saturated NaHCO$_3$ solution, combined with 30 mL water, the aqueous phase is extracted exhaustively with DCM and the combined organic phases are dried over MgSO$_4$. After the desiccant and solvent have been eliminated the desired product is obtained.

Yield: 127 mg (76.3% of theory)

$C_{31}H_{34}ClN_3O$ (M=500.089)

Calc.: molpeak (M+H)$^+$: 500/502 Found: molpeak (M+H)$^+$: 500/502

R$_f$ value: 0.10 (silica gel, DCM/MeOH/NH$_3$ 9:1:0.1)

Example 4.46

(R)-1-(2-{4-[5-(4-chloro-phenyl)-pyridin-2-ylethynyl]-phenoxy}-ethyl)-piperidin-3-ylamine

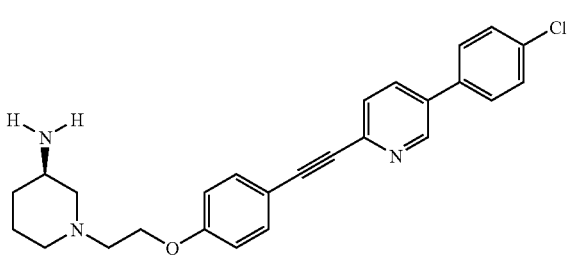 [SMILES: N[C@@H]1CCCN(CCOc2ccc(C#Cc3ccc(-c4ccc(Cl)cc4)cn3)cc2)C1]

1.5 mL of a 5 N HCl solution in isopropanol are added to a solution of 110 mg (0.21 mmol) tert-butyl [(R)-1-(2-{4-[5-(4-chloro-phenyl)-pyridin-2-ylethynyl]-phenoxy}-ethyl)-piperidin-3-yl]-carbaminate (Example 4.19) in 5 mL DCM and the reaction mixture is stirred for 4 h at RT. The precipitate formed is combined with a little tert-butylmethylether, filtered, washed with tert-butylmethylether and dried at 30° C.

Yield: 104 mg (99.5% of theory)
$C_{26}H_{26}ClN_3O*2HCl$ (M=504.892)
Calc.: molpeak (M+H)$^+$: 432/434 Found: molpeak (M+H)$^+$: 432/434
$R_f$ value: 0.27 (silica gel, DCM/MeOH/NH$_3$ 9:1:0.1)

Example 4.47

[1-(2-{4-[5-(4-chloro-phenyl)-pyridin-2-ylethynyl]-phenoxy}-ethyl)-piperidin-4-ylmethyl]-methyl-amine

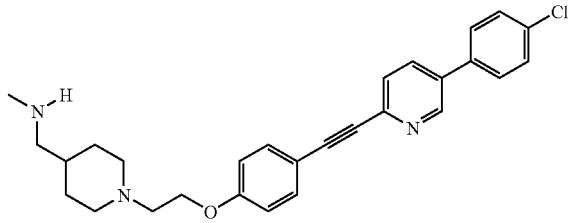 [SMILES: CNCC1CCN(CCOc2ccc(C#Cc3ccc(-c4ccc(Cl)cc4)cn3)cc2)CC1]

Prepared analogously to Example 4.46 from 160 mg (0.29 mmol) tert-butyl [1-(2-{4-[5-(4-chloro-phenyl)-pyridin-2-ylethynyl]-phenoxy}-ethyl)-piperidin-4-ylmethyl]-methyl-carbaminate (Example 4.18).

Yield: 156 mg (100% of theory)
$C_{28}H_{30}ClN_3O*2HCl$ (M=532.946)
Calc.: molpeak (M+H)$^+$: 460/462 Found: molpeak (M+H)$^+$: 460/462
$R_f$ value: 0.13 (silica gel, DCM/MeOH/NH$_3$ 9:1:0.1)

Example 4.48

1-(2-{4-[5-(4-chloro-phenyl)-pyridin-2-ylethynyl]-phenoxy}-ethyl)-pyrrolidin-3-ylamine

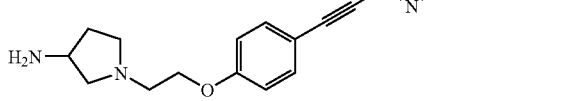

1 mL trifluoroacetic acid are added to a solution of 45 mg (0.09 mmol) tert-butyl [1-(2-{4-[5-(4-chloro-phenyl)-pyridin-2-ylethynyl]-phenoxy}-ethyl)-pyrrolidin-3-yl]-carbaminate (Example 4.15) in 5 mL DCM and the reaction mixture is stirred for 24 h at RT. The mixture is evaporated down i. vac., the residue is combined with 20 mL DCM, the organic phase is washed with saturated NaHCO$_3$ solution and dried over Na$_2$SO$_4$. After the desiccant and solvent have been eliminated the desired product is obtained.

Yield: 15 mg (41.3% of theory)
$C_{25}H_{24}ClN_3O$ (M=417.943)
Calc.: molpeak (M+H)$^+$: 418/420 Found: molpeak (M+H)$^+$: 418/420
HPLC retention time: 5.86 min (method A)

Example 4.49

(2-{4-[5-(4-chloro-phenyl)-pyridin-2-ylethynyl]-phenoxy}-ethyl)-methyl-piperidin-4-yl-amine

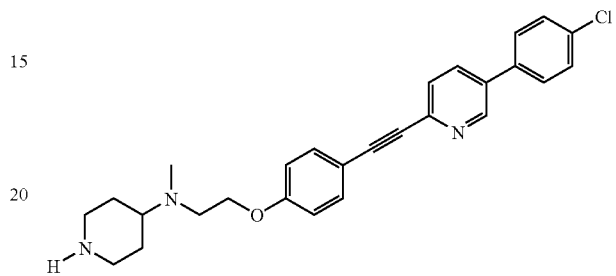

60 µL (0.8 mmol) trifluoroacetic acid are added to a solution of 22 mg (0.04 mmol) tert-butyl 4-[(2-{4-[5-(4-chloro-phenyl)-pyridin-2-ylethynyl]-phenoxy}-ethyl)-methyl-amino]-piperidin-1-carboxylate in 5 mL DCM and the reaction mixture is stirred for 24 h at RT. The mixture is evaporated down i. vac. and the residue is stirred with diethyl ether. The precipitate is suction filtered, washed with diethyl ether and dried.

Yield: 12 mg (67.3% of theory)
$C_{27}H_{28}ClN_3O*CF_3COOH$ (M=560.017)
Calc.: molpeak (M+H)$^+$: 445/447 Found: molpeak (M+H)$^+$: 445/447
$R_f$ value: 0.07 (silica gel, EtOAc/MeOH/NH$_3$ 80:20:2)

Example 4.50 methyl 1-(2-{4-[5-(4-chloro-phenyl)-pyridin-2-yl-ethynyl]-phenoxy}-ethyl)-pyrrolidine-2-carboxylate

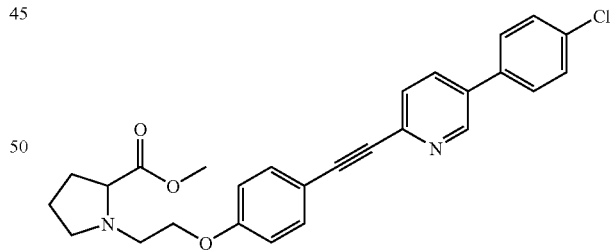

0.15 mL ethyldiisopropylamine and 73 mg (0.44 mmol) proline-methyl ester (used as the hydrochloride) are added to a solution of 171 mg (0.4 mmol) 2-{4-[5-(4-chloro-phenyl)-pyridin-2-ylethynyl]-phenoxy}-ethyl methanesulphonate in 2 mL DMF and the reaction mixture is stirred for 18 h at RT. The mixture is evaporated down i. vac. and the residue is purified by HPLC.

Yield: 10 mg (5.4% of theory)
$C_{27}H_{25}ClN_2O_3$ (M=460.965)
Calc.: molpeak (M+H)$^+$: 461/463 Found: molpeak (M+H)$^+$: 461/463
$R_f$ value: 0.79 (silica gel, cyc/EtOAc 1:1)

The following compounds may be prepared by the methods described:

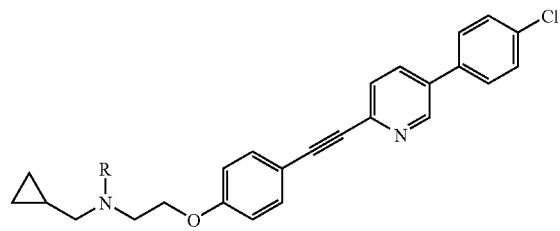

| Example | R |
|---|---|
| 4.51 | 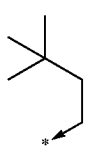 |
| 4.52 | 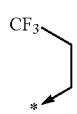 |
| 4.53 | 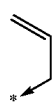 |
| 4.54 | 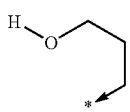 |
| 4.55 | 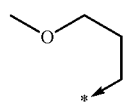 |
| 4.56 |  |
| 4.57 | 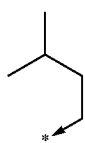 |

Example 4.58

[1-(2-{4-[5-(4-chloro-phenyl)-pyridin-2-ylethynyl]-phenoxy}-ethyl)-piperidin-4-ylmethyl]-dimethyl-amine hydrochloride

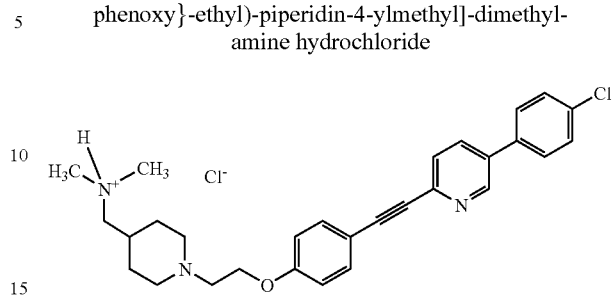

Saturated ethereal HCl solution is added to a solution of 15 mg (0.03 mmol) [1-(2-{4-[5-(4-chloro-phenyl)-pyridin-2-yl-ethynyl]-phenoxy}-ethyl)-piperidin-4-ylmethyl]-dimethyl-amine (Example 4.41) in 6 mL DCM and 4 mL acetone until no more precipitate is formed during the addition. The salt formed is suction filtered in a nitrogen current and dried.

Yield: 10 mg (61.2% of theory)

$C_{29}H_{32}ClN_3O$*HCl (M=510.512)

Calc.: molpeak $(M+H)^+$: 474/476 Found: molpeak $(M+H)^+$: 474/476

Fp: >250° C.

Example 5

5-(4-chloro-phenyl)-2-[3-methyl-4-(2-pyrrolidin-1-yl-ethoxy)-phenylethynyl]-pyridine

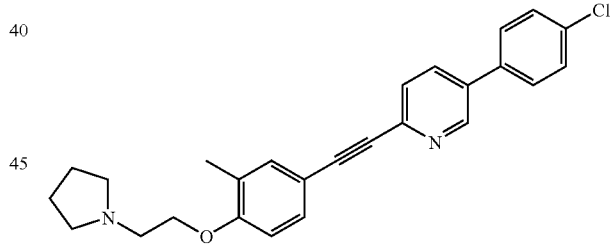

5a 2-(4-iodo-2-methyl-phenoxy)-ethanol

Under an $N_2$ atmosphere 2.34 g (10 mmol) 4-iodo-2-methyl-phenol are added to a suspension batchwise, cooled to 0° C., of 0.48 g (11 mmol) NaH in 50 mL THF and stirred for a further 30 min at this temperature. Then 0.85 mL (12 mmol) 2-bromoethanol, dissolved in 5 mL THF, are added dropwise and the mixture is stirred for 18 h at RT. 5 mL of DMF are added and the reaction mixture is heated to 70° C. for 8 h. The mixture is evaporated down i. vac., the residue is taken up in water, extracted exhaustively with EtOAc and dried with Na$_2$SO$_4$. After the desiccant and solvent have been eliminated the residue is purified by chromatography on silica gel (cyc/EtOAc 7:3).

Yield: 0.39 g (14.0% of theory)

C$_9$H$_{11}$IO$_2$ (M=278.091)

Calc.: molpeak (M+H)$^+$: 279 Found: molpeak (M+H)$^+$: 279

R$_f$ value: 0.28 (silica gel, cyc/EtOAc 2:1)

5b

2-{4-[5-(4-chloro-phenyl)-pyridin-2-ylethynyl]-2-methyl-phenoxy}-ethanol

Prepared analogously to Example 4b from 380 mg (1.37 mmol) 2-(4-iodo-2-methyl-phenoxy)-ethanol and 292 mg (1.37 mmol) 5-(4-chloro-phenyl)-2-ethynyl-pyridine in 38 mL piperidine.

Yield: 340 mg (68.4% of theory)

C$_{22}$H$_{18}$ClNO$_2$ (M=363.847)

Calc.: molpeak (M+H)$^+$: 364 Found: molpeak (M+H)$^+$: 364

R$_f$ value: 0.26 (silica gel, cyc/EtOAc 1:1)

5c

2-{4-[5-(4-chloro-phenyl)-pyridin-2-ylethynyl]-2-methyl-phenoxy}-ethyl methanesulphonate Prepared analogously to Example 4.1a from 310 mg (0.93 mmol) 2-{4-[5-(4-chloro-phenyl)-pyridin-2-ylethynyl]-2-methyl-phenoxy}-ethanol and 88 µL (1.12 mmol) methanesulphonic acid chloride.

Yield: 300 mg (72.7% of theory)

C$_{23}$H$_{20}$ClNO$_4$S (M=441.937)

Calc.: molpeak (M+H)$^+$: 442/444 Found: molpeak (M+H)$^+$: 442/444

R$_f$ value: 0.35 (silica gel, cyc/EtOAc 1:1)

5d 5-(4-chloro-phenyl)-2-[3-methyl-4-(2-pyrrolidin-1-yl-ethoxy)-phenylethynyl]-pyridine A solution of 110 mg (0.25 mmol) 2-{4-[5-(4-chloro-phenyl)-pyridin-2-ylethynyl]-2-methyl-phenoxy}-ethyl methanesulphonate in 2.11 mL (25 mmol) pyrrolidine is heated to 70° C. for 3 h. The mixture is evaporated down i. vac., the residue is combined with water, extracted exhaustively with DCM and the organic phase is dried over Na$_2$SO$_4$. After the desiccant and solvent have been eliminated and after recrystallisation from EtOH the desired product is obtained.

Yield: 55 mg (52.8% of theory)

C$_{26}$H$_{25}$ClN$_2$O (M=416.955)

Calc.: molpeak (M+H)$^+$: 417/419 Found: molpeak (M+H)$^+$: 417/419

HPLC retention time: 7.19 min (method A)

Example 5.1

5-(4-chloro-phenyl)-2-{4-[2-(2,5-dihydro-pyrrol-1-yl)-ethoxy]-3-methyl-phenylethynyl}-pyridine

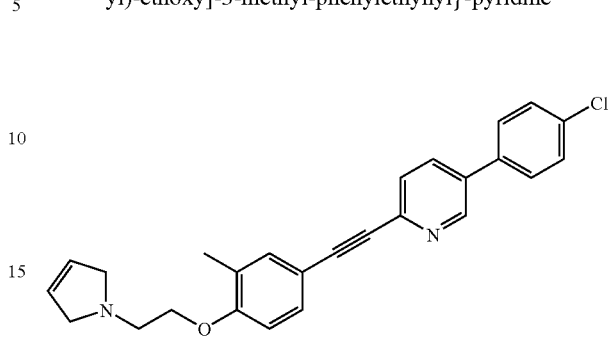

Prepared analogously to Example 5d from 110 mg (0.25 mmol) 2-{4-[5-(4-chloro-phenyl)-pyridin-2-ylethynyl]-2-methyl-phenoxy}-ethyl methanesulphonate and 1.92 mL (25 mmol) 2,5-dihydro-1H-pyrrole.

Yield: 10 mg (9.6% of theory)

C$_{26}$H$_{23}$ClN$_2$O (M=414.939)

Calc.: molpeak (M+H)$^+$: 415/417 Found: molpeak (M+H)$^+$: 415/417

R$_f$ value: 0.50 (silica gel, EtOAc/MeOH/NH$_3$ 95:5:0.5)

Example 5.2

5-(4-chloro-phenyl)-2-{4-[2-(4-isopropyl-piperidin-1-yl)-ethoxy]-3-methyl-phenylethynyl}-pyridine

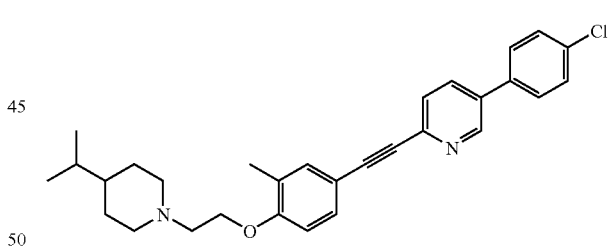

164 mg (1.0 mmol) 4-isopropyl-piperidine (used as the hydrochloride) are added to a solution of 88 mg (0.2 mmol) 2-{4-[5-(4-chloro-phenyl)-pyridin-2-ylethynyl]-2-methyl-phenoxy}-ethyl methanesulphonate and 0.34 mL (2 mmol) ethyldiisopropylamine in 1.8 mL DMF and the reaction mixture is stirred for 24 h at RT. It is filtered using an injection filter and the reaction mixture is purified by HPLC.

Yield: 18 mg (19.4% of theory)

C$_{30}$H$_{33}$ClN$_2$O (M=473.063)

Calc.: molpeak (M+H)$^+$: 473/475 Found: molpeak (M+H)$^+$: 473/475

HPLC retention time: 5.70 min (method B)

The following compounds are prepared as described in Example 5.2:
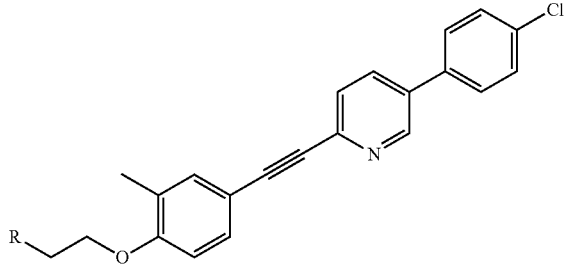
| Example | R | Yield (%) | empirical formula | mass spectrum | HPLC retention time in min (method) |
|---|---|---|---|---|---|
| 5.3 | | 18.3 | $C_{32}H_{29}ClN_2O$ | 493/495 $[M + H]^+$ | 5.70 (B) |
| 5.4 | | 48.9 | $C_{28}H_{30}ClN_3O$ | 460/462 $[M + H]^+$ | 4.22 (B) |
| 5.5 | | 10.9 | $C_{29}H_{31}ClN_2O$ | 459/461 $[M + H]^+$ | 5.49 (B) |
| 5.6 | | 25.6 | $C_{33}H_{31}ClN_2O$ | 507/509 $[M + H]^+$ | 5.73 (B) |
| 5.7 | | 20.2 | $C_{27}H_{25}ClN_2O_2$ | 445/447 $[M + H]^+$ | 4.82 (B) |
| 5.8 | | 24.6 | $C_{27}H_{27}ClN_2O_2$ | 447/449 $[M + H]^+$ | 4.69 (B) |
| 5.9 | | 17.3 | $C_{34}H_{33}ClN_2O$ | 521/523 $[M + H]^+$ | 5.83 (B) |
| 5.10 | | 40.0 | $C_{32}H_{31}ClN_4O$ | 523/525 $[M + H]^+$ | 4.25 (B) |

-continued

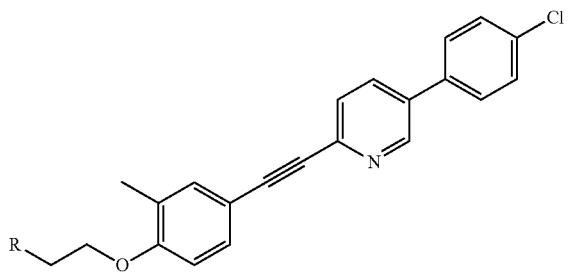

| Example | R | Yield (%) | empirical formula | mass spectrum | HPLC retention time in min (method) |
|---|---|---|---|---|---|
| 5.11 | (S)-pyrrolidin-2-yl-methanol group | 12.3 | $C_{27}H_{27}ClN_2O_2$ | 447/449 [M + H]$^+$ | 4.89 (B) |
| 5.12 | bis(2-hydroxyethyl)amino | 31.0 | $C_{26}H_{27}ClN_2O_3$ | 451/453 [M + H]$^+$ | 4.62 (B) |
| 5.13 | N-methyl-N-propargylamino | 17.7 | $C_{26}H_{23}ClN_2O$ | 415/417 [M + H]$^+$ | 5.03 (B) |
| 5.14 | N-(cyclopropylmethyl)-N-propylamino | 29.8 | $C_{29}H_{31}ClN_2O$ | 459/461 [M + H]$^+$ | 5.46 (B) |
| 5.15 | 3-(dimethylamino)pyrrolidin-1-yl | 52.9 | $C_{28}H_{30}ClN_3O$ | 460/462 [M + H]$^+$ | 4.15 (B) |
| 5.16 | 4-Boc-piperazin-1-yl | 21.4 | $C_{31}H_{34}ClN_3O_3$ | 532/534 [M + H]$^+$ | 5.43 (B) |
| 5.17 | 3,3-dimethylpiperidin-1-yl | 19.8 | $C_{29}H_{31}ClN_2O$ | 459/461 [M + H]$^+$ | 5.43 (B) |
| 5.18 | 4-acetylpiperazin-1-yl | 28.1 | $C_{28}H_{28}ClN_3O_2$ | 474/476 [M + H]$^+$ | 4.66 (B) |

-continued

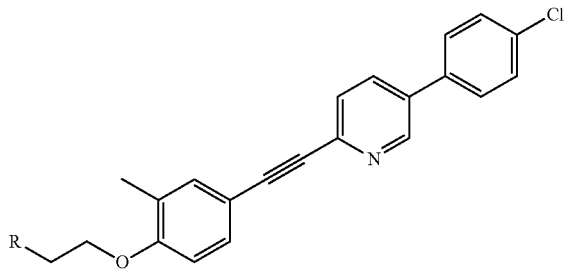

| Example | R | Yield (%) | empirical formula | mass spectrum | HPLC retention time in min (method) |
|---|---|---|---|---|---|
| 5.19 | *tert-butyl N-(piperidin-4-yl)carbamate group* | 11.4 | $C_{33}H_{38}ClN_3O_3$ | 560/562 $[M + H]^+$ | 5.60 (B) |
| 5.20 | *methanesulfonamido-piperidinyl group* | 7.4 | $C_{28}H_{30}ClN_3O_3S$ | 524/526 $[M + H]^+$ | 4.79 (B) |
| 5.21 | *methyl 2-(piperidin-4-yl)acetate group* | 13.5 | $C_{30}H_{31}ClN_2O_3$ | 503/505 $[M + H]^+$ | 5.16 (B) |
| 5.22 | *methyl 4-(piperidin-4-yl)butanoate group* | 14.0 | $C_{32}H_{35}ClN_2O_3$ | 531/533 $[M + H]^+$ | 5.39 (B) |
| 5.23 | *tert-butylamino-piperidinyl group* | 16.6 | $C_{31}H_{36}ClN_3O$ | 502/504 $[M + H]^+$ | 4.15 (B) |
| 5.24 | *diethylamino-ethyl-piperidinyl group* | 24.5 | $C_{33}H_{40}ClN_3O$ | 530/532 $[M + H]^+$ | 4.19 (B) |
| 5.25 | *N-cyclopentyl-N-methyl-piperidin-4-amine group* | 4.8 | $C_{33}H_{38}ClN_3O$ | 528/530 $[M + H]^+$ | 4.22 (B) |

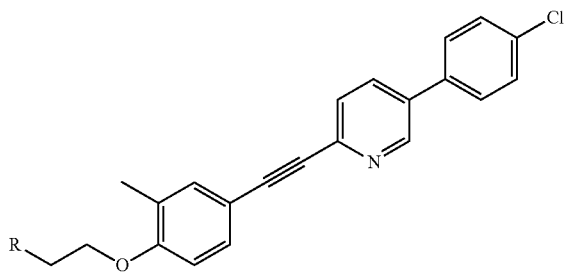

| Example | R | Yield (%) | empirical formula | mass spectrum | HPLC retention time in min (method) |
|---|---|---|---|---|---|
| 5.26 | (3,4-dihydroquinazolin-4-one spiro-piperidine) | 24.0 | $C_{34}H_{31}ClN_4O_2$ | 536/565 [M + H]$^+$ | 4.92 (B) |
| 5.27 | (1-methanesulfonyl-spiroindoline-piperidine) | 36.8 | $C_{35}H_{34}ClN_3O_3S$ | 612/614 [M + H]$^+$ | 5.43 (B) |

The following compounds are prepared as described in Example 5.2, while after the reaction has ended the reaction mixture is evaporated down i.vac., the residue is combined with water, the aqueous phase is exhaustively extracted with DCM and the organic phase is dried over Na$_2$SO$_4$. After the desiccant and solvent have been eliminated the residue is purified by chromatography on silica gel (DCM/MeOH 95:5 or 8:2).

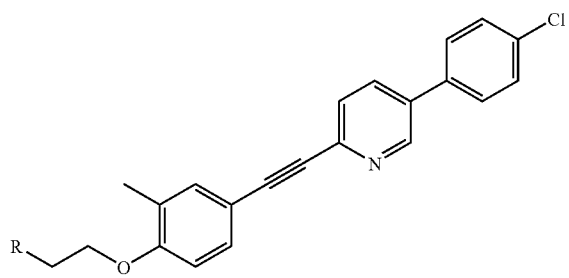

| Example | R | Yield (%) | empirical formula | mass spectrum | HPLC retention time in min (method) |
|---|---|---|---|---|---|
| 5.28 | H$_3$C-N (2-azaspiro[3.4]octane) | 37.6 | $C_{29}H_{30}ClN_3O$ | 472/474 [M + H]$^+$ | 4.05 (B) |

-continued

[Structure: 4-chlorophenyl-pyridine-alkyne-methylphenyl-O-CH2CH2-R scaffold]

| Example | R | Yield (%) | empirical formula | mass spectrum | HPLC retention time in min (method) |
|---|---|---|---|---|---|
| 5.29 | 2-(pyridin-2-yloxy)piperidin-1-yl | 35.8 | $C_{32}H_{30}ClN_3O_2$ | 524/526 $[M + H]^+$ | 5.43 (B) |
| 5.30 | azepan-1-yl | 60.7 | $C_{28}H_{29}ClN_2O$ | 446/448 $[M + H]^+$ | 5.26 (B) |
| 5.31 | 4-hydroxy-4-phenylpiperidin-1-yl | 37.1 | $C_{33}H_{31}ClN_2O_2$ | 523/525 $[M + H]^+$ | 5.33 (B) |
| 5.32 | 3,5-dimethylpiperidin-1-yl | 53.2 | $C_{29}H_{31}ClN_2O$ | 459/461 $[M + H]^+$ | 5.53 (B) |
| 5.33 | 4-methylpiperidin-1-yl | 48.8 | $C_{28}H_{29}ClN_2O$ | 445/447 $[M + H]^+$ | 5.26 (B) |
| 5.34 | isoindolin-2-yl | 46.1 | $C_{30}H_{25}ClN_2O$ | 465/467 $[M + H]^+$ | 5.33 (B) |

The following compounds are prepared as described in Example 5.2, while the reaction mixture is heated to 60° C. for between 4 and 18 h as necessary. After the reaction has ended the reaction mixture is evaporated down i.vac., the residue is combined with water, the aqueous phase is extracted exhaustively with DCM and the organic phase is dried over $Na_2SO_4$. After the desiccant and solvent have been eliminated the residue is purified by chromatography on Alox.

| Example | R | Yield (%) | empirical formula | mass spectrum | $R_f$ value on Alox (eluant) |
|---|---|---|---|---|---|
| 5.35 | (3R)-3-hydroxypyrrolidin-1-yl | 64.7 | $C_{26}H_{25}ClN_2O_2$ | 433/435 $[M + H]^+$ | 0.52 (EtOAc) |

-continued

| Example | R | Yield (%) | empirical formula | mass spectrum | $R_f$ value on Alox (eluant) |
|---|---|---|---|---|---|
| 5.36 | 4-hydroxy-4-methylpiperidinyl | 74.8 | $C_{28}H_{29}ClN_2O_2$ | 461/463 $[M+H]^+$ | 0.31 (cyc/EtOAc 1:1) |
| 5.37 | 3-hydroxypyrrolidinyl | 48.5 | $C_{26}H_{25}ClN_2O_2$ | 433/435 $[M+H]^+$ | 0.52 (cyc/EtOAc 1:2) |
| 5.38 | 4-(hydroxymethyl)piperidinyl | 78.1 | $C_{28}H_{29}ClN_2O_2$ | 461/463 $[M+H]+$ | 0.38 (cyc/EtOAc 1:3) |
| 5.39 | 1,2,3,6-tetrahydropyridinyl | 65.3 | $C_{27}H_{25}ClN_2O$ | 429/431 $[M+H]+$ | 0.70 (cyc/EtOAc 2:1) |
| 5.40 | hydroxy-tropanyl | 49.7 | $C_{29}H_{29}ClN_2O_2$ | 473/475 $[M+H]+$ | 0.34 (cyc/EtOAc 1:1) |
| 5.41 | 3-hydroxypiperidinyl | 52.6 | $C_{27}H_{27}ClN_2O_2$ | 447/449 $[M+H]+$ | 0.21 (cyc/EtOAc 1:1) |
| 5.42 | 4-(trifluoromethyl)piperidinyl | 81.8 | $C_{28}H_{26}ClF_3N_2O_2$ | 499/501 $[M+H]+$ | 0.57 (cyc/EtOAc 3:1) |
| 5.43 | piperidinyl | 47.0 | $C_{27}H_{27}ClN_2O$ | 431/433 $[M+H]+$ | 0.72 (cyc/EtOAc 2:1) |
| 5.44 | N-methyl-N-cyclopropylamino | 12.0 | $C_{26}H_{25}ClN_2O$ | 417/419 $[M+H]+$ | 0.52 (cyc/EtOAc 4:1) |
| 5.45 | 4-(hydroxyimino)piperidinyl | 32.6 | $C_{27}H_{26}ClN_3O_2$ | 461/463 $[M+H]+$ | 0.27 (cyc/EtOAc 1:1) |
| 5.46 | 4-(methoxyimino)piperidinyl | 44.3 | $C_{28}H_{28}ClN_3O_2$ | 474/476 $[M+H]+$ | 0.25 (cyc/EtOAc 4:1) |

The following compounds are prepared as described in Example 5.2, while the reaction mixture is heated to 60° C. for 18 h.

| Example | R | Yield (%) | empirical formula | mass spectrum | $R_f$ value on Alox (eluant) |
|---|---|---|---|---|---|
| 5.47 | 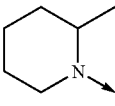 | 28.2 | $C_{28}H_{29}ClN_2O_2$ | 461/463 $[M + H]^+$ | 0.40 (cyc/EtOAc 1:1) |
| 5.48 | 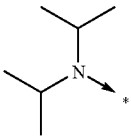 | 6.7 | $C_{28}H_{31}ClN_2O$ | 447/449 $[M + H]+$ | 0.63 (cyc/EtOAc (4:1) |

The following compounds are prepared as described in Example 5.2, heating the reaction mixture to 60° C. for between 6 and 14 h as necessary. After the reaction has ended the reaction mixture is evaporated down i. vac., the residue is combined with saturated $K_2CO_3$ solution, the aqueous phase exhaustively extracted with DCM and the organic phase is dried over $Na_2SO_4$. After the desiccant and solvent have been eliminated the residue is purified by chromatography on Alox.

The following compounds are prepared as described in Example 5.2, heating the reaction mixture to 100° C. for between 3 and 18 h as necessary. After the reaction has ended the reaction mixture is evaporated down i. vac., the residue is combined with saturated $K_2CO_3$ solution, the aqueous phase is exhaustively extracted with DCM and the organic phase is dried over $Na_2SO_4$. After the desiccant and solvent have been eliminated the residue is purified by chromatography on Alox.

| Example | R | Yield (%) | empirical formula | mass spectrum | $R_f$ value on Alox (eluant) or HPLC retention time in min (method) |
|---|---|---|---|---|---|
| 5.49 | 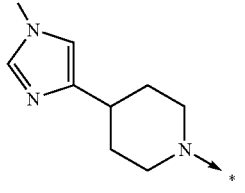 | 5.5 | $C_{30}H_{29}ClN_4O$ | 497/499 $[M + H]^+$ | 0.36 (cyc/EtOAc 1:1) |
| 5.50 | 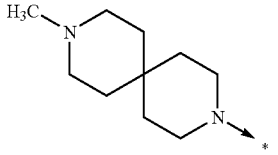 | 8.3 | $C_{32}H_{36}ClN_3O$ | 514/516 $[M + H]^+$ | 4.12 (B) |
| 5.51 | 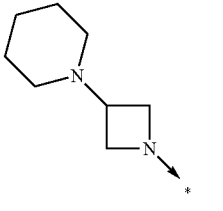 | 3.9 | $C_{30}H_{32}ClN_3O$ | 486/488 $[M + H]^+$ | 4.46 (B) |
| 5.52 | 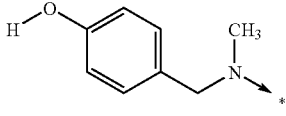 | 36.2 | $C_{30}H_{27}ClN_2O_2$ | 483/485 $[M + H]^+$ | 0.54 (cyc/EtOAc 1:1) |

| Example | R | Yield (%) | empirical formula | mass spectrum | $R_f$ value on Alox (eluant) or HPLC retention time in min (method) |
|---|---|---|---|---|---|
| 5.53 | | 75.7 | $C_{30}H_{32}ClN_3O_2$ | 502/504 $[M + H]^+$ | 0.31 (cyc/EtOAc 1:1) |
| 5.54 | | 23.3 | $C_{32}H_{36}ClN_3O$ | 514/516 $[M + H]^+$ | 4.22 (B) |
| 5.55 | | 15.2 | $C_{29}H_{31}ClN_2O$ | 459/461 $[M + H]^+$ | 5.39 (B) |

Example 5.56

1-(2-{4-[5-(4-chloro-phenyl)-pyridin-2-ylethynyl]-2-methyl-phenoxy}-ethyl)-4-methyl-piperidin-4-ylamine

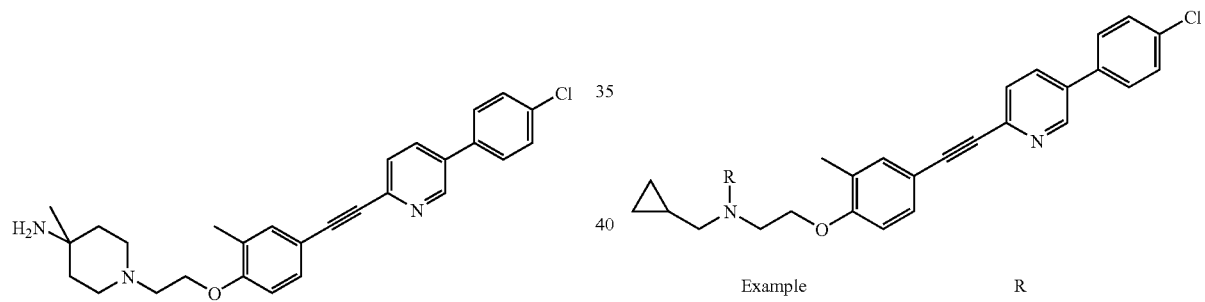

1 mL trifluoroacetic acid is added to a solution of 130 mg (0.23 mmol) tert. butyl [1-(2-{4-[5-(4-chloro-phenyl)-pyridin-2-ylethynyl]-2-methyl-phenoxy}-ethyl)-4-methyl-piperidin-4-yl]-carbaminate (Example 5.19) in 10 mL DCM and the reaction mixture is stirred for 14 h at RT. The mixture is evaporated down i. vac. (water bath temperature max. 30° C.), the residue is combined with dilute $K_2CO_3$ solution, extracted exhaustively with DCM and the organic phase is dried with $Na_2SO_4$. After the desiccant and solvent have been eliminated the residue is triturated with diisopropylether, the precipitate is suction filtered and dried in the air.

Yield: 65 mg (60.9% of theory)

$C_{28}H_{30}ClN_3O$ (M=460.024)

Calc.: molpeak $(M+H)^+$: 460/462 Found: molpeak $(M+H)^+$: 460/462

HPLC retention time: 4.09 min (method B)

The following compounds may be prepared by the processes described:

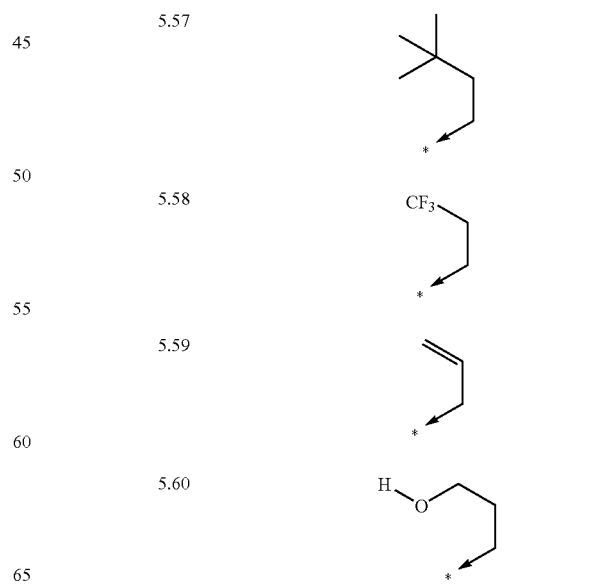

-continued

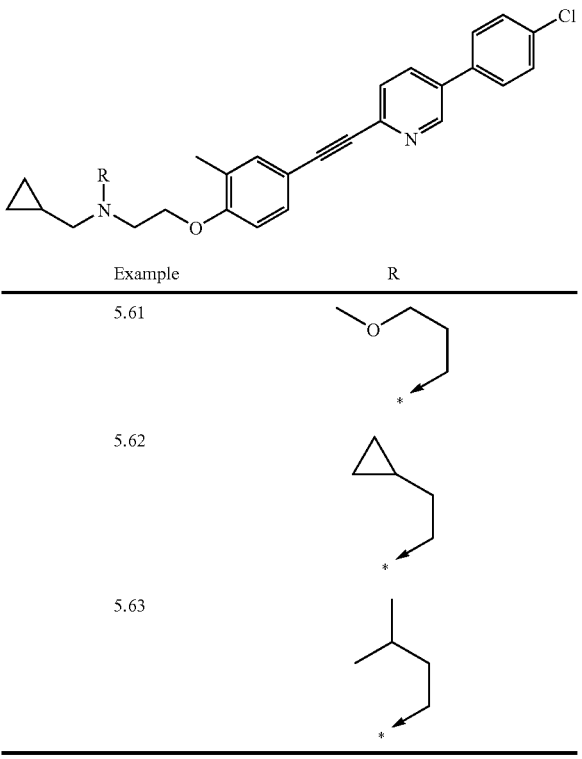

| Example | R |
|---|---|
| 5.61 | ![structure] (methoxypropyl) |
| 5.62 | ![structure] (cyclopropylmethyl) |
| 5.63 | ![structure] (isopentyl) |

Example 6

5-[5-(4-chloro-phenyl)-pyridin-2-ylethynyl]-1-(2-pyrrolidin-1-yl-ethyl)-1H-indole

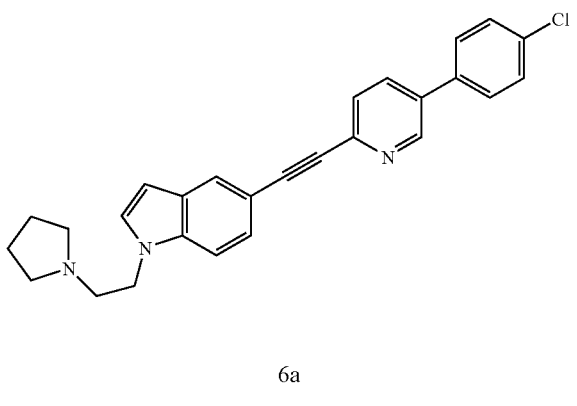

6a 2-(5-iodo-indol-1-yl)-ethanol

Under an $N_2$ atmosphere 30 g (121 mmol) 5-iodoindole are added to a suspension of 27.1 g (484 mmol) KOH in 150 mL DMSO. The reaction mixture is kept for 1 h at RT, cooled to 0° C. with ice water, 9.7 mL (145 mmol) of 2-chloroethanol in 30 mL DMSO are slowly added dropwise and stirred for 4.5 h at RT. The reaction mixture is combined with 1 L EtOAc, washed four times with in each case 800 mL water and once with 400 mL saturated NaCl solution and the organic phase is dried over $Na_2SO_4$. After the desiccant and solvent have been eliminated the residue is purified by chromatography (silica gel, cyc/EtOAc 3:1).

Yield: 20.5 g (59.1% of theory)
$C_{10}H_{10}INO$ (M=287.102)
Calc.: molpeak $(M+H)^+$: 288 Found: molpeak $(M+H)^+$: 288
HPLC retention time: 7.98 min (method A)

6b 2-(5-trimethylsilanylethynyl-indol-1-yl)-ethanol 398 mg (2.1 mmol) CuI and 1.47 g (2.1 mmol) Pd(PPh$_3$)$_2$Cl$_2$ are added to a solution, cooled to 0° C., of 30 g (104 mmol) 2-(5-iodo-indol-1-yl)-ethanol and 18 mL (125 mmol) ethynyl-trimethyl-silane in 480 mL triethylamine and 120 mL THF and stirred for 30 min at 0° C. and 2 h at RT. The mixture is evaporated down i. vac., the residue is taken up in 300 mL EtOAc, the organic phase is washed with 150 mL water and dried over $Na_2SO_4$. After the desiccant and solvent have been eliminated the residue is purified by chromatography (silica gel, gradient: cyc/EtOAc 4:1 to 2:1).

Yield: 26.85 g (100% of theory)
$C_{15}H_{19}NOSi$ (M=257.411)
Calc.: molpeak $(M+H)^+$: 258 Found: molpeak $(M+H)^+$: 258
$R_f$ value: 0.25 (silica gel, cyc/EtOAc 2:1)

6c 2-(5-ethynyl-indol-1-yl)-ethanol

Under an $N_2$ atmosphere 29 g (91.8 mmol) TBAF are added to a solution of 21.5 g (83.5 mmol) 2-(5-trimethylsilanylethynyl-indol-1-yl)-ethanol in 500 mL THF and the reaction mixture is stirred for 1.5 h at RT. The mixture is evaporated down i. vac., the residue is taken up in 300 mL EtOAc, the organic phase is washed twice with in each case 200 mL water and once with 200 mL saturated NaCl solution and dried over $Na_2SO_4$. After the desiccant and solvent have been eliminated the desired product is obtained in the form of a brown oil.

Yield: 15.46 g (100% of theory)
$C_{12}H_{11}NO$ (M=185.228)
Calc.: molpeak $(M+H)^+$: 186 Found: molpeak $(M+H)^+$: 186
HPLC retention time: 7.04 min (method A)

6d

2-[5-(5-bromo-pyridin-2-ylethynyl)-indol-1-yl]-ethanol

Under an $N_2$ atmosphere 29.4 g (124 mmol) 2,5-dibromo-pyridine, 241 mg (1.3 mmol) CuI and 888 mg (1.3 mmol) Pd(PPh$_3$)$_2$Cl$_2$ are added to a solution of 23.0 g (124 mmol) 2-(5-ethynyl-indol-1-yl)-ethanol and 35 mL (248 mmol) diisopropylamine in 1150 mL THF and the reaction mixture is heated to 50° C. for 3.5 h. Another 241 mg CuI and 888 mg Pd(PPh$_3$)$_2$Cl$_2$ and 9 g (38 mmol) 2,5-dibromo-pyridine are added, the mixture is stirred for a further 2.5 h at 50° C., 64 h at RT and a further 8 h at 60° C. The mixture is evaporated down i. vac., the residue is combined with 500 mL 3% $NH_3$ solution and 800 mL EtOAc. The precipitate formed is filtered off, washed with water and dried at 50° C. The two phases of the filtrate are separated and the organic phase is evaporated down i.vac. The residue is stirred vigorously with 500 mL PE/diisopropylether (1:1) and suction filtered. The two product fractions are then combined.

Yield: 24.96 g (58.9% of theory)

$C_{17}H_{13}BrN_2O$ (M=341.210)
Calc.: molpeak (M+H)$^+$: 340/342 Found: molpeak (M+H)$^+$: 340/342
R$_f$ value: 0.39 (silica gel, cyc/EtOAc 1:1)

6e

2-{5-[5-(4-chloro-phenyl)-pyridin-2-ylethynyl]-indol-1-yl}-ethanol

Under an N$_2$ atmosphere 56 mL 2 M Na$_2$CO$_3$ solution and 1.29 g (1.1 mmol) tetrakis-triphenylphosphane-palladium are added to a solution of 19.0 g (55.7 mmol) 2-[5-(5-bromo-pyridin-2-ylethynyl)-indol-1-yl]-ethanol and 11.55 g (72.4 mmol) 4-chlorophenyl-boric acid in 320 mL 1,4-dioxane and 80 mL MeOH and the reaction mixture is heated to 110° C. for 16 h. The mixture is evaporated down i. vac., the residue is combined with 300 mL water and the suspension is stirred vigorously. The precipitate is filtered off and washed with 200 mL water. The precipitate is suspended three times, each time with 600 mL PE/DCM (5:1), suction filtered and finally dried in the air until a constant weight is obtained.
Yield: 17.11 g (82.4% of theory)
$C_{23}H_{17}ClN_2O$ (M=372.858)
Calc.: molpeak (M+H)$^+$: 373/375 Found: molpeak (M+H)$^+$: 373/375
R$_f$ value: 0.42 (silica gel, DCM/MeOH/NH$_3$ 19:1:0.1)

6f

2-{5-[5-(4-chloro-phenyl)-pyridin-2-ylethynyl]-indol-1-yl}-ethyl methanesulphonate Under an argon atmosphere 7.1 mL (51.5 mmol) triethylamine are added to a solution of 16.0 g (42.9 mmol) 2-{5-[5-(4-chloro-phenyl)-pyridin-2-ylethynyl]-indol-1-yl}-ethanol in 480 mL THF and 30 mL pyridine and this is cooled to 0° C. Then a solution of 4 mL (51.5 mmol) methanesulphonic acid chloride in 20 mL THF is slowly added dropwise, the mixture is allowed to warm up to RT and stirred for a further 2 h at RT. The reaction solution is filtered and evaporated down i.vac. The residue is combined with 1 L DCM, washed with 400 mL water and the organic phase is dried over Na$_2$SO$_4$. After the desiccant and solvent have been eliminated the residue is suspended with 600 mL PE/DCM (5:1), suction filtered and finally dried in the air until a constant weight is obtained.
Yield: 17.10 g (88.4% of theory)
$C_{24}H_{19}ClN_2O_3S$ (M=450.948)
Calc.: molpeak (M+H)$^+$: 451/453 Found: molpeak (M+H)$^+$: 451/453
R$_f$ value: 0.9 (silica gel, EtOAc/MeOH/NH$_3$ 19:1:0.1)

6g

5-[5-(4-chloro-phenyl)-pyridin-2-ylethynyl]-1-(2-pyrrolidin-1-yl-ethyl)-1H-indole 1.1 mL (13.3 mmol) pyrrolidine are added to a solution of 600 mg (1.33 mmol) 2-{5-[5-(4-chloro-phenyl)-pyridin-2-ylethynyl]-indol-1-yl}-ethyl methanesulphonate in 12 mL DMF and the reaction mixture is stirred for 24 h at RT. The mixture is evaporated down i. vac., the residue is taken up in a little DCM and the product is purified by chromatography (silica gel, cyc/EtOAc 2:1)
Yield: 301 mg (53.1% of theory)
$C_{27}H_{24}ClN_3$ (M=425.965)
Calc.: molpeak (M+H)$^+$: 426/428 Found: molpeak (M+H)$^+$: 426/428
R$_f$ value: 0.44 (silica gel, cyc/EtOAc 2:1)

The following compounds are prepared as described in Example 6g, in each case using 5-20 eq. of the amine and stirring the reaction mixture for 24 h at RT (method A) or for 24 h at RT and for 24 h at 60° C. (method B) or for 7.5 h at 80° C. (method C) or for 48 h at 80° C. (method D). DCM and water are added, the phases are separated and the organic phase is dried over Na$_2$SO$_4$. After the desiccant and solvent have been eliminated the residue is purified by chromatography on Alox.

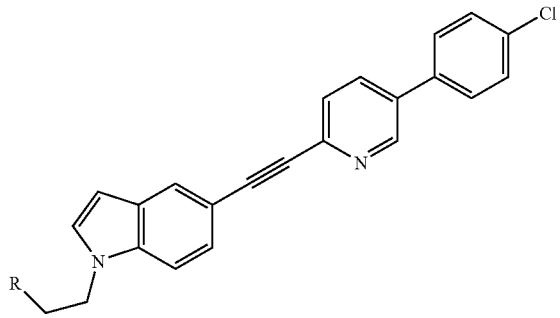

| Example (method) | R | Yield (%) | empirical formula | mass spectrum | R$_f$ value on Alox (eluant) or HPLC retention time in min (method) |
|---|---|---|---|---|---|
| 6.1 (A) |  | 33.1 | $C_{27}H_{24}ClN_3O$ | 442/444 [M + H]$^+$ | 0.24 (DCM/MeOH/NH$_3$ 19:1:0.1) |

-continued

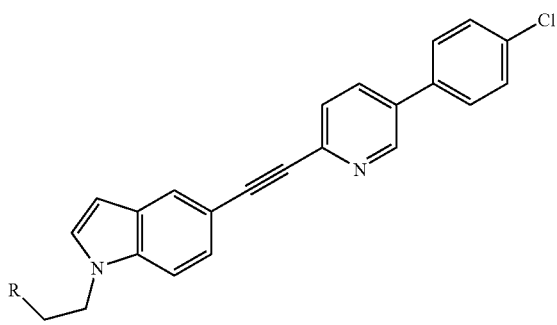

| Example (method) | R | Yield (%) | empirical formula | mass spectrum | R$_f$-value on Alox (eluant) or HPLC retention time in min (method) |
| --- | --- | --- | --- | --- | --- |
| 6.2 (B) | (S)-3-hydroxypyrrolidin-1-yl | 35.2 | C$_{27}$H$_{24}$ClN$_3$O | 442/444 [M + H]$^+$ | 0.46 (DCM/MeOH/NH$_3$ 9:1:0.1) |
| 6.3 (B) | 4-hydroxypiperidin-1-yl | 34.7 | C$_{28}$H$_{26}$ClN$_3$O | 456/458 [M + H]$^+$ | 0.32 (DCM/MeOH/NH$_3$ 9:1:0.1) |
| 6.4 (B) | piperidin-1-yl | 22.1 | C$_{28}$H$_{26}$ClN$_3$ | 440/442 [M + H]$^+$ | 0.85 (DCM/MeOH/NH$_3$ 9:1:0.1) |
| 6.5 (B) | 2-(hydroxymethyl)pyrrolidin-1-yl | 26.3 | C$_{28}$H$_{26}$ClN$_3$O | 456/458 [M + H]$^+$ | 0.42 (DCM/MeOH/NH$_3$ 19:1:0.1) |
| 6.6 (B) | 4-hydroxy-4-methylpiperidin-1-yl | 21.9 | C$_{29}$H$_{28}$ClN$_3$O | 470/472 [M + H]$^+$ | 0.21 (DCM/MeOH/NH$_3$ 19:1:0.1) |
| 6.7 (B) | 4-(hydroxymethyl)piperidin-1-yl | 27.0 | C$_{29}$H$_{28}$ClN$_3$O | 470/472 [M + H]$^+$ | 0.07 (DCM/MeOH/NH$_3$ 19:1:0.1) |
| 6.8 (B) | 3-hydroxypiperidin-1-yl | 21.1 | C$_{28}$H$_{26}$ClN$_3$O | 456/458 [M + H]$^+$ | 0.28 (DCM/MeOH/NH$_3$ 19:1:0.1) |
| 6.9 (B) | 4-methylpiperidin-1-yl | 17.2 | C$_{29}$H$_{28}$ClN$_3$ | 454/456 [M + H]$^+$ | 0.33 (DCM/MeOH/NH$_3$ 19:1:0.1) |

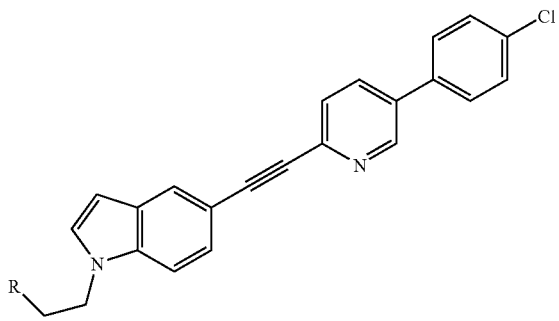

| Example (method) | R | Yield (%) | empirical formula | mass spectrum | $R_f$-value on Alox (eluant) or HPLC retention time in min (method) |
|---|---|---|---|---|---|
| 6.10 (C) | | 55.7 | $C_{29}H_{28}ClN_3$ | 454/456 $[M + H]^+$ | 0.16 (DCM/MeOH/NH$_3$ 19:1:0.1) |
| 6.11 (D) | | 11.6 | $C_{30}H_{30}ClN_3$ | 468/470 $[M + H]^+$ | 0.18 (DCM/MeOH/NH$_3$ 19:1:0.1) |

Example 6.12

(2-{5-[5-(4-chloro-phenyl)-pyridin-2-ylethynyl]-indol-1-yl}-ethyl)-cyclopropylmethyl-propyl-amine

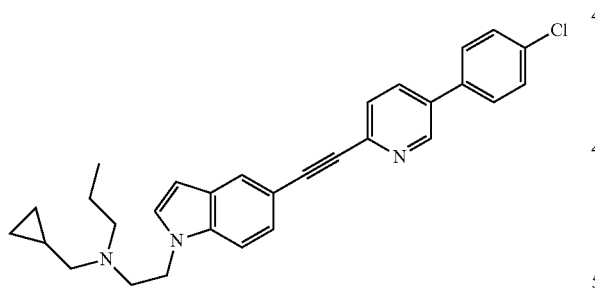

63 µL (0.44 mmol) cyclopropylmethyl-propyl-amine are added to a solution of 100 mg (0.22 mmol) 2-{5-[5-(4-chloro-phenyl)-pyridin-2-ylethynyl]-indol-1-yl}-ethyl methane-sulphonate in 2 mL DMF and the reaction mixture is stirred for 16 h at 60° C. The mixture is evaporated down i. vac., the residue is taken up in DCM, the organic phase is washed with water and dilute K$_2$CO$_3$ solution and dried over Na$_2$SO$_4$. After the desiccant and solvent have been eliminated the residue is purified twice by chromatography (Alox, cyc/EtOAc 8:2 and cyc/DCM 1:1).

Yield: 21 mg (20.2% of theory)

$C_{30}H_{30}ClN_3$ (M=468.047)

Calc.: molpeak (M+H)$^+$: 468/470 Found: molpeak (M+H)$^+$: 468/470

$R_f$-value: 0.37 (Alox, cyc/EtOAc 8:2)

Example 6.13

(2-{5-[5-(4-chloro-phenyl)-pyridin-2-ylethynyl]-indol-1-yl}-ethyl)-cyclopropylmethyl-amine

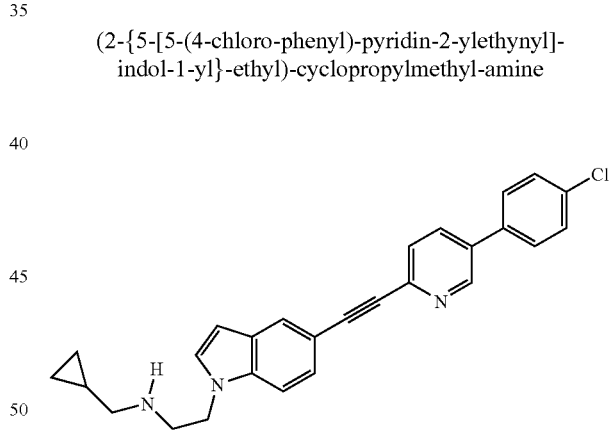

0.46 mL (5.4 mmol) C-cyclopropyl-methylamine are added to a solution of 2.03 g (4.5 mmol) 2-{5-[5-(4-chloro-phenyl)-pyridin-2-ylethynyl]-indol-1-yl}-ethyl methane-sulphonate in 20 mL DMF and the reaction mixture is stirred for 4 h at 60° C. The mixture is evaporated down i. vac., the residue is stirred with DCM, the precipitate is suction filtered and dried in the air. The product is precipitated as the methanesulphonic acid salt.

Yield: 600 mg (25.5% of theory)

$C_{27}H_{24}ClN_3*CH_4O_3S$ (M=522.07)

Calc.: molpeak (M+H)$^+$: 426/428 Found: molpeak (M+H)$^+$: 426/428

HPLC retention time: 5.23 min (method B)

Example 6.14

(2-{5-[5-(4-chloro-phenyl)-pyridin-2-ylethynyl]-indol-1-yl}-ethyl)-bis-cyclopropylmethyl-amine

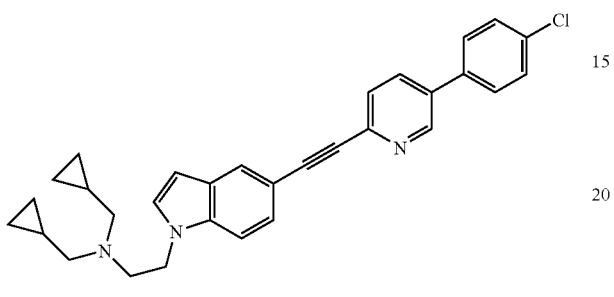

36 µL (0.47 mmol) cyclopropanecarbaldehyde are added to a solution of 100 mg (0.24 m mol) (2-{5-[5-(4-chloro-phenyl)-pyridin-2-ylethynyl]-indol-1-yl}-ethyl)-cyclopropylmethyl-amine in 20 mL MeOH at RT and 15 min later 59 mg (0.94 mmol) NaBH$_4$ and one drop of glacial acetic acid are added. The mixture is stirred for 1 h at RT, evaporated down i.vac., the residue is taken up in dilute K$_2$CO$_3$ solution, extracted exhaustively with EtOAc and dried over Na$_2$SO$_4$. After the desiccant and solvent have been eliminated the residue is triturated with PE, suction filtered and dried.

Yield: 105 mg (93.1% of theory)

C$_{31}$H$_{30}$ClN$_3$ (M=480.058)

Calc.: molpeak (M+H)$^+$: 480/482 Found: molpeak (M+H)$^+$: 480/482

HPLC retention time: 5.53 min (method B)

Example 6.15

(2-{5-[5-(4-chloro-phenyl)-pyridin-2-ylethynyl]-indol-1-yl}-ethyl)-cyclopropylmethyl-isobutyl-amine

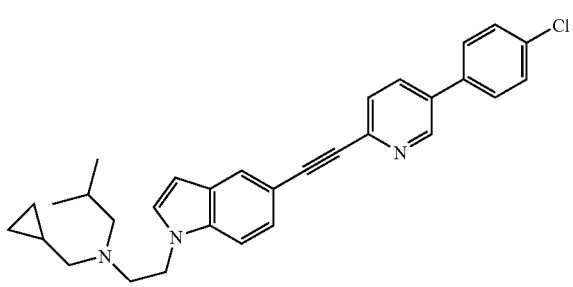 [SMILES: CCCN(CCn1ccc2cc(C#Cc3ccc(-c4ccc(Cl)cc4)cn3)ccc21)CC1CC1]

Prepared analogously to Example 6.14; after the working up described, the crude product is purified by chromatography (Alox, cyc/EtOAc 4:1).

Yield: 35 mg (41.5% of theory)

C$_{31}$H$_{32}$ClN$_3$ (M=482.074)

Calc.: molpeak (M+H)$^+$: 482/484 Found: molpeak (M+H)$^+$: 482/484

R$_f$ value: 0.83 (Alox, cyc/EtOAc 4:1)

HPLC retention time: 5.7 min (method B)

Example 6.16

(2-{5-[5-(4-chloro-phenyl)-pyridin-2-ylethynyl]-indol-1-yl}-ethyl)-cyclopropylmethyl-prop-2-ynyl-amine

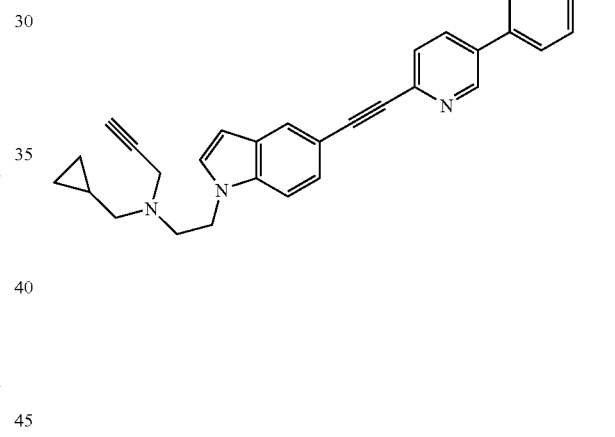

45 mg (0.33 mmol) K$_2$CO$_3$ and 13 µL (0.18 mmol) 3-bromo-propyne are added at RT to a solution of 70 mg (0.16 mmol) (2-{5-[5-(4-chloro-phenyl)-pyridin-2-ylethynyl]-indol-1-yl}-ethyl)-cyclopropylmethyl-amine in 2 mL DMF and the reaction mixture is stirred for 4 h at RT. The mixture is evaporated down i. vac., the residue is taken up in water, extracted exhaustively with DCM and the organic phase is dried over Na$_2$SO$_4$. After the desiccant and solvent have been eliminated the residue is purified by chromatography (Alox, cyc/EtOAc 4:1).

Yield: 32 mg (42.1% of theory)

C$_{30}$H$_{26}$ClN$_3$ (M=464.015)

Calc.: molpeak (M+H)$^+$: 464/466 Found: molpeak (M+H)$^+$: 464/466

R$_f$ value: 0.35 (Alox, cyc/EtOAc 4:1)

HPLC retention time: 5.86 min (method B)

The following compounds may be prepared by the methods described in Examples 6.14 and 6.16:

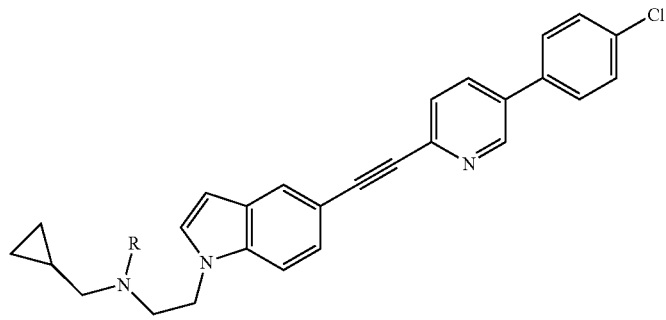

| Example | R | Yield (%) | empirical formula | mass spectrum | HPLC retention time in min (method) |
|---|---|---|---|---|---|
| 6.17 | | | | | |
| 6.18 | | | | | |
| 6.19 | | 30.1 | $C_{30}H_{28}ClN_3$ | 466/468 [M + H]$^+$ | 5.5 (B) |
| 6.20 | | | | | |
| 6.21 | | | | | |

Example 7

1-{3-[5-(4-chloro-phenyl)-pyridin-2-yl]-prop-2-ynyl}-5-pyrrolidin-1-ylmethyl-1H-indole

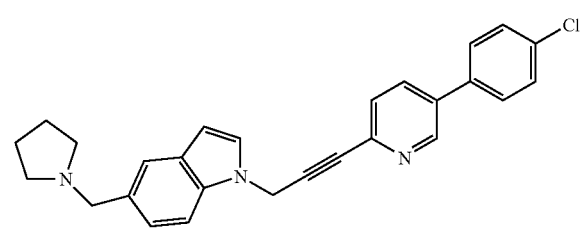 [SMILES: Clc1ccc(-c2ccc(C#CCn3ccc4cc(CN5CCCC5)ccc43)nc2)cc1]

7a 1-prop-2-ynyl-1H-indole-5-carbaldehyde 0.65 g (50% in mineral oil, 13.5 mmol) NaH are batchwise added to a solution, cooled to 0° C., of 2.0 g (13.5 mmol) 1H-indole-5-carbaldehyde in 80 mL THF and after heating to RT stirred for 15 min. Then a solution of 1.6 mL (80% in toluene, 15 mmol) propargyl bromide in 20 mL THF is slowly added dropwise and the reaction mixture is stirred overnight at RT. The mixture is evaporated down i. vac., the residue is combined with water, the aqueous phase is exhaustively extracted with EtOAc and the organic phase is dried over $Na_2SO_4$. After the desiccant and solvent have been eliminated the residue is purified by chromatography (silica gel, gradient: cyc/EtOAc 4:1 to 2:1).

Yield: 0.65 g (26.4% of theory)
$C_{12}H_9NO$ (M=183.212)
Calc.: molpeak (M+H)$^+$: 184 Found: molpeak (M+H)$^+$: 184
$R_f$ value: 0.34 (silica gel, cyc/EtOAc 3:1)

7b 1-prop-2-ynyl-5-pyrrolidin-1-ylmethyl-1H-indole

A solution of 250 mg (1.37 mmol) 1-prop-2-ynyl-1H-indole-5-carbaldehyde and 200 μL (2.37 mmol) pyrrolidine in 50 mL THF is adjusted to pH 5 with glacial acetic acid, combined with 550 mg (2.47 mmol) NaBH(OAc)$_3$ and stirred for 24 h at RT. 20 mL of saturated K$_2$CO$_3$ solution are added, the mixture is extracted with 50 mL EtOAc and the organic phase is dried over Na$_2$SO$_4$. After the desiccant and solvent have been eliminated the residue is purified by chromatography (silica gel, EtOAc/MeOH/NH$_3$ 95:5:0.5).

Yield: 325 mg (100% of theory)

C$_{16}$H$_{18}$N$_2$ (M=238.335)

Calc.: molpeak (M+H)$^+$: 239 Found: molpeak (M+H)$^+$: 239

R$_f$ value: 0.38 (silica gel, EtOAc/MeOH/NH$_3$ 95:5:0.5)

7c

1-[3-(5-bromo-pyridin-2-yl)-prop-2-ynyl]-5-pyrrolidin-1-ylmethyl-1H-indole

Under an argon atmosphere 5 mg (0.03 mmol) CuI and 18 mg (0.03 mmol) Pd(PPh$_3$)$_2$Cl$_2$ are added to a solution of 337 mg (1.41 mmol) 1-prop-2-ynyl-5-pyrrolidin-1-ylmethyl-1H-indole and 345 mg (1.41 mmol) 2,5-dibromo-pyridine in 50 mL THF and 0.4 mL diisopropylamine and the reaction mixture is stirred for 17 h at RT. The mixture is evaporated down i. vac., the residue is taken up in 30 mL EtOAc, the organic phase is washed with 30 mL water and 30 mL saturated NaCl solution and dried over Na$_2$SO$_4$. After the desiccant and solvent have been eliminated the residue is purified by chromatography (silica gel, EtOAc/MeOH/NH$_3$ 95:5:0.5).

Yield: 145 mg (26.0% of theory)

C$_{21}$H$_{20}$BrN$_3$ (M=394.318)

Calc.: molpeak (M+H)$^+$: 394/396 Found: molpeak (M+H)$^+$: 394/396

R$_f$ value: 0.62 (silica gel, EtOAc/MeOH/NH$_3$ 90:10:1)

7d

1-{3-[5-(4-chloro-phenyl)-pyridin-2-yl]-prop-2-ynyl}-5-pyrrolidin-1-ylmethyl-1H-indole Under an argon atmosphere 0.5 mL 2 M Na$_2$CO$_3$ solution and 10 mg (0.01 mmol) tetrakis-triphenylphosphane-palladium are added to a solution of 59 mg (0.15 mmol) 1-[3-(5-bromo-pyridin-2-yl)-prop-2-ynyl]-5-pyrrolidin-1-ylmethyl-1H-indole and 50 mg (0.32 mmol) 4-chlorophenyl-boric acid in 5 mL 1,4-dioxane and the reaction mixture is stirred for 2.5 h at 110° C. The mixture is evaporated down i. vac., the residue is combined with 3 mL water, extracted with 5 mL EtOAc, the organic phase is washed with saturated NaCl solution and dried over Na$_2$SO$_4$. After the desiccant and solvent have been eliminated the residue is purified by HPLC.

Yield: 21.8 mg (34.1% of theory)

C$_{27}$H$_{24}$ClN$_3$ (M=425.965)

Calc.: molpeak (M+H)$^+$: 426/428 Found: molpeak (M+H)$^+$: 426/428

HPLC retention time: 6.75 min (method A).

Example 8

5-(4-chloro-phenyl)-2-[3-(4-pyrrolidin-1-ylmethyl-phenoxy)-prop-1-ynyl]-pyridine

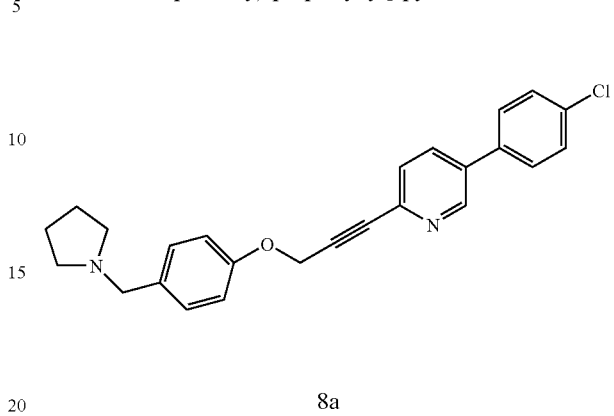

8a

3-[5-(4-chloro-phenyl)-pyridin-2-yl]-prop-2-yn-1-ol

Under an N$_2$ atmosphere 1 mL (7.22 mmol) triethylamine, 23 mg (0.1 mmol) Pd(OAc)$_2$ and 57.5 mg (0.19 mmol) biphenyl-2-yl-di-tert-butyl-phosphane are added to a solution of 500 mg (2.36 mmol) 3-(5-bromo-pyridin-2-yl)-prop-2-yn-1-ol and 600 mg (3.72 mmol) 4-chlorophenyl-boric acid in 10 mL DMF and 2.5 mL water and the reaction mixture is stirred for 8 h at 60° C. Then 400 mg (2.48 mmol) 4-chlorophenyl-boric acid are added and the mixture is stirred for a further 19 h at 60° C. The mixture is evaporated down i. vac., the residue is combined with 10 mL water and 10 mL EtOAc, the aqueous phase is saturated with NaCl, the organic phase is separated off and dried over Na$_2$SO$_4$. After the desiccant and solvent have been eliminated the residue is purified by chromatography (silica gel, cyc/EtOAc$_3$ 2:1).

Yield: 228 mg (39.6% of theory)

C$_{14}$H$_{10}$ClNO (M=243.695)

Calc.: molpeak (M+H)$^+$: 244/246 Found: molpeak (M+H)$^+$: 244/246

R$_f$ value: 0.23 (silica gel, cyc/EtOAc 1:1)

8b 5-(4-chloro-phenyl)-2-[3-(4-pyrrolidin-1-ylmethyl-phenoxy)-prop-1-ynyl]-pyridine 131 mg (0.5 mmol) triphenylphosphane are added to a solution of 100 mg (0.41 mmol) 3-[5-(4-chloro-phenyl)-pyridin-2-yl]-prop-2-yn-1-ol and 88 mg (0.5 mmol) 4-pyrrolidin-1-ylmethyl-phenol in 4 mL THF. Then 0.1 mL (0.5 mmol) diisopropyl azo-dicarboxylate is slowly added dropwise and the reaction mixture is stirred for 3 h at RT. The mixture is evaporated down i. vac., the residue is taken up in 1 mL DMF and purified by HPLC. The product obtained, which still contains triphenylphosphane oxide, is again purified by chromatography (silica gel, EtOAc after EtOAc/MeOH/NH$_3$ 9:1:0.1).

Yield: 6.5 mg (3.9% of theory)

C$_{25}$H$_{23}$ClN$_2$O (M=402.928)

Calc.: molpeak (M+H)$^+$: 403/405 Found: molpeak (M+H)$^+$: 403/405

R$_f$ value: 0.72 (silica gel, EtOAc/MeOH/NH$_3$ 9:1:0.1)

Example 9

5-(4-chloro-phenyl)-2-[3-methyl-3-(4-pyrrolidin-1-ylmethyl-phenoxy)-but-1-ynyl]-pyridine

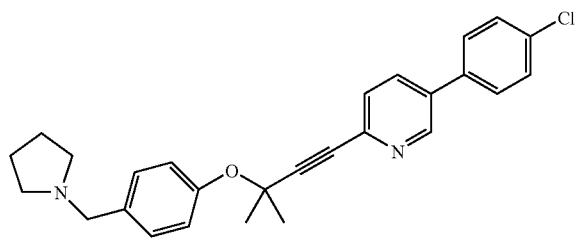 [SMILES: CC(C)(C#Cc1ccc(-c2ccc(Cl)cc2)cn1)Oc1ccc(CN2CCCC2)cc1]

9a 4-(5-bromo-pyridin-2-yl)-2-methyl-but-3-yn-2-ol

Under an argon atmosphere 38 mg (0.2 mmol) CuI and 143 mg (0.2 mmol) Pd(PPh$_3$)$_2$Cl$_2$ are added to a solution of 0.99 mL (10.0 mmol) 2-methyl-but-3-yn-2-ol and 2.44 g (10.0 mmol) 2,5-dibromo-pyridine in 50 mL THF and 2.8 mL (20 mmol) diisopropylamine and the reaction mixture is stirred for 15 min at RT. The reaction mixture is combined with water, exhaustively extracted with EtOAc and the organic phase is dried over Na$_2$SO$_4$. After the desiccant and solvent have been eliminated the residue is purified by chromatography (silica gel, cyc/EtOAc 2:1).

Yield: 2.0 g (83.3% of theory)
C$_{10}$H$_{10}$BrNO (M=240.101)
Calc.: molpeak (M+H)$^+$: 240/242 Found: molpeak (M+H)$^+$: 240/242
R$_f$ value: 0.29 (silica gel, cyc/EtOAc 2:1)

9b

4-[5-(4-chloro-phenyl)-pyridin-2-yl]-2-methyl-but-3-yn-2-ol

Under an argon atmosphere 3 mL 2 M Na$_2$CO$_3$ solution and 173 mg (0.15 mmol) tetrakis-triphenylphosphane-palladium are added to a solution of 720 mg (3.0 mmol) 4-(5-bromo-pyridin-2-yl)-2-methyl-but-3-yn-2-ol and 593 mg (3.6 mmol) 4-chlorophenyl-boric acid in 60 mL 1,4-dioxane and the reaction mixture is stirred for 18 h at 85° C. The mixture is evaporated down i. vac., the residue is combined with water, extracted with EtOAc, the organic phase is washed with water and dried over Na$_2$SO$_4$. After the desiccant and solvent have been eliminated the residue is purified by chromatography (silica gel, PE/EtOAc 1:1).

Yield: 420 mg (51.5% of theory)
C$_{16}$H$_{14}$ClNO (M=271.749)
Calc.: molpeak (M+H)$^+$: 272/274 Found: molpeak (M+H)$^+$: 272/274
R$_f$ value: 0.42 (silica gel, PE/EtOAc 1:1)

9c 5-(4-chloro-phenyl)-2-[3-methyl-3-(4-pyrrolidin-1-ylmethyl-phenoxy)-but-1-ynyl]-pyridine 131 mg (0.5 mmol) triphenylphosphane are added to a solution of 136 mg (0.5 mmol) 4-[5-(4-chloro-phenyl)-pyridin-2-yl]-2-methyl-but-3-yn-2-ol and 88 mg (0.5 mmol) 4-pyrrolidin-1-ylmethyl-phenol in 20 ml THF. Then 0.1 mL (0.5 mmol) diisopropyl azo-dicarboxylate is slowly added dropwise and the reaction mixture is stirred for 24 h at RT. The mixture is evaporated down i. vac., the residue is taken up in water, extracted exhaustively with EtOAc, the organic phase is washed with saturated NaCl solution and dried over Na$_2$SO$_4$. After the desiccant and solvent have been eliminated the residue is purified by HPLC.

Yield: 3 mg (1.4% of theory)
C$_{27}$H$_{27}$ClN$_2$O (M=430.982)
Calc.: molpeak (M+H)$^+$: 431/433 Found: molpeak (M+H)$^+$: 431/433
HPLC retention time: 7.78 min (method A)

Example 10

5-(4-chloro-phenyl)-2-[3-(4-pyrrolidin-1-ylmethyl-phenyl)-prop-2-ynyloxy]-pyridine

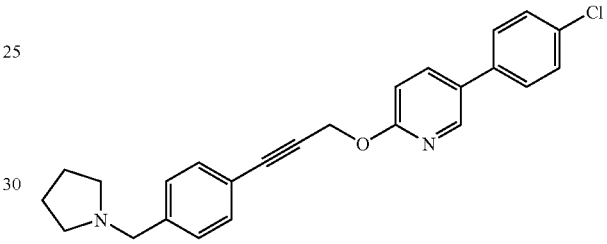

10a 5-(4-chloro-phenyl)-pyridin-2-ol

Under an N$_2$ atmosphere 21.7 mL 2 M Na$_2$CO$_3$ solution and 250 mg (0.22 mmol) tetrakis-triphenylphosphane-palladium are added to a solution of 8.0 g (21.7 mmol) 5-iodo-pyridin-2-ol and 3.81 g (23.9 mmol) 4-chlorophenyl-boric acid in 120 mL 1,4-dioxane and 30 mL dry MeOH and the reaction mixture is stirred for 19 h at 110° C. The mixture is evaporated down i. vac., the residue is combined with water, the precipitate is filtered off, washed with water and dried at 40° C. in the circulating air dryer until a constant weight is obtained.

Yield: 3.8 g (85.1% of theory)
C$_{11}$H$_8$ClNO (M=205.646)
Calc.: molpeak (M+H)$^+$: 206/208 Found: molpeak (M+H)$^+$: 206/208
R$_f$ value: 0.56 (silica gel, EtOAc/MeOH/NH$_3$ 9:1:0.1)

10b 5-(4-chloro-phenyl)-2-prop-2-ynyloxy-pyridine 2 mL (80% in toluene, 18.5 mmol) 3-bromo-propyne are added to a suspension of 3.8 g (18.5 mmol) 5-(4-chloro-phenyl)-pyridin-2-ol and 5.1 g (37 mmol) K$_2$CO$_3$ in 50 mL DMF and the reaction mixture is stirred for 64 h at RT. The mixture is evaporated down i. vac., the residue is combined with 80 mL water, extracted with 150 mL EtOAc and the organic phase is dried over Na$_2$SO$_4$. After the desiccant and solvent have been eliminated the residue is purified by chromatography (silica gel, cyc/EtOAc 2:1).

Yield: 216 mg (4.8% of theory)
$C_{14}H_{10}ClNO$ (M=243.695)
Calc.: molpeak $(M+H)^+$: 244/246 Found: molpeak $(M+H)^+$: 244/246
$R_f$ value: 0.16 (silica gel, cyc/EtOAc 2:1)

10c 5-(4-chloro-phenyl)-2-[3-(4-pyrrolidin-1-ylmethyl-phenyl)-prop-2-ynyloxy]-pyridine Under an $N_2$ atmosphere 221 mg (0.68 mmol) $Cs_2CO_3$, 4 mg (0.02 mmol) CuI and 23 mg (0.02 mmol) tetrakis-triphenylphosphane-palladium are added to a solution of 110 mg (0.45 mmol) 5-(4-chloro-phenyl)-2-prop-2-ynyloxy-pyridine and 129 mg (0.45 mmol) 1-(4-iodo-benzyl)-pyrrolidine in 9 mL THF and the reaction mixture is stirred for 4.5 h at RT. The mixture is evaporated down i. vac., the residue is combined with 20 mL 3% $NH_3$ solution and 40 mL EtOAc, the organic phase is separated off and dried over $Na_2SO_4$. After the desiccant and solvent have been eliminated the residue is purified first by HPLC and then by chromatography (silica gel, $DCM/MeOH/NH_3$ 19:1:0.1).
Yield: 28 mg (15.5% of theory)
$C_{25}H_{23}ClN_2O$ (M=402.928)
Calc.: molpeak $(M+H)^+$: 403/405 Found: molpeak $(M+H)^+$: 403/405
$R_f$ value: 0.33 (silica gel, $DCM/MeOH/NH_3$ 19:1:0.1)
HPLC retention time: 6.43 min (method A)

Example 11

1-(2-{4-[4-(4-chloro-phenyl)-thiophen-2-ylethynyl]-phenoxy}-ethyl)-pyrrolidine

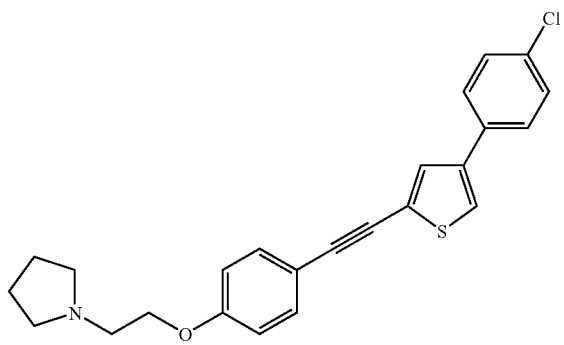 [SMILES: Clc1ccc(-c2csc(C#Cc3ccc(OCCN4CCCC4)cc3)c2)cc1]

11a (4-bromo-thiophen-2-ylethynyl)-trimethyl-silane

Under an argon atmosphere 0.37 g (1.94 mmol) CuI, 2.24 g (1.94 mmol) tetrakis-triphenylphosphane-palladium and 16.2 mL triethylamine are added to a solution of 10.0 g (38.85 mmol) 2,4-dibromothiophene in 300 mL THF, the reaction mixture is cooled to −78° C. and then at this temperature a solution of 5.6 mL (38.85 mmol)) ethynyl-trimethyl-silane in 250 mL THF is slowly added dropwise. After the addition has ended the mixture is allowed to heat up slowly to RT and stirred overnight. The mixture is evaporated down i. vac., the residue is combined with water, extracted exhaustively with DCM and the combined organic phases are dried over $MgSO_4$. After the desiccant and solvent have been eliminated the residue is triturated with PE, filtered to remove insoluble ingredients and the solvent is evaporated down. The residue is purified by chromatography (silica gel, PE).
Yield: 9.5 g (56.6% of theory)
$C_9H_{11}BrSSi$ (M=259.242)
$R_f$ value: 0.77 (silica gel, PE)

11b 4-bromo-2-ethynyl-thiophene 4.6 g (14.58 mmol) TBAF are added to a solution, cooled to 0° C., of 6.3 g (14.58 mmol) (4-bromo-thiophen-2-ylethynyl)-trimethyl-silane in 60 mL THF. The cooling bath is removed and the mixture is stirred for a further 30 min. The reaction mixture is combined with EtOAc, washed with water and the organic phase is dried over $MgSO_4$. After the desiccant and solvent have been eliminated the residue is purified by chromatography (silica gel, PE).
Yield: 1.9 g (69.7% of theory)
$C_6H_3BrS$ (M=187.059)
Calc.: molpeak $(M+H)^+$: 186/188 Found: molpeak $(M+H)^+$: 186/188

11c

1-{2-[4-(4-bromo-thiophen-2-ylethynyl)-phenoxy]-ethyl}-pyrrolidine

Under an argon atmosphere 0.3 mL (3.13 mmol) piperidine, 14.9 mg (0.08 mmol) CuI and 90.3 mg (0.08 mmol) tetrakis-triphenylphosphane-palladium are added to a solution of 293 mg (1.56 mmol) 4-bromo-2-ethynyl-thiophene and 620 mg (1.56 mmol) 1-[2-(4-iodo-phenoxy)-ethyl]-pyrrolidine in 10 mL THF and the reaction mixture is stirred overnight at RT. To complete the reaction another 150 mg (0.8 mmol) 4-bromo-2-ethynyl-thiophene are added and the mixture is stirred for a further 24 h at RT. The mixture is evaporated down i. vac., the residue is triturated with EtOAc and the insoluble ingredients are filtered off. After the solvent has been eliminated the residue is purified by chromatography (silica gel, $EtOAc/MeOH/NH_3$ 8:2:0.2).
Yield: 300 mg (51.0% of theory)
$C_{18}H_{18}BrNOS$ (M=376.318)
Calc.: molpeak $(M+H)^+$: 376/378 Found: molpeak $(M+H)^+$: 376/378
$R_f$ value: 0.52 (silica gel, $EtOAc/MeOH/NH_3$ 9:1:0.1)

11d 1-(2-{4-[4-(4-chloro-phenyl)-thiophen-2-ylethynyl]-phenoxy}-ethyl)-pyrrolidine Under an $N_2$ atmosphere 5 mL 2 M $Na_2CO_3$ solution and 47 mg (0.41 mmol) tetrakis-triphenylphosphane-palladium are added to a solution of 310 mg (0.82 mmol) 1-{2-[4-(4-bromo-thiophen-2-ylethynyl)-phenoxy]-ethyl}-pyrrolidine and 129 mg (0.82 mmol) 4-chlorophenyl-boric acid in 10 mL 1,4-dioxane and the reaction mixture is refluxed for 1 h. The hot solution is filtered through a fibreglass filter, the filtrate is extracted with EtOAc, the organic phase is washed with water and dried over $MgSO_4$. After the desiccant and solvent have been eliminated the residue is purified by chromatography (silica gel, $EtOAc/MeOH/NH_3$ 8:2:0.2).
Yield: 23 mg (6.8% of theory)
$C_{24}H_{22}ClNOS$ (M=407.966)

Calc.: molpeak (M+H)⁺: 408/410 Found: molpeak (M+H)⁺: 408/410

HPLC retention time: 5.35 min (method B)

Example 12

2-(4-chloro-phenyl)-5-[4-(2-pyrrolidin-1-yl-ethoxy)-phenylethynyl]-pyrazine

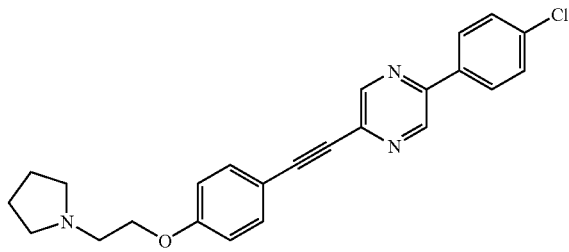

12a 5-(4-chloro-phenyl)-pyrazin-2-ylamine

Under an argon atmosphere 50 mL 2 M Na₂CO₃ solution and 1.2 g (1.0 mmol) tetrakis-triphenylphosphane-palladium are added to a solution of 8.7 g (50.0 mmol) 5-bromo-pyrazin-2-ylamine and 8.0 g (50.0 mmol) 4-chlorophenyl-boric acid in 150 mL 1,4-dioxane and 50 mL MeOH and the reaction mixture is heated to 110° C. for 2.5 h. The mixture is evaporated down i. vac., the residue is combined with water, extracted exhaustively with EtOAc and the organic phase is dried over Na₂SO₄. After the desiccant and solvent have been eliminated the residue is purified by chromatography (silica gel, gradient: DCM to DCM/MeOH 20:1).

Yield: 8.3 g (80.7% of theory)

$C_{10}H_8ClN_3$ (M=205.648)

Calc.: molpeak (M+H)⁺: 206/208 Found: molpeak (M+H)⁺: 206/208

HPLC retention time: 7.15 min (method A)

12b 2-(4-chloro-phenyl)-5-iodo-pyrazine

With the exclusion of light, 4.9 mL (40.0 mmol) tert-butylnitrite and 7.6 g (30 mmol) iodine are added to a solution of 4.8 g (23.3 mmol) 5-(4-chloro-phenyl)-pyrazin-2-ylamine in 100 mL CCl₄ and 50 mL DCM and the reaction mixture is stirred overnight at RT. It is combined with 100 mL water and 50 mL 10% Na₂S₂O₃ solution, the organic phase is separated off, washed again with 50 mL 10% Na₂S₂O₃ solution and twice with 50 mL water and dried over MgSO₄. It is filtered through activated charcoal, evaporated down i.vac. and the residue is purified by chromatography (silica gel, gradient: PE to PE/EtOAc 8:2).

Yield: 3.4 g (46.0% of theory)

$C_{10}H_6ClIN_2$ (M=316.530)

Calc.: molpeak (M+H)⁺: 317/319 Found: molpeak (M+H)⁺: 317/319

$R_f$ value: 0.55 (silica gel, PE/EtOAc 9:1)

12c 2-(4-chloro-phenyl)-5-[4-(2-pyrrolidin-1-yl-ethoxy)-phenylethynyl]-pyrazine

Under an N₂ atmosphere 19 mg (0.1 mmol) CuI, 82 mg (0.1 mmol) [1,1'-bis-(diphenylphosphine)-ferrocene]-palladium (II)-chloride are added to a solution of 316 mg (1.0 mmol) 2-(4-chloro-phenyl)-5-iodo-pyrazine and 215 mg (1.0 mmol) 1-[2-(4-ethynyl-phenoxy)-ethyl]-pyrrolidine in 50 mL THF and 0.4 mL (3 mmol) triethylamine and the reaction mixture is stirred overnight at RT. To complete the reaction another 100 mg (0.32 mmol) 2-(4-chloro-phenyl)-5-iodo-pyrazine are added and the mixture is again stirred overnight. It is evaporated down i. vac., the residue is combined with 10% Na₂CO₃ solution, extracted exhaustively with DCM, the combined organic phases are washed three times with water and dried over MgSO₄. This is filtered through activated charcoal, evaporated down i.vac. and the residue is purified by chromatography (silica gel, gradient: EtOAc to EtOAc/MeOH/NH₃ 9:9:1).

Yield: 170 mg (42.1% of theory)

$C_{24}H_{22}ClN_3O$ (M=403.915)

Calc.: molpeak (M+H)⁺: 404/406 Found: molpeak (M+H)⁺: 404/406

$R_f$ value: 0.58 (silica gel, DCM/MeOH/NH₃ 9:1:0.1)

Example 13

2-(4-chloro-phenyl)-5-[4-(2-pyrrolidin-1-yl-ethoxy)-phenylethynyl]-pyridine

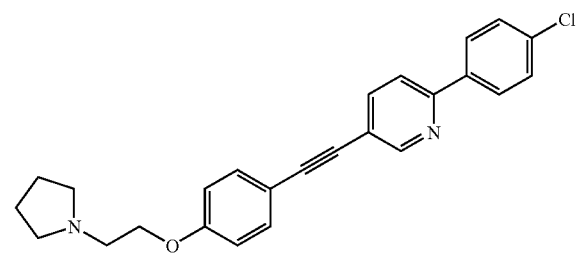 [SMILES: Clc1ccc(-c2ccc(C#Cc3ccc(OCCN4CCCC4)cc3)cn2)cc1]

13a 5-bromo-2-(4-chloro-phenyl)-pyridine

Under an N₂ atmosphere 11 mL 2 M Na₂CO₃ solution and 240 mg (0.21 mmol) tetrakis-triphenylphosphane-palladium are added to a solution of 3.00 g (10.6 mmol) 5-bromo-2-iodo-pyridine and 3.37 g (21.1 mmol) 4-chlorophenyl-boric acid in 60 mL 1,4-dioxane and 15 mL MeOH and the reaction mixture is heated to 110° C. for 3 h. The mixture is evaporated down i. vac., the residue is combined with 50 mL water, 10 mL 3% NH₃ solution and 150 mL EtOAc, the organic phase is separated off and dried over Na₂SO₄. After the desiccant and solvent have been eliminated the residue is purified by chromatography (silica gel, cyc).

Yield: 1.52 g (53.6% of theory)

$C_{11}H_7BrClN$ (M=268.542)

Calc.: molpeak $(M+H)^+$: 268/270/272 Found: molpeak $(M+H)^+$: 268/270/272

$R_f$ value: 0.1 (silica gel, cyc)

13b 2-(4-chloro-phenyl)-5-[4-(2-pyrrolidin-1-yl-ethoxy)-phenylethynyl]-pyridine

Under an $N_2$ atmosphere 773 mg (2.25 mmol) $Cs_2CO_3$, 14 mg (0.08 mmol) CuI and 87 mg (0.08 mmol) tetrakis-triphenylphosphane-palladium are added to a solution of 403 mg (1.5 mmol) 5-bromo-2-(4-chloro-phenyl)-pyridine and 322 mg (1.5 mmol) 1-[2-(4-ethynyl-phenoxy)-ethyl]-pyrrolidine in 10 mL THF and the reaction mixture is stirred for 4 h at RT. Then it is heated to 60° C. for 16 h. The mixture is evaporated down i. vac., the residue is combined with 30 mL water, 5 mL 3% $NH_3$ solution and 60 mL EtOAc, the organic phase is separated off and dried over $Na_2SO_4$. After the desiccant and solvent have been eliminated the residue is purified first by chromatography (silica gel, EtOAc/MeOH/$NH_3$ 19:1:0.1) and then by HPLC.

Yield: 9 mg (2.2% of theory)

$C_{25}H_{23}ClN_2O$ (M=402.928)

Calc.: molpeak $(M+H)^+$: 403/405 Found: molpeak $(M+H)^+$: 403/405

HPLC retention time: 8.11 min (method A)

Example 14 ethyl 5-[5-(4-chloro-phenyl)-pyridin-2-ylethynyl]-3-methyl-1-(2-pyrrolidin-1-yl-ethyl)-1H-indole-2-carboxylate

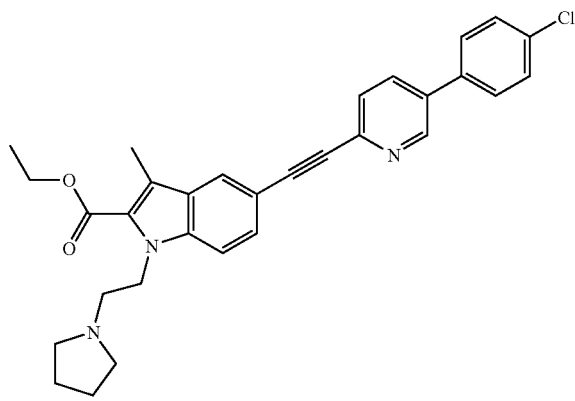 [SMILES: CCOC(=O)c1c(C)c2cc(C#Cc3ccc(-c4ccc(Cl)cc4)cn3)ccc2n1CCN1CCCC1]

14a ethyl 3-methyl-1-(2-pyrrolidin-1-yl-ethyl)-5-trimethylsilanylethynyl-1H-indole-2-carboxylate Under an argon atmosphere 577 mg (0.5 mmol) tetrakis-triphenylphosphane-palladium and 95 mg (0.5 mmol) CuI are added to a solution of 2.82 g (10 mmol) ethyl 5-bromo-3-methyl-1H-indole-2-carboxylate and 1.52 mL (11 mmol) ethynyl-trimethyl-silane in 3 mL (30 mmol) piperidine and 30 mL THF and the reaction mixture is stirred for 14 h at 60° C. It is diluted with water, extracted exhaustively with EtOAc, the combined organic phases are washed with saturated NaCl solution and dried over $Na_2SO_4$. After the desiccant and solvent have been eliminated the residue is purified by chromatography (silica gel, cyc/EtOAc 9:1).

Yield: 1.3 g (43.4% of theory)

$C_{17}H_{21}NO_2Si$ (M=299.448)

Calc.: molpeak $(M+H)^+$: 300 Found: molpeak $(M+H)^+$: 300

$R_f$ value: 0.61 (silica gel, cyc/EtOAc 7:3)

14b ethyl 5-ethynyl-3-methyl-1-(2-pyrrolidin-1-yl-ethyl)-1H-indole-2-carboxylate Under an argon atmosphere 562 mg (3.3 mmol) 1-(2-chloro-ethyl)-pyrrolidine (used as the hydrochloride) are added to a suspension of 900 mg (3.0 mmol) ethyl 3-methyl-1-(2-pyrrolidin-1-yl-ethyl)-5-trimethylsilanylethynyl-1H-indole-2-carboxylate and 457 mg (3.3 mmol) $K_2CO_3$ in 10 mL DMF and the reaction mixture is stirred for 42 h at 60° C. It is diluted with water, extracted exhaustively with EtOAc, the combined organic phases are washed with water and dried over $Na_2SO_4$. After the desiccant and solvent have been eliminated the residue is purified by chromatography (silica gel, EtOAc/MeOH/$NH_3$ 90:10:1).

Yield: 250 mg (25.6% of theory)

$C_{20}H_{24}N_2O_2$ (M=324.426)

Calc.: molpeak $(M+H)^+$: 325 Found: molpeak $(M+H)^+$: 325

HPLC retention time: 4.59 min (method B)

14c ethyl 5-[5-(4-chloro-phenyl)-pyridin-2-ylethynyl]-3-methyl-1-(2-pyrrolidin-1-yl-ethyl)-1H-indole-2-carboxylate Under an argon atmosphere 11 mg (0.02 mmol) $Pd(PPh_3)_2Cl_2$ and 3 mg (0.02 mmol) CuI are added to a solution of 250 mg (0.77 mmol) ethyl 5-ethynyl-3-methyl-1-(2-pyrrolidin-1-yl-ethyl)-1H-indole-2-carboxylate and 243 mg (0.77 mmol) 5-(4-chloro-phenyl)-2-iodo-pyridine in 1.52 mL (15.4 mmol) piperidine and 25 mL THF and the reaction mixture is stirred for 4 h at RT. It is diluted with water, extracted exhaustively with EtOAc, the combined organic phases are washed with water and saturated NaCl solution and dried over $Na_2SO_4$. After the desiccant and solvent have been eliminated the residue is purified first by chromatography (silica gel, cyc/EtOAc 2:1) and then by HPLC.

Yield: 7 mg (1.8% of theory)

$C_{31}H_{30}ClN_3O_2$ (M=512.057)

Calc.: molpeak $(M+H)^+$: 512/514 Found: molpeak $(M+H)^+$: 512/514

$R_f$ value: 0.67 (Alox, cyc/EtOAc 2:1)

HPLC retention time: 5.96 min (method B)

Example 15

N-{5-[5-(4-chloro-phenyl)-pyridin-2-ylethynyl]-3-methyl-pyridin-2-yl}-2-pyrrolidin-1-yl-acetamide

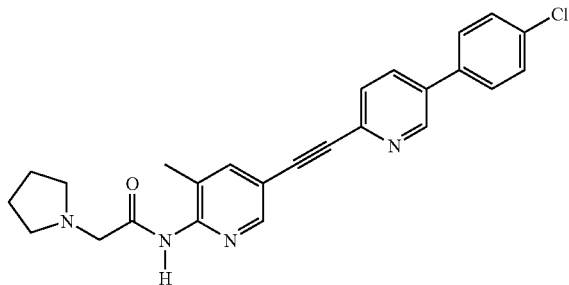 [SMILES: Cc1cc(C#Cc2ccc(-c3ccc(Cl)cc3)cn2)cnc1NC(=O)CN1CCCC1]

15a

N-(5-bromo-3-methyl-pyridin-2-yl)-2-chloro-acetamide 1.75 mL (22 mmol) chloroacetyl chloride are added to a solution, cooled to 0° C., of 3.74 g (20 mmol) 2-amino-5-bromo-3-methylpyridine in 50 mL DCM and then 6.1 mL (44 mmol) triethylamine are slowly added dropwise. After the addition has ended the ice bath is removed and the reaction mixture is stirred for 4 h at RT. It is poured onto water, extracted exhaustively with DCM, the combined organic phases are washed with water and saturated NaCl solution and dried over $Na_2SO_4$. After the desiccant and solvent have been eliminated the residue is purified by chromatography (silica gel, cyc/EtOAc 2:1).

Yield: 2.7 g (51.2% of theory)
$C_8H_8BrClN_2O$ (M=263.523)
Calc.: molpeak $(M+H)^+$: 263/265/267 Found: molpeak $(M+H)^+$: 263/265/267
$R_f$ value: 0.48 (silica gel, cyc/EtOAc 1:1)

15b

N-(5-bromo-3-methyl-pyridin-2-yl)-2-pyrrolidin-1-yl-acetamide 0.81 mL (9.9 mmol) pyrrolidine are added to a suspension of 2.37 g (9.0 mmol) N-(5-bromo-3-methyl-pyridin-2-yl)-2-chloro-acetamide and 2.49 g (18 mmol) $K_2CO_3$ in 22.5 mL DMF and the reaction mixture is stirred for 20 h at RT. It is diluted with water, extracted exhaustively with EtOAc, the combined organic phases are washed with water and dried over $Na_2SO_4$. After the desiccant and solvent have been eliminated the residue is taken up in a little diisopropylether, cooled to 0° C., the crystals precipitated are suction filtered and dried in the air.

Yield: 1.4 g (52.2% of theory)
$C_{12}H_{16}BrN_3O$ (M=298.185)
Calc.: molpeak $(M+H)^+$: 298/300 Found: molpeak $(M+H)^+$: 298/300
$R_f$ value: 0.48 (silica gel, EtOAc/MeOH/$NH_3$ 90:10:1)

15c

N-(3-methyl-5-trimethylsilanylethynyl-pyridin-2-yl)-2-pyrrolidin-1-yl-acetamide

Under an argon atmosphere 35 mg (0.03 mmol) tetrakis-triphenylphosphane-palladium and 5.7 mg (0.03 mmol) CuI are added to a solution of 447 mg (1.5 mmol) N-(5-bromo-3-methyl-pyridin-2-yl)-2-pyrrolidin-1-yl-acetamide and 0.23 mL (1.65 mmol) ethynyl-trimethyl-silane in 0.45 mL (4.5 mmol) piperidine and 10 mL THF and the reaction mixture is stirred for 14 h at RT. To complete the reaction a further 35 mg tetrakis-triphenylphosphane-palladium are added and the reaction mixture is heated to 50° C. for 4 h. It is diluted with water, extracted exhaustively with EtOAc, the combined organic phases are washed with saturated NaCl solution and dried over $Na_2SO_4$. After the desiccant and solvent have been eliminated the residue is purified by chromatography (silica gel, EtOAc/MeOH/$NH_3$ 90:10:1).

Yield: 210 mg (44.4% of theory)
$C_{17}H_{25}N_3OSi$ (M=315.494)
Calc.: molpeak $(M+H)^+$: 316 Found: molpeak $(M+H)^+$: 316
$R_f$ value: 0.65 (silica gel, EtOAc/MeOH/$NH_3$ 90:10:1)

15d

N-(5-ethynyl-3-methyl-pyridin-2-yl)-2-pyrrolidin-1-yl-acetamide

Under an argon atmosphere 132 mg (0.48 mmol) TBAF are added to a solution of 150 mg (0.48 mmol) N-(3-methyl-5-trimethylsilanylethynyl-pyridin-2-yl)-2-pyrrolidin-1-yl-acetamide in 10 mL THF and the reaction mixture is stirred overnight at RT. The mixture is evaporated down i. vac., the residue is taken up in EtOAc, the organic phase is washed with water and saturated NaCl solution and dried over $Na_2SO_4$. After the desiccant and solvent have been eliminated the desired product is obtained.

Yield: 110 mg (95.2% of theory)
$C_{14}H_{17}N_3O$ (M=243.311)
Calc.: molpeak $(M+H)^+$: 244 Found: molpeak $(M+H)^+$: 244
$R_f$ value: 0.48 (silica gel, EtOAc/MeOH/$NH_3$ 90:10:1)

15e

N-{5-[5-(4-chloro-phenyl)-pyridin-2-ylethynyl]-3-methyl-pyridin-2-yl}-2-pyrrolidin-1-yl-acetamide Under an argon atmosphere 4 mg (0.01 mmol) $Pd(PPh_3)_2Cl_2$ and 1 mg (0.01 mmol) CuI are added to a solution of 73 mg (0.3 mmol) N-(5-ethynyl-3-methyl-pyridin-2-yl)-2-pyrrolidin-1-yl-acetamide and 95 mg (0.3 mmol) 5-(4-chloro-phenyl)-2-iodo-pyridine in 59 μL (0.6 mmol) piperidine and 10 mL THF and the reaction mixture is stirred for 30 min at RT. It is evaporated down i.vac., the residue is taken up in EtOAc, the organic phase is washed with water and saturated NaCl solution and dried over $Na_2SO_4$. After the desiccant and solvent have been eliminated the residue is purified first by chromatography (silica gel, EtOAc/MeOH/$NH_3$ 95:5:0.5) and then by HPLC.

Yield: 22 mg (17.0% of theory)
$C_{25}H_{23}ClN_4O$ (M=430.941)
Calc.: molpeak $(M+H)^+$: 431/433 Found: molpeak $(M+H)^+$: 431/433
$R_f$ value: 0.39 (silica gel, EtOAc/MeOH/$NH_3$ 90:10:1)

Example 16

{5-[5-(4-chloro-phenyl)-pyridin-2-ylethynyl]-3-methyl-pyridin-2-yl}-(2-pyrrolidin-1-yl-ethyl)-amine

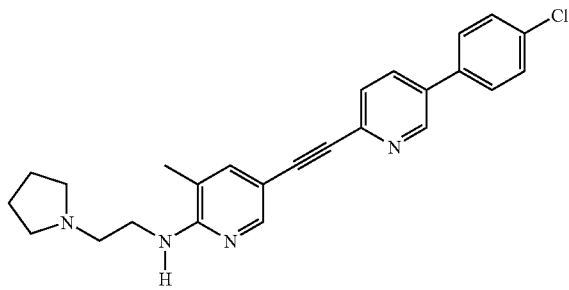 [SMILES: Cc1cc(C#Cc2ccc(-c3ccc(Cl)cc3)cn2)cnc1NCCN1CCCC1]

16a (5-bromo-3-methyl-pyridin-2-yl)-(2-pyrrolidin-1-yl-ethyl)-amine

Under an argon atmosphere 2 mL of a 1 M solution of LiAlH$_4$ in THF are slowly added dropwise to a solution, cooled to 0° C., of 800 mg (2.68 mmol) N-(5-bromo-3-methyl-pyridin-2-yl)-2-pyrrolidin-1-yl-acetamide (Example 15b) in 10 mL THF and the reaction mixture is stirred for 3 h at this temperature. 20% NaOH is slowly added dropwise, solid K$_2$CO$_3$ is added to the suspension and this is stirred vigorously. The precipitate is filtered off, the filtrate is evaporated down and the residue is purified by chromatography (silica gel, EtOAc/MeOH/NH$_3$ 80:20:2).

Yield: 500 mg (65.6% of theory)
C$_{12}$H$_{18}$BrN$_3$ (M=284.201)
Calc.: molpeak (M+H)$^+$: 284/286 Found: molpeak (M+H)$^+$: 284/286
R$_f$ value: 0.25 (silica gel, EtOAc/MeOH/NH$_3$ 80:20:2)

16b (3-methyl-5-trimethylsilanylethynyl-pyridin-2-yl)-(2-pyrrolidin-1-yl-ethyl)-amine Prepared analogously to Example 15c from 500 mg (1.76 mmol) (5-bromo-3-methyl-pyridin-2-yl)-(2-pyrrolidin-1-yl-ethyl)-amine and 0.29 mL (2.11 mmol) ethynyl-trimethylsilane, while the reaction mixture is heated to 50° C. for 12 h.

Yield: 400 mg (75.4% of theory)
C$_{17}$H$_{27}$N$_3$Si (M=301.511)
Calc.: molpeak (M+H)$^+$: 302 Found: molpeak (M+H)$^+$: 302
R$_f$ value: 0.27 (silica gel, EtOAc/MeOH/NH$_3$ 90:10:1)

16c (5-ethynyl-3-methyl-pyridin-2-yl)-(2-pyrrolidin-1-yl-ethyl)-amine

Prepared analogously to Example 15d from 400 mg (1.33 mmol) (3-methyl-5-trimethylsilanyl-ethynyl-pyridin-2-yl)-(2-pyrrolidin-1-yl-ethyl)-amine.

Yield: 250 mg (82.2% of theory)
C$_{14}$H$_{19}$N$_3$ (M=229.328)
R$_f$ value: 0.51 (silica gel, EtOAc/MeOH/NH$_3$ 80:20:2)

16d

{5-[5-(4-chloro-phenyl)-pyridin-2-ylethynyl]-3-methyl-pyridin-2-yl}-(2-pyrrolidin-1-yl-ethyl)-amine Prepared analogously to Example 15e from 69 mg (0.3 mmol) (5-ethynyl-3-methyl-pyridin-2-yl)-(2-pyrrolidin-1-yl-ethyl)-amine and 95 mg (0.3 mmol) 5-(4-chloro-phenyl)-2-iodo-pyridine, while after working up the crude product is purified by chromatography on Alox (cyc/EtOAc 6:4).

Yield: 12 mg (9.6% of theory)
C$_{25}$H$_{25}$ClN$_4$ (M=416.958)
Calc.: molpeak (M+H)$^+$: 417/419 Found: molpeak (M+H)$^+$: 417/419
R$_f$ value: 0.42 (Alox, cyc/EtOAc 1:1)

Example 17

6-(4-chloro-phenyl)-2-(4-pyrrolidin-1-ylmethyl-phenylethynyl)-quinoline

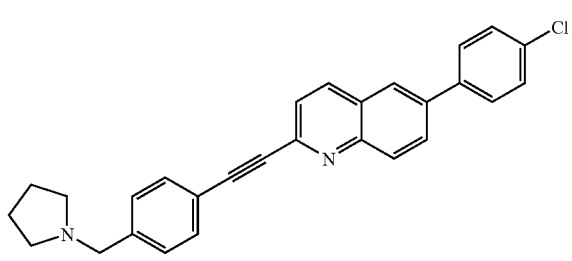 [SMILES: Clc1ccc(-c2ccc3nc(C#Cc4ccc(CN5CCCC5)cc4)ccc3c2)cc1]

17a (E)-3-ethoxy-acrylic acid chloride 20 g (0.172 mol) (E)-3-ethoxy-acrylic acid are added batchwise to a solution of 14.99 mL (0.206 mol) thionyl chloride in 300 ml of toluene at RT and heated to 90° C. for 2 h. The reaction mixture is evaporated to dryness and the yellow oil remaining is further reacted without any more purification.

17b (E)-N-(4-bromo-phenyl)-3-ethoxy-acrylamide 26.63 g (0.155 mol) of 4-bromoaniline are dissolved in 120 ml of pyridine and 23.14 g (0.172 mol) (E)-3-ethoxy-acrylic acid chloride are added dropwise at a temperature between 0° C. and 5° C. and the mixture is stirred for one hour at 0° C. Then the reaction mixture is allowed to warm up to RT and stirred for 14 h. The reaction mixture is combined with water, the precipitate formed is filtered off and washed with water. The solid is dried at 65° C. in the drying cupboard.

Yield: 37.84 g (90.4% of theory)
C$_{11}$H$_{12}$BrNO$_2$ (M=270.12)
Calc.: molpeak (M+H)$^+$: 270/272 Found: molpeak (M+H)$^+$: 270/272
R$_f$ value: 0.7 (silica gel, cyc/EtOAc 1:1)

17c

6-bromo-1H-quinolin-2-one 37.8 g (0.14 mol) (E)-N-(4-bromo-phenyl)-3-ethoxy-acrylamide are added batchwise to 200 mL concentrated sulphuric acid and stirred for 2 h at RT. Then the reaction mixture is poured into ice water, the precipitate is filtered off and washed with water. The solid is dried at 70° C. in the drying cupboard.

Yield: 28.6 g (91.2% of theory)
$C_9H_6BrNO$ (M=224.05)
Calc.: molpeak $(M+H)^+$: 224/226 Found: molpeak $(M+H)^+$: 224/226
$R_f$ value: 0.6 (silica gel, EtOAc)

17d

6-(4-chloro-phenyl)-1H-quinolin-2-one

A solution of 22.7 g (0.101 mol) 6-bromo-1H-quinolin-2-one in 380 mL 1,4-dioxane and 380 mL MeOH is combined with 141.5 ml (0.283 ml) 2 M $Na_2CO_3$ solution and saturated with argon. Then 3.735 g (3.23 mmol) tetrakis-triphenylphosphane-palladium and 4-chlorophenylboric acid are added successively. The reaction mixture is heated to 110° C. for four hours and then evaporated down to a volume of 300 mL. 1.2 L water are added and the precipitate is filtered off. The solid is dried at 55° C. in the drying cupboard, washed with diisopropylether and dried again.

Yield: 25.4 (89.5% of theory)
$C_{15}H_{10}ClNO$ (M=255.70)
Calc.: molpeak $(M+H)^+$: 256/258 Found: molpeak $(M+H)^+$: 256/258
$R_f$ value: 0.6 (silica gel, EtOAc/PE 3:1)

17e

2-bromo-6-(4-chloro-phenyl)-quinoline 50 g (0.174 mol) phosphorus oxybromide are heated to 65° C., combined with 10 g (0.039 mol) 6-(4-chloro-phenyl)-1H-quinolin-2-one and heated to 110° C. for 3 h. The reaction mixture is then poured onto ice water and made alkaline with ammonia solution. The precipitate is filtered off and dried in the drying cupboard at 60° C.

Yield: 12.28 g (98.8% of theory)
$C_{15}H_9BrClN$ (M=318.60)
Calc.: molpeak $(M+H)^+$: 318/320/322 Found: molpeak $(M+H)^+$: 318/320/322
$R_f$ value: 0.8 (silica gel, cyc/EtOAc 3:1)

17f

4-[6-(4-chloro-phenyl)-quinolin-2-ylethynyl]-benzaldehyde

Under a nitrogen atmosphere 0.6 mg CuI, 9.3 mg $Pd(PPh_3)_2Cl_2$ and 318 mg (1 mmol) 2-bromo-6-(4-chloro-phenyl)-quinoline are added successively to a solution of 85 mg (0.66 mmol) 4-ethynyl-benzaldehyde and 2.6 mL (18.67 mmol) triethylamine in 5 mL absolute DMF and 10 mL acetonitrile. The reaction mixture is stirred for 14 hours at RT and evaporated down. The purification is carried out by column chromatography on silica gel (PE/EtOAc 1:1).

Yield: 290 mg (78.8% of theory)
$C_{24}H_{14}ClNO$ (M=367.83)
Calc.: molpeak $(M+H)^+$: 368/370 Found: molpeak $(M+H)^+$: 368/370
$R_f$ value: 0.84 (silica gel, DCM/MeOH/$NH_3$ 90:10:1)

17g

6-(4-chloro-phenyl)-2-(4-pyrrolidin-1-ylmethyl-phenylethynyl)-quinoline 3 mg p-toluenesulphonic acid and 100 µL glacial acetic acid are added to a solution of 290 mg (0.78 mmol) 4-[6-(4-chloro-phenyl)-quinoline-2-ylethynyl]-benzaldehyde and 56 mg (0.78 mmol) pyrrolidine in 10 mL THF at RT and stirred for 30 minutes. Then 334 mg (1.57 mmol) $NaBH(OAc)_3$ are added batchwise and the reaction mixture is stirred for 14 h. A few drops of water are added dropwise to the reaction mixture and this is stirred for 15 minutes. The reaction mixture is then combined with $K_2CO_3$ and filtered. The filtrate is evaporated down. The purification is carried out by column chromatography on silica gel (DCM/MeOH/$NH_3$ 90:10:1).

Yield: 150 mg (45% of theory)
melting point: 170-193° C.
$C_{28}H_{23}ClN_2$ (M=422.96)
Calc.: molpeak $(M+H)^+$: 423/425 Found: molpeak $(M+H)^+$: 423/425
$R_f$ value: 0.49 (silica gel, DCM/MeOH/$NH_3$ 90:10:1)

The following compounds are prepared analogously to Example 17g with 17f as educt:

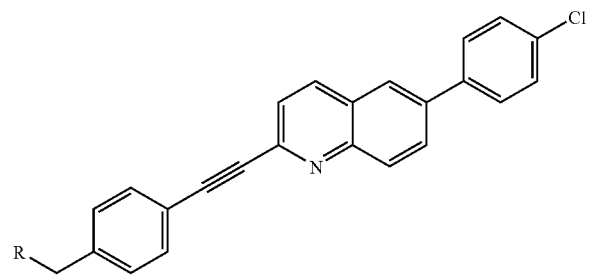

| Example | R | empirical formula | mass spectrum | mp [° C.] | $R_f$ value |
|---|---|---|---|---|---|
| 17.1 | * | $C_{29}H_{26}ClN_3$ | 452/54 $[M + H]^+$ | 176-182 | 0.33 |

-continued

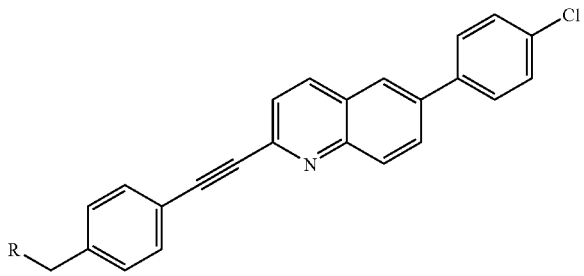

| Example | R | empirical formula | mass spectrum | mp [° C.] | R_f value |
|---|---|---|---|---|---|
| 17.2 | morpholine | $C_{28}H_{23}ClN_2O$ | 439/41 [M + H]$^+$ | 170-174 | 0.45 |
| 17.3 | 4-methoxypiperidine | $C_{30}H_{27}ClN_2O$ | 467/69 [M + H]$^+$ | 159-165 | 0.52 |
| 17.4 | 2-methyl-2,7-diazaspiro[4.4]nonane | $C_{32}H_{30}ClN_3$ | 492/94 [M + H]$^+$ | 140-148 | 0.21 |
| 17.5 | (S)-2-(methoxymethyl)pyrrolidine | $C_{30}H_{27}ClN_2O$ | 467/69 [M + H]$^+$ | 139-147 | 0.61 |
| 17.6 | (R)-2-(methoxymethyl)pyrrolidine | $C_{30}H_{27}ClN_2O$ | 467/69 [M + H]$^+$ | 143-173 | 0.61 |
| 17.7 | (S)-N,N-dimethylpyrrolidine-2-carboxamide | $C_{31}H_{28}ClN_3O$ | 494/96 [M + H]$^+$ | 142-145 | 0.31 |
| 17.8 | 4-acetylpiperazine | $C_{30}H_{26}ClN_3O$ | 480/82 [M + H]$^+$ | 165-170 | 0.30 |
| 17.9 | 1-methyl-3-oxopiperazine | $C_{29}H_{24}ClN_3O$ | 466/68 [M + H]$^+$ | 152-157 | 0.45 |

-continued

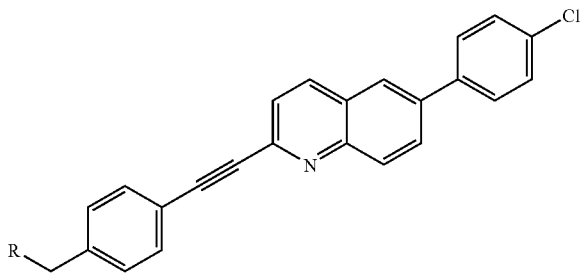

| Example | R | empirical formula | mass spectrum | mp [° C.] | $R_f$ value |
|---|---|---|---|---|---|
| 17.10 | (piperazinyl-pyridin-4-yl) | *$C_{33}H_{27}ClN_4$ | 515/17 [M + H]$^+$ | 214-219 | 0.47 |
| 17.11 | (N-methyl-N-(2-methoxyethyl)amino) | $C_{28}H_{25}ClN_2O$ | 441/43 [M + H]$^+$ | 153 | 0.38 |
| 17.12 | (N-methyl-(tetrahydropyran-4-yl)amino) | $C_{30}H_{27}ClN_2O$ | 467/69 [M + H]$^+$ | 130-136 | 0.32 |
| 17.13 | (N-methyl-(pyridin-4-ylmethyl)amino) | $C_{31}H_{24}ClN_3$ | 474/476 [M + H]$^+$ | 140-149 | 0.43 |
| 17.14 | (4-hydroxy-4-methylpiperidin-1-yl) | $C_{30}H_{27}ClN_2O$ | 467/69 [M + H]$^+$ | 190-192 | 0.30 |
| 17.15 | (thiomorpholin-4-yl S-oxide) | $C_{28}H_{23}ClN_2OS$ | 471/73 [M + H]$^+$ | 170-174 | 0.38 |
| 17.16 | (thiomorpholin-4-yl S,S-dioxide) | $C_{28}H_{23}ClN_2OS$ | 487/89 [M + H]$^+$ | 216-220 | 0.61 |

-continued

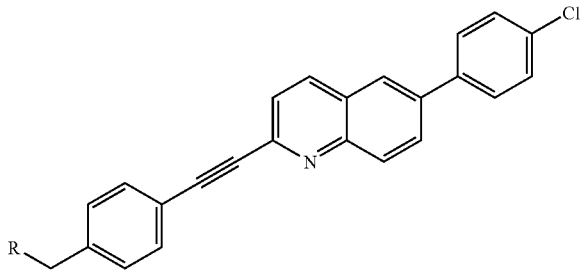

| Example | R | empirical formula | mass spectrum | mp [° C.] | $R_f$ value |
|---|---|---|---|---|---|
| 17.17 | (piperidine with phenyl and OH, N-CH2 linker) | $C_{35}H_{29}ClN_2O$ | 529/31 $[M + H]^+$ | 208-219 | 0.34 |

The $R_f$ values specified are obtained on silica gel with DCM/MeOH/NH$_3$ 90:10:1 as the mobile phase.

Example 18

6-(4-chloro-phenyl)-2-[4-(2-pyrrolidin-1-yl-ethoxy)-phenylethynyl]-quinoline

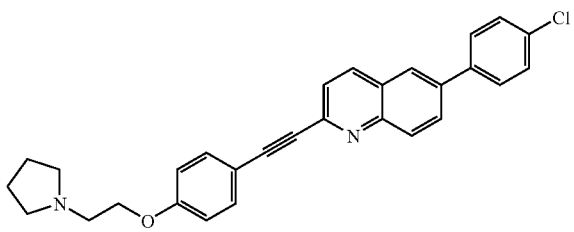 [SMILES: Clc1ccc(-c2ccc3nc(C#Cc4ccc(OCCN5CCCC5)cc4)ccc3c2)cc1]

18a

1-[2-(4-iodo-phenoxy)-ethyl]-pyrrolidine

A reaction mixture of 44 g (0.2 mol) 4-iodophenol, 34 g (0.2 mol) 1-(2-chloro-ethyl)-pyrrolidine-hydrochloride, 110.56 g (0.8 mol) K$_2$CO$_3$ and 800 mL DMF is stirred for 48 h at RT. The reaction mixture is filtered and the filtrate is evaporated down. The residue is taken up in water and extracted with EtOAc. The organic phase is extracted with saturated NaCl solution and dried over Na$_2$SO$_4$. The purification is carried out by column chromatography on silica gel (EtOAc/MeOH/NH$_3$ 85:15:1.5).

Yield: 34.8 g (54.9% of theory)

$C_{12}H_{16}INO$ (M=317.17)

$R_f$ value: 0.49 (silica gel, EtOAc/MeOH/NH$_3$ 90:10:1)

18b

1-[2-(4-trimethylsilanylethynyl-phenoxy)-ethyl]-pyrrolidine

Under a nitrogen atmosphere and while cooling with ice a reaction mixture of 1.5 g (4.72 mmol) 1-[2-(4-iodo-phenoxy)-ethyl]-pyrrolidine, 0.735 ml (5.2 mmol) ethynyl-trimethyl-silane, 15 mL piperidine, 115.5 mg (0.1 mmol) tetrakis-triphenylphosphane-palladium and 19 mg (0.1 mmol) CuI is stirred for 1 h. Then the reaction mixture is evaporated down, the residue is taken up in 20 mL water and extracted with EtOAc. The organic phase is dried over Na$_2$SO$_4$. The purification is carried out by column chromatography on silica gel (EtOAc/MeOH/NH$_3$ 95:5:0.5).

Yield: 1.244 g (91.5% of theory)

$C_{17}H_{25}NOSi$ (M=287.48)

Calc.: molpeak $(M+H)^+$: 288 Found: molpeak $(M+H)^+$: 288

$R_f$ value: 0.45 (silica gel, EtOAc/MeOH/NH$_3$ 90:10:1)

18c

1-[2-(4-ethynyl-phenoxy)-ethyl]-pyrrolidine

A reaction mixture of 1.22 g (4.24 mmol) 1-[2-(4-trimethylsilanylethynyl-phenoxy)-ethyl]-pyrrolidine, 1.47 g (4.67 mmol) TBAF and 25 mL THF is stirred for 3 h at RT. Then the reaction mixture is evaporated down and the residue is combined with 20 mL saturated NaCl solution and 50 mL EtOAc. The organic phase is dried over Na$_2$SO$_4$. The purification is carried out by column chromatography on silica gel (EtOAc/MeOH/NH$_3$ 90:10:1).

Yield: 0.91 g (100% of theory)

$C_{14}H_{17}NO$ (M=215.29)

Calc.: molpeak $(M+H)^+$: 216 Found: molpeak $(M+H)^+$: 216

$R_f$ value: 0.33 (silica gel, EtOAc/MeOH/NH$_3$ 90:10:1)

18d 6-(4-chloro-phenyl)-2-[4-(2-pyrrolidin-1-yl-ethoxy)-phenylethynyl]-quinoline In a nitrogen atmosphere, 0.6 mg CuI, 9.3 mg Pd(PPh$_3$)$_2$Cl$_2$ and 318 mg (1 mmol) 2-bromo-6-(4-chloro-phenyl)-quinoline are added successively to a solution of 142 mg (0.66 mmol) 1-[2-(4-ethynyl-phenoxy)-ethyl]-pyrrolidine and 2.6 mL (18.67 mmol) triethylamine in 5 mL absolute DMF and 10 mL acetonitrile. The reaction mixture is stirred for 14 h at RT and evaporated down. The purification is carried out by column chromatography on silica gel (DCM/MeOH/NH$_3$ 90:10:1).

Yield: 148 mg (32.7% of theory)
melting point: 176-185° C.
C$_{29}$H$_{25}$ClN$_2$O (M=452.98)
Calc.: molpeak (M+H)$^+$: 453/455 Found: molpeak (M+H)$^+$: 453/455
R$_f$ value: 0.71 (silica gel, DCM/MeOH/NH$_3$ 80:20:1)

Example 19

6-(4-chloro-phenyl)-2-[3-(2-pyrrolidin-1-yl-ethoxy)-phenylethynyl]-quinoline

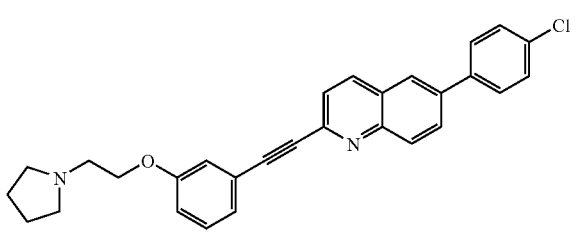 [SMILES: Clc1ccc(-c2ccc3nc(C#Cc4cccc(OCCN5CCCC5)c4)ccc3c2)cc1]

19a

1-[2-(3-ethynyl-phenoxy)-ethyl]-pyrrolidine

Prepared analogously to Example 18a from 1-(2-chloro-ethyl)-pyrrolidine-hydrochloride and 3-ethynyl-phenol.

Yield: 1.44 g (79% of theory)
C$_{14}$H$_{17}$NO (M=215.29)
Calc.: molpeak (M+H)$^+$: 216 Found: molpeak (M+H)$^+$: 216
R$_f$ value: 0.37 (silica gel, DCM/MeOH/NH$_3$ 90:10:1)

19b 6-(4-chloro-phenyl)-2-[3-(2-pyrrolidin-1-yl-ethoxy)-phenylethynyl]-quinoline Prepared analogously to Example 18d from 1-[2-(3-ethynyl-phenoxy)-ethyl]-pyrrolidine and 2-bromo-6-(4-chloro-phenyl)-quinoline.

Yield: 135 mg (29.8% of theory)
melting point: 114-117° C.
C$_{29}$H$_{25}$ClN$_2$O (M=452.98)
Calc.: molpeak (M+H)$^+$: 453/455 Found: molpeak (M+H)$^+$: 453/455
R$_f$ value: 0.61 (silica gel, DCM/MeOH/NH$_3$ 80:20:1)

Example 20

6-(4-chloro-phenyl)-2-(2-pyrrolidin-1-ylmethyl-benzoxazol-5-ylethynyl)-quinoline

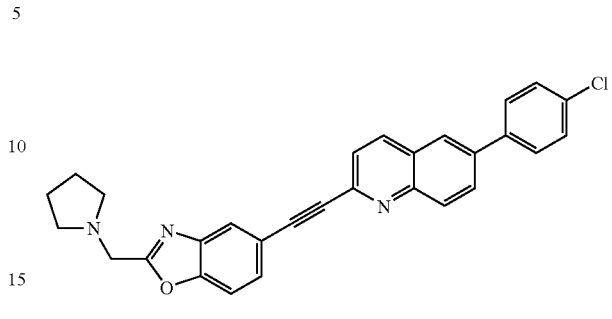

20a 5-bromo-2-chloromethyl-benzoxazole 1.79 mL (13.3 mmol) 2-chloro-1,1,1-trimethoxy-ethane are added dropwise at RT to a solution of 2.5 g (13.29 mmol) 2-amino-4-bromophenol in 20 mL ethanol and stirred for 48 h. Then 0.4 mL 2-chloro-1,1,1-trimethoxy-ethane are added and stirred for 20 h. The reaction mixture is evaporated down. The purification is carried out by column chromatography on silica gel (DCM/ethanol 80:1).

Yield: 2 g (60.9% of theory)
C$_8$H$_5$BrClNO (M=246.49)
Calc.: molpeak (M+H)$^+$: 246/248/250 Found: molpeak (M+H)$^+$: 246/248/250
R$_f$ value: 0.95 (silica gel, DCM/ethanol 20:1)

20b 5-bromo-2-pyrrolidin-1-ylmethyl-benzoxazole

A solution of 2 g (8.11 mmol) 5-bromo-2-chloromethyl-benzoxazole in 30 mL DMF is combined with 2.24 g (16.22 mmol) K$_2$CO$_3$ and 0.9 mL (10.78 mmol) pyrrolidine and stirred for 24 hours at RT. The reaction mixture is diluted with water and extracted with EtOAc. The organic phase is dried over Na$_2$SO$_4$, the desiccant is filtered off and the filtrate is evaporated down.

Yield: 2.2 g (96.4% of theory)
C$_{12}$H$_{13}$BrN$_2$O (M=281.15)
Calc.: molpeak (M+H)$^+$: 281/283 Found: molpeak (M+H)$^+$: 281/283
R$_f$ value: 0.15 (silica gel, DCM/ethanol 50:1)

20c 5-iodo-2-pyrrolidin-1-ylmethyl-benzoxazole 71 mg (0.36 mmol) CuI, 1 g (3.55 mmol) 5-bromo-2-pyrrolidin-1-ylmethyl-benzoxazole and 1.07 g (7.15 mmol) NaI are successively placed in a flask in an argon atmosphere. Then 0.08 mL (0.73 mmol) N,N'-dimethylethylenediamine and 3.5 mL 1,4-dioxane are added and the reaction mixture is refluxed for 14 h. The reaction mixture is then combined with 20 mL concentrated ammonia solution at RT, diluted with 100 mL water and extracted with DCM. The organic phase is extracted three times with water and dried over Na$_2$SO$_4$.

Yield: 1 g (72.8% of theory)
C$_{12}$H$_{13}$IN$_2$O (M=328.15)
Calc.: molpeak (M+H)$^+$: 329 Found: molpeak (M+H)$^+$: 329
R$_f$ value: 0.35 (silica gel, cyc/EtOAc 1:1)

20d

2-pyrrolidin-1-ylmethyl-5-trimethylsilanylethynyl-benzoxazole

Prepared analogously to Example 18b from 5-iodo-2-pyrrolidin-1-ylmethyl-benzoxazole and ethynyl-trimethyl-silane.

Yield: 0.5 g (91.6% of theory)
$C_{17}H_{22}N_2OSi$ (M=298.46)
Calc.: molpeak (M+H)$^+$: 299 Found: molpeak (M+H)$^+$: 299
$R_f$ value: 0.5 (silica gel, DCM/MeOH/NH$_3$ 90:10:1)

20e

5-ethynyl-2-pyrrolidin-1-ylmethyl-benzoxazole

Prepared analogously to Example 18c from 2-pyrrolidin-1-ylmethyl-5-trimethylsilanylethynyl-benzoxazole.

Yield: 0.265 g (69.9% of theory)
$C_{14}H_{14}N_2O$ (M=226.28)
Calc.: molpeak (M+H)$^+$: 227 Found: molpeak (M+H)$^+$: 227
$R_f$ value: 0.79 (silica gel, DCM/MeOH/NH$_3$ 80:20:1)

20f

6-(4-chloro-phenyl)-2-(2-pyrrolidin-1-ylmethyl-benzoxazol-5-ylethynyl)-quinoline Prepared analogously to Example 18d from 5-ethynyl-2-pyrrolidin-1-ylmethyl-benzoxazole and 2-bromo-6-(4-chloro-phenyl)-quinoline.

Yield: 90 mg (13.9% of theory)
melting point: 151-153° C.
$C_{29}H_{22}ClN_3O$ (M=463.97)
Calc.: molpeak (M+H)$^+$: 464/466 Found: molpeak (M+H)$^+$: 464/466
$R_f$ value: 0.53 (silica gel, DCM/MeOH/NH$_3$ 90:10:1)

Example 21

5-[5-(4-chloro-phenyl)-pyridin-2-ylethynyl]-2-pyrrolidin-1-ylmethyl-benzoxazole

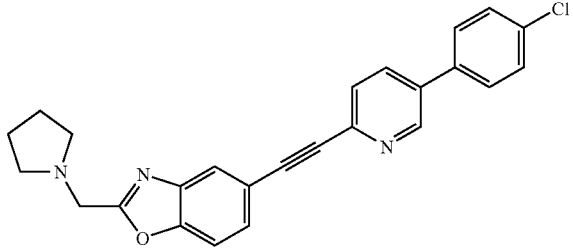 [SMILES: Clc1ccc(-c2ccc(C#Cc3ccc4oc(CN5CCCC5)nc4c3)nc2)cc1]

A reaction mixture of 260 mg (0.792 mmol) 5-iodo-2-pyrrolidin-1-ylmethyl-benzoxazole, 171 mg (0.8 mmol) 5-(4-chloro-phenyl)-2-ethynyl-pyridine, 23 mg (0.02 mmol) tetrakis-triphenylphosphane-palladium, 3.8 mg (0.02 mmol) CuI and 350 mg (1.075 mmol) Cs$_2$CO$_3$ in 10 mL THF is stirred for 14 h in an argon atmosphere at RT. Then the reaction mixture is evaporated down and the residue is purified by column chromatography on silica gel (DCM/MeOH 80:1).

Yield: 140 mg (42.7% of theory)
melting point: 145° C.
$C_{25}H_{20}ClN_3O$ (M=413.91)
Calc.: molpeak (M+H)$^+$: 414/416 Found: molpeak (M+H)$^+$: 414/416
$R_f$ value: 0.1 (silica gel, DCM/MeOH 50:1)

Example 22

5-[5-(4-chloro-phenyl)-pyridin-2-ylethynyl]-2-(2-pyrrolidin-1-yl-ethoxy)-benzoic acid

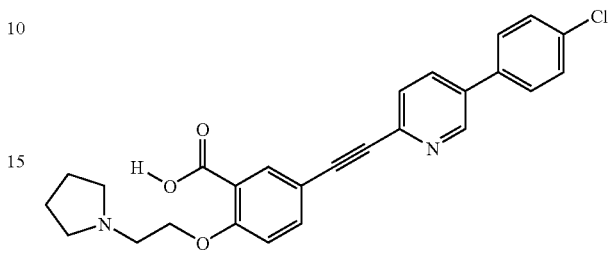

1.6 mL aqueous 1 M NaOH are added to a solution of 369 mg (0.8 mmol) methyl 5-[5-(4-chloro-phenyl)-pyridin-2-ylethynyl]-2-(2-pyrrolidin-1-yl-ethoxy)-benzoate (Example 3.4) in 20 mL MeOH and the reaction mixture is heated to 70° C. for 3 h. It is combined with 1.6 mL 1 M HCl, evaporated down i.vac. and the residue is coevaporated twice with in each case 20 mL MeOH. The residue is triturated with EtOH with heating and suction filtered.

Yield: 340 mg (95.1% of theory)
$C_{26}H_{23}ClN_2O_3$ (M=446.938)
Calc.: molpeak (M+H)$^+$: 447/449 Found: molpeak (M+H)$^+$: 447/449
HPLC retention time: 7.0 min (method A)

Example 22.1

5-[5-(4-chloro-phenyl)-pyridin-2-ylethynyl]-N-methyl-2-(2-pyrrolidin-1-yl-ethoxy)-benzamide

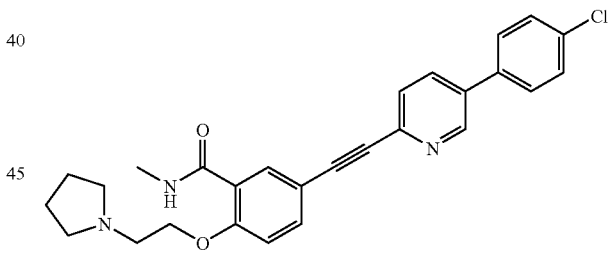

80 mg (0.25 mmol) TBTU and 69 μL triethylamine are added to a solution of 112 mg (0.25 mmol) 5-[5-(4-chloro-phenyl)-pyridin-2-ylethynyl]-2-(2-pyrrolidin-1-yl-ethoxy)-benzoic acid (Example 22) in 5 mL DMF and the reaction mixture is stirred for 2 h at RT. Then 31 mg (1.0 mmol) methylamine are added and stirring is continued for a further 2 h at RT. The mixture is evaporated down i. vac., the residue is combined with dilute Na$_2$CO$_3$ solution, extracted exhaustively with DCM and the organic phase is dried over Na$_2$SO$_4$. After the desiccant and solvent have been eliminated the residue is purified by chromatography (silica gel, DCM to DCM/MeOH/NH$_3$ 7:3:0.3).

Yield: 45 mg (39.1% of theory)
$C_{27}H_{26}ClN_3O_2$ (M=459.980)
Calc.: molpeak (M+H)$^+$: 460/462 Found: molpeak (M+H)$^+$: 460/462
HPLC retention time: 6.8 min (method A)

The following compounds are prepared as described in Example 22.1, while in Example 22.5 ammonium carbonate is used as the ammonia source:

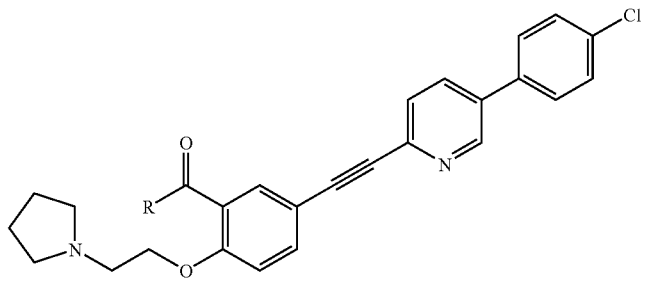

| Example | R | Yield (%) | empirical formula | mass spectrum | HPLC retention time in min (method) |
|---|---|---|---|---|---|
| 22.2 | H₃C−N(CH₃)−* | 42.2 | C₂₈H₂₈ClN₃O₂ | 474/476 [M + H]⁺ | 6.95 (A) |
| 22.3 | pyrrolidinyl-ethyl-NH− | 9.3 | C₃₂H₃₅ClN₄O₂ | 543/545 [M + H]⁺ | 5.30 (A) |
| 22.4 | cyclopropyl-NH−* | 6.9 | C₂₉H₂₈ClN₃O₂ | 486/488 [M + H]⁺ | 7.07 (A) |
| 22.5 | H₂N−NH−* | 4.0 | C₂₆H₂₄ClN₃O₂ | 446/446 [M + H]⁺ | 6.10 (A) |

Example 23

5-[5-(4-chloro-phenyl)-pyridin-2-ylethynyl]-2-(2-pyrrolidin-1-yl-ethoxy)-phenylamine

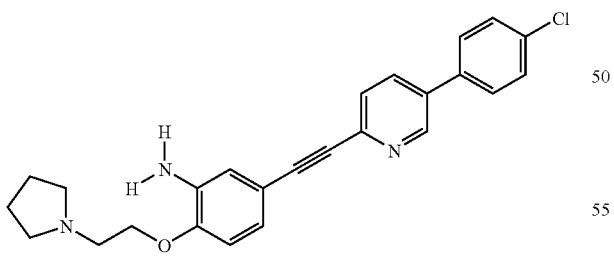

200 mg (2.5 mmol) NaHCO₃ and 300 mg (1.1 mmol) tin-(II)-chloride dihydrate are added to a solution of 100 mg (0.22 mmol) 5-(4-chloro-phenyl)-2-[3-nitro-4-(2-pyrrolidin-1-yl-ethoxy)-phenylethynyl]-pyridine (Example 3.13) in 10 mL EtOAc and the reaction mixture is refluxed for 2 h. To complete the reaction a further 200 mg (2.5 mmol) NaHCO₃, 300 mg (1.1 mmol) tin-(II)-chloride dihydrate and 1 mL MeOH are added and the mixture is refluxed for a further 2 h. After cooling, 4 g of silica gel are added, the solvent is eliminated i.vac. and the residue is purified by chromatography (silica gel, DCM/MeOH/NH₃ 8:2:0.2).

Yield: 85 mg (39.1% of theory)

C₂₅H₂₄ClN₃O (M=417.943)

Calc.: molpeak (M+H)⁺: 418/420 Found: molpeak (M+H)⁺: 418/420

HPLC retention time: 7.1 min (method A)

Example 23.1

N-[5-[5-(4-chloro-phenyl)-pyridin-2-ylethynyl]-2-(2-pyrrolidin-1-yl-ethoxy)-phenyl]-acetamide 16 μL (170 μmol) acetic anhydride are added to a solution of 35 mg (84 μmol) 5-[5-(4-chloro-phenyl)-pyridin-2-ylethynyl]-2-(2-pyrrolidin-1-yl-ethoxy)-phenylamine in 2 mL DCM and the reaction mixture is stirred overnight at RT and then purified by chromatography on silica gel (gradient: EtOAc to EtOAc/MeOH/NH$_3$ 7:3:0.3) without any further working up Yield: 10 mg (26.0% of theory)

$C_{27}H_{26}ClN_3O_2$ (M=459.980)

Calc.: molpeak (M+H)$^+$: 460/462 Found: molpeak (M+H)$^+$: 460/462

R$_f$ value: 0.55 (silica gel, DCM/MeOH/NH$_3$ 90:10:1)

Example 23.2

N-[5-[5-(4-chloro-phenyl)-pyridin-2-ylethynyl]-2-(2-pyrrolidin-1-yl-ethoxy)-phenyl]-methanesulphonamide

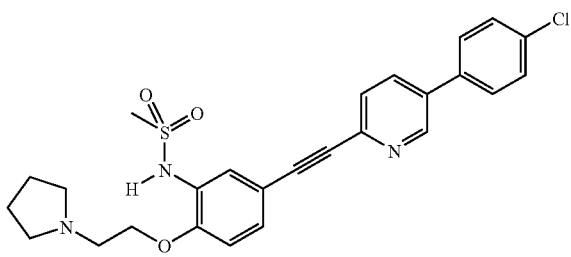 [SMILES: CS(=O)(=O)Nc1cc(C#Cc2ccc(-c3ccc(Cl)cc3)cn2)ccc1OCCN1CCCC1]

Under an N$_2$ atmosphere 39 μL (0.5 mmol) methanesulphonic acid chloride are added to a solution of 100 mg (0.24 mmol) 5-[5-(4-chloro-phenyl)-pyridin-2-ylethynyl]-2-(2-pyrrolidin-1-yl-ethoxy)-phenylamine and 161 μL (2 mmol) pyridine in 10 mL DCM and the reaction mixture is stirred for 2 h at RT. To complete the reaction a further 160 μL pyridine and 39 μL methanesulphonic acid chloride are added and the mixture is stirred overnight. It is combined with 10% Na$_2$CO$_3$ solution, the organic phase is separated off and the solvent is eliminated i.vac. The residue is purified by HPLC.

Yield: 15 mg (13.0% of theory)

$C_{26}H_{26}ClN_3O_3S$ (M=496.032)

Calc.: molpeak (M+H)$^+$: 496/498 Found: molpeak (M+H)$^+$: 496/498

HPLC retention time: 6.8 min (method A)

Example 23.3

[5-[5-(4-chloro-phenyl)-pyridin-2-ylethynyl]-2-(2-pyrrolidin-1-yl-ethoxy)-phenyl]-dimethyl-amine

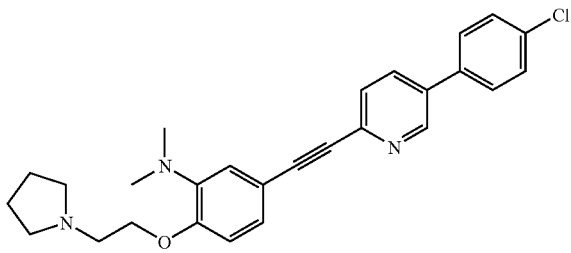

180 μL (2.4 mmol) formalin solution (37% in water), 63 mg (1.0 mmol) NaBH$_3$CN and 57 μL (1.0 mmol) acetic acid are added to a solution of 100 mg (0.24 mmol) 5-[5-(4-chloro-phenyl)-pyridin-2-ylethynyl]-2-(2-pyrrolidin-1-yl-ethoxy)-phenylamine in 5 mL acetonitrile and the reaction mixture is stirred overnight at RT. It is acidified with 12% HCl, stirred vigorously for one hour, combined with saturated Na$_2$CO$_3$ solution until an alkaline reaction is obtained and extracted exhaustively with DCM. After elimination of the solvent the residue is purified by HPLC.

Yield: 9 mg (8.4% of theory)

$C_{27}H_{28}ClN_3O$ (M=445.997)

Calc.: molpeak (M+H)$^+$: 446/448 Found: molpeak (M+H)$^+$: 446/448

HPLC retention time: 6.7 min (method A)

Example 23.4

[5-[5-(4-chloro-phenyl)-pyridin-2-ylethynyl]-2-(2-pyrrolidin-1-yl-ethoxy)-phenyl]-methyl-amine

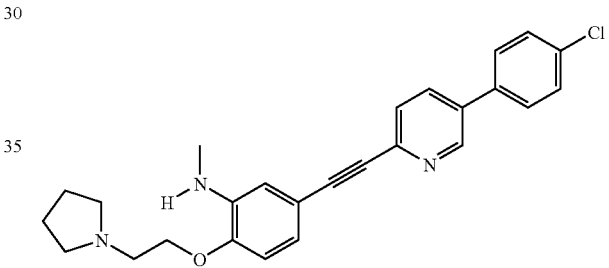

Under a nitrogen atmosphere 178 μL (1.35 mmol) N,N-dimethylformamide dimethylacetal are added to a solution of 100 mg (0.24 mmol) 5-[5-(4-chloro-phenyl)-pyridin-2-ylethynyl]-2-(2-pyrrolidin-1-yl-ethoxy)-phenylamine in 2 mL DMF, the reaction mixture is stirred for 5 h at 60° C. and cooled to RT overnight. Then 32 mg (0.85 mmol) NaBH$_4$ are added and the mixture is again heated to 60° C. for 1 h. To complete the reaction a further 32 mg NaBH$_4$ are added and the mixture is heated to 60° C. for a further 4 h. After cooling it is combined with saturated NaHCO$_3$ solution, exhaustively extracted with EtOAc and the organic phase is dried over MgSO$_4$. After the desiccant and solvent have been eliminated the residue is purified by HPLC.

Yield: 0.5 mg (0.5% of theory)

$C_{26}H_{26}ClN_3O$ (M=431.970)

Calc.: molpeak (M+H)$^+$: 432/434 Found: molpeak (M+H)$^+$: 432/434

HPLC retention time: 7.5 min (method A)

The following compounds may also be obtained by the processes described in the foregoing experimental section:
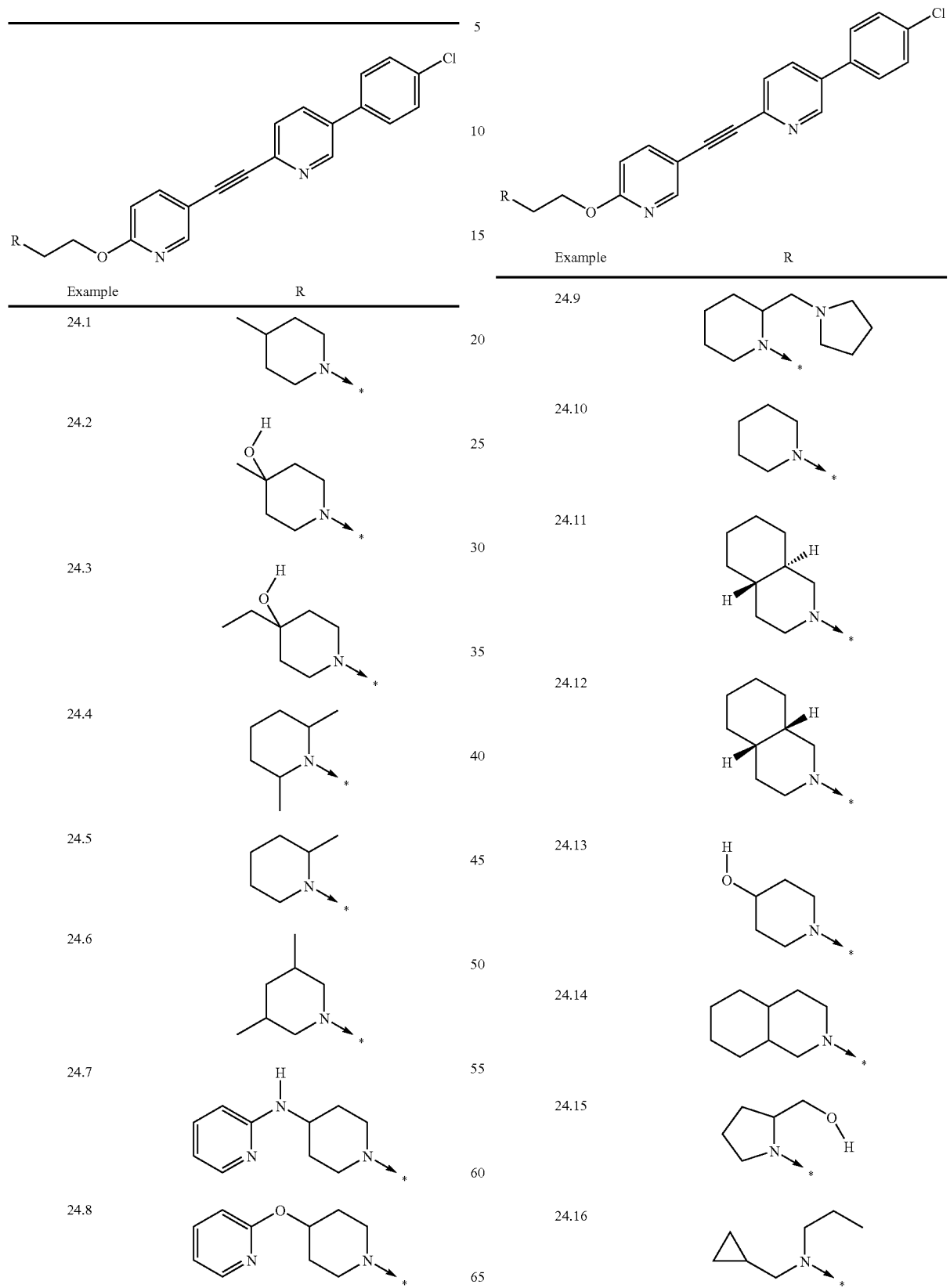

-continued
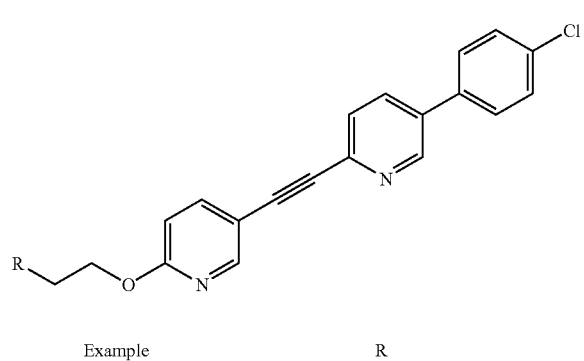
| Example | R |
|---|---|
| 24.17 | 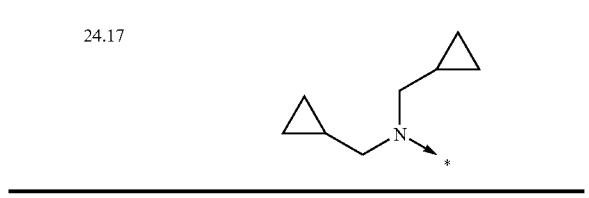 |
The following compounds may also be obtained by the processes described in the foregoing experimental section:
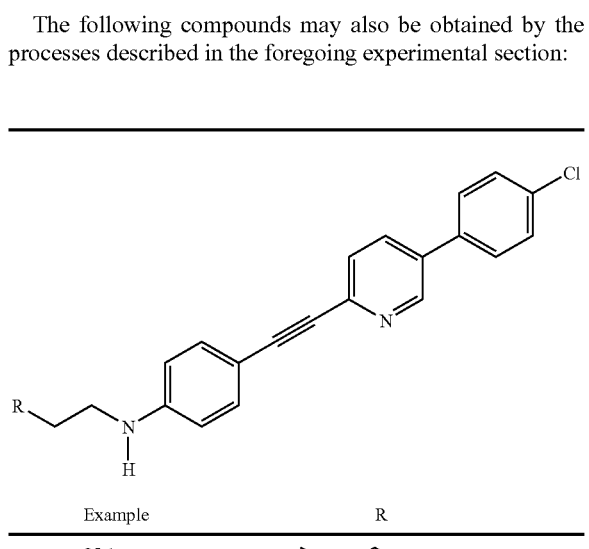
| Example | R |
|---|---|
| 25.1 | 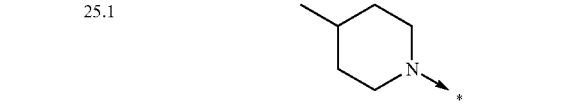 |
| 25.2 | |
| 25.3 | 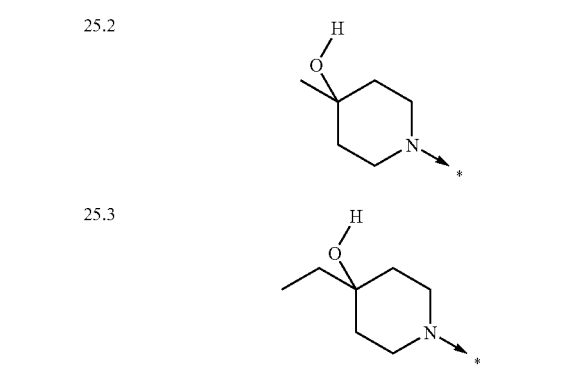 |
-continued
| Example | R |
|---|---|
| 25.4 | |
| 25.5 | |
| 25.6 | |
| 25.7 | |
| 25.8 | |
| 25.9 | |
| 25.10 | |
| 25.11 | |

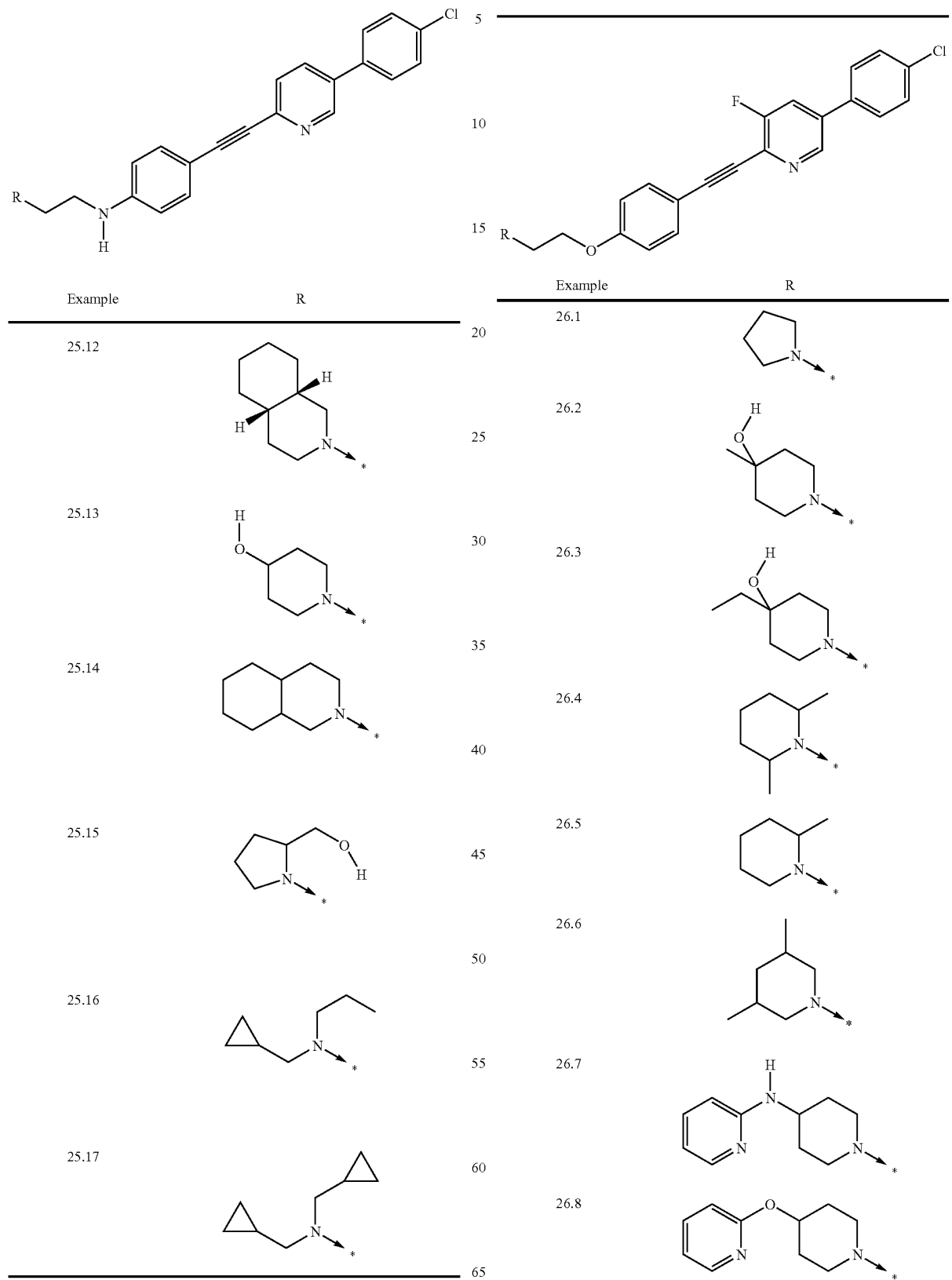

267
-continued

| Example | R |
|---|---|
| 26.9 | (2-(pyrrolidin-1-ylmethyl)piperidin-1-yl) |
| 26.10 | piperidin-1-yl |
| 26.11 | trans-decahydroisoquinolin-2-yl |
| 26.12 | cis-decahydroisoquinolin-2-yl |
| 26.13 | 4-hydroxypiperidin-1-yl |
| 26.14 | decahydroisoquinolin-2-yl |
| 26.15 | 2-(hydroxymethyl)pyrrolidin-1-yl |
| 26.16 | N-(cyclopropylmethyl)-N-propylamino |
| 26.17 | N,N-bis(cyclopropylmethyl)amino |

268

The following compounds may also be obtained by the processes described in the foregoing experimental section:

| Example | R |
|---|---|
| 27.1 | 4-methylpiperidin-1-yl |
| 27.2 | 4-hydroxypiperidin-1-yl |
| 27.3 | 4-ethyl-4-hydroxypiperidin-1-yl |
| 27.4 | 2,6-dimethylpiperidin-1-yl |
| 27.5 | 2-methylpiperidin-1-yl |
| 27.6 | 3,5-dimethylpiperidin-1-yl |
| 27.7 | 4-(pyridin-2-ylamino)piperidin-1-yl |

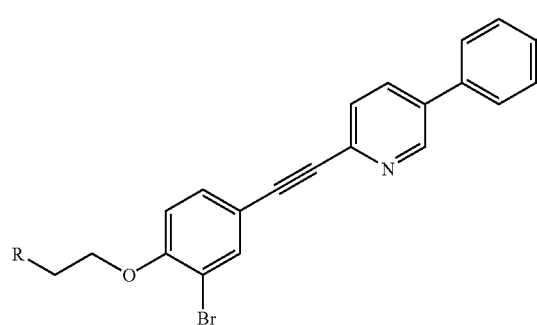
| Example | R |
|---|---|
| 27.8 | 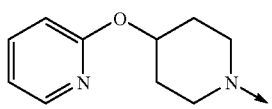 |
| 27.9 | 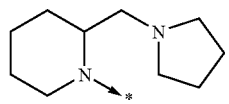 |
| 27.10 | 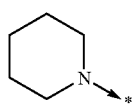 |
| 27.11 | 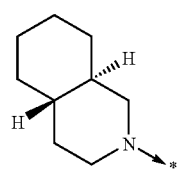 |
| 27.12 | 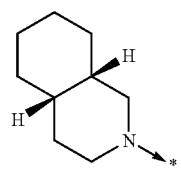 |
| 27.13 | 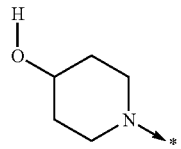 |
| 27.14 | 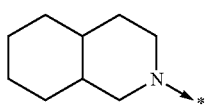 |
| 27.15 | 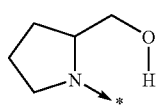 |
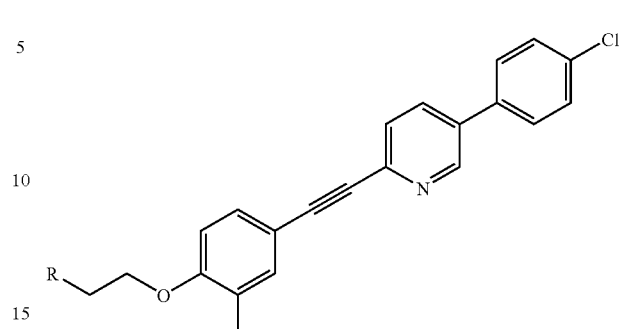
| Example | R |
|---|---|
| 27.16 | 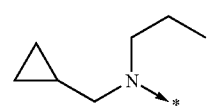 |
| 27.17 | 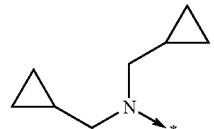 |
The following compounds may also be obtained by the processes described in the foregoing experimental section:
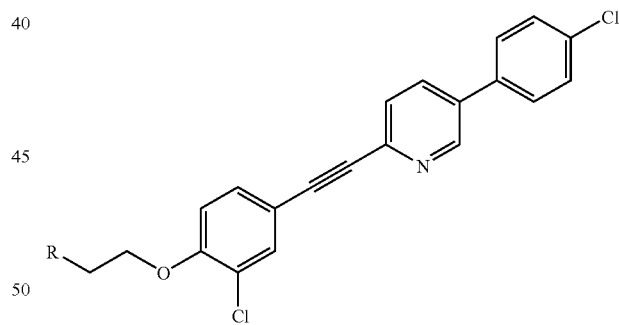
| Example | R |
|---|---|
| 28.1 | 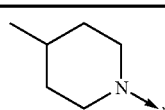 |
| 28.2 | 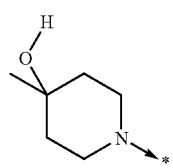 |

271
-continued
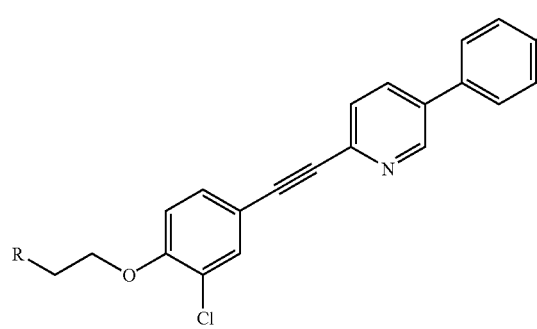
| Example | R |
|---|---|
| 28.3 | 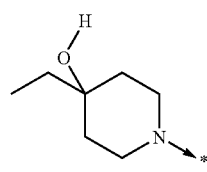 |
| 28.4 | 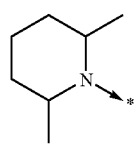 |
| 28.5 | 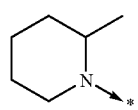 |
| 28.6 | 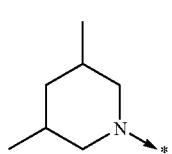 |
| 28.7 | 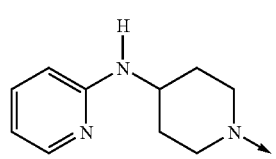 |
| 28.8 | 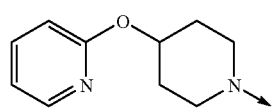 |
| 28.9 | 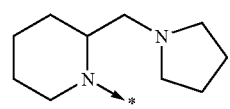 |
| 28.10 | 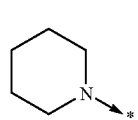 |
272
-continued
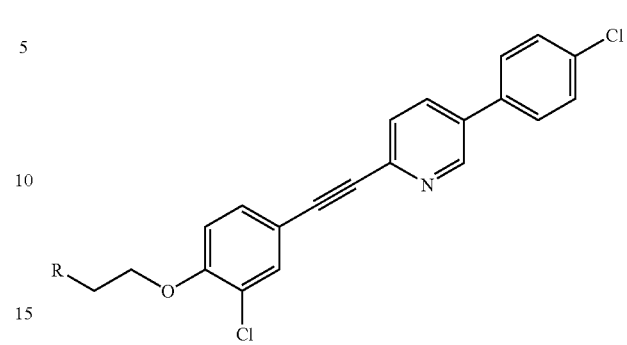
| Example | R |
|---|---|
| 28.11 | 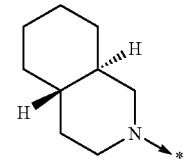 |
| 28.12 | 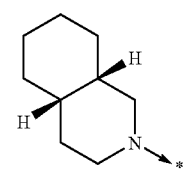 |
| 28.13 | 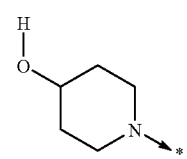 |
| 28.14 | 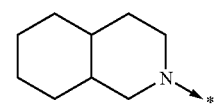 |
| 28.15 | 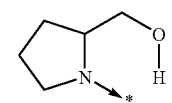 |
| 28.16 | 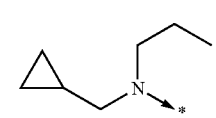 |
| 28.17 | 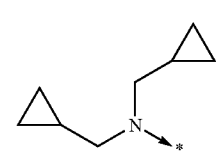 |

The following compounds may also be obtained by the processes described in the foregoing experimental section:
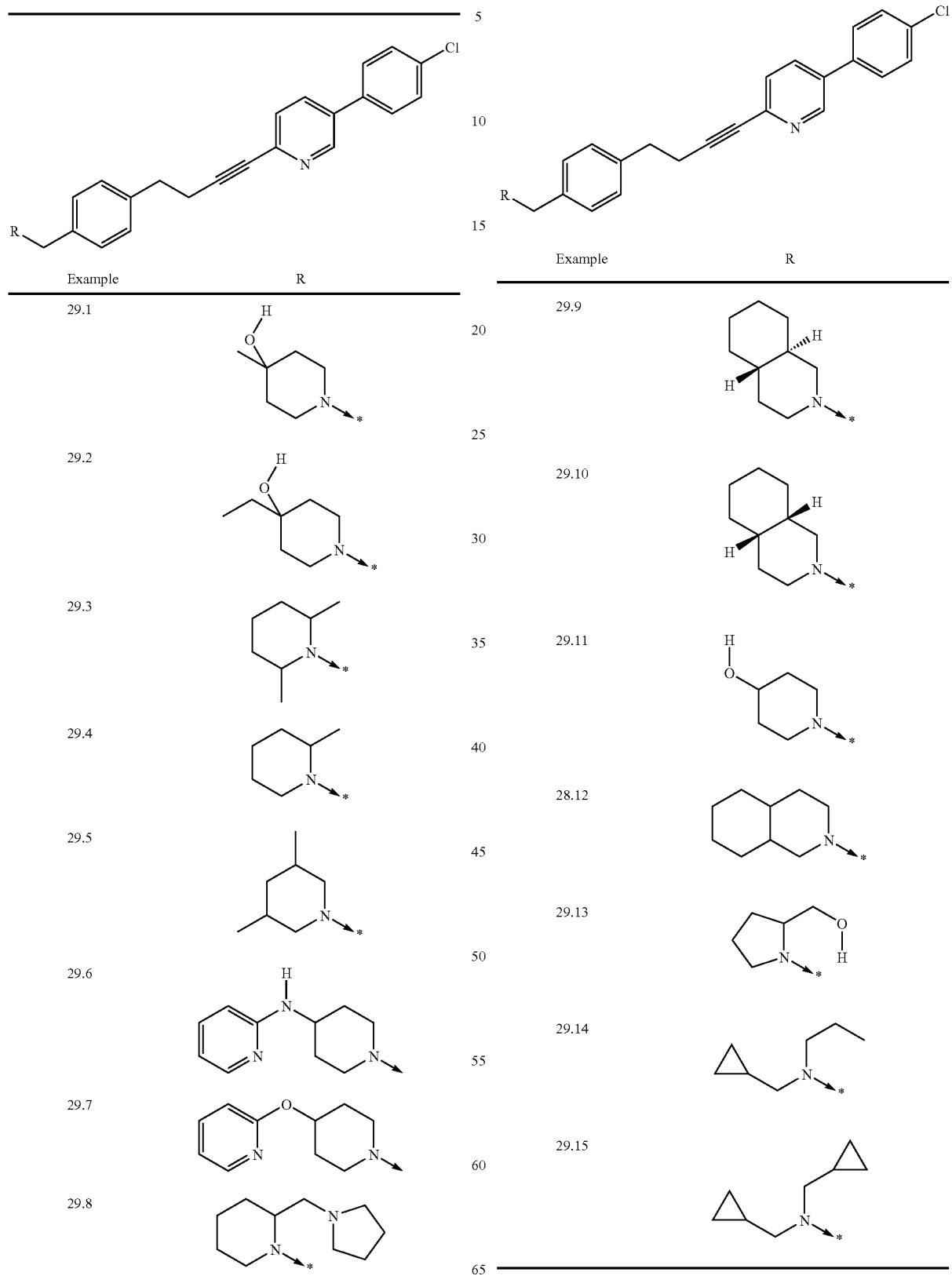

The following compounds may also be obtained by the processes described in the foregoing experimental section:
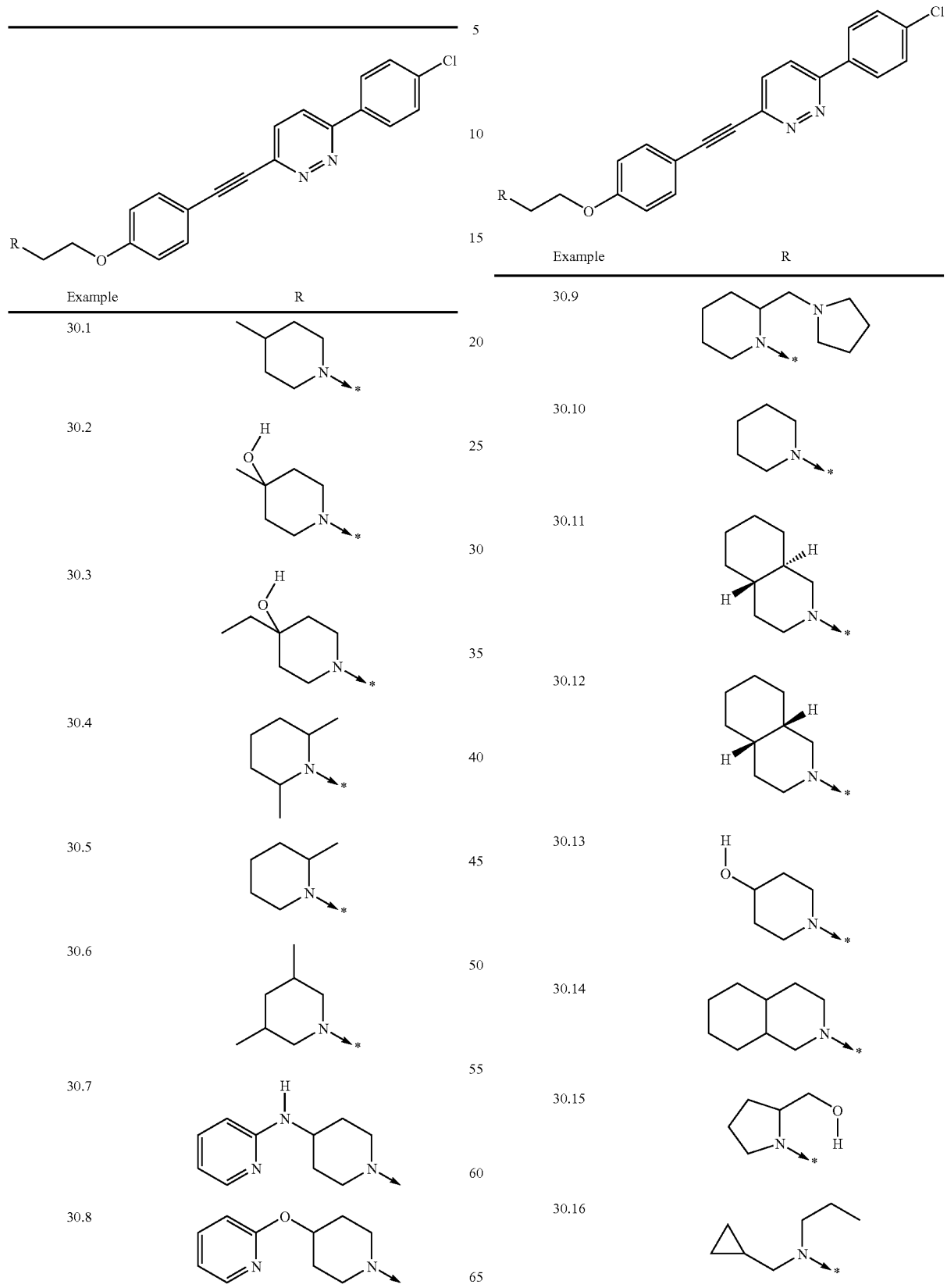

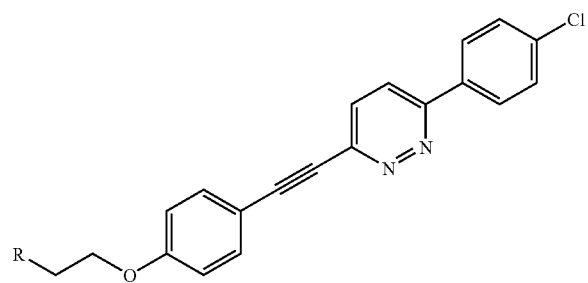
| Example | R |
|---|---|
| 30.17 | 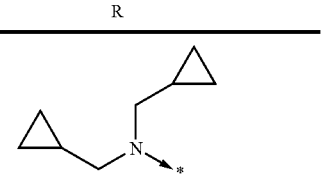 |
The following compounds may also be obtained by the processes described in the foregoing experimental section:
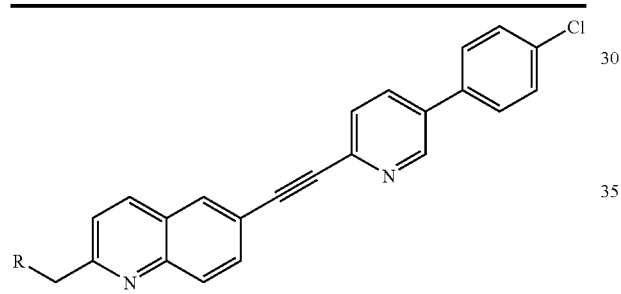
| Example | R |
|---|---|
| 31.1 | 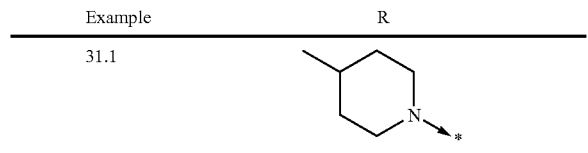 |
| 31.2 | 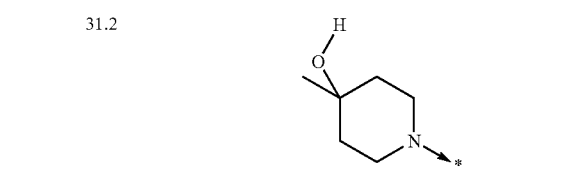 |
| 31.3 | 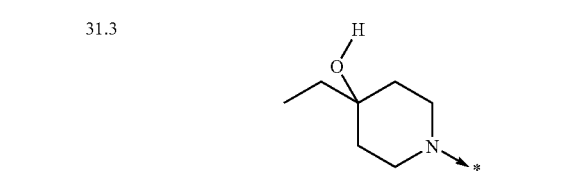 |
| 31.4 | 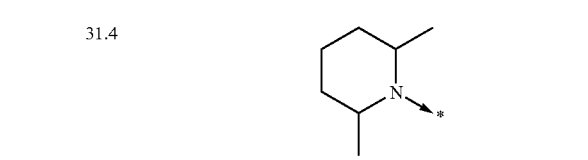 |
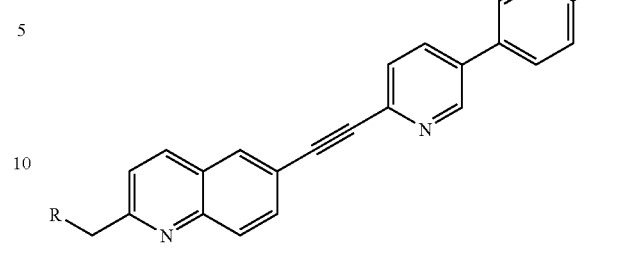
| Example | R |
|---|---|
| 31.5 | 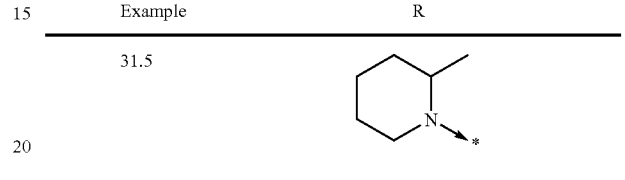 |
| 31.6 | 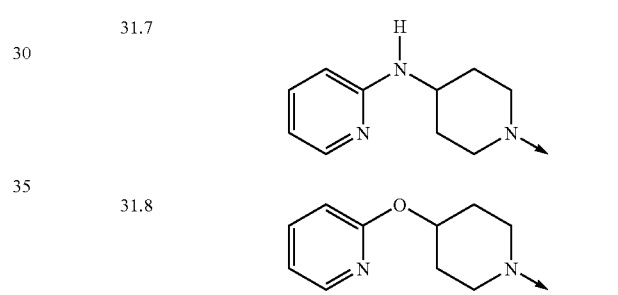 |
| 31.7 | 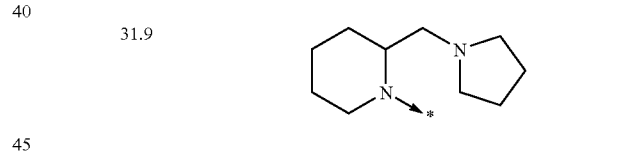 |
| 31.8 | 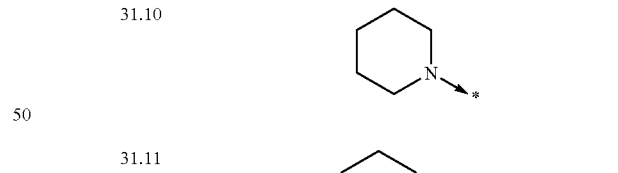 |
| 31.9 | 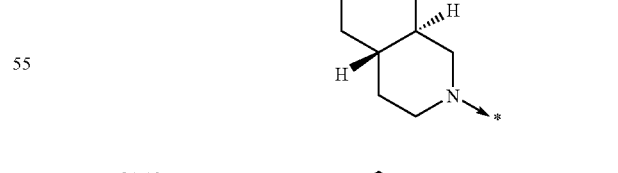 |
| 31.10 | 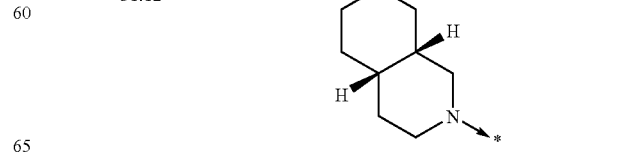 |
| 31.11 | |
| 31.12 | |

-continued
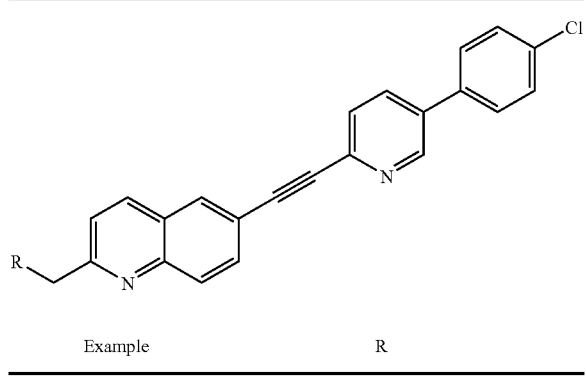
| Example | R |
|---|---|
| 31.13 | 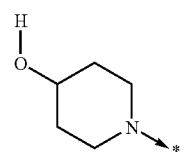 |
| 31.14 | 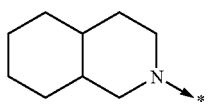 |
| 31.15 | 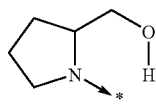 |
| 31.16 | 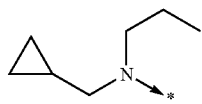 |
| 31.17 | 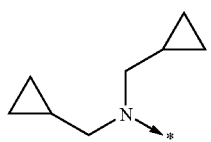 |
The compounds of Examples 32 to 32.12 may also be obtained by the processes described in the foregoing experimental section:
Example 32
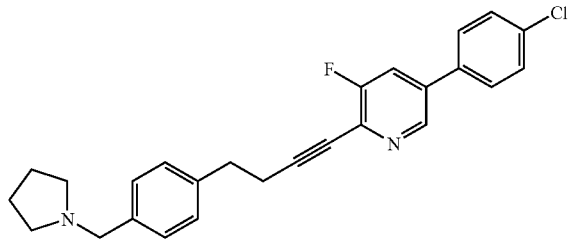 [SMILES: Fc1cc(-c2ccc(Cl)cc2)cnc1C#CCCc1ccc(CN2CCCC2)cc1]
Example 32.1
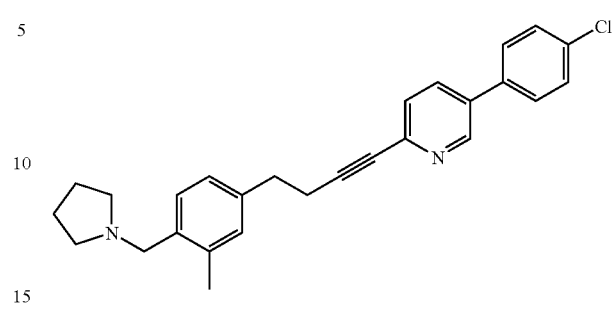
Example 32.2
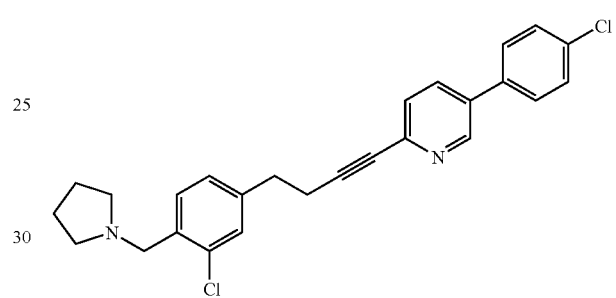
Example 32.3
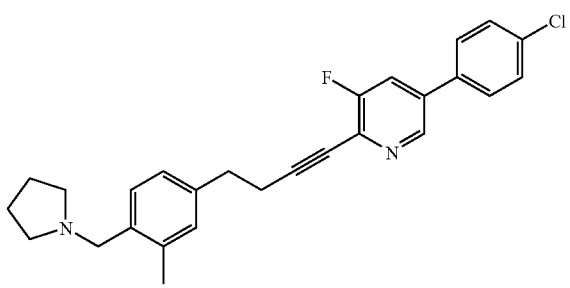 [SMILES: Cc1cc(CCC#Cc2ncc(-c3ccc(Cl)cc3)cc2F)ccc1CN1CCCC1]
Example 32.4
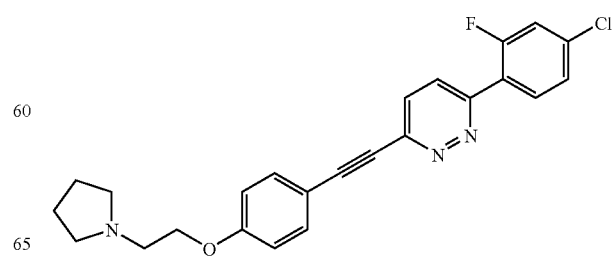

Example 32.5
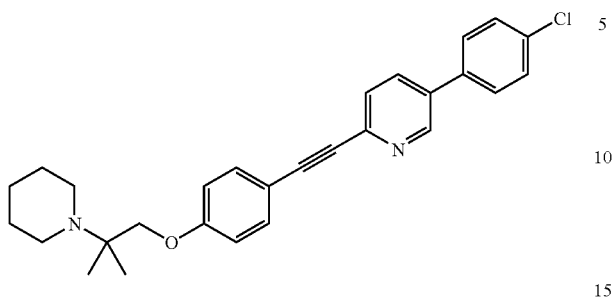
Example 32.9
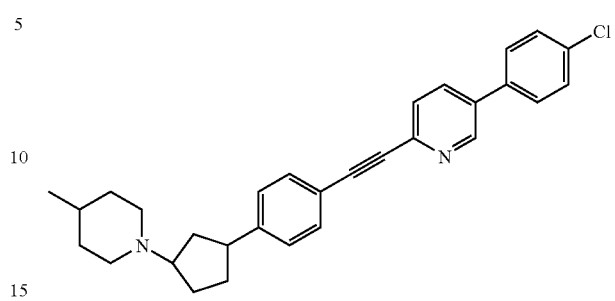
Example 32.6
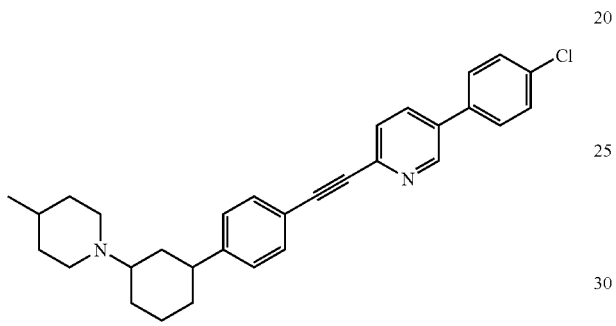
Example 32.10
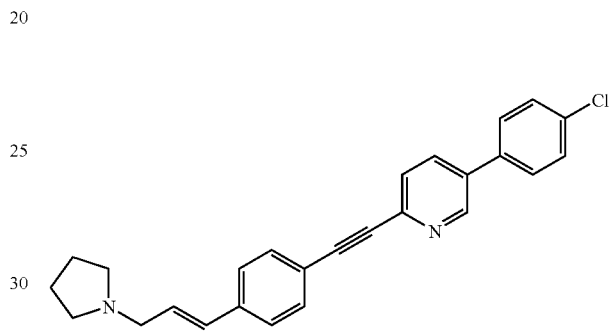
Example 32.7
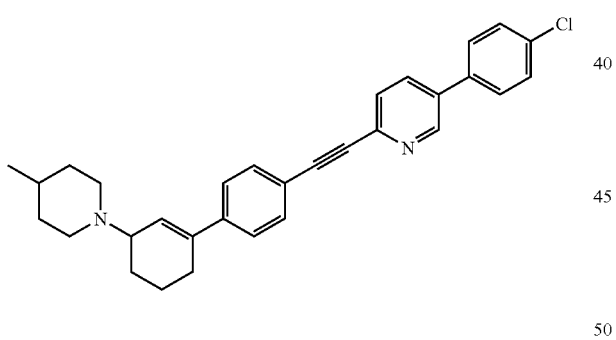
Example 32.11
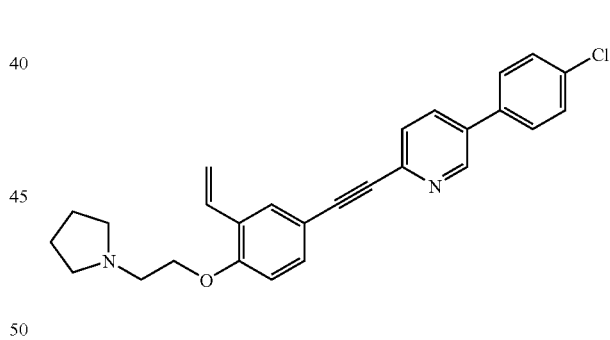
Example 32.8
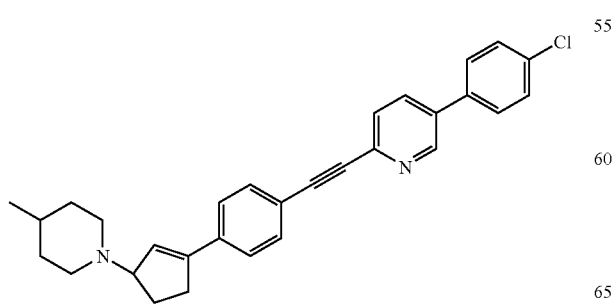
Example 32.12
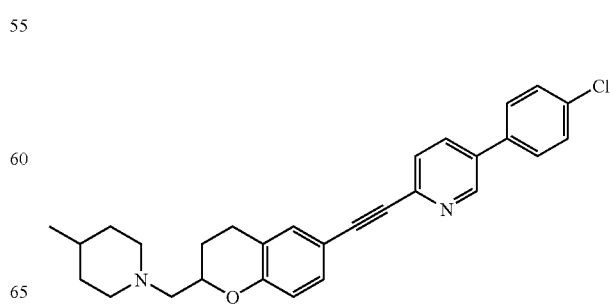

The following compounds may also be obtained by the processes described in the foregoing experimental section:

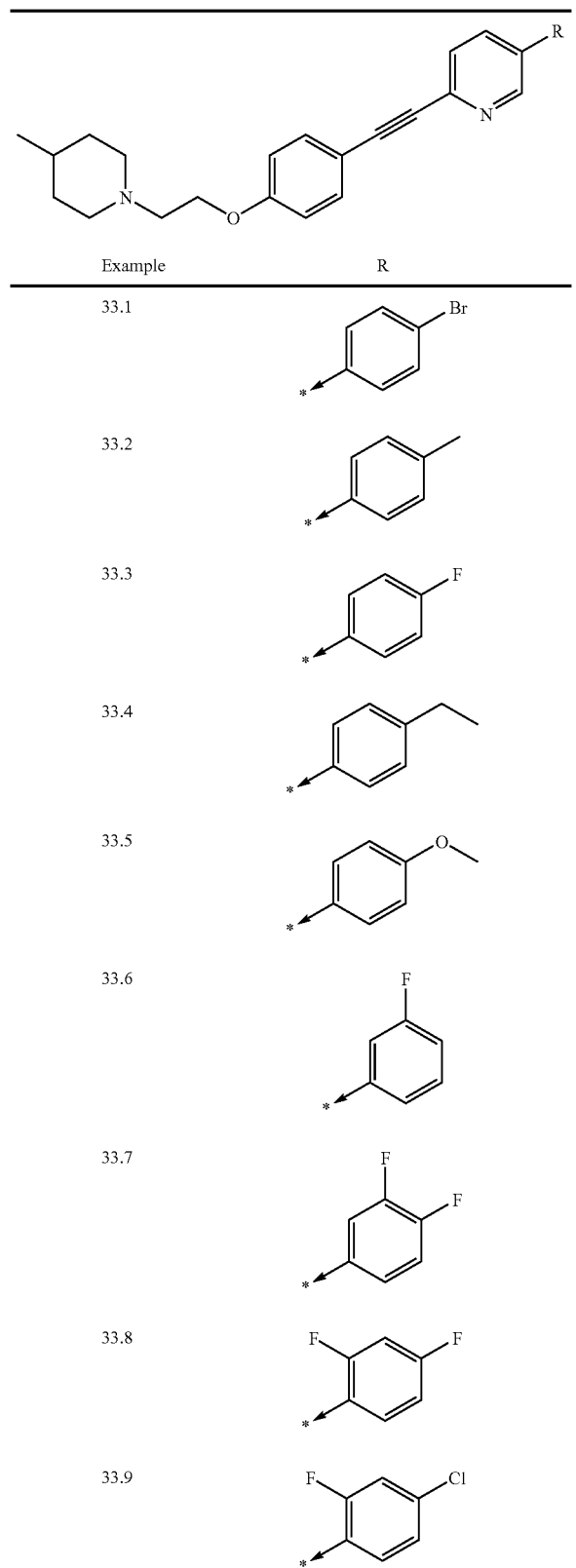

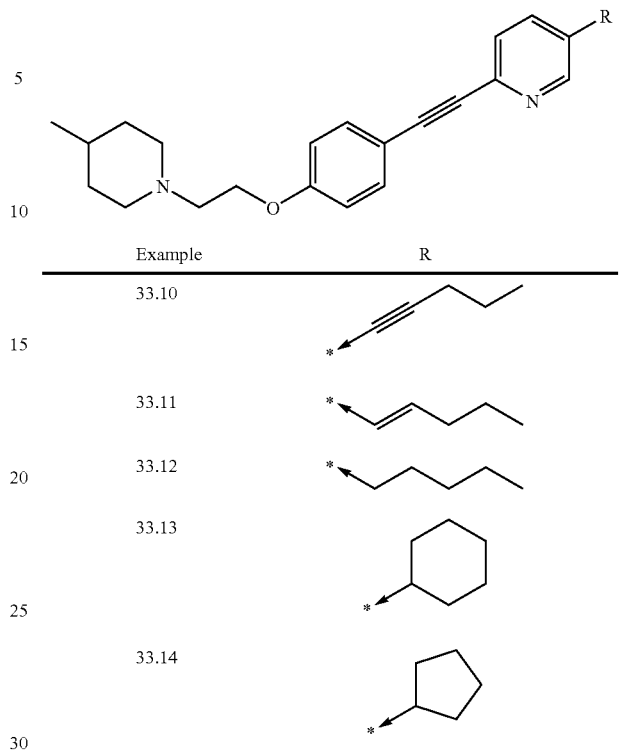

Some test methods for determining an MCH-receptor antagonistic activity will now be described. In addition, other test methods known to the skilled man are used, e.g. by inhibiting the MCH-receptor-mediated inhibition of cAMP production, as described by Hoogduijn M et al. in "Melanin-concentrating hormone and its receptor are expressed and functional in human skin", Biochem. Biophys. Res Commun. 296 (2002) 698-701 and by biosensory measurement of the binding of MCH to the MCH receptor in the presence of antagonistic substances by plasmon resonance, as described by Karlsson O P and Lofas S. in "Flow-Mediated On-Surface Reconstitution of G-Protein Coupled Receptors for Applications in Surface Plasmon Resonance Biosensors", Anal. Biochem. 300 (2002), 132-138. Other methods of testing antagonistic activity to MCH receptors are contained in the references and patent documents mentioned hereinbefore, and the description of the test methods used is hereby incorporated in this application.

| MCH-1 receptor binding test | |
|---|---|
| Method: | MCH binding to hMCH-1R transfected cells |
| Species: | Human |
| Test cell: | hMCH-1R stably transfected into CHO/Galpha16 cells |
| Results: | IC50 values |

Membranes from CHO/Galpha16 cells stably transfected with human hMCH-1R are resuspended using a syringe (needle 0.6×25 mm) and diluted in test buffer (50 mM HEPES, 10 mM $MgCl_2$, 2 mM EGTA, pH 7.00; 0.1% bovine serum albumin (protease-free), 0.021% bacitracin, 1 μg/ml aprotinin, 1 μg/ml leupeptin and 1 μM phosphoramidone) to a concentration of 5 to 15 μg/ml. 200 microliters of this membrane fraction (contains 1 to 3 μg of protein) are incubated for 60 minutes at ambient temperature with 100 μM of $^{125}$I-tyrosyl melanin concentrating hormone ($^{125}$I-MCH commercially obtainable from NEN) and increasing concentrations of the test compound in a final volume of 250 microliters. After the incubation the reaction is filtered using a cell harvester through 0.5% PEI treated glass fibre filters (GF/B, Unifilter Packard). The membrane-bound radioactivity retained on the filter is then determined after the addition of scintillator substance (Packard Microscint 20) in a measuring device (TopCount of Packard).

The non-specific binding is defined as bound radioactivity in the presence of 1 micromolar MCH during the incubation period.

The analysis of the concentration binding curve is carried out on the assumption of one receptor binding site.

Standard:

Non-labelled MCH competes with labelled $^{125}$I-MCH for the receptor binding with an IC50 value of between 0.06 and 0.15 nM.

The KD value of the radioligand is 0.156 nM.

| MCH-1 receptor-coupled $Ca^{2+}$ mobilisation test | |
|---|---|
| Method: | Calcium mobilisation test with human MCH (FLIPR$^{384}$) |
| Species: | Human |
| Test cells: | CHO/Galpha 16 cells stably transfected with hMCH-R1 |
| Results: | 1st measurement: % stimulation of the reference (MCH $10^{-6}$M) |
| | 2nd measurement: pKB value |
| Reagents: | HBSS (10x) (GIBCO) |
| | HEPES buffer (1M) (GIBCO) |
| | Pluronic F-127 (Molecular Probes) |
| | Fluo-4 (Molecular Probes) |
| | Probenecid (Sigma) |
| | MCH (Bachem) |
| | bovine serum albumin (Serva) |
| | (protease-free) |
| | DMSO (Serva) |
| | Ham's F12 (BioWhittaker) |
| | FCS (BioWhittaker) |
| | L-Glutamine (GIBCO) |
| | Hygromycin B (GIBCO) |
| | PENStrep (BioWhittaker) |
| | Zeocin (Invitrogen) |

Clonal CHO/Galpha16 hMCH-R1 cells are cultivated in Ham's F12 cell culture medium (with L-glutamine; BioWhittaker; Cat. No.: BE12-615F). This contains per 500 ml 10% FCS, 1% PENStrep, 5 ml L-glutamine (200 mM stock solution), 3 ml hygromycin B (50 mg/ml in PBS) and 1.25 ml zeocin (100 μg/ml stock solution). One day before the experiment the cells are plated on a 384-well microtitre plate (black-walled with a transparent base, made by Costar) in a density of 2500 cells per cavity and cultivated in the above medium overnight at 37° C., 5% $CO_2$ and 95% relative humidity. On the day of the experiment the cells are incubated with cell culture medium to which 2 mM Fluo-4 and 4.6 mM Probenicid have been added, at 37° C. for 45 minutes. After charging with fluorescent dye the cells are washed four times with Hanks buffer solution (1×HBSS, 20 mM HEPES), which is combined with 0.07% Probenicid. The test substances are diluted in Hanks buffer solution, combined with 2.5% DMSO. The background fluorescence of non-stimulated cells is measured in the presence of substance in the 384-well microtitre plate five minutes after the last washing step in the FLIPR$^{384}$ apparatus (Molecular Devices; excitation wavelength: 488 nm; emission wavelength: bandpass 510 to 570 nm). To stimulate the cells MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:

1st measurement: The cellular $Ca^{2+}$ mobilisation is measured as the peak of the relative fluorescence minus the background and is expressed as the percentage of the maximum signal of the reference (MCH $10^{-6}$M). This measurement serves to identify any possible agonistic effect of a test substance.

2nd measurement: The cellular $Ca^{2+}$ mobilisation is measured as the peak of the relative fluorescence minus the background and is expressed as the percentage of the maximum signal of the reference (MCH $10^{-6}$M, signal is standardised to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+MCH)}/EC_{50(MCH)} - 1) - \log c_{(testsubstance)}$$

The compounds according to the invention, including their salts, exhibit an MCH-receptor antagonistic activity in the tests mentioned above. Using the MCH-1 receptor binding test described above an antagonistic activity is obtained in a dosage range from about $10^{-10}$ to $10^{-5}$ M, particularly from $10^{-9}$ to $10^{-6}$ M.

The following IC50 values were determined using the MCH-1 receptor binding test described above:

| Compound according to Example No. | Name of substance | IC50 value |
|---|---|---|
| 1.8 | 5-(4-bromo-phenyl)-2-[4-(2-pyrrolidin-1-yl-ethoxy)-phenylethynyl]-pyridine | 8 nM |
| 1.3 | (2-{4-[5-(3,4-difluorophenyl)-pyridin-2-ylethynyl]-phenoxy}-ethyl)-diethyl-amine | 74 nM |

Some examples of formulations will be described hereinafter, wherein the term "active substance" denotes one or more compounds according to the invention, including their salts. In the case of one of the combinations with one or more active substances described, the term "active substance" also includes the additional active substances.

Example A

Capsules for Powder Inhalation Containing 1 mg Active Substance

Composition:

1 capsule for powder inhalation contains:

| | |
|---|---|
| active substance | 1.0 mg |
| lactose | 20.0 mg |
| hard gelatine capsules | 50.0 mg |
| | 71.0 mg |

Method of Preparation:

The active substance is ground to the particle size required for inhalation. The ground active substance is homogeneously mixed with the lactose. The mixture is packed into hard gelatine capsules.

Example B

Inhalable Solution for Respimat® Containing 1 mg Active Substance

Composition:

1 spray contains:

| | | |
|---|---|---|
| active substance | 1.0 | mg |
| benzalkonium chloride | 0.002 | mg |
| disodium edetate | 0.0075 | mg |
| purified water ad | 15.0 | µl |

Method of Preparation:

The active substance and benzalkonium chloride are dissolved in water and packed into Respimat® cartridges.

Example C

Inhalable Solution for Nebulisers Containing 1 mg Active Substance

Composition:

1 vial contains:

| | | |
|---|---|---|
| active substance | 0.1 | g |
| sodium chloride | 0.18 | g |
| benzalkonium chloride | 0.002 | g |
| purified water ad | 20.0 | ml |

Method of Preparation:

The active substance, sodium chloride and benzalkonium chloride are dissolved in water.

Example D

Propellant Type Metered Dose Aerosol Containing 1 mg Active Substance

Composition:

1 spray contains:

| | |
|---|---|
| active substance | 1.0 mg |
| lecithin | 0.1% |
| propellant gas ad | 50.0 µl |

Method of Preparation:

The micronised active substance is homogeneously suspended in the mixture of lecithin and propellant gas. The suspension is transferred into a pressurised contained with a metering valve.

Example E

Nasal Spray Containing 1 mg Active Substance

Composition:

| | | |
|---|---|---|
| active substance | 1.0 | mg |
| sodium chloride | 0.9 | mg |
| benzalkonium chloride | 0.025 | mg |
| disodium edetate | 0.05 | mg |
| purified water ad | 0.1 | ml |

Method of Preparation:

The active substance and the excipients are dissolved in water and transferred into a corresponding container.

Example F

Injectable Solution Containing 5 mg of Active Substance Per 5 ml

Composition:

| | | |
|---|---|---|
| active substance | 5 | mg |
| glucose | 250 | mg |
| human serum albumin | 10 | mg |
| glycofurol | 250 | mg |
| water for injections ad | 5 | ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

Example G

Injectable Solution Containing 100 mg of Active Substance Per 20 ml

Composition:

| | | |
|---|---|---|
| active substance | 100 | mg |
| monopotassium dihydrogen phosphate = $KH_2PO_4$ | 12 | mg |
| disodium hydrogen phosphate = $Na_2HPO_4 \cdot 2H_2O$ | 2 | mg |
| sodium chloride | 180 | mg |
| human serum albumin | 50 | mg |
| Polysorbate 80 | 20 | mg |
| water for injections ad | 20 | ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example H

Lyophilisate Containing 10 mg of Active Substance
Composition:

| Active substance | 10 mg |
|---|---|
| Mannitol | 300 mg |
| human serum albumin | 20 mg |

Preparation:

Mannitol is dissolved in water for injections (Wfl); human serum albumin is added; active ingredient is dissolved with heating; made up to specified volume with Wfl; transferred into vials; freeze-dried.

Solvent for Lyophilisate:

| Polysorbate 80 = Tween 80 | 20 mg |
|---|---|
| mannitol | 200 mg |
| water for injections ad | 10 ml |

Preparation:

Polysorbate 80 and mannitol are dissolved in water for injections (Wfl); transferred into ampoules.

Example I

Tablets Containing 20 mg of Active Substance
Composition:

| active substance | 20 mg |
|---|---|
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

Example J

Capsules Containing 20 mg Active Substance
Composition:

| active substance | 20 mg |
|---|---|
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size 3 hard gelatine capsules in a capsule filling machine.

Example K

Suppositories Containing 50 mg of Active Substance
Composition:

| active substance | 50 mg |
|---|---|
| hard fat (Adeps solidus) q.s. ad | 1700 mg |

Preparation:

Hard fat is melted at about 38° C.; ground active substance is homogeneously dispersed in the molten hard fat; after cooling to about 35° C. it is poured into chilled moulds.

Example L

Injectable Solution Containing 10 mg of Active Substance Per 1 ml
Composition:

| active substance | 10 mg |
|---|---|
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

What is claimed is:

1. An alkyne compound of formula IIa:

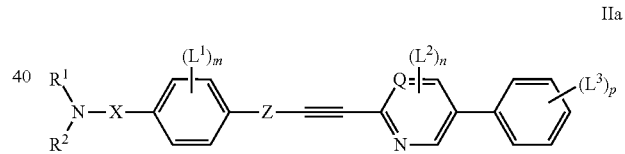

IIa wherein
$R^1$ and $R^2$ together form an alkylene bridge in such a way that $R^1R^2N$-denotes a piperidine group, wherein one or more H atoms are optionally replaced by $R^{14}$,
X is $C_2$-$C_4$-alkylenoxy,
Z is a single bond,
$R^{14}$ denotes $C_{1-4}$-alkyl, $C_{2-4}$-alkenyl, $C_{2-4}$-alkynyl, $C_{3-7}$-cycloalkyl, $C_{3-7}$cycloalkyl-$C_{1-3}$-alkyl, hydroxy, ω-hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, carboxy, $C_{1-4}$-alkoxycarbonyl, hydroxy-carbonyl-$C_{1-3}$-alkyl, $C_{1-4}$-alkoxycarbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkyl-amino, $C_{3-7}$-cycloalkyl-amino, N—($C_{3-7}$-cycloalkyl)-N—($C_{1-4}$-alkyl)-amino, di($C_{1-4}$-alkyl)-amino, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-14}$-alkyl)-amino-$C_{1-3}$-alkyl, di-($C_{1-4}$-alkyl)-amino-$C_{1-3}$-alkyl, cyclo-$C_{3-6}$-alkylene-imino-$C_{1-3}$-alkyl, aminocarbonyl, $C_{1-4}$-alkyl-amino-carbonyl, $C_{3-7}$-cycloalkyl-amino-carbonyl, N—($C_{3-7}$-cycloalkyl)-N—($C_{1-4}$-alkyl)-amino-carbonyl, or di-($C_{1-4}$-alkyl)-amino-carbonyl, Q is CH, L¹, L², and L³, independently of one another are F, Cl, Br, I, OH, cyano, $C_{1-4}$-alkyl, $C_{2-4}$-alkynyl, $C_{1-4}$-alkoxy, difluoromethyl, trifluoromethyl, amino, $C_{1-4}$-alkylamino, di-($C_{1-4}$-alkyl)-amino, acetylamino, aminocarbonyl, difluoromethoxy, trifluoromethoxy, amino-$C_{1-3}$-alkyl, $C_{1-4}$-alkylamino-$C_{1-3}$-alkyl or di-($C_{1-4}$-alkyl)-amino-$C_{1-3}$-alkyl or nitro, with the proviso that a phenyl may only be monosubstituted by nitro, m, n, and p, independently of one another represent the values 0, 1 or 2, and may also have the value 3, while the above-mentioned groups X, Z, R¹, R² and R¹⁴ one or more C atoms are optionally additionally mono- or polysubstituted by F and/or one or two C atoms, independently of one another, are optionally additionally monosubstituted by Cl or Br, or a tautomer, a diastereomer, an enantiomer, a mixture thereof or a salt thereof.

2. An alkyne compound according to claim 1, which is in a physiologically acceptable salt form.

3. A composition comprising an alkyne compound according to claim 1, together with one or more inert carriers and/or diluents.

4. An alkyne compound according to claim 1, wherein X is —CH₂—CH₂—O—.

5. An alkyne compound according to claim 1, wherein R¹⁴ is $C_{1-4}$-alkyl, hydroxy, ω-hydroxy-$C_{1-3}$-alkyl, $C_{1-4}$-alkoxy and ω-($C_{1-4}$-alkoxy)-$C_{1-3}$-alkyl.

6. An alkyne compound according to claim 1, wherein

L¹, L² and L³ independently of each other denote F, Cl, Br, I, OH, cyano, methyl, difluoromethyl, trifluoromethyl, ethyl, n-propyl, iso-propyl, methoxy, difluoromethoxy, trifluoromethoxy, ethoxy, n-propoxy or iso-propoxy, while any substituents L1, L2 and L3 occurring repeatedly may have identical or different meanings.

7. An alkyne compound according to claim 1 selected from the following formulae:

(1) [1-(2-{4-[5-(4-chloro-phenyl)-pyridine-2-ylethynyl]-phenoxy}-ethyl)-piperidin-4-yl]-methanol (2) 1-(2-{4-[5-(4-chloro-phenyl)-pyridine-2-ylethynyl]-2-methyl-phenoxy}ethyl)-piperidin-3-ol (3) 5-(4-chloro-phenyl)-2-{4-[2-(4-propyl-piperidine-1-yl)-ethoxy]-phenylethynyl}-pyridine (4) 5-(4-chloro-phenyl)-2-{4-[2-(2,6-dimethyl-piperidine-1-yl)-ethoxy]-3-methyl-phenylethynyl}-pyridine (5) 5-(4-chloro-phenyl)-2-[3-methyl-4-(2-piperidine-1-yl-ethoxy)-phenylethynyl]-pyridine (6) 1-(2-{4-[5-(4-chloro-phenyl)-pyridin-2-ylethynyl]-2-methyl-phenoxy}-ethyl)-piperidin-4-ol (9) 1-(2-{4-[5-(4-chloro-phenyl)-pyridin-2-ylethynyl]-phenoxy}-ethyl)-4-methyl-piperidin-4-ol

(10) 5-(4-chloro-phenyl)-2-{3-methyl-4-[2-(4-methyl-piperidin-1-yl)-ethoxy]-phenylethynyl}-pyridine

(11) 5-(4-chloro-phenyl)-3-fluoro-2-{4-[2-(4-methyl-piperidin-1-yl)-ethoxy]phenylethynyl}-pyridine

(12) methyl [1-(2-{4-[5-(4-chloro-phenyl)-pyridin-2-yiethynyl]-2-methyl-phenoxy}-ethyl)-piperidin-4-yl]-acetate

(13) 5-(4-chloro-phenyl)-2-[4-(2-piperidin-1-yl-ethoxy)-phenylethynyl]-pyridine

(14) N-[1-(2-{4-[5-(4-chloro-phenyl)-pyridin-2-ylethynyl]-phenoxy}-ethyl)-piperidin-4-ylmethyl]-N-methyl-acetamide

(15) 5-(4-chloro-phenyl)-2-{4-[2-(4-ethyl-piperidin-1-yl)-ethoxy]-phenylethynyl}-pyridine

(16) [1-(2-{4-[5-(4-chloro-phenyl)-pyridin-2-ylethynyl]-2-methyl-phenoxy}-ethyl)-piperidin-4-yl]-methanol

(17) 1-(2-{4-[5-(4-chloro-phenyl)-pyridin-2-ylethynyl]-2-methyl-phenoxy}-ethyl)-4-methyl-piperidin-4-ol

(18) 1-(2-{4-[5-(4-chloro-phenyl)-pyridin-2-ylethynyl]-phenoxy}-ethyl)-piperidin-4-ol

(21) 1-(2-{4-[5-(4-chloro-phenyl)-pyridin-2-ylethynyl]-2-methyl-phenoxy}-ethyl)-4-methyl-piperidin-4-ylamine

(22) 5-(4-chloro-phenyl)-2-{4-[2-(2,6-dimethyl-piperidin-1-yl)-ethoxy]-phenylethynyl}-pyridine

(23) [1-(2-{4-[5-(4-chloro-phenyl)-pyridin-2-ylethynyl]-2-methyl-phenoxy}-ethyl)-piperidin-2-yl]-methanol

(24) 1-(2-{4-[5-(4-chloro-phenyl)-pyridin-2-ylethynyl]-phenoxy}-ethyl)-piperidin-4-carboxylic acid amide

(25) 5-(4-chloro-phenyl)-2-{4-[2-(4-methyl-piperidin-1-yl)-ethoxy]-phenylethynyl}-pyridine

(26) {2-[1-(2-{4-[5-(4-chloro-phenyl)-pyridin-2-ylethynyl]-2-methyl-phenoxy}-ethyl)-piperidin-4-yl]ethyl}-diethyl-amine

(27) 5-(4-chloro-phenyl)-2-{4-[2-(2,4,6-trimethyl-piperidin-1-yl)-ethoxy]-phenylethynyl}-pyridine

(28) 5-(4-chloro-phenyl)-2-{4-[2-(3,5-dimethyl-piperidin-1-yl)-ethoxy]-3-methyl-phenylethynyl}-pyridine

(29) [1-(2-{4-[5-(4-chloro-phenyl)-pyridin-2-ylethynyl]-2-methyl-phenoxy}-ethyl)-piperidin-4-yl]-cyclopentyl-methyl-amine

(30) 5-(4-chloro-phenyl)-2-{4-[2-(4-pyrrolidin-1-yl-piperidin-1-yl)-ethoxy]-phenylethynyl}-pyridine

(31) [1-(2-{4-[5-(4-chloro-phenyl)-pyridin-2-ylethynyl]-phenoxy}-ethyl)-piperidin-4-ylmethyl]-dimethyl-amine or an enantiomer, a mixture thereof or a salt thereof.

8. An alkyne compound, which compound is 5-(4-chloro-phenyl)-2-{4-[2-(4-methyl-piperidin-1-yl)-ethoxy]-phenylethynyl}-pyridine, or an enantiomer thereof, or a mixture of enantiomers thereof, or a salt thereof.

* * * * *